United States Patent
Axford et al.

(10) Patent No.: US 9,040,712 B2
(45) Date of Patent: May 26, 2015

(54) THIADIAZOLE ANALOGS THEREOF AND METHODS FOR TREATING SMN-DEFICIENCY-RELATED-CONDITIONS

(71) Applicants: Jake Axford, Boston, MA (US); Natalie Dales, Arlington, MA (US); Moo Je Sung, Belmont, MA (US)

(72) Inventors: Jake Axford, Boston, MA (US); Natalie Dales, Arlington, MA (US); Moo Je Sung, Belmont, MA (US)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 14/160,180

(22) Filed: Jan. 21, 2014

(65) Prior Publication Data

US 2014/0206661 A1 Jul. 24, 2014

Related U.S. Application Data

(60) Provisional application No. 61/755,680, filed on Jan. 23, 2013.

(51) Int. Cl.

| | |
|---|---|
| *C07D 417/14* | (2006.01) |
| *A61K 31/433* | (2006.01) |
| *A61K 31/435* | (2006.01) |
| *A61K 31/437* | (2006.01) |
| *A61K 31/454* | (2006.01) |
| *A61K 31/4709* | (2006.01) |
| *A61K 31/506* | (2006.01) |
| *A61K 31/5377* | (2006.01) |
| *A61K 45/06* | (2006.01) |
| *C07D 417/12* | (2006.01) |
| *C07D 471/04* | (2006.01) |
| *C07D 471/10* | (2006.01) |
| *C07D 487/04* | (2006.01) |
| *A61K 31/438* | (2006.01) |
| *C07D 487/20* | (2006.01) |
| *A61K 31/496* | (2006.01) |
| *A61K 31/4436* | (2006.01) |
| *C07D 487/10* | (2006.01) |

(52) U.S. Cl.
CPC ............ *C07D 417/14* (2013.01); *A61K 31/433* (2013.01); *A61K 31/435* (2013.01); *A61K 31/437* (2013.01); *A61K 31/454* (2013.01); *A61K 31/4709* (2013.01); *A61K 31/506* (2013.01); *A61K 31/5377* (2013.01); *A61K 45/06* (2013.01); *C07D 417/12* (2013.01); *C07D 471/04* (2013.01); *C07D 471/10* (2013.01); *C07D 487/04* (2013.01); *A61K 31/438* (2013.01); *C07D 487/20* (2013.01); *A61K 31/496* (2013.01); *A61K 31/4436* (2013.01); *C07D 487/10* (2013.01)

(58) Field of Classification Search
CPC .. C07D 417/12; C07D 417/14; C07D 487/04; C07D 487/20; A61K 31/5377; A61K 31/506; A61K 31/496; A61K 31/4709; A61K 31/454; A61K 31/4436; A61K 31/438; A61K 31/433
See application file for complete search history.

(56) References Cited

U.S. PATENT DOCUMENTS

| | | | |
|---|---|---|---|
| 3,677,737 A | 7/1972 | Dahle et al. | |
| 5,086,053 A | 2/1992 | Brodin et al. | |
| 2005/0065178 A1* | 3/2005 | Basha et al. | 514/300 |
| 2005/0101602 A1 | 5/2005 | Bunnelle et al. | |
| 2011/0224187 A1* | 9/2011 | Palani et al. | 514/210.05 |

FOREIGN PATENT DOCUMENTS

| | | |
|---|---|---|
| DE | 136963 | 8/1979 |
| WO | 03/094831 | 11/2003 |
| WO | 2004014370 | 2/2004 |
| WO | 2004014881 | 2/2004 |
| WO | 2004014902 | 2/2004 |
| WO | 2004110351 | 12/2004 |
| WO | 2005077368 | 8/2005 |
| WO | 2005077373 | 8/2005 |
| WO | 2006/008259 | 1/2006 |
| WO | 2006034341 | 3/2006 |
| WO | 2006044860 | 4/2006 |
| WO | 2008107677 | 9/2008 |
| WO | 2009/058348 | 5/2009 |
| WO | 2010/022055 | 2/2010 |
| WO | 2010/045303 | 4/2010 |
| WO | 2011/082732 | 7/2011 |
| WO | 2011107530 | 9/2011 |
| WO | 2011133882 | 10/2011 |
| WO | WO 2011130515 A1 * | 10/2011 |

(Continued)

OTHER PUBLICATIONS

Corcia et al. Amyotrophic Lateral Sclerosis 2009, 10, 436-440.*

(Continued)

*Primary Examiner* — Joseph Kosack
*Assistant Examiner* — Matthew Coughlin
(74) *Attorney, Agent, or Firm* — Joshua Roth

(57) ABSTRACT

The present invention provides a compound of Formula (X) or a pharmaceutically acceptable salt thereof;

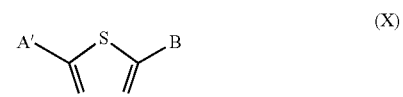

(X)

a method for manufacturing the compounds of the invention, and its therapeutic uses. The present invention further provides a combination of pharmacologically active agents and a pharmaceutical composition.

16 Claims, No Drawings

(56) References Cited

FOREIGN PATENT DOCUMENTS

| WO | 2012/129338 | 9/2012 |
| WO | 2013149121 | 10/2013 |

OTHER PUBLICATIONS

Motor Neurone Disease Assocation (Living with Motor Neurone Disease, 2013, pp. 1-117.*
CAS Registry No. 1031061-23-0, which entered STN on Jun. 26, 2008.*
Srihari et al. Synthesis, 2006, 16, 2646-2648.*
Xiao et al. J. Med. Chem. 2011, 54, 6215-6233.*
Alemagna et al., Tetrahedron, 24(8):3209-3217 (1968).
Xiao et al., ioorganic & Medicinal Chemistry Letters, 21(2):861-864 (2011).
Hwang et al., J. Comb. Chem./, 7:816-819 (2005).
Lalezari et al., Journal of Pharmaceutical Sciences, 64(7):1250-1252 (1975).
Rusu et al., Russian Chemical Bulletin, 49(10):1763-1766 (2000).
Database Registry Chemical Abstracts Service, XP002722070, Database Accession No. 1031061-23-0 (2008).
Database Registry Chemical Abstracts Service, XP02722071, Database Accession No. 942659-39-4 (2007).
Database Registry Chemical Abstracts Service, XP002722072, Database Accession No. 1181524-94-6 (2009).
Database Registry Chemical Abstracts Service, XP002722073, Database Accession No. 1254358-28-5 (2010).
Database Registry Chemical Abstracts Service, XP002722074, Database Accession No. 1422647-09-3 (2013).
Database Registry Chemical Abstracts Service, XP002722075, Database Accession No. 1453002-96-4 (2013).
Lipunova et al., Russian Journal of Organic Chemistry, 38(12):1790-1796 (2002).
Turner et al., Neurobiology of Disease, 34(3):511-517 (2009).

* cited by examiner

THIADIAZOLE ANALOGS THEREOF AND METHODS FOR TREATING SMN-DEFICIENCY-RELATED-CONDITIONS

BACKGROUND OF THE INVENTION

Proximal spinal muscular atrophy (SMA) is an inherited, clinically heterogeneous group of neuromuscular disorders characterized by degeneration of the anterior horn cells of the spinal cord. Patients suffer from symmetrical weakness of trunk and limb muscles, the legs being more affected than the arms and the proximal muscles weaker than the distal ones; diaphragm, facial and ocular muscles are spared. There are three forms of childhood-onset SMA (types I, II and III), and a relatively recently categorized adult-onset form IV, all of which can be distinguished on the basis of age of onset and severity of the clinical course assessed by clinical examination, muscle biopsy and electromyography (EMG) (Munsat T L, Davies K E (1992)).

Type I (Werdnig-Hoffmann disease) is the most acute and severe form, with onset before six months and death usually before two years; children are never able to sit without support. Symptoms of the disease can be present in utero, as reduction of fetal movements; at birth; or more often, within the first four months of life. Affected infants are particularly floppy, experience feeding difficulties and diaphragmatic breathing, and are characterized by a general weakness in the intercostals and accessory respiratory muscles. Affected children never sit or stand and usually die before the age of 2; death is generally due to respiratory insufficiency.

Type II (intermediate, chronic form) has onset between six and eighteen months of age; muscular fasciculations are common, and tendon reflexes progressively reduce. Children are unable to stand or walk without aid. Feeding and swallowing problems are not usually present in Type II SMA, although in some patients a feeding tube may become necessary. Most patients generally develop a progressive muscular scoliosis which can require surgical correction. Like patients with type I disease, clearing of tracheal secretions and coughing might become difficult because of poor bulbar function and weak intercostal muscles. These patients have profound hypotonia, symmetrical flaccid paralysis, and no control of head movement.

Type III (Kugelberg-Welander disease, or Juvenile Spinal Muscular Atrophy) is a mild, chronic form, with onset after the age of 18 months; motor milestones achievement is normal, and deambulation can be preserved until variable ages. These patients often develop scoliosis, and symptoms of joint overuse, generally caused by weakness, are frequently seen. Life expectancy is almost normal but quality of life is markedly compromised.

Types I, II and III SMA progress over time, accompanied by deterioration of the patient's condition.

Adult-onset type IV is characterized by weakness in the second or third decade of life, with mild motor impairment not accompanied by respiratory or nutritional problems. Adult SMA is characterized by insidious onset and very slow progression. The bulbar muscles are rarely affected in Type IV. It is not clear that Type IV SMA is etiologically related to the Type I-III forms.

Other forms of spinal muscular atrophy include X-linked disease, spinal muscular atrophy with respiratory distress (SMARD), spinal and bulbar muscular atrophy (Kennedy's disease, or Bulbo-Spinal Muscular Atrophy), and distal spinal muscular atrophy.

SMA is due to mutations in the Survival of Motor Neuron (SMN) gene, which exists in two forms in humans (SMN1 and SMN2). Loss of SMN is deleterious to motor neurons and results in neuromuscular insufficiency, a hallmark of the disease. From a genetic point of view, SMA is an autosomal recessive condition, caused by disruption of SMN1 gene, located in 5q13 (Lefebvre S., et al. (1995) Cell 80: 155-165). More than 98% of patients with spinal muscular atrophy have a homozygous disruption of SMN1 by deletion, rearrangement, or mutation. All these patients, however, retain at least one copy of SMN2.

At the genomic level, only five nucleotides have been found that differentiate the SMN1 gene from the SMN2 gene. Furthermore, the two genes produce identical mRNAs, except for a silent nucleotide change in exon 7, i.e., a C→T change six base pairs inside exon 7 in SMN2. This mutation modulates the activity of an exon splicing enhancer (Lorson and Androphy (2000) Hum. Mol. Genet. 9:259-265). The result of this and the other nucleotide changes in the intronic and promoter regions is that most SMN2 are alternatively spliced, and their transcripts lack exons 3, 5, or 7. In contrast, the mRNA transcribed from the SMN1 gene is generally a full-length mRNA with only a small fraction of its transcripts spliced to remove exon 3, 5, or 7 (Gennarelli et al. (1995) Biochem. Biophys. Res. Commun. 213:342-348; Jong et al. (2000) J. Neurol. Sci. 173:147-153). All SMA subjects have at least one, and generally two to four copies of the SMN2 gene, which encodes the same protein as SMN1; however, the SMN2 gene produces predominantly truncated protein (SMNΔ7) and only low levels of full-length SMN protein.

The SMNΔ7 protein is non-functional and thought to be rapidly degraded. About 10% of SMN2 pre-mRNA is properly spliced and subsequently translated into full length SMN protein (FL-SMN), and the rest being the SMNΔ7 copy. The efficiency of SMN2 splicing might be dependent on severity of disease, and production of a full length transcript of SMN2 could range from 10% to 50%. Furthermore, presence or absence of the SMN1 gene, roughly 90% of which becomes the FL-SMN gene product and protein, influences the severity of SMA by whether or not it can compensate for the truncated SMNΔ7 copies. A low level of SMN protein allows embryonic development, but is not sufficient to sustain the survival of motor neurons of the spinal cord.

The clinical severity of SMA patients inversely correlates with the number of SMN2 genes and with the level of functional SMN protein produced (Lorson C L, et al. (1999) PNAS; 96:6307-6311) (Vitali T. et al. (1999) Hum Mol Genet; 8:2525-2532) (Brahe C. (2000) Neuromusc. Disord.; 10:274-275) (Feldkotter M, et al. (2002) Am J Hum Genet; 70:358-368) (Lefebvre S, et al. (1997) Nature Genet; 16:265-269) (Coovert D D, et al. (1997) Hum Mol Genet; 6:1205-1214) (Patrizi A L, et al. (1999) Eur J Hum Genet; 7:301-309).

Current therapeutic strategies for SMA are mostly centered on elevating full length (wild type) SMN protein levels, modulating splicing towards exon 7 inclusion, stabilizing the wild type protein, and to a lesser extent, on restoring muscle function in SMA by providing trophic support or by inhibiting skeletal muscle atrophy.

The mechanism leading to motorneuron loss and to muscular atrophy still remains obscure, although the availability of animal models of the disease is rapidly increasing knowledge in this field (Frugier T, et al. (2000) Hum Mol. Genet. 9:849-58; Monani U R, et al. (2000) Hum Mol Genet 9:333-9; Hsieh-Li H M, et al. (2000) Nat Genet 24:66-70; Jablonka S, et al. (2000) Hum Mol. Genet. 9:341-6). Also the function of SMN protein is still partially unknown, and studies indicate that it can be involved in mRNA metabolism (Meister G, et al. (2002). Trends Cell Biol. 12:472-8; Pellizzoni L, et al. (2002). Science. 298: 1775-9), and probably in transport of proteins/ mRNA to neuromuscular junctions (Ci-fuentes-Diaz C, et al. (2002) Hum Mol. Genet. 11: 1439-47; Chan Y B, et al. (2003) Hum Mol. Genet. 12:1367-76; McWhorter M L, et al. (2003) J. Cell Biol. 162:919-31; Rossoll W, et al. (2003) J. Cell Biol. 163:801-812).

In addition to the SMAs, a subclass of neurogenic-type arthrogryposis multiplex congenita (congenital AMC) has separately been reported to involve SMN1 gene deletion, suggesting that some degree of pathology in those afflicted is likely due to low levels of motor neuron SMN. (L. Burgien et al., (1996) J. Clin. Invest. 98(5):1130-32. Congenital AMC affects humans and animals, e.g., horses, cattle, sheep, goats, pigs, dogs, and cats. (M. Longeri et al., (2003) Genet. Sel. Evol. 35:S167-S175). Also, the risk of development or the severity of amyotrophic lateral sclerosis (ALS) has been found to be correlated with low levels of motor neuron SMN.

There is no cure or effective treatment for SMA available to date and therefore it would be advantageous to provide novel methods for modulating SMN in order to treat those afflicted with SMA, with neurogenic congenital AMC, ALS, or with other SMN-deficiency-related conditions. It would further be advantageous to provide novel drug targets that could be used as a basis for developing effective therapeutics or diagnostics for such neuronal conditions.

SUMMARY OF THE INVENTION

There is a need for new treatments and therapies for Spinal Muscular Atrophy. The invention provides compounds, salts thereof, pharmaceutical formulations thereof and combinations thereof which compounds are Spinal Muscular Atrophy modulators. The invention further provides methods of treating, preventing, or ameliorating Spinal Muscular Atrophy, comprising administering to a subject in need thereof an effective amount of an SMN modulator (e.g., a compound of the invention).

Various embodiments of the invention are described herein. It will be recognized that features specified in each embodiment may be combined with other specified features to provide further embodiments.

Within certain aspects, SMN modulators provided herein are compounds of Formula X and salts thereof:

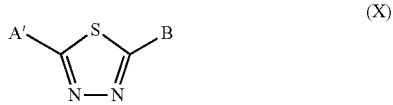
(X)

wherein A' is phenyl which is substituted with 0, 1, 2, or 3 substituents independently selected from $C_1$-$C_4$alkyl, wherein 2 $C_1$-$C_4$alkyl groups can combine with the atoms to which they are bound to form a 5-6 membered ring and is substituted with 0 or 1 substituents selected from oxo, oxime and, hydroxy, halo$C_1$-$C_4$alkyl, dihalo$C_1$-$C_4$alkyl, trihalo$C_1$-$C_4$alkyl, $C_1$-$C_4$alkoxy, $C_1$-$C_4$alkoxy-$C_3$-$C_7$cycloalkyl, halo$C_1$-$C_4$alkoxy, dihalo$C_1$-$C_4$alkoxy, trihalo$C_1$-$C_4$alkoxy, hydroxy, cyano, halogen, amino, mono- and di-$C_1$-$C_4$alkylamino, heteroaryl, $C_1$-$C_4$alkyl substituted with hydroxy, $C_1$-$C_4$alkoxy substituted with aryl, amino, —C(O)NH$C_1$-$C_4$alkyl-heteroaryl, —NHC(O)—$C_1$-$C_4$alkyl-heteroaryl, $C_1$-$C_4$alkyl C(O)NH— heteroaryl, $C_1$-$C_4$alkyl NHC (O)— heteroaryl, 3-7 membered cycloalkyl, 5-7 membered cycloalkenyl or 5, 6 or 9 membered heterocycle containing 1 or 2 heteroatoms, independently, selected from S, O and N, wherein heteroaryl has 5, 6 or 9 ring atoms, 1, 2 or 3 ring heteroatoms selected from N, O and S and substituted with 0, 1, or 2 substituents independently selected from oxo, hydroxy, nitro, halogen, $C_1$-$C_4$alkyl, $C_1$-$C_4$alkenyl, $C_1$-$C_4$alkoxy, $C_3$-$C_7$cycloalkyl, $C_1$-$C_4$alkyl-OH, trihalo$C_1$-$C_4$alkyl, mono- and di-$C_1$-$C_4$alkylamino, —C(O)NH$_2$, —NH$_2$, —NO$_2$, hydroxyC1-$C_4$alkylamino, hydroxy$C_1$-$C_4$alkyl, 4-7 member heterocycle$C_1$-$C_4$alkyl, amino$C_1$-$C_4$alkyl and mono- and di-$C_1$-$C_4$alkylamino$C_1$-$C_4$alkyl; or A' is 6 member heteroaryl having 1-3 ring nitrogen atoms, which 6 member heteroaryl is substituted by phenyl or a heteroaryl having 5 or 6 ring atoms, 1 or 2 ring heteroatoms independently selected from N, O and S and substituted with 0, 1, or 2 substituents independently selected from $C_1$-$C_4$alkyl, mono- and di-$C_1$-$C_4$alkylamino, hydroxy$C_1$-$C_4$alkylamino, hydroxy$C_1$-$C_4$alkyl, amino$C_1$-$C_4$alkyl and mono- and di-$C_1$-$C_4$alkylamino$C_1$-$C_4$alkyl; or A' is bicyclic heteroaryl having 9 to 10 ring atoms and 1, 2, or 3 ring heteroatoms independently selected from N, O or S, which bicyclic heteroaryl is substituted with 0, 1, or 2 substituents independently selected from oxo, cyano, halogen, hydroxy, $C_1$-$C_4$alkyl, $C_2$-$C_4$alkenyl, $C_2$-$C_4$alkynyl, $C_1$-$C_4$alkoxy and $C_1$-$C_4$alkoxy substituted with hydroxy, $C_1$-$C_4$alkoxy, amino and mono- and di-$C_1$-$C_4$alkylamino; B is a group of the formula:

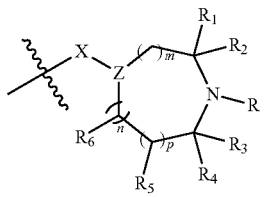

wherein m, n and p are independently selected from 0 or 1; R, $R_1$, $R_2$, $R_3$, and $R_4$ are independently selected from the group consisting of hydrogen, $C_1$-$C_4$alkyl, which alkyl is optionally substituted with hydroxy, amino or mono- and di-$C_1$-$C_4$alkylamino; $R_5$ and $R_6$ are independently selected from hydrogen and fluorine; or R and $R_3$, taken in combination form a fused 5 or 6 member heterocyclic ring having 0 or 1 additional ring heteroatoms selected from N, O or S; $R_1$ and $R_3$, taken in combination form a $C_1$-$C_3$alkylene group; $R_1$ and $R_5$, taken in combination form a $C_1$-$C_3$alkylene group; $R_3$ and $R_4$, taken in combination with the carbon atom to which they attach, form a spirocyclic$C_3$-$C_6$cycloalkyl; X is $CR_AR_{B''}$, $NR_7$ or a bond; $R_7$ is hydrogen, or $C_1$-$C_4$alkyl; $R_{A'}$ and $R_{B'}$ are independently selected from hydrogen and $C_1$-$C_4$alkyl, or $R_{A'}$ and $R_{B''}$ taken in combination, form a divalent $C_2$-$C_5$alkylene group; Z is $CR_8$ or N; when Z is N, X is a bond; $R_8$ is hydrogen or taken in combination with $R_6$ form a double bond; or B is a group of the formula:

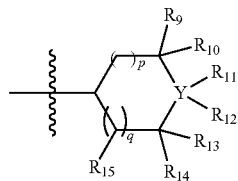

wherein Y is C or O and when Y is O $R_{11}$ and $R_{12}$ are both absent; p and q are independently selected from the group consisting of 0, 1, and 2; $R_9$ and $R_{13}$ are independently selected from hydrogen and $C_1$-$C_4$alkyl; $R_{10}$ and $R_{14}$ are independently selected from hydrogen, amino, mono- and di-$C_1$-$C_4$alkylamino and $C_1$-$C_4$alkyl, which alkyl is optionally substituted with hydroxy, amino or mono- and di-$C_1$-$C_4$alkylamino; $R_{11}$ is hydrogen, $C_1$-$C_4$alkyl, amino or mono- and di-$C_1$-$C_4$alkylamino; $R_{12}$ is hydrogen or $C_1$-$C_4$alkyl; or $R_9$ and $R_{11}$, taken in combination form a saturated azacycle having 4 to 7 ring atoms which is optionally substituted with 1-3 $C_1$-$C_4$alkyl groups; or $R_{11}$ and $R_{12}$, taken in combination form a saturated azacycle having 4 to 7 ring atoms which is optionally substituted with 1-3 $C_1$-$C_4$alkyl groups.

In another embodiment, the invention provides a pharmaceutical composition comprising a therapeutically effective amount of a compound according to the definition of Formula (X) or subformulae thereof and one or more pharmaceutically acceptable carriers.

In another embodiment, the invention provides a combination, in particular a pharmaceutical combination, comprising a therapeutically effective amount of the compound according to the definition of Formula (X) or subformulae thereof and one or more therapeutically active.

One embodiment of the invention is to provide a method for treating, preventing, or ameliorating an SMN-deficiency-related condition, comprising administering to a subject in need thereof an effective amount of an SMN modulator, or a pharmaceutical composition comprising the same.

Another embodiment of the invention is a method of modulating SMN protein through the administration of an SMN modulator. In another embodiment, said SMN modulator is capable of increasing one or more of FL-SMN or SMNΔ7 levels. In still another embodiment, said SMN modulator is capable of preventing exon 7 from being spliced from the SMN transcript.

The present invention is based on the discovery that the SMN modulators of the invention (e.g., compounds of formula (X) and/or subformulae thereof) are capable of modulating SMN proteins, e.g., through SMN promoter activation, splicing modulation (e.g., preventing exon7 from being spliced out of the SMN gene), and/or SMN protein stability modulation.

DETAILED DESCRIPTION OF THE INVENTION

As noted above, the present invention provides compounds that modulate SMN activity. Such compounds may be used in vitro or in vivo to modulate (preferably increase) SMN production and activity in a variety of contexts.

In a first embodiment, the invention provides compounds of Formula X and pharmaceutically acceptable salts thereof, which modulate SMN activity. Compounds of Formula X are represented by the structure:

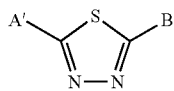

(X)

wherein A' is phenyl which is substituted with 0, 1, 2, or 3 substituents independently selected from $C_1$-$C_4$alkyl, wherein 2 $C_1$-$C_4$alkyl groups can combine with the atoms to which they are bound to form a 5-6 membered ring and is substituted with 0 or 1 substituents selected from oxo, oxime and, hydroxy, halo$C_1$-$C_4$alkyl, dihalo$C_1$-$C_4$alkyl, trihalo$C_1$-$C_4$alkyl, $C_1$-$C_4$alkoxy, $C_1$-$C_4$alkoxy-$C_3$-$C_7$cycloalkyl, halo$C_1$-$C_4$alkoxy, dihalo$C_1$-$C_4$alkoxy, trihalo$C_1$-$C_4$alkoxy, hydroxy, cyano, halogen, amino, mono- and di-$C_1$-$C_4$alkylamino, heteroaryl, $C_1$-$C_4$alkyl substituted with hydroxy, $C_1$-$C_4$alkoxy substituted with aryl, amino, —C(O)NH $C_1$-$C_4$alkyl-heteroaryl, —NHC(O)—$C_1$-$C_4$alkyl-heteroaryl, $C_1$-$C_4$alkyl C(O)NH— heteroaryl, $C_1$-$C_4$alkyl NHC(O)— heteroaryl, 3-7 membered cycloalkyl, 5-7 membered cycloalkenyl or 5, 6 or 9 membered heterocycle containing 1 or 2 heteroatoms, independently, selected from S, O and N, wherein heteroaryl has 5, 6 or 9 ring atoms, 1, 2 or 3 ring heteroatoms selected from N, O and S and substituted with 0, 1, or 2 substituents independently selected from oxo, hydroxy, nitro, halogen, $C_1$-$C_4$alkyl, $C_1$-$C_4$alkenyl, $C_1$-$C_4$alkoxy, $C_3$-$C_7$cycloalkyl, $C_1$-$C_4$alkyl-OH, trihalo$C_1$-$C_4$alkyl, mono- and di-$C_1$-$C_4$alkylamino, —C(O)NH$_2$, —NH$_2$, —NO$_2$, hydroxyC1-$C_4$alkylamino, hydroxyC$_1$-$C_4$alkyl, 4-7 member heterocycleC$_1$-$C_4$alkyl, aminoC$_1$-$C_4$alkyl and mono- and di-$C_1$-$C_4$alkylaminoC$_1$-$C_4$alkyl; or A' is 6 member heteroaryl having 1-3 ring nitrogen atoms, which 6 member heteroaryl is substituted by phenyl or a heteroaryl having 5 or 6 ring atoms, 1 or 2 ring heteroatoms independently selected from N, O and S and substituted with 0, 1, or 2 substituents independently selected from $C_1$-$C_4$alkyl, mono- and di-$C_1$-$C_4$alkylamino, hydroxy$C_1$-$C_4$alkylamino, hydroxyC$_1$-$C_4$alkyl, aminoC$_1$-$C_4$alkyl and mono- and di-$C_1$-$C_4$alkylaminoC$_1$-$C_4$alkyl; or A' is bicyclic heteroaryl having 9 to 10 ring atoms and 1, 2, or 3 ring heteroatoms independently selected from N, O or S, which bicyclic heteroaryl is substituted with 0, 1, or 2 substituents independently selected from oxo, cyano, halogen, hydroxy, $C_1$-$C_4$alkyl, $C_2$-$C_4$alkenyl, $C_2$-$C_4$alkynyl, $C_1$-$C_4$alkoxy and $C_1$-$C_4$alkoxy substituted with hydroxy, $C_1$-$C_4$alkoxy, amino and mono- and di-$C_1$-$C_4$alkylamino; B is a group of the formula:

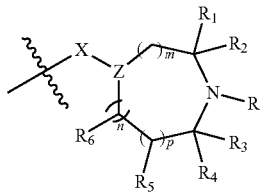

wherein m, n and p are independently selected from 0 or 1; R, $R_1$, $R_2$, $R_3$, and $R_4$ are independently selected from the group consisting of hydrogen, $C_1$-$C_4$alkyl, which alkyl is optionally substituted with hydroxy, amino or mono- and di-$C_1$-$C_4$alkylamino; $R_5$ and $R_6$ are independently selected from hydrogen and fluorine; or R and $R_3$, taken in combination form a fused 5 or 6 member heterocyclic ring having 0 or 1 additional ring heteroatoms selected from N, O or S; $R_1$ and $R_3$, taken in combination form a $C_1$-$C_3$alkylene group; $R_1$ and $R_5$, taken in combination form a $C_1$-$C_3$alkylene group; $R_3$ and $R_4$, taken in combination with the carbon atom to which they attach, form a spirocyclic$C_3$-$C_6$cycloalkyl; X is $CR_{A'}R_{B'}$, $NR_7$ or a bond; $R_7$ is hydrogen, or $C_1$-$C_4$alkyl; $R_{A'}$ and $R_{B'}$ are independently selected from hydrogen and $C_1$-$C_4$alkyl, or $R_{A'}$ and $R_{B'}$, taken in combination, form a divalent $C_2$-$C_5$alkylene group; Z is $CR_8$ or N; when Z is N, X is a bond; $R_8$ is hydrogen or taken in combination with $R_6$ form a double bond; or B is a group of the formula:

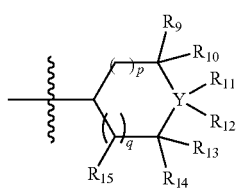

wherein Y is C or O and when Y is O $R_{11}$ and $R_{12}$ are both absent; p and q are independently selected from the group consisting of 0, 1, and 2; $R_9$ and $R_{13}$ are independently selected from hydrogen and $C_1$-$C_4$alkyl; $R_{10}$ and $R_{14}$ are independently selected from hydrogen, amino, mono- and di-$C_1$-$C_4$alkylamino and $C_1$-$C_4$alkyl, which alkyl is optionally substituted with hydroxy, amino or mono- and di-$C_1$-$C_4$alkylamino; $R_{11}$ is hydrogen, $C_1$-$C_4$alkyl, amino or mono- and di-$C_1$-$C_4$alkylamino; $R_{12}$ is hydrogen or $C_1$-$C_4$alkyl; or $R_9$ and $R_{11}$, taken in combination form a saturated azacycle having 4 to 7 ring atoms which is optionally substituted with 1-3 $C_1$-$C_4$alkyl groups; or $R_{11}$ and $R_{12}$, taken in combination form a saturated azacycle having 4 to 7 ring atoms which is optionally substituted with 1-3 $C_1$-$C_4$alkyl groups.

In a second embodiment, the invention a compound, or salt thereof, according to the first embodiment wherein A' is selected from:

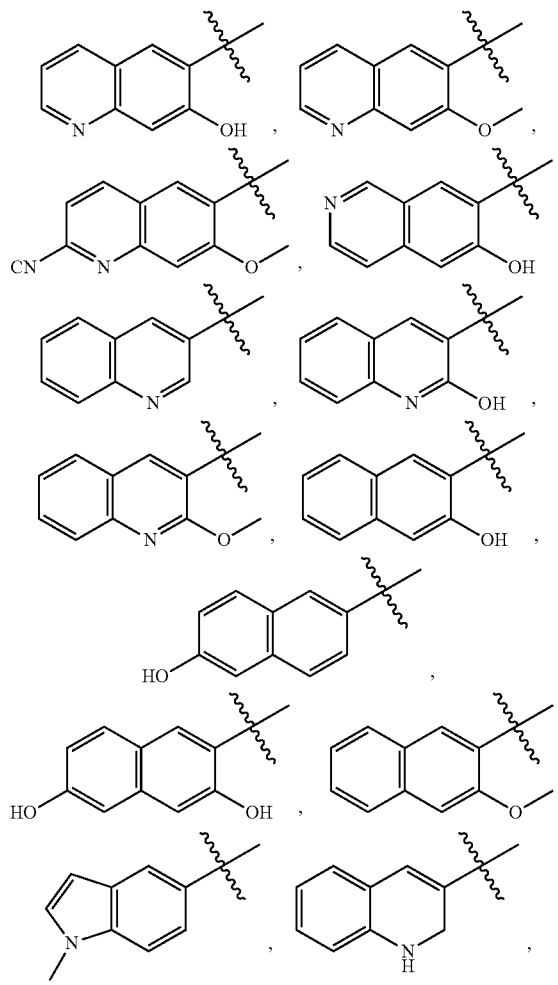

-continued

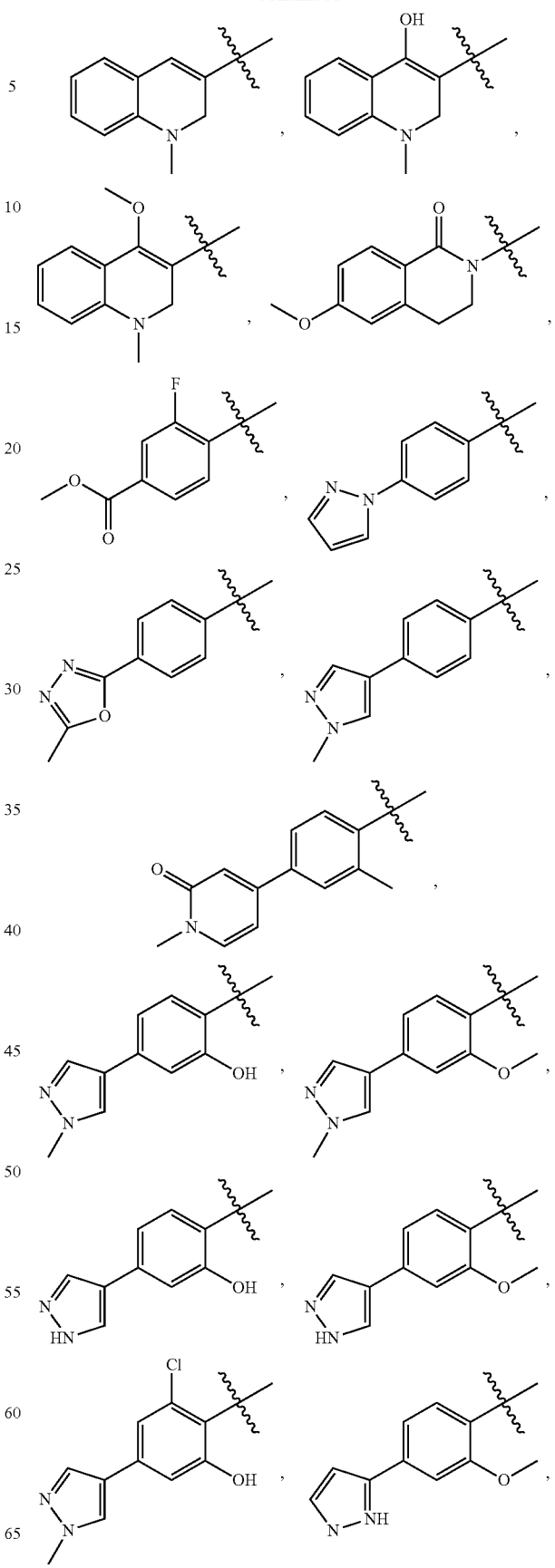

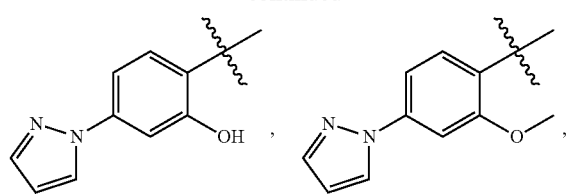
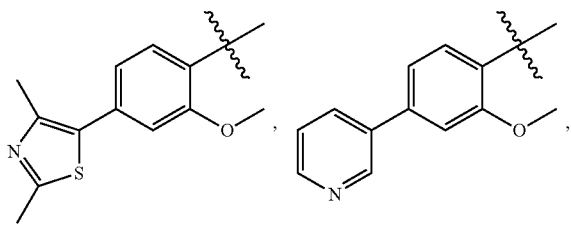
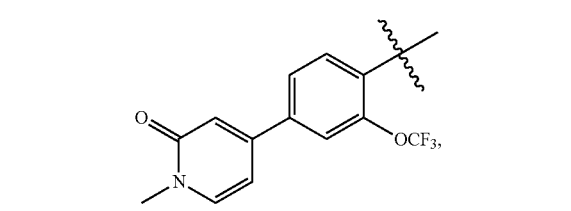
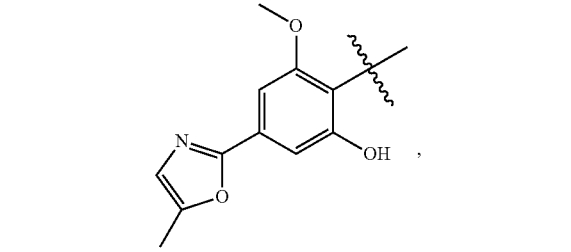
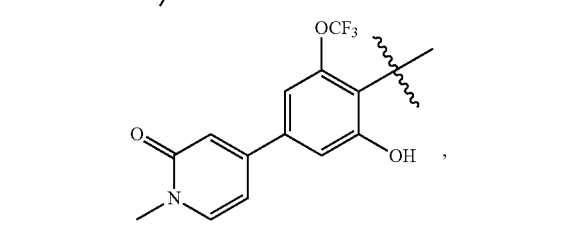
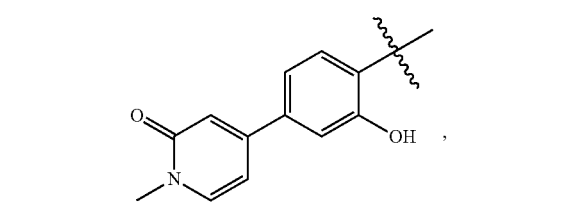
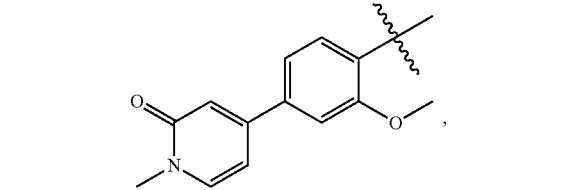
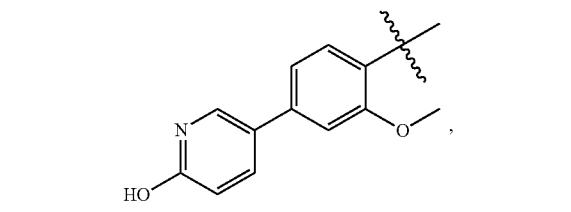
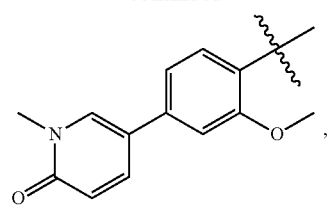
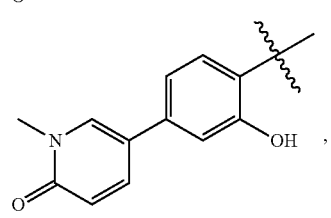
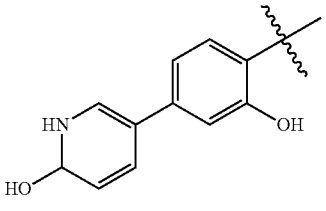
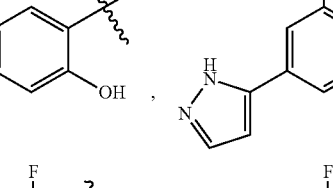
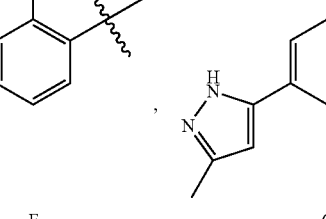
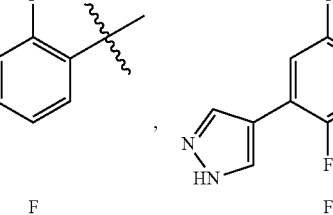
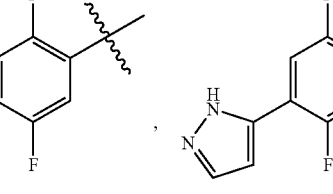
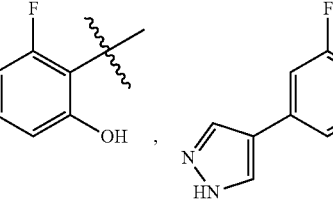

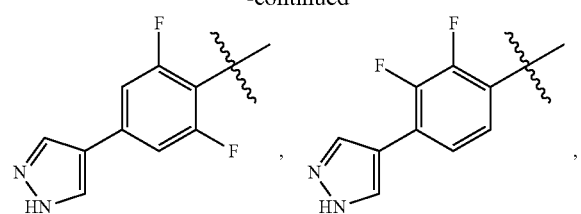
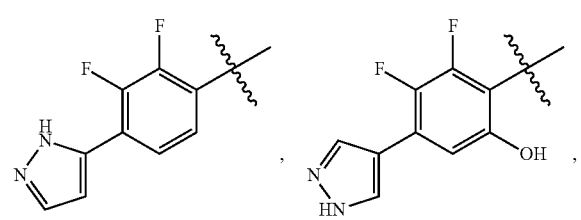
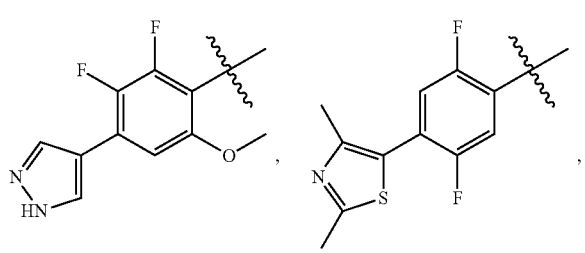
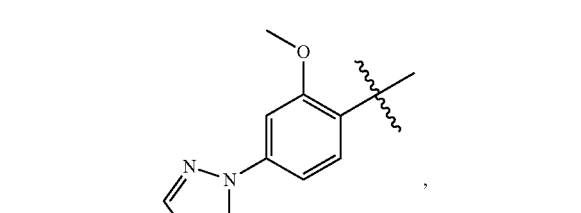
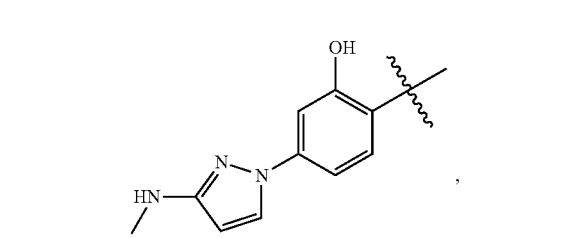
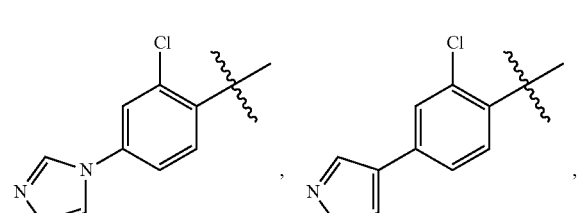
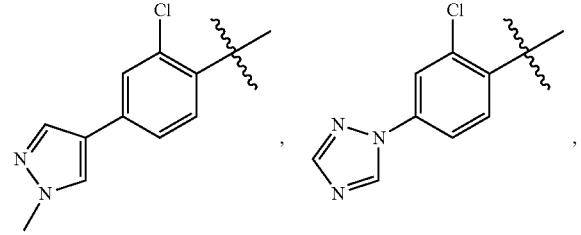
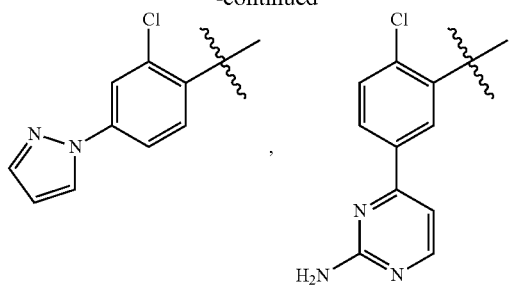
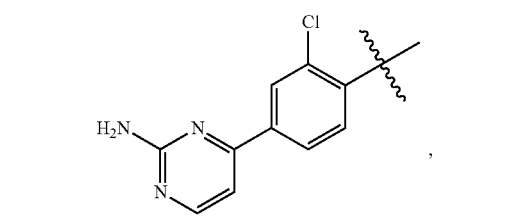
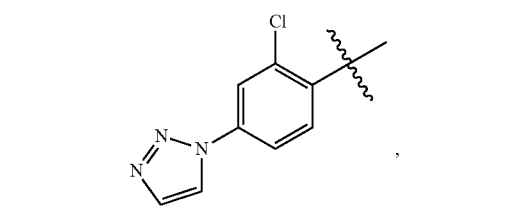
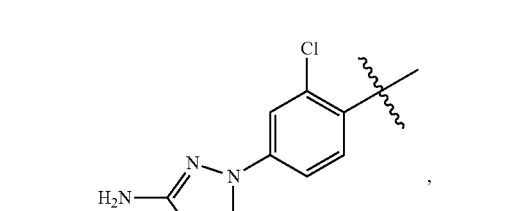
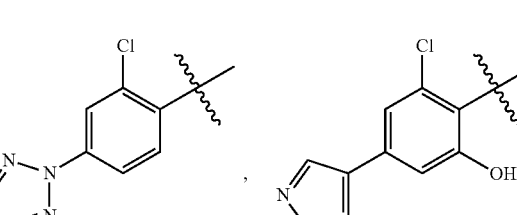
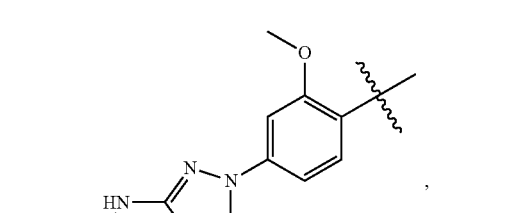
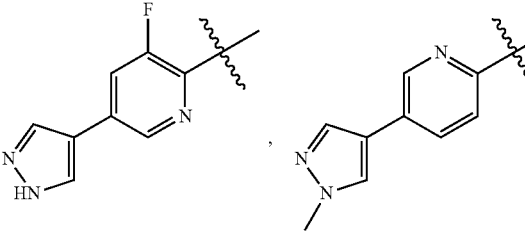

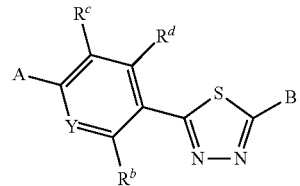

(I)

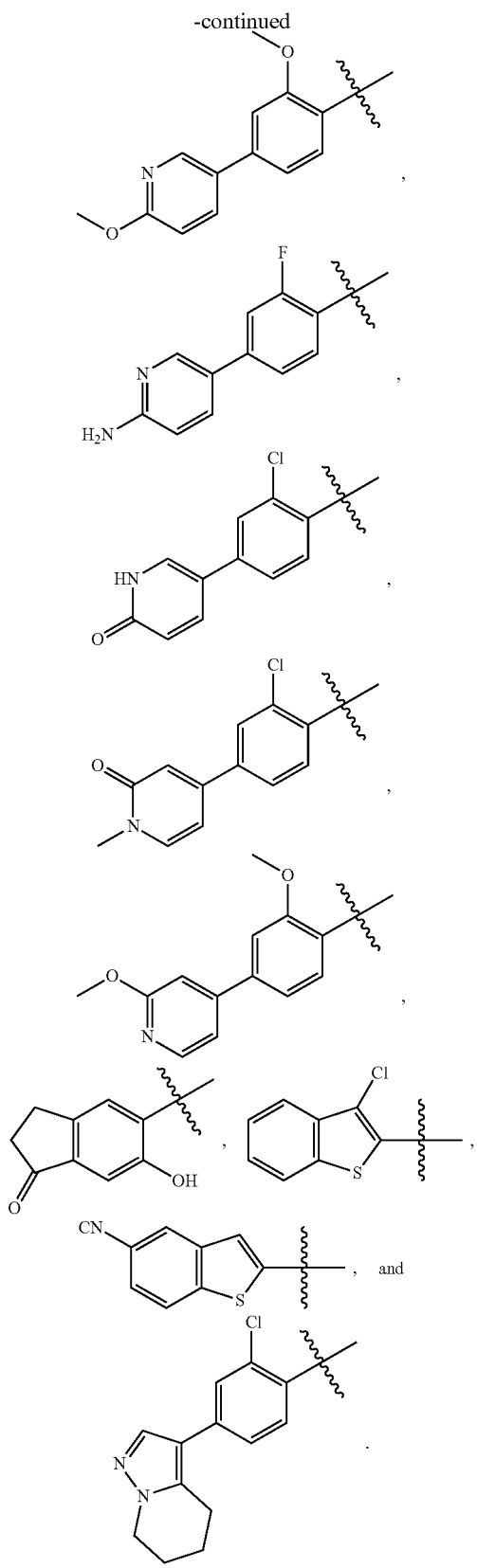

Wherein Y is N or C—$R^a$; $R^a$ is hydrogen or $C_1$-$C_4$alkyl; $R^b$ is hydrogen, $C_1$-$C_4$alkyl, $C_1$-$C_4$alkoxy, hydroxy, cyano, halogen, trihalo $C_1$-$C_4$alkyl or trihalo $C_1$-$C_4$alkoxy; $R^c$ and $R^d$ are each, independently, hydrogen, $C_1$-$C_4$alkyl, $C_1$-$C_4$alkoxy, hydroxy, trihalo $C_1$-$C_4$alkyl, trihalo $C_1$-$C_4$alkoxy or heteroaryl; A is 6 member heteroaryl having 1-3 ring nitrogen atoms, which 6 member heteroaryl is substituted with 0, 1, or 2 substituents independently selected from oxo, $C_1$-$C_4$alkyl, mono- and di-$C_1$-$C_4$alkylamino, hydroxy$C_1$-$C_4$alkylamino, hydroxy$C_1$-$C_4$alkyl, amino$C_1$-$C_4$alkyl and mono- and di-$C_1$-$C_4$alkylamino$C_1$-$C_4$alkyl; or A is 5 member heteroaryl having 1-3 ring heteroatoms independently selected from N, O and S and substituted with 0, 1, or 2 substituents independently selected from $C_1$-$C_4$alkyl, hydroxyl, mono- and di-$C_1$-$C_4$alkylamino, hydroxy$C_1$-$C_4$alkylamino, hydroxy$C_1$-$C_4$alkyl, amino$C_1$-$C_4$alkyl and mono- and di-$C_1$-$C_4$alkylamino$C_1$-$C_4$alkyl; or A and $R^c$, together with the atoms to which they are bound, form a 6 member aryl with 0, 1, or 2 substituents independently selected from cyano, halogen, hydroxy, $C_1$-$C_4$alkyl, $C_2$-$C_4$alkenyl, $C_2$-$C_4$alkynyl, $C_1$-$C_4$alkoxy and $C_1$-$C_4$alkoxy substituted with hydroxy, $C_1$-$C_4$alkoxy, amino and mono- and di-$C_1$-$C_4$alkylamino; B is a group of the formula:

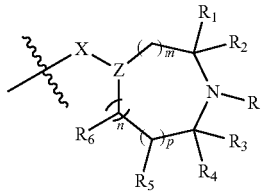

wherein m, n and p are independently selected from 0 or 1; R, $R_1$, $R_2$, $R_3$, and $R_4$ are independently selected from the group consisting of hydrogen, $C_1$-$C_4$alkyl, which alkyl is optionally substituted with hydroxy, amino or mono- and di-$C_1$-$C_4$alkylamino; $R_5$ and $R_6$ are independently selected from hydrogen and fluorine; or R and $R_3$, taken in combination form a fused 5 or 6 member heterocyclic ring having 0 or 1 additional ring heteroatoms selected from N, O or S; $R_1$ and $R_3$, taken in combination form a $C_1$-$C_3$alkylene group; $R_1$ and $R_5$, taken in combination form a $C_1$-$C_3$alkylene group; $R_3$ and $R_4$, taken in combination with the carbon atom to which they attach, form a spirocyclic$C_3$-$C_6$cycloalkyl; X is $CR_{A'}R_{B''}$, $NR_7$ or a bond; $R_7$ is hydrogen, or $C_1$-$C_4$alkyl; $R_{A'}$ and $R_{B'}$ are independently selected from hydrogen and $C_1$-$C_4$alkyl, or $R_{A'}$ and $R_{B''}$, taken in combination, form a divalent $C_2$-$C_5$alkylene group; Z is $CR_8$ or N; when Z is N, X is a bond; $R_8$ is hydrogen or taken in combination with $R_6$ form a double bond; or B is a group of the formula:

In a third embodiment, the invention is a compound, or salt thereof, according any one of the first or second embodiments, which compound is represented by Formula (I)

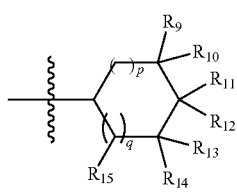

wherein p and q are independently selected from the group consisting of 0, 1, and 2; $R_9$ and $R_{13}$ are independently selected from hydrogen and $C_1$-$C_4$alkyl; $R_{10}$ and $R_{14}$ are independently selected from hydrogen, amino, mono- and di-$C_1$-$C_4$alkylamino and $C_1$-$C_4$alkyl, which alkyl is optionally substituted with hydroxy, amino or mono- and di-$C_1$-$C_4$alkylamino; $R_{11}$ is hydrogen, $C_1$-$C_4$alkyl, amino or mono- and di-$C_1$-$C_4$alkylamino; $R_{12}$ is hydrogen or $C_1$-$C_4$alkyl; or $R_9$ and $R_{11}$, taken in combination form a saturated azacycle having 4 to 7 ring atoms which is optionally substituted with 1-3 $C_1$-$C_4$alkyl groups; or $R_{11}$ and $R_{12}$, taken in combination form a saturated azacycle having 4 to 7 ring atoms which is optionally substituted with 1-3 $C_1$-$C_4$alkyl groups.

In a fourth embodiment, the invention is a compound, or a salt thereof, according to the third embodiment, wherein A is 6 member heteroaryl having 1-3 ring nitrogen atoms, which 6 member heteroaryl is substituted with 0, 1, or 2 substituents independently selected from oxo, $C_1$-$C_4$alkyl, mono- and di-$C_1$-$C_4$alkylamino, hydroxy$C_1$-$C_4$alkylamino, hydroxy$C_1$-$C_4$alkyl, amino$C_1$-$C_4$alkyl and mono- and di-$C_1$-$C_4$alkylamino$C_1$-$C_4$alkyl.

In a fifth embodiment, the invention is a compound, or a salt thereof, according to any one of the third or fourth embodiments, wherein A is selected from:

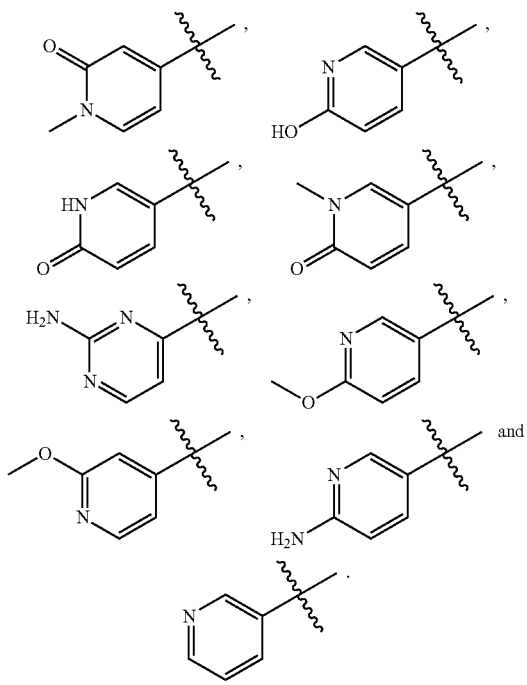

In a sixth embodiment, the invention is a compound, or a salt thereof, according to the third embodiment, wherein A is 5 member heteroaryl having 1-3 ring heteroatoms independently selected from N, O and S and substituted with 0, 1, or 2 substituents independently selected from $C_1$-$C_4$alkyl, hydroxyl, mono- and di-$C_1$-$C_4$alkylamino, hydroxy$C_1$-$C_4$alkylamino, hydroxy$C_1$-$C_4$alkyl, amino$C_1$-$C_4$alkyl and mono- and di-$C_1$-$C_4$alkylamino$C_1$-$C_4$alkyl.

In a seventh embodiment, the invention is a compound, or a salt thereof, according to any one of the third or sixth embodiments, wherein A is selected from:

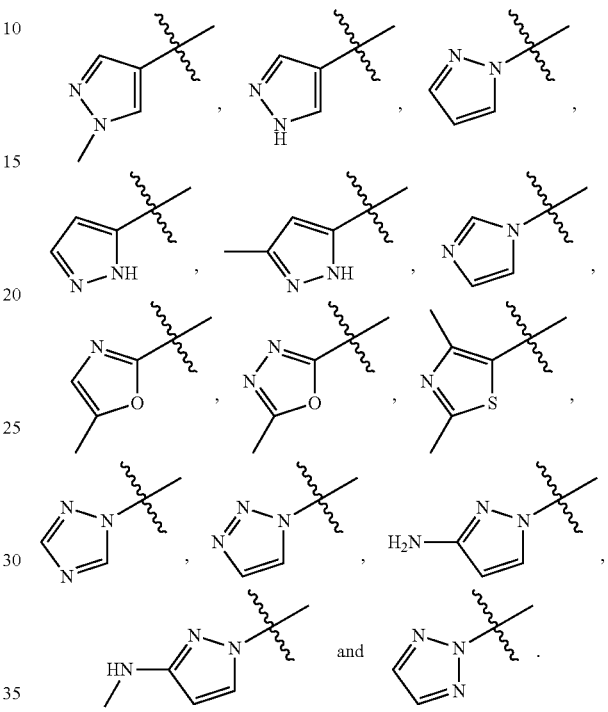

In an eighth embodiment, the invention is a compound, or salt thereof, according to any one of the first through seventh embodiments, wherein B is a group of the formula:

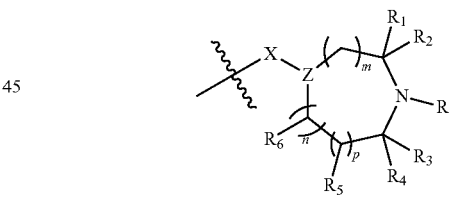

wherein m, n and p are independently selected from 0 or 1; R, $R_1$, $R_2$, $R_3$, and $R_4$ are independently selected from the group consisting of hydrogen, $C_1$-$C_4$alkyl, which alkyl is optionally substituted with hydroxy, amino or mono- and di-$C_1$-$C_4$alkylamino; $R_5$ and $R_6$ are hydrogen; or R and $R_3$, taken in combination form a fused 5 or 6 member heterocyclic ring having 0 or 1 additional ring heteroatoms selected from N, O or S; $R_1$ and $R_3$, taken in combination form a $C_1$-$C_3$alkylene group; $R_1$ and $R_5$, taken in combination form a $C_1$-$C_3$alkylene group; $R_3$ and $R_4$, taken in combination with the carbon atom to which they attach, form a spirocyclic$C_3$-$C_6$cycloalkyl; X is $CR_{A'}R_{B'}$, O, $NR_7$ or a bond; $R_{A'}$ and $R_{B'}$ are independently selected from hydrogen and $C_1$-$C_4$alkyl, or $R_{A'}$ and $R_{B'}$, taken in combination, form a divalent $C_2$-$C_5$alkylene group; Z is $CR_8$ or N; when Z is N, X is a bond; $R_8$ is hydrogen or taken in combination with $R_6$ form a double bond.

In a ninth embodiment, the invention is a compound, or salt thereof, according to any one of the first through seventh embodiments, wherein B is a group of the formula:

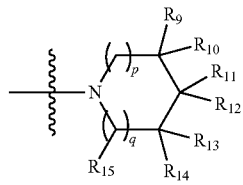

wherein p and q are independently selected from the group consisting of 0, 1, and 2; $R_9$ and $R_{13}$ are independently selected from hydrogen and $C_1$-$C_4$alkyl; $R_{10}$ and $R_{14}$ are independently selected from hydrogen, amino, mono- and di-$C_1$-$C_4$alkylamino and $C_1$-$C_4$alkyl, which alkyl is optionally substituted with hydroxy, amino or mono- and di-$C_1$-$C_4$alkylamino; $R_{11}$ is hydrogen, $C_1$-$C_4$alkyl, amino or mono- and di-$C_1$-$C_4$alkylamino; $R_{12}$ is hydrogen or $C_1$-$C_4$alkyl; or $R_9$ and $R_{11}$, taken in combination form a saturated azacycle having 4 to 7 ring atoms which is optionally substituted with 1-3 $C_1$-$C_4$alkyl groups; or $R_{11}$ and $R_{12}$, taken in combination form a saturated azacycle having 4 to 7 ring atoms which is optionally substituted with 1-3 $C_1$-$C_4$alkyl groups.

In a tenth embodiment, the invention is a compound, or a salt thereof, according to any one of the first through ninth embodiments, which compound is represented by Formula (XX):

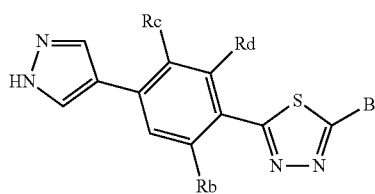

(XX)

wherein $R^b$ is hydrogen or hydroxy; $R^c$ is hydrogen or halogen; and $R^d$ is halogen.

In an eleventh embodiment, the invention is a compound, or salt thereof according to any one of the first through ninth embodiments, which compound is represented by Formula (II):

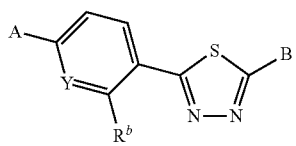

(II)

wherein $R^b$ is hydroxyl, methoxy, trifluoromethyl or trifluoromethoxy.

In a twelfth embodiment, the invention is a compound, or salt thereof, according to any one of the first through ninth embodiments, which compound is represented by Formula (III):

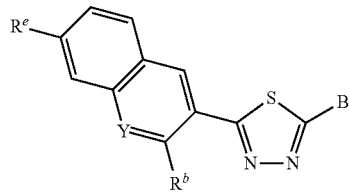

(III)

wherein $R^b$ is hydroxyl, methoxy, trifluoromethyl or trifluoromethoxy; and $R^e$ is hydrogen, hydroxy or methoxy.

In a thirteenth embodiment, the invention is a compound, or salt thereof, according to any one of the third through ninth or eleventh through twelfth embodiments, wherein Y is N.

In a fourteenth embodiment, the invention is a compound, or salt thereof, according to any one of the third through ninth or eleventh through twelfth embodiments, wherein Y is CH.

In a fifteenth embodiment, the invention is a compound, or salt thereof, according of any one of the first through eighth or tenth through fourteenth embodiments, wherein B is selected from

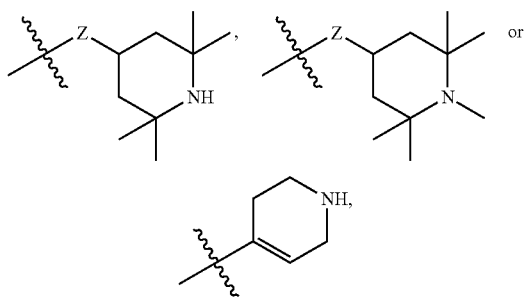

wherein Z is NH or N(Me).

In a sixteenth embodiment, the invention is a compound, or salt thereof, according of any one of the first through eighth or tenth through fifteenth embodiments, wherein B is

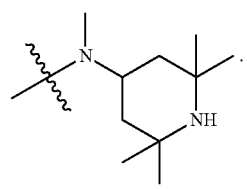 [SMILES: *N(C)C1CC(C)(C)NC(C)(C)C1]

In a seventeenth embodiment compound, or salt thereof, according of any one of the first through seventh or ninth through fourteenth embodiments, wherein B is selected from

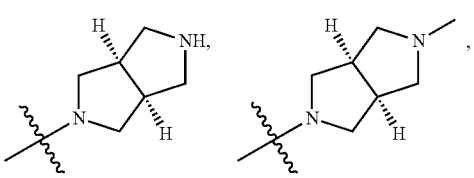

-continued

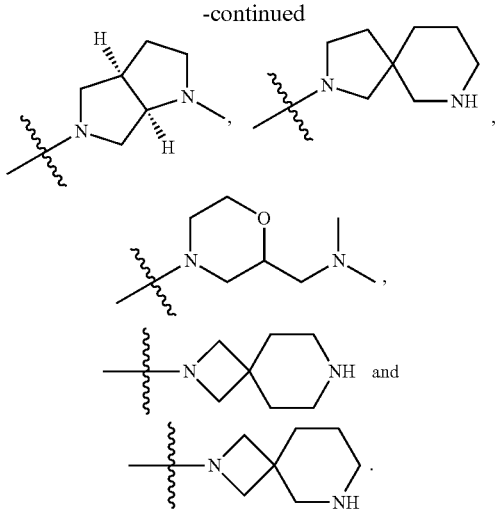

In an eighteenth embodiment, the invention is a compound, or salt thereof, according of any one of the first through seventh, ninth through fourteenth or seventeenth embodiments wherein B is

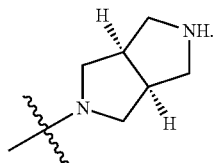 [SMILES: *N1C[C@H]2CNC[C@H]2C1]

In a nineteenth embodiment, the invention is a compound or salt thereof selected from the group consisting of:

5-(2-Methoxy-4-(1H-pyrazol-1-yl)phenyl)-N-methyl-N-(2,2,6,6-tetramethylpiperidin-4-yl)-1,3,4-thiadiazol-2-amine;
6-(5-(Methyl(2,2,6,6-tetramethylpiperidin-4-yl)amino)-1,3,4-thiadiazol-2-yl)naphthalen-2-ol;
5-(2-Methoxyquinolin-3-yl)-N-methyl-N-(2,2,6,6-tetramethylpiperidin-4-yl)-1,3,4-thiadiazol-2-amine;
5-(3-Methoxynaphthalen-2-yl)-N-methyl-N-(2,2,6,6-tetramethylpiperidin-4-yl)-1,3,4-thiadiazol-2-amine;
5-(2-Methoxy-4-(1H-pyrazol-1-yl)phenyl)-N-(1,2,2,6,6-pentamethylpiperidin-4-yl)-1,3,4-thiadiazol-2-amine;
5-(2-Methoxy-4-(1-methyl-1H-pyrazol-4-yl)phenyl)-N-methyl-N-(2,2,6,6-tetramethylpiperidin-4-yl)-1,3,4-thiadiazol-2-amine;
5-(2-Methoxy-4-(1H-pyrazol-4-yl)phenyl)-N-methyl-N-(2,2,6,6-tetramethylpiperidin-4-yl)-1,3,4-thiadiazol-2-amine;
4-(3-Methoxy-4-(5-(methyl(2,2,6,6-tetramethylpiperidin-4-yl)amino)-1,3,4-thiadiazol-2-yl)phenyl)-1-methylpyridin-2(1H)-one;
5-(3-Methoxy-4-(5-(methyl(2,2,6,6-tetramethylpiperidin-4-yl)amino)-1,3,4-thiadiazol-2-yl)phenyl)pyridin-2-ol;
5-(3-Methoxy-4-(5-(methyl(2,2,6,6-tetramethylpiperidin-4-yl)amino)-1,3,4-thiadiazol-2-yl)phenyl)-1-methylpyridin-2(1H)-one;
N-Methyl-5-(2-methyl-4-(1-methyl-1H-pyrazol-4-yl)phenyl)-N-(2,2,6,6-tetramethylpiperidin-4-yl)-1,3,4-thiadiazol-2-amine;
1-Methyl-4-(4-(5-(methyl(2,2,6,6-tetramethylpiperidin-4-yl)amino)-1,3,4-thiadiazol-2-yl)-3-(trifluoromethoxy)phenyl)pyridin-2(1H)-one;
5-(4-(3,5-Dimethyl-1H-pyrazol-4-yl)-2-methoxyphenyl)-N-methyl-N-(2,2,6,6-tetramethylpiperidin-4-yl)-1,3,4-thiadiazol-2-amine;
5-(2-Methoxy-4-(1-methyl-1H-pyrazol-4-yl)phenyl)-N-methyl-N-(2,2,6,6-tetramethylpiperidin-4-yl)-1,3,4-thiadiazol-2-amine;
2-(5-(Methyl(2,2,6,6-tetramethylpiperidin-4-yl)amino)-1,3,4-thiadiazol-2-yl)-5-(1-methyl-1H-pyrazol-4-yl)phenol;
2-(5-(Methyl(2,2,6,6-tetramethylpiperidin-4-yl)amino)-1,3,4-thiadiazol-2-yl)-5-(1H-pyrazol-1-yl)phenol;
5-(3-Hydroxy-4-(5-(methyl(2,2,6,6-tetramethylpiperidin-4-yl)amino)-1,3,4-thiadiazol-2-yl)phenyl)-1-methylpyridin-2(1H)-one;
4-(3-Hydroxy-4-(5-(methyl(2,2,6,6-tetramethylpiperidin-4-yl)amino)-1,3,4-thiadiazol-2-yl)phenyl)-1-methylpyridin-2(1H)-one;
5-(3-Hydroxy-4-(5-(methyl(2,2,6,6-tetramethylpiperidin-4-yl)amino)-1,3,4-thiadiazol-2-yl)phenyl)pyridin-2-ol;
3-(5-(Methyl(2,2,6,6-tetramethylpiperidin-4-yl)amino)-1,3,4-thiadiazol-2-yl)naphthalene-2,7-diol;
3-(5-((3aR,6aS)-Hexahydropyrrolo[3,4-c]pyrrol-2(1H)-yl)-1,3,4-thiadiazol-2-yl)naphthalene-2,7-diol;
3-(5-(Methyl(2,2,6,6-tetramethylpiperidin-4-yl)amino)-1,3,4-thiadiazol-2-yl)naphthalen-2-ol.hydrobromide salt;
3-(5-(Methyl(2,2,6,6-tetramethylpiperidin-4-yl)amino)-1,3,4-thiadiazol-2-yl)quinolin-2-ol;
2-(5-(Methyl(2,2,6,6-tetramethylpiperidin-4-yl)amino)-1,3,4-thiadiazol-2-yl)-4-(1H-pyrazol-1-yl)phenol;
5-(2-Chloro-4-(1-methyl-1H-pyrazol-4-yl)phenyl)-N-methyl-N-(2,2,6,6-tetramethylpiperidin-4-yl)-1,3,4-thiadiazol-2-amine;
3-Chloro-2-(5-(methyl(2,2,6,6-tetramethylpiperidin-4-yl)amino)-1,3,4-thiadiazol-2-yl)-5-(1-methyl-1H-pyrazol-4-yl)phenol;
5-(2-chloro-4-(1-methyl-1H-pyrazol-4-yl)phenyl)-N-(2,2,6,6-tetramethylpiperidin-4-yl)-1,3,4-thiadiazol-2-amine;
3-Methoxy-2-(5-(methyl(2,2,6,6-tetramethylpiperidin-4-yl)amino)-1,3,4-thiadiazol-2-yl)-5-(5-methyloxazol-2-yl)phenol;
2-(2-Methoxy-4-(1H-pyrazol-1-yl)phenyl)-5-(1,2,3,6-tetrahydropyridin-4-yl)-1,3,4-thiadiazole
2-(5-(piperazin-1-yl)-1,3,4-thiadiazol-2-yl)-5-(1H-pyrazol-1-yl)phenol;
5-(7-Methoxyquinolin-6-yl)-N-methyl-N-(2,2,6,6-tetramethylpiperidin-4-yl)-1,3,4-thiadiazol-2-amine;
6-(5-(Methyl(2,2,6,6-tetramethylpiperidin-4-yl)amino)-1,3,4-thiadiazol-2-yl)quinolin-7-ol;
3-methoxy-4-(5-(methyl(2,2,6,6-tetramethylpiperidin-4-yl)amino)-1,3,4-thiadiazol-2-yl)benzonitrile;
3-fluoro-4-(5-(methyl(2,2,6,6-tetramethylpiperidin-4-yl)amino)-1,3,4-thiadiazol-2-yl)benzonitrile;
methyl 3-fluoro-4-(5-(methyl(2,2,6,6-tetramethylpiperidin-4-yl)amino)-1,3,4-thiadiazol-2-yl)benzoate;
5-(2-methoxy-4-(3-(methylamino)-1H-pyrazol-1-yl)phenyl)-N-methyl-N-(2,2,6,6-tetramethylpiperidin-4-yl)-1,3,4-thiadiazol-2-amine;
7-methoxy-6-(5-(methyl(2,2,6,6-tetramethylpiperidin-4-yl)amino)-1,3,4-thiadiazol-2-yl)quinoline-2-carbonitrile;
4-(3-methoxy-4-(5-((2,2,6,6-tetramethylpiperidin-4-yl)oxy)-1,3,4-thiadiazol-2-yl)phenyl)-1-methylpyridin-2(1H)-one;
4-(3-chloro-4-(5-(methyl(2,2,6,6-tetramethylpiperidin-4-yl)amino)-1,3,4-thiadiazol-2-yl)phenyl)-1-methylpyridin-2(1H)-one;
5-(2-chloro-4-(1H-pyrazol-4-yl)phenyl)-N-methyl-N-(2,2,6,6-tetramethylpiperidin-4-yl)-1,3,4-thiadiazol-2-amine;

5-(2-chloro-4-(4,5,6,7-tetrahydropyrazolo[1,5-a]pyridin-3-yl)phenyl)-N-methyl-N-(2,2,6,6-tetramethylpiperidin-4-yl)-1,3,4-thiadiazol-2-amine;

N-methyl-5-(5-(1-methyl-1H-pyrazol-4-yl)pyridin-2-yl)-N-(2,2,6,6-tetramethylpiperidin-4-yl)-1,3,4-thiadiazol-2-amine Hydrochloride salt;

2-(2-chloro-4-(1-methyl-1H-pyrazol-4-yl)phenyl)-5-((2,2,6,6-tetramethylpiperidin-4-yl)oxy)-1,3,4-thiadiazole;

5-(2-chloro-4-(6-methoxypyridin-3-yl)phenyl)-N-methyl-N-(2,2,6,6-tetramethylpiperidin-4-yl)-1,3,4-thiadiazol-2-amine;

5-(4-(6-aminopyridin-3-yl)-2-fluorophenyl)-N-methyl-N-(2,2,6,6-tetramethylpiperidin-4-yl)-1,3,4-thiadiazol-2-amine;

5-(2-fluoro-4-(3-methyl-1H-pyrazol-5-yl)phenyl)-N-methyl-N-(2,2,6,6-tetramethylpiperidin-4-yl)-1,3,4-thiadiazol-2-amine;

5-(2-fluoro-4-(1H-pyrazol-5-yl)phenyl)-N-methyl-N-(2,2,6,6-tetramethylpiperidin-4-yl)-1,3,4-thiadiazol-2-amine;

5-(2,3-difluoro-4-(1H-pyrazol-4-yl)phenyl)-N-methyl-N-(2,2,6,6-tetramethylpiperidin-4-yl)-1,3,4-thiadiazol-2-amine;

5-(2,3-difluoro-4-(1H-pyrazol-5-yl)phenyl)-N-methyl-N-(2,2,6,6-tetramethylpiperidin-4-yl)-1,3,4-thiadiazol-2-amine;

5-(2,5-difluoro-4-(1H-pyrazol-4-yl)phenyl)-N-methyl-N-(2,2,6,6-tetramethylpiperidin-4-yl)-1,3,4-thiadiazol-2-amine;

5-(2,5-difluoro-4-(1H-pyrazol-5-yl)phenyl)-N-methyl-N-(2,2,6,6-tetramethylpiperidin-4-yl)-1,3,4-thiadiazol-2-amine;

5-(2,6-difluoro-4-(1H-pyrazol-4-yl)phenyl)-N-methyl-N-(2,2,6,6-tetramethylpiperidin-4-yl)-1,3,4-thiadiazol-2-amine;

2-(2,5-difluoro-4-(1H-pyrazol-4-yl)phenyl)-5-((3aR,6aS)-hexahydropyrrolo[3,4-c]pyrrol-2(1H)-yl)-1,3,4-thiadiazole;

5-(2-chloro-5-fluoro-4-(1H-pyrazol-4-yl)phenyl)-N-methyl-N-(2,2,6,6-tetramethylpiperidin-4-yl)-1,3,4-thiadiazol-2-amine;

5-(3-fluoro-5-(1H-pyrazol-4-yl)pyridin-2-yl)-N-methyl-N-(2,2,6,6-tetramethylpiperidin-4-yl)-1,3,4-thiadiazol-2-amine;

5-(4-(2-aminopyrimidin-4-yl)-2-chlorophenyl)-N-methyl-N-(2,2,6,6-tetramethylpiperidin-4-yl)-1,3,4-thiadiazol-2-amine;

5-(5-(2-aminopyrimidin-4-yl)-2-chlorophenyl)-N-methyl-N-(2,2,6,6-tetramethylpiperidin-4-yl)-1,3,4-thiadiazol-2-amine;

5-(4-(2,4-dimethylthiazol-5-yl)-2,5-difluorophenyl)-N-methyl-N-(2,2,6,6-tetramethylpiperidin-4-yl)-1,3,4-thiadiazol-2-amine;

5-(4-(2,4-dimethylthiazol-5-yl)-2,3-difluorophenyl)-N-methyl-N-(2,2,6,6-tetramethylpiperidin-4-yl)-1,3,4-thiadiazol-2-amine;

4-(3-hydroxy-4-(5-(methyl(2,2,6,6-tetramethylpiperidin-4-yl)amino)-1,3,4-thiadiazol-2-yl)-5-(trifluoromethoxy)phenyl)-1-methylpyridin-2(1H)-one;

5-(2-fluoro-6-methoxy-4-(1H-pyrazol-4-yl)phenyl)-N-methyl-N-(2,2,6,6-tetramethylpiperidin-4-yl)-1,3,4-thiadiazol-2-amine;

2-(2-fluoro-6-methoxy-4-(1H-pyrazol-4-yl)phenyl)-5-((3aR,6aS)-5-methylhexahydropyrrolo[3,4-c]pyrrol-2(1H)-yl)-1,3,4-thiadiazole;

5-(2,3-difluoro-6-methoxy-4-(1H-pyrazol-4-yl)phenyl)-N-methyl-N-(2,2,6,6-tetramethylpiperidin-4-yl)-1,3,4-thiadiazol-2-amine;

6-methoxy-2-(5-(methyl(2,2,6,6-tetramethylpiperidin-4-yl)amino)-1,3,4-thiadiazol-2-yl)-3,4-dihydroisoquinolin-1(2H)-one;

5-(2-chloro-4-(1H-pyrazol-1-yl)phenyl)-N-methyl-N-(2,2,6,6-tetramethylpiperidin-4-yl)-1,3,4-thiadiazol-2-amine;

5-(2-chloro-4-(1H-1,2,3-triazol-1-yl)phenyl)-N-methyl-N-(2,2,6,6-tetramethylpiperidin-4-yl)-1,3,4-thiadiazol-2-amine;

5-(2-chloro-4-(2H-1,2,3-triazol-2-yl)phenyl)-N-methyl-N-(2,2,6,6-tetramethylpiperidin-4-yl)-1,3,4-thiadiazol-2-amine;

5-(2-chloro-4-(1H-1,2,4-triazol-1-yl)phenyl)-N-methyl-N-(2,2,6,6-tetramethylpiperidin-4-yl)-1,3,4-thiadiazol-2-amine;

5-(4-(3-amino-1H-pyrazol-1-yl)-2-chlorophenyl)-N-methyl-N-(2,2,6,6-tetramethylpiperidin-4-yl)-1,3,4-thiadiazol-2-amine;

2-(2-chloro-4-(1H-imidazol-1-yl)phenyl)-5-((3aR,6aS)-5-methylhexahydropyrrolo[3,4-c]pyrrol-2(1H)-yl)-1,3,4-thiadiazole;

5-(2-chloro-4-(1H-imidazol-1-yl)phenyl)-N-methyl-N-(2,2,6,6-tetramethylpiperidin-4-yl)-1,3,4-thiadiazol-2-amine;

5-(2-fluoro-4-(1H-imidazol-1-yl)phenyl)-N-methyl-N-(2,2,6,6-tetramethylpiperidin-4-yl)-1,3,4-thiadiazol-2-amine;

5-(2-methoxy-4-(1H-pyrazol-5-yl)phenyl)-N-methyl-N-(2,2,6,6-tetramethylpiperidin-4-yl)-1,3,4-thiadiazol-2-amine;

5-(4-(2,4-dimethylthiazol-5-yl)-2-methoxyphenyl)-N-methyl-N-(2,2,6,6-tetramethylpiperidin-4-yl)-1,3,4-thiadiazol-2-amine;

5-(2-methoxy-4-(pyridin-3-yl)phenyl)-N-methyl-N-(2,2,6,6-tetramethylpiperidin-4-yl)-1,3,4-thiadiazol-2-amine;

5-(2-fluoro-4-(1H-pyrazol-4-yl)phenyl)-N-methyl-N-(2,2,6,6-tetramethylpiperidin-4-yl)-1,3,4-thiadiazol-2-amine;

5-(2-methoxy-4-(2-methoxypyridin-4-yl)phenyl)-N-methyl-N-(2,2,6,6-tetramethylpiperidin-4-yl)-1,3,4-thiadiazol-2-amine;

5-(2-methoxy-4-(6-methoxypyridin-3-yl)phenyl)-N-methyl-N-(2,2,6,6-tetramethylpiperidin-4-yl)-1,3,4-thiadiazol-2-amine;

2-(2-chloro-4-(1-methyl-1H-pyrazol-4-yl)phenyl)-5-((3aR,6aS)-5-methylhexahydropyrrolo[3,4-c]pyrrol-2(1H)-yl)-1,3,4-thiadiazole;

2-(2-chloro-4-(1H-pyrazol-4-yl)phenyl)-5-((3aR,6aS)-5-methylhexahydropyrrolo[3,4-c]pyrrol-2(1H)-yl)-1,3,4-thiadiazole;

2-(2-chloro-4-(1H-pyrazol-4-yl)phenyl)-5-((3aR,6aR)-1-methylhexahydropyrrolo[3,4-c]pyrrol-5(1H)-yl)-1,3,4-thiadiazole;

1-(4-(5-(2-chloro-4-(1H-pyrazol-4-yl)phenyl)-1,3,4-thiadiazol-2-yl)morpholin-2-yl)-N,N-dimethylmethanamine;

2-(2-chloro-4-(1H-pyrazol-4-yl)phenyl)-5-(2-methyl-2,7-diazaspiro[4.5]decan-7-yl)-1,3,4-thiadiazole;

2-(2-fluoro-4-(1H-pyrazol-4-yl)phenyl)-5-((3aR,6aS)-5-methylhexahydropyrrolo[3,4-c]pyrrol-2(1H)-yl)-1,3,4-thiadiazole;

2-(2-methoxy-4-(1-methyl-1H-pyrazol-4-yl)phenyl)-5-(2,6-diazaspiro[3.5]nonan-2-yl)-1,3,4-thiadiazole;

2-(2-methoxy-4-(1-methyl-1H-pyrazol-4-yl)phenyl)-5-(2,7-diazaspiro[3.5]nonan-2-yl)-1,3,4-thiadiazole;

2-(5-(Methyl(2,2,6,6-tetramethylpiperidin-4-yl)amino)-1,3,4-thiadiazol-2-yl)-5-(1H-pyrazol-1-yl)phenol;

5-(3-chloro-4-(5-(methyl(2,2,6,6-tetramethylpiperidin-4-yl)amino)-1,3,4-thiadiazol-2-yl)phenyl)pyridin-2(1H)-one;

2-(5-(methyl(2,2,6,6-tetramethylpiperidin-4-yl)amino)-1,3,4-thiadiazol-2-yl)-5-(3-(methylamino)-1H-pyrazol-1-yl)phenol;

3-fluoro-2-(5-(methyl(2,2,6,6-tetramethylpiperidin-4-yl) amino)-1,3,4-thiadiazol-2-yl)-5-(1H-pyrazol-4-yl)phenol;

3,4-difluoro-2-(5-(methyl(2,2,6,6-tetramethylpiperidin-4-yl)amino)-1,3,4-thiadiazol-2-yl)-5-(1H-pyrazol-4-yl)phenol;

6-hydroxy-5-(5-(methyl(2,2,6,6-tetramethylpiperidin-4-yl) amino)-1,3,4-thiadiazol-2-yl)-2,3-dihydro-1H-inden-1-one;

2-(5-(methyl(2,2,6,6-tetramethylpiperidin-4-yl)amino)-1,3,4-thiadiazol-2-yl)-5-(1H-pyrazol-4-yl)phenol;

2-(5-(2,6-diazaspiro[3.5]nonan-2-yl)-1,3,4-thiadiazol-2-yl)-5-(1-methyl-1H-pyrazol-4-yl)phenol;

2-(5-(2,7-diazaspiro[3.5]nonan-2-yl)-1,3,4-thiadiazol-2-yl)-5-(1-methyl-1H-pyrazol-4-yl)phenol;

3-fluoro-2-(5-((3aR,6aS)-hexahydropyrrolo[3,4-c]pyrrol-2 (1H)-yl)-1,3,4-thiadiazol-2-yl)-5-(1H-pyrazol-4-yl)phenol Di-hydrochloride salt;

3-chloro-2-(5-(methyl(2,2,6,6-tetramethylpiperidin-4-yl) amino)-1,3,4-thiadiazol-2-yl)-5-(1H-pyrazol-4-yl)phenol;

2-(2-methoxy-4-(1H-pyrazol-1-yl)phenyl)-5-((2,2,6,6-tetramethylpiperidin-4-yl)methyl)-1,3,4-thiadiazole;

2-(2,3-difluoro-4-(1H-pyrazol-4-yl)phenyl)-5-(2,7-diazaspiro[3.5]nonan-2-yl)-1,3,4-thiadiazole;

2-(5-(2,7-diazaspiro[3.5]nonan-2-yl)-1,3,4-thiadiazol-2-yl)-3-fluoro-5-(1H-pyrazol-4-yl)phenol;

4-methoxy-1-methyl-3-(5-(methyl(2,2,6,6-tetramethylpiperidin-4-yl)amino)-1,3,4-thiadiazol-2-yl)quinolin-2(1H)-one;

4-hydroxy-1-methyl-3-(5-(methyl(2,2,6,6-tetramethylpiperidin-4-yl)amino)-1,3,4-thiadiazol-2-yl)quinolin-2(1H)-one;

3-(5-(methyl(2,2,6,6-tetramethylpiperidin-4-yl)amino)-1,3,4-thiadiazol-2-yl)quinolin-2(1H)-one;

1-methyl-3-(5-(methyl(2,2,6,6-tetramethylpiperidin-4-yl) amino)-1,3,4-thiadiazol-2-yl)quinolin-2(1H)-one;

2-(2-chloro-4-(1H-pyrazol-4-yl)phenyl)-5-((3aR,6aS)-hexahydropyrrolo[3,4-c]pyrrol-2(1H)-yl)-1,3,4-thiadiazole Hydrochloride Salt;

2-(2-chloro-4-(1H-pyrazol-4-yl)phenyl)-5-(2,7-diazaspiro [4.5]decan-2-yl)-1,3,4-thiadiazole Hydrochloride Salt;

(R)-(4-(5-(2-chloro-4-(1H-pyrazol-4-yl)phenyl)-1,3,4-thiadiazol-2-yl)piperazin-2-yl)methanol Hydrochloride Salt;

2-(5-(methyl(2,2,6,6-tetramethylpiperidin-4-yl)amino)-1,3,4-thiadiazol-2-yl)benzo[b]thiophene-5-carbonitrile; and 5-(3-chlorobenzo[b]thiophen-2-yl)-N-methyl-N-(2,2,6,6-tetramethylpiperidin-4-yl)-1,3,4-thiadiazol-2-amine.

In another embodiment, the invention is a compound or salt thereof selected from the group consisting of:

5-(2,3-difluoro-4-(1H-pyrazol-4-yl)phenyl)-N-methyl-N-(2,2,6,6-tetramethylpiperidin-4-yl)-1,3,4-thiadiazol-2-amine;

5-(2,5-difluoro-4-(1H-pyrazol-4-yl)phenyl)-N-methyl-N-(2,2,6,6-tetramethylpiperidin-4-yl)-1,3,4-thiadiazol-2-amine;

3-fluoro-2-(5-((3aR,6aS)-hexahydropyrrolo[3,4-c]pyrrol-2 (1H)-yl)-1,3,4-thiadiazol-2-yl)-5-(1H-pyrazol-4-yl)phenol;

3-fluoro-2-(5-(methyl(2,2,6,6-tetramethylpiperidin-4-yl) amino)-1,3,4-thiadiazol-2-yl)-5-(1H-pyrazol-4-yl)phenol;

5-(2-chloro-5-fluoro-4-(1H-pyrazol-4-yl)phenyl)-N-methyl-N-(2,2,6,6-tetramethylpiperidin-4-yl)-1,3,4-thiadiazol-2-amine; and Synthesis of 4-hydroxy-1-methyl-3-(5-(methyl(2,2,6,6-tetramethylpiperidin-4-yl)amino)-1,3,4-thiadiazol-2-yl) quinolin-2(1H)-one.

In a twentieth embodiment, the invention is a pharmaceutical composition comprising a therapeutically effective amount of a compound according to any one of the first through nineteenth embodiments, or a pharmaceutically acceptable salt thereof and one or more pharmaceutically acceptable carriers.

In a twentyfirst embodiment, the invention is a combination comprising a therapeutically effective amount of a compound according to any one of the first through nineteenth embodiments or a pharmaceutically acceptable salt thereof and one or more therapeutically active co-agents.

In a twentysecond embodiment, the invention is a method to treat, prevent or ameliorate an SMN-deficiency-related condition, comprising administering to a subject in need thereof an effective amount of a compound or salt thereof of any one of the first through nineteenth embodiments.

In a twentythird embodiment, the invention is the method of the twentysecond embodiment, wherein said SMN-deficiency-related condition is Spinal Muscular Atrophy.

In a twentyfourth embodiment, the invention is a compound according to any one of claims the first through nineteenth embodiments or a pharmaceutically acceptable salt thereof, for use as a medicament.

In a twentyfifth embodiment, the invention is a compound according to any one of the first through nineteenth embodiments or a pharmaceutically acceptable salt thereof, for use in the treatment of an SMN-deficiency-related condition.

In a twentysixth embodiment, the invention is the compound according to the twentyfifth embodiment, or pharmaceutically acceptable salt thereof, for use in the treatment of spinal muscular atrophy.

In a twentyseventh embodiment, the invention is the use of a compound according to any one of the first through nineteenth embodiments or a pharmaceutically acceptable salt thereof in the manufacture of a medicament for the treatment of spinal muscular atrophy.

For purposes of interpreting this specification, the following definitions will apply and whenever appropriate, terms used in the singular will also include the plural and vice versa.

As used herein, the term "SMN modulator" includes agents, such as the compounds of the invention, which possess the ability to modulate, e.g., increase, SMN protein levels by at least one of multiple possible mechanisms. A non-limiting set of mechanisms includes SMN promoter activation, splicing modulation (e.g., preventing exon7 from being spliced out of the SMN gene), and SMN protein stability modulation. SMN modulators can modulate, e.g., increase FL-SMN and/or SMNΔ7 levels via any of said mechanisms, and/or can prevent SMNΔ7 from being degraded.

As used herein, the term "compounds of the invention" include but are not limited to the compounds of formula (X).

As used herein, the term "SMN-deficiency-related conditions" includes but is not limited to Spinal Muscular Atrophy (SMA), neurogenic-type arthrogryposis multiplex congenita (congenital AMC), and amyotrophic lateral sclerosis (ALS).

As used herein, the term "Spinal Muscular Atrophy", "SMA," include three forms of childhood-onset SMA: Type I (Werdnig-Hoffmann disease); Type II (intermediate, chronic form), Type III (Kugelberg-Welander disease, or Juvenile Spinal Muscular Atrophy); Adult-onset type IV; as well as other forms of SMA, including X-linked disease, Spinal Muscular Atrophy with respiratory distress (SMARD), spinal and bulbar muscular atrophy (Kennedy's disease, or Bulbo-Spinal Muscular Atrophy), and distal spinal muscular atrophy.

For purposes of interpreting this specification, the following definitions will apply and whenever appropriate, terms used in the singular will also include the plural and vice versa.

As used herein, the term "$C_{1-10}$alkyl" refers to a fully saturated branched or unbranched hydrocarbon moiety having 1 to 10 carbon atoms. The terms "$C_{1-6}$alkyl" and "$C_{1-4}$alkyl" are to be construed accordingly. Representative examples of $C_{1-10}$alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl and n-decyl.

As used herein, the term "$C_{1-10}$alkylene" refers to divalent alkyl group as defined herein above having 1 to 10 carbon atoms. The terms "$C_{1-6}$alkylene" and "$C_{1-4}$alkylene" are to be construed accordingly. Representative examples of $C_{1-10}$alkylene include, but are not limited to, methylene, ethylene, n-propylene, iso-propylene, n-butylene, sec-butylene, iso-butylene, tert-butylene, n-pentylene, isopentylene, neopentylene, n-hexylene, 3-methylhexylene, 2,2-dimethylpentylene, 2,3-dimethylpentylene, n-heptylene, n-octylene, n-nonylene and n-decylene.

As used herein, the term "halo$C_{1-4}$alkyl" refers to a $C_{1-4}$alkyl group as defined herein, wherein at least one of the hydrogen atoms is replaced by a halo atom. The halo$C_{1-4}$alkyl group can be monohalo$C_{1-4}$alkyl, dihalo$C_{1-4}$alkyl or polyhalo$C_{1-4}$alkyl including perhalo$C_{1-4}$alkyl. A monohalo$C_{1-4}$alkyl can have one iodo, bromo, chloro or fluoro within the alkyl group. Dihalo$C_{1-4}$alkyl and polyhalo$C_{1-4}$alkyl groups can have two or more of the same halo atoms or a combination of different halo groups within the alkyl. Typically the polyhalo$C_{1-4}$alkyl group contains up to 12, or 10, or 8, or 6, or 4, or 3, or 2 halo groups. Non-limiting examples of halo$C_{1-4}$alkyl include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhalo$C_{1-4}$alkyl group refers to an $C_{1-4}$alkyl group having all hydrogen atoms replaced with halo atoms.

The term "aryl" refers to an aromatic hydrocarbon group having 6-20 carbon atoms in the ring portion. Typically, aryl is monocyclic, bicyclic or tricyclic aryl having 6-20 carbon atoms and includes one or more aromatic rings fused to one or more non-aromatic hydrocarbon rings. Non-limiting examples include phenyl, naphthyl or tetrahydronaphthyl.

As used herein, the term "$C_{1-10}$alkoxy" refers to $C_{1-10}$alkyl-O—, wherein $C_{1-10}$alkyl is defined herein above. The term "$C_{1-4}$alkoxy" refers to $C_{1-4}$alkyl-O—, wherein $C_{1-4}$alkyl is defined herein above. Representative examples of $C_{1-10}$alkoxy include, but are not limited to, methoxy, ethoxy, propoxy, 2-propoxy, butoxy, tert-butoxy, pentyloxy, hexyloxy, heptyloxy, octyloxy- and decyloxy-.

As used herein, the term "heterocyclyl" or "heterocyclo" refers to a saturated or unsaturated non-aromatic ring or ring system, which is a 4-, 5-, 6-, or 7-membered monocyclic ring containing 1, 2 or 3 heteroatoms selected from O, S and N, a 7-, 8-, 9-, 10-, 11-, or 12-membered bicyclic ring system containing 1, 2, 3, 4 or 5 heteroatoms selected from O, S and N, or a 10-, 11-, 12-, 13-, 14- or 15-membered tricyclic ring system and containing 1, 2, 3, 4, 5, 6 or 7 heteroatoms selected from O, S and N, where the N and S can also optionally be oxidized to various oxidation states. The heterocyclic group can be attached via a heteroatom or a carbon atom. The heterocyclyl can include fused or bridged rings as well as spirocyclic rings. Examples of heterocycles include tetrahydrofuran (THF), dihydrofuran, 1,4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane and thiomorpholine.

As used herein, the term "$C_{3-12}$cycloalkyl" refers to saturated or unsaturated monocyclic, bicyclic or tricyclic hydrocarbon groups of 3-12 carbon atoms. The term "$C_{3-18}$cycloalkyl" refers to a fully saturated or unsaturated monocyclic hydrocarbon group of 3-8 carbon atoms. The term "$C_{3-7}$cycloalkyl" refers to saturated or unsaturated monocyclic, bicyclic or tricyclic hydrocarbon groups of 3-7 carbon atoms. Exemplary monocyclic hydrocarbon groups include, but are not limited to, cyclopropyl, cyclobutyl, cyclopentyl, cyclopentenyl, cyclohexyl and cyclohexenyl. Exemplary bicyclic hydrocarbon groups include bornyl, indyl, hexahydroindyl, tetrahydronaphthyl, decahydronaphthyl, bicyclo[2.1.1]hexyl, bicyclo[2.2.1]heptyl, bicyclo[2.2.1]heptenyl, 6,6-dimethylbicyclo[3.1.1]heptyl, 2,6,6-trimethylbicyclo[3.1.1]heptyl, bicyclo[2.2.2]octyl. Exemplary tricyclic hydrocarbon groups include, for example, adamantyl.

As used herein the term "$C_{3-12}$cycloalklyoxy" refers to $C_{3-12}$cycloalkyl-O—, wherein $C_{3-12}$cycloalkyl is defined herein above. Representative examples of $C_{3-12}$cycloalklyoxy include, but are not limited to monocyclic groups such as cyclopropoxy, cyclobutoxy, cyclopentyloxy, cyclopentenyloxy, cyclohexyloxy and cyclohexenyloxy and the like. Exemplary bicyclic hydrocarbon groups include bornyloxy, indyloxy, hexahydroindyloxy, tetrahydronaphthyloxy, decahydronaphthyloxy, bicyclo[2.1.1]hexyloxy, bicyclo[2.2.1]heptyloxy, bicyclo[2.2.1]heptenyloxy, 6,6-dimethylbicyclo[3.1.1]heptyloxy, 2,6,6-trimethylbicyclo[3.1.1]heptyloxy, bicyclo[2.2.2]octyloxy and the like. Exemplary tricyclic hydrocarbon groups include, for example, adamantyloxy.

As used herein, the term "aryloxy" refers to both an —O-aryl and an —O-heteroaryl group, wherein aryl and heteroaryl are defined herein.

As used herein, the term "heteroaryl" refers to a 5-, 6-, or 7-membered monocyclic aromatic ring containing 1, 2, 3 or 4 heteroatoms selected from O, S and N, an 8-, 9-, or 10-membered fused bicyclic ring system containing 1, 2, 3, 4 or 5 heteroatoms selected from O, S and N, or an 11-, 12-, 13-, or 14-membered fused tricyclic ring system containing 1, 2, 3, 4, 5 or 6 heteroatoms selected from O, S and N, wherein at least one of the rings of the bicyclic or tricyclic ring systems is fully aromatic. Typical heteroaryl groups include 2- or 3-thienyl, 2- or 3-furyl, 2- or 3-pyrrolyl, 2-, 4-, or 5-imidazolyl, 3-, 4-, or 5-pyrazolyl, 2-, 4-, or 5-thiazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridyl, 3- or 4-pyridazinyl, 3-, 4-, or 5-pyrazinyl, 2-pyrazinyl, 2-, 4-, or 5-pyrimidinyl, 1-, 2-, 3-, 5-, 6-, 7-, or 8-indolizinyl, 1-, 3-, 4-, 5-, 6-, or 7-isoindolyl, 2-, 3-, 4-, 5-, 6-, or 7-indolyl, 2-, 3-, 4-, 5-, 6-, or 7-indazolyl, 2-, 4-, 5-, 6-, 7-, or 8-purinyl, 1-, 2-, 3-, 4-, 6-, 7-, 8-, or 9-quinolizinyl, 2-, 3-, 4-, 5-, 6-, 7-, or 8-quinoliyl, 1-, 3-, 4-, 5-, 6-, 7-, or 8-isoquinolinyl, 1-, 4-, 5-, 6-, 7-, or 8-phthalazinyl, 2-, 3-, 4-, 5-, or 6-naphthyridinyl, 2-, 3-, 5-, 6-, 7-, or 8-quinazolinyl, 3-, 4-, 5-, 6-, 7-, or 8-cinnolinyl, 2-, 4-, 6-, or 7-pteridinyl, 1-, 2-, 3-, 4-, 5-, 6-, 7-, or 8-4-aH carbazolyl, 1-, 2-, 3-, 4-, 5-, 6-, 7-, or 8-carbazolyl, 1-, 3-, 4-, 5-, 6-, 7-, 8-, or 9-carbolinyl, 1-, 2-, 3-, 4-, 6-, 7-, 8-, 9-, or 10-phenanthridinyl, 1-, 2-, 3-, 4-, 5-, 6-, 7-, 8-, or 9-acridinyl, 1-, 2-, 4-, 5-, 6-, 7-, 8-, or 9-perimidinyl, 2-, 3-, 4-, 5-, 6-, 8-, 9-, or 10-phenathrolinyl, 1-, 2-, 3-, 4-, 6-, 7-, 8-, or 9-phenazinyl, 1-, 2-, 3-, 4-, 6-, 7-, 8-, 9-, or 10-phenothiazinyl, 1-, 2-, 3-, 4-, 6-, 7-, 8-, 9-, or 10-phenoxazinyl, 2-, 3-, 4-, 5-, 6-, or 1-, 3-, 4-, 5-, 6-, 7-, 8-, 9-, or 10-benzisoqinolinyl, 2-, 3-, 4-, or thieno[2,3-b]furanyl, 2-, 3-, 5-, 6-, 7-, 8-, 9-, 10-, or 11-7H-pyrazino[2,3-c]carbazolyl, 2-, 3-, 5-, 6-, or 7-2H-furo[3,2-b]pyranyl, 2-, 3-, 4-, 5-, 7-, or 8-5H-pyrido[2,3-d]-o-oxazinyl, 1-, 3-, or 5-1H-pyrazolo[4,3-d]-oxazolyl, 2-, 4-, or 54H-imidazo[4,5-d]thiazolyl, 3-, 5-, or 8-pyrazino[2,3-d]pyridazinyl, 2-, 3-, 5-, or 6-imidazo[2,1-b]thiazolyl, 1-, 3-, 6-, 7-, 8-, or 9-furo[3,4-c]cinnolinyl, 1-, 2-, 3-, 4-, 5-, 6-, 8-, 9-, 10, or 11-4H-pyrido[2,3-c]carbazolyl, 2-, 3-, 6-, or 7-imidazo[1,2-b][1,2,4]triazinyl, 7-benzo[b]thienyl, 2-, 4-, 5-, 6-, or 7-benzoxazolyl, 2-, 4-, 5-, 6-, or 7-benzimidazolyl, 2-, 4-, 4-, 5-, 6-, or 7-benzothiazolyl, 1-, 2-, 4-, 5-, 6-, 7-, 8-, or 9-benzoxapinyl, 2-, 4-, 5-, 6-, 7-, or 8-benzoxazinyl, 1-, 2-, 3-, 5-, 6-, 7-, 8-, 9-, 10-, or 11-1H-pyrrolo[1,2-b][2]benzazapinyl, 2-, 3-, 4-, 5-, 6-, 7-, or 8-quinolinyl, 1-, 3-, 4-, 5-, 6-, 7-, or 8-isoquinolinyl, 2-, 3-, 4-, 5-, 6-, or 7-indolyl, 2-, 3-, 4-, 5-, 6-, or 7-benzo[b]thienyl, 2-, 4-, 5-, 6-, or 7-benzoxazolyl, 2-, 4-, 5-, 6-, or 7-benzimidazolyl, and 2-, 4-, 5-, 6-, or 7-benzothiazolyl.

As used herein, the term "halogen" or "halo" refers to fluoro, chloro, bromo, and iodo.

As used herein, the term "isomers" refers to different compounds that have the same molecular formula but differ in arrangement and configuration of the atoms. Also as used herein, the term "an optical isomer" or "a stereoisomer" refers to any of the various stereoisomeric configurations which may exist for a given compound of the present invention and includes geometric isomers. It is understood that a substituent may be attached at a chiral center of a carbon atom. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R—S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers or axes and may thus give rise to enantiomers, diastereomers, and other stereoisomeric forms that may be defined, in terms of absolute stereochemistry, as (R)- or (S)-. The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the terms "salt" or "salts" refers to an acid addition or base addition salt of a compound of the invention. "Salts" include in particular "pharmaceutical acceptable salts." The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulformate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^{2}H$, $^{3}H$, $^{11}C$, $^{13}C$, $^{14}C$, $^{15}N$, $^{18}F$ $^{31}P$, $^{32}P$, $^{35}S$, $^{36}Cl$, $^{125}I$ respectively. The invention includes various isotopically labeled compounds as defined herein, for example those into which radioactive isotopes, such as $^{3}H$, $^{13}$C, and $^{14}$C, are present. Such isotopically labelled compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F or labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

Further, substitution with heavier isotopes, particularly deuterium (i.e., $^2$H or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the Formula (X). The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Isotopically-labeled compounds of Formula (X) can generally be prepared by conventional techniques known to those skilled in the art or by processes analogous to those described in the accompanying Examples and Preparations using an appropriate isotopically-labeled reagents in place of the non-labeled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e. compounds of Formula (X) that contain groups capable of acting as donors and/or acceptors for hydrogen bonds may be capable of forming co-crystals with suitable co-crystal formers. These co-crystals may be prepared from compounds of Formula (X) by known co-crystal forming procedures. Such procedures include grinding, heating, co-subliming, co-melting, or contacting in solution compounds of Formula (X) with the co-crystal former under crystallization conditions and isolating co-crystals thereby formed. Suitable co-crystal formers include those described in WO 2004/078163. Hence the invention further provides co-crystals comprising a compound of Formula (X).

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviate, inhibit, prevent and/or ameliorate a condition, or a disorder or a disease (i) mediated by Survival of Motor Neuron (SMN) gene or gene product, or by SMNΔ7 degradation, or by the relative levels of FL-SMN and SMNΔ7 (ii) associated with SMN activity, or (iii) characterized by activity (normal or abnormal) of SMN; or (2) reducing or inhibiting the activity of SMN; or (3) reducing or inhibiting the expression of SMN1 or SMN2.

In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of SMN; or at least partially reducing or inhibiting the expression of SMN, in both cases by modulating the relative levels of FL-SMN and SMNΔ7.

The phrases "therapeutically effective amount" and "effective amount" are used herein to mean an amount sufficient to reduce by at least about 15 percent, preferably by at least 50 percent, more preferably by at least 90 percent, and most preferably prevent, a clinically significant deficit in the activity, function and response of the host. Alternatively, a therapeutically effective amount is sufficient to cause an improvement in a clinically significant condition/symptom in the host.

The effective amount can vary depending on such factors as the size and weight of the subject, the type of illness, or the particular compound of the invention. For example, the choice of the compound of the invention can affect what constitutes an "effective amount." One of ordinary skill in the art would be able to study the factors contained herein and make the determination regarding the effective amount of the compounds of the invention without undue experimentation.

The regimen of administration can affect what constitutes an effective amount. The compound of the invention can be administered to the subject either prior to or after the onset of an SMN-deficiency-related condition. Further, several divided dosages, as well as staggered dosages, can be administered daily or sequentially, or the dose can be continuously infused, or can be a bolus injection. Further, the dosages of the compound(s) of the invention can be proportionally increased or decreased as indicated by the exigencies of the therapeutic or prophylactic situation.

As used herein, the term "subject" refers to an animal. Typically the animal is a mammal. A subject also refers to for example, primates (e.g., humans, male or female), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat," "treating," or "treatment" refers to alleviating or ameliorating at least one physical parameter including those which may not be discernible by the patient. In yet another embodiment, "treat", "treating" or "treatment" refers to modulating the disease or disorder, either physically (e.g., through stabilization of a discernible symptom), physiologically, (e.g., through stabilization of a physical parameter), or both. In yet another embodiment, "treat," "treating," or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Compounds of the present invention are either obtained in the free form, as a salt thereof, or as prodrug derivatives thereof.

When both a basic group and an acid group are present in the same molecule, the compounds of the present invention may also form internal salts, e.g., zwitterionic molecules.

Furthermore, the compounds of the present invention, including their salts, can also be obtained in the form of their hydrates, or include other solvents used for their crystallization. The compounds of the present invention may inherently or by design form solvates with pharmaceutically acceptable solvents (including water); therefore, it is intended that the invention embrace both solvated and unsolvated forms. The term "solvate" refers to a molecular complex of a compound of the present invention (including pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The compounds of the present invention, including salts, hydrates and solvates thereof, may inherently or by design form polymorphs.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure material.

Compounds of the invention and intermediates can also be converted into each other according to methods generally known to those skilled in the art.

In another aspect, the present invention provides a pharmaceutical composition comprising a compound of the present invention, or a pharmaceutically acceptable salt thereof, and a pharmaceutically acceptable carrier. The pharmaceutical composition can be formulated for particular routes of administration such as oral administration, parenteral administration, and rectal administration, etc. In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifiers and buffers, etc.

Typically, the pharmaceutical compositions are tablets or gelatin capsules comprising the active ingredient together with diluents, e.g., lactose, dextrose, sucrose, mannitol, sorbitol, cellulose and/or glycine;

lubricants, e.g., silica, talcum, stearic acid, its magnesium or calcium salt and/or polyethyleneglycol; for tablets also binders, e.g., magnesium aluminum silicate, starch paste, gelatin, tragacanth, methylcellulose, sodium carboxymethylcellulose and/or polyvinylpyrrolidone; if desired disintegrants, e.g., starches, agar, alginic acid or its sodium salt, or effervescent mixtures; and/or absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems, will in particular, be appropriate for dermal application, e.g., for the treatment of skin cancer, e.g., for prophylactic use in sun creams, lotions, sprays and the like. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The compounds of Formula I in free form or in salt form, exhibit valuable pharmacological properties, e.g. full length SMN protein production modulating properties, e.g. as indicated in in vitro and in vivo tests as provided in the next sections, and are therefore indicated for therapy or for use as research chemicals, e.g. as tool compounds.

Thus, as a further embodiment, the present invention provides the use of a compound of Formula (X) or a salt thereof in therapy. In a further embodiment, the therapy is selected from a disease which may be treated by modulating full length SMN protein production. In another embodiment, the disease is selected from the afore-mentioned list, suitably Spinal Muscular Atrophy.

In another embodiment, the invention provides a method of treating a disease which is treated by modulating full length SMN protein production comprising administration of a therapeutically acceptable amount of a compound of Formula (X) or salt thereof to a patient in need of such therapy. In a further embodiment, the disease is selected from the afore-mentioned list, suitably Spinal Muscular Atrophy.

Thus, as a further embodiment, the present invention provides the use of a compound of Formula (X) or salt thereof for the manufacture of a medicament. In a further embodiment, the medicament is for treatment of a disease which may be treated by modulation of SMN protein production. In another embodiment, the disease is selected from the afore-mentioned list, suitably Spinal Muscular Atrophy.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

The compound of the present invention may be administered either simultaneously with, or before or after, one or more other therapeutic agent. The compound of the present invention may be administered separately, by the same or different route of administration, or together in the same pharmaceutical composition as the other agents.

In one embodiment, the invention provides a product comprising a compound of Formula (X) and at least one other therapeutic agent as a combined preparation for simultaneous, separate or sequential use in therapy. In one embodiment, the therapy is the treatment of a Spinal Muscular Atrophy. Products provided as a combined preparation include a composition comprising the compound of Formula (X) and the other therapeutic agent(s) together in the same pharmaceutical composition, or the compound of Formula (X) and the other therapeutic agent(s) in separate form, e.g. in the form of a kit.

In one embodiment, the invention provides a pharmaceutical composition comprising a compound of Formula (X) and another therapeutic agent(s). Optionally, the pharmaceutical composition may comprise a pharmaceutically acceptable carrier, as described above.

In one embodiment, the invention provides a kit comprising two or more separate pharmaceutical compositions, at least one of which contains a compound of Formula (X). In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

Preparations of Compounds

It is understood that in the following description, combinations of substituents and/or variables of the depicted formulae are permissible only if such contributions result in stable compounds.

It will also be appreciated by those skilled in the art that in the processes described below the functional groups of intermediate compounds may need to be protected by suitable protecting groups. Such functional groups include hydroxy, phenol, amino and carboxylic acid. Suitable protecting groups for hydroxy or phenol include trialkylsilyl or diaryalkylsilyl (e.g., t-butyldimethylsilyl, t-butyldiphenylsilyl or trimethylsilyl), tetrahydropyranyl, benzyl, substituted benzyl, methyl, and the like. Suitable protecting groups for amino, amidino and guanidino include t-butoxycarbonyl, benzyloxycarbonyl, and the like. Suitable protecting groups for carboxylic acid include alkyl, aryl or arylalkyl esters.

Protecting groups may be added or removed in accordance with standard techniques, which are well-known to those skilled in the art and as described herein. The use of protecting groups is described in detail in Green, T. W. and P. G. M. Wutz, *Protective Groups in Organic Synthesis* (1999), 3rd Ed., Wiley. The protecting group may also be a polymer resin, such as a Wang resin or a 2-chlorotrityl-chloride resin.

It will also be appreciated by those skilled in the art, although such protected derivatives of compounds of this invention may not possess pharmacological activity as such, they may be administered to a subject and thereafter metabolized in the body to form compounds of the invention which are pharmacologically active. Such derivatives may therefore be described as "prodrugs". All prodrugs of compounds of this invention are included within the scope of the invention.

The following reaction schemes illustrate methods to make compounds of this invention. It is understood that one skilled in the art would be able to make these compounds by similar methods or by methods known to one skilled in the art. In general, starting components and reagents may be obtained from sources such as Sigma Aldrich, Lancaster Synthesis, Inc., Maybridge, Matrix Scientific, TCI, and Fluorochem USA, Strem, other commercial vendors, or synthesized according to sources known to those skilled in the art, or prepared as described in this invention. A, B, X, R, $R^1$, $R^2$, $R^3$, $R^4$, are defined as in the Specification unless specifically defined.

In general, thiadiazole compounds of Formula (X) of this invention can be synthesized following the general procedure described in Scheme 1.

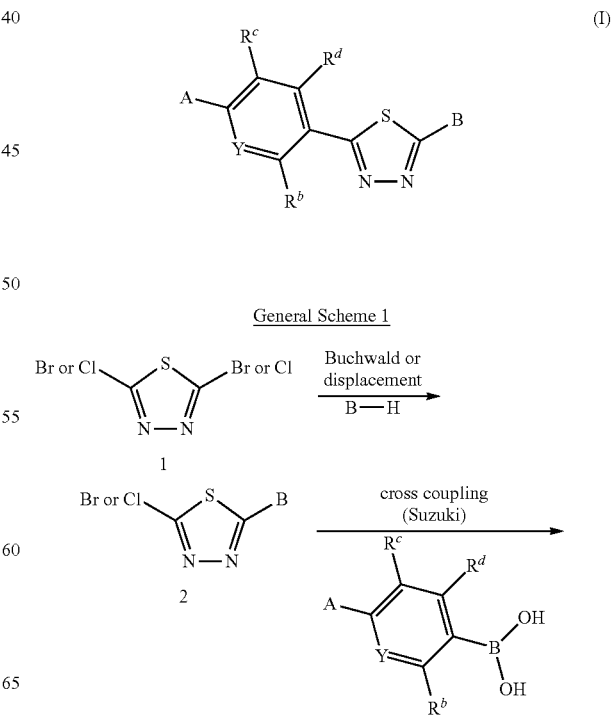

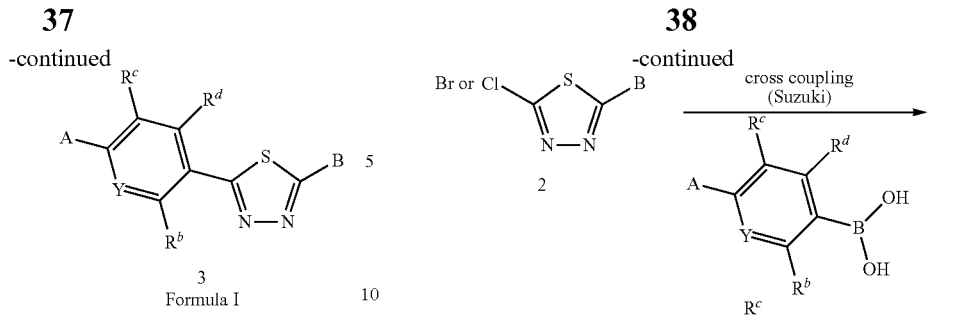

The starting materials for the above reaction scheme are commercially available or can be prepared according to methods known to one skilled in the art or by methods disclosed herein. In general, the compounds of the invention are prepared in the above reaction Scheme 1 as follows:

Di-halothiadiazole (1) reacts in a displacement reaction or a metal-mediated cross coupling reaction (Buchwald) with an alcohol or an amine (B) to provide thiadiazole intermediate (2). Transition metal-mediated cross coupling reaction, such as a Suzuki reaction, between halide compound (2) and a substituted aryl or heteroaryl compound A, such as a boronate acid or boronate ester, provides compound (3) of Formula (X) of the invention.

In an alternative manner, compounds of Formula (X) can be synthesized following the general procedure described in Scheme 2.

General Scheme 2

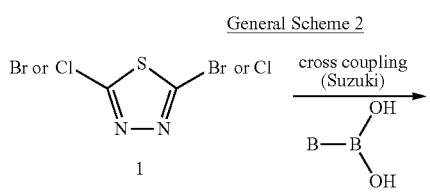

The starting materials for the above reaction scheme are commercially available or can be prepared according to methods known to one skilled in the art or by methods disclosed herein. In general, the compounds of the invention are prepared in the above reaction Scheme 2 as follows:

Di-halothiadiazole (1) reacts in a transition metal-mediated cross coupling reaction, such as a Suzuki reaction, with a boronate acid or ester, to provide thiadiazole intermediate (2). Thiadiazole intermediate (2) reacts via second metal-mediated cross coupling, such as a Suzuki reaction, to provide thiadiazole (3) of Formula (X) of the invention.

Compounds of Formula (X) can also be prepared following the general procedure described in Scheme 3.

General Scheme 3

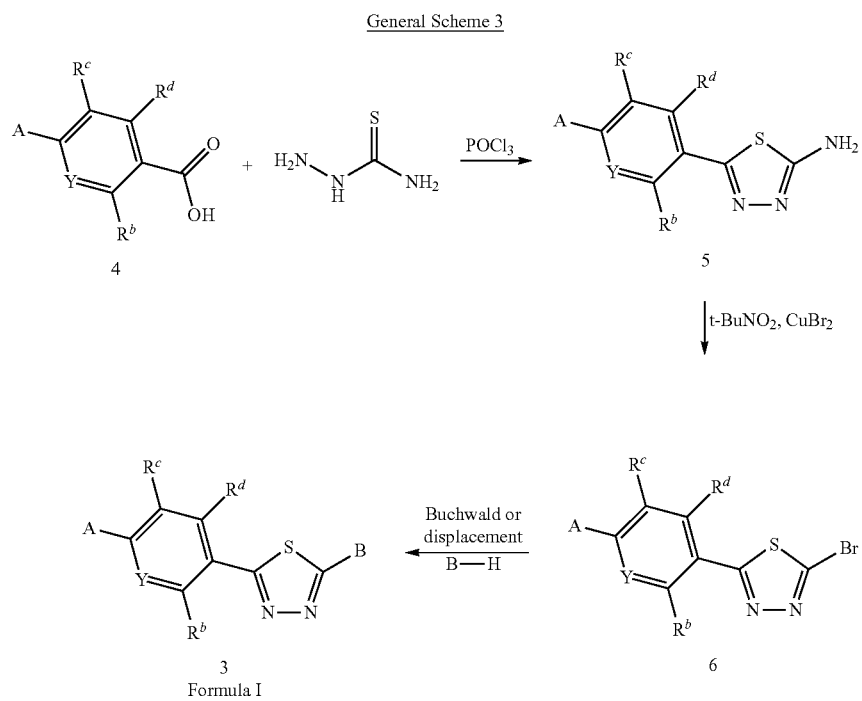

The starting materials for the above reaction scheme are commercially available or can be prepared according to methods known to one skilled in the art or by methods disclosed herein. In general, the compounds of the invention are prepared in the above reaction Scheme 3 as follows:

Substituted aryl or heteroaryl carboxylic acid (4) reacts with hydrazinecarbothioamide and phosphoryl chloride to form amino thiadiazole intermediate (5). Thiadiazole intermediate (5) is then reacted with tert-butylnitrile and $CuBr_2$ to provide thiadiazole intermediate (6). Thiadiazole intermediate (6) reacts in a displacement reaction or a metal-mediated cross coupling reaction (Buchwald) with an alcohol or an amine (B) to provide thiadiazole (3) of Formula (X) of the invention.

General Schemes 1, 2 and 3 can be followed for a variety of aromatic A groups such as substituted phenols, naphthyls, heteroaryls, and the like, and for a variety of amine B groups such as substituted aminopiperidines, piperidines, piperazines, homopiperazines, pyrrolidines, bicyclic amines, and the like, to provide compounds of Formula (X) of the invention. Routine protecting group strategies may be required to achieve final compounds of Formula (X).

All starting materials, building blocks, reagents, acids, bases, dehydrating agents, solvents, catalysts and scavengers utilized to synthesize the compounds of the present invention are either commercially available or can be produced by organic synthesis methods known to one of ordinary skill in the art. Further, the compounds of the present invention can be produced by organic synthesis methods known to one of ordinary skill in the art as shown in the following examples.

The following examples are intended to illustrate the invention and are not to be construed as being limitations thereon. Temperatures are given in degrees centigrade. If not mentioned otherwise, all evaporations are performed under reduced pressure, preferably between about 15 mm Hg and 100 mm Hg (=20-133 mbar). The structure of final products, intermediates and starting materials is confirmed by standard analytical methods, e.g., microanalysis and spectroscopic characteristics, e.g., LCMS, NMR, CHN. Abbreviations used are those conventional in the art, a list of which is provided at the end of the experimental section.

Synthesis of intermediates

Intermediate 1: Synthesis of 1-(3-Methoxy-4-(4,4,5,5-tetramethyl-1,3,2-dioxaborolan-2-yl)phenyl)-1H-pyrazole

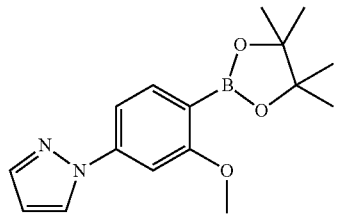 [SMILES: COc1cc(-n2cccn2)ccc1B1OC(C)(C)C(C)(C)O1]

Step 1: (4-Bromo-3-methoxyphenyl)hydrazine

4-Bromo-3-methoxyaniline (3.0 g, 14.85 mmol) was suspended in concentrated HCl (50 mL) and the mixture was cooled to 0° C. in the ice-water bath. A solution of sodium nitrite (1.23 g, 17.82 mmol) in 10 mL water was added very slowly to the reaction mixture. The mixture turned yellow, then brown with a yellow haze indicating diazotization. The diazonium salt was held at 0° C. for an hour and then a solution of tin(II) chloride dihydrate (10.05 g, 44.5 mmol) in concentrated HCl (20 mL) was added very slowly (caution, extremely exothermic). The reaction was stirred for 2 h at 0° C. then at RT overnight. The reaction was filtered and the filter cake was washed with cold $H_2O$ to afford (4-bromo-3-methoxyphenyl)hydrazine as a tan solid (3.1 g, MS: 218 [M+H$^+$]).

Step 2: 1-(4-Bromo-3-methoxyphenyl)-1H-pyrazole

To a solution of (4-bromo-3-methoxyphenyl)hydrazine (62 g, 245 mmol) in ethanol (310 mL) was added tetramethoxypropane (40.2 g, 245 mmol) over a few minutes, and the mixture was heated to an internal temperature of 70° C. The mixture was stirred at 70° C. for 1.5 h then slowly cooled to RT. Ethanol was removed in vacuo and the residue was slurried in EtOAc. The residue was neutralized with 1M aqueous sodium hydroxide (~700 mL) to cause precipitation. The biphasic mixture was filtered and the filtrate was extracted with EtOAc, dried over sodium sulfate and concentrated to provide 30 g of 1-(4-bromo-3-methoxyphenyl)-1H-pyrazole as a black solid (30 g, MS: 254 [M+H$^+$].).

Step 3: 1-(3-Methoxy-4-(4,4,5,5-tetramethyl-1,3,2-dioxaborolan-2-yl)phenyl)-1H-pyrazole 1-(4-Bromo-3-methoxyphenyl)-1H-pyrazole (28.5 g, 113 mmol), bis(pinacolato)diboron (42.9 g, 169 mmol), potassium carbonate (15.56 g, 113 mmol), and $PdCl_2$(dppf). $CH_2Cl_2$ adduct (9.20 g, 11.26 mmol) were added to a 2 L round bottom flask, followed by addition of dioxane (700 mL). The reaction mixture was purged by $N_2$ and stirred under $N_2$ at an internal temperature of 84° C. overnight. The reaction mixture was filtered through a disposable filter funnel and concentrated onto silica gel. The mixture was purified using column chromatography (20% EtOAc in heptanes). The desired fractions were collected and concentrated to provide 13.5 g of 1-(3-methoxy-4-(4,4,5,5-tetramethyl-1,3,2-dioxaborolan-2-yl)phenyl)-1H-pyrazole.

Intermediate 2: Synthesis of (2-(Benzyloxy)-6-methoxy-4-(5-methyloxazol-2-yl)phenyl)boronic acid

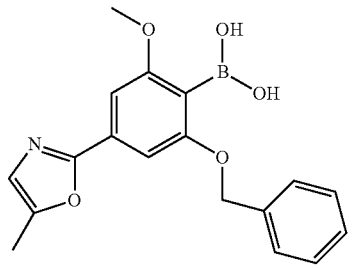 [SMILES: COc1cc(-c2ncc(C)o2)cc(OCc2ccccc2)c1B(O)O]

Step 1: Methyl 3-(benzyloxy)-4-bromo-5-hydroxybenzoate

To a mixture of methyl 4-bromo-3,5-dihydroxybenzoate (18.8 g, 76 mmol) and potassium carbonate (5.26 g, 38.1 mmol) in DMF (190 mL) was added benzyl bromide (3.17 mL, 26.6 mmol). The mixture was stirred overnight, diluted with 200 mL water and acidified to pH 1 by slow addition of concentrated hydrochloric acid. The solution was extracted with 1:1 ethyl acetate/ether (6×) and the combined extracts were washed with water (8×), saturated sodium bicarbonate, brine, then dried over magnesium sulfate and concentrated to provide an orange solid. The solid was suspended in DCM (200 mL) and stirred overnight. The solid (primarily unreacted 4-bromo-3,5-dihydroxybenzoate) was removed by filtration and the filtrate was concentrated to provide an orange oil which was purified by column chromatography (80 g silica gel, 2:1 DCM in heptane elution, followed by DCM elution) to provide methyl 3-(benzyloxy)-4-bromo-5-hydroxybenzoate (4.66 g). MS (M+1)=337.0. $^1$H NMR (400 MHz, CHLOROFORM-d) δ ppm 7.32-7.57 (m, 6H), 7.26 (d, J=1.52 Hz, 1H), 5.77 (s, 1H), 5.22 (s, 2H), 3.93 (s, 3H) as well as the di-benzylated methyl 3,5-bis(benzyloxy)-4-bromobenzoate (1.8 g).

Step 2: Methyl 3-(benzyloxy)-4-bromo-5-methoxybenzoate

To a mixture of methyl 3-(benzyloxy)-4-bromo-5-hydroxybenzoate (3.69 g, 10.94 mmol) and potassium carbonate (3.03 g, 21.98 mmol) in DMF (27 mL) was added methyl iodide (0.753 mL, 12.04 mmol). The mixture was stirred overnight after which time it was diluted with water and extracted with ethyl acetate (4×). The combined extracts were washed with water (8×), brine, dried over magnesium sulfate and concentrated to provide methyl 3-(benzyloxy)-4-bromo-5-methoxybenzoate as a white solid (3.72 g). MS (M+1)= 351.1; $^1$H NMR (400 MHz, CHLOROFORM-d) δ ppm 7.31-7.59 (m, 7H), 5.24 (s, 2H), 3.99 (s, 3H), 3.95 (s, 3H).

Step 3: 3-(Benzyloxy)-4-bromo-5-methoxybenzoic acid

To a solution of methyl 3-(benzyloxy)-4-bromo-5-methoxybenzoate (3.72 g, 10.59 mmol) in 1:1 MeOH/THF (50 mL) was added aqueous sodium hydroxide (1 M, 53.0 mL, 53.0 mmol). After 10 minutes the volatiles were removed under reduced pressure and the solution acidified to pH 1 by addition of concentrated hydrochloric acid resulting in formation of a thick white precipitate. The mixture was extracted with ethyl acetate (2×), and DCM (3×). The combined extracts were washed with brine, dried over magnesium sulfate and concentrated to provide 3-(benzyloxy)-4-bromo-5-methoxybenzoic acid as a white solid (3.41 g). MS (M−1)= 335.0. $^1$H NMR (400 MHz, CHLOROFORM-d) δ ppm 7.21-7.49 (m, 7H), 5.16 (s, 2H), 3.91 (s, 3H).

Step 4: 3-(Benzyloxy)-4-bromo-5-methoxy-N-(prop-2-yn-1-yl)benzamide

To a suspension of 3-(benzyloxy)-4-bromo-5-methoxybenzoic acid (2.0 g, 5.93 mmol) and 4 drops of DMF in DCM (40 mL) was slowly added oxalyl chloride (0.57 mL, 6.52 mmol). After three hours the solvent was removed and the residue was redissolved in DCM (10 mL). To this solution was slowly added a mixture of propargylamine (0.46 mL, 7.12 mmol) and triethylamine (2.5 mL, 17.8 mmol) in DCM (2 mL). After 30 minutes the solution was diluted with ether, washed with water (2×), 1 M hydrochloric acid (2×), water, saturated sodium bicarbonate, brine, then dried over magnesium sulfate and concentrated to a yellow solid. The solid was triturated with diethyl ether and dried under vacuum to provide 3-(benzyloxy)-4-bromo-5-methoxy-N-(prop-2-yn-1-yl)benzamide (1.88 g) as an off-white solid. MS=374.0 (M+1).

Step 5: 2-(3-(Benzyloxy)-4-bromo-5-methoxyphenyl)-5-methyloxazole

To a solution of 3-(benzyloxy)-4-bromo-5-methoxy-N-(prop-2-yn-1-yl)benzamide (0.455 g, 1.22 mmol) in dioxane (12 mL) was added sodium hydride (60% wt, 0.146 g, 3.65 mmol) and the mixture was heated at reflux for six hours. The mixture was cooled to room temperature, quenched by slow addition of water, and diluted with ethyl acetate. The mixture was washed with water, saturated sodium bicarbonate, brine, then dried over magnesium sulfate and concentrated. Flash column chromatography (12 g silica, 2% ethyl acetate in DCM) provided 2-(3-(benzyloxy)-4-bromo-5-methoxyphenyl)-5-methyloxazole (198 mg) as an off-white solid. MS=374 (M+1). $^1$H NMR (400 MHz, CHLOROFORM-d) δ ppm 7.55 (d, J=7.58 Hz, 2H), 7.43 (t, J=7.33 Hz, 2H), 7.32-7.39 (m, 2H), 7.27 (d, J=2.02 Hz, 1H), 6.89 (d, J=1.01 Hz, 1H), 5.27 (s, 2H), 4.02 (s, 3H), 2.44 (d, J=1.52 Hz, 3H).

Step 6: (2-(Benzyloxy)-6-methoxy-4-(5-methyloxazol-2-yl)phenyl)boronic acid

To a stirred solution of 2-(3-(benzyloxy)-4-bromo-5-methoxyphenyl)-5-methyloxazole (197 mg, 0.526 mmol) in THF (1.3 mL) cooled to −78° C. was added n-butyl lithium (2.5 M in hexanes, 232 uL, 0.579 mmol). The solution was stirred for 15 minutes after which time trimethyl borate (235 uL, 2.11 mmol) was added and the solution was allowed to slowly warm to room temperature overnight. The reaction was quenched by addition of 0.1 M HCl and was diluted with ethyl acetate, washed with water, brine, dried over magnesium sulfate and concentrated. Flash column chromatography (12 g silica, 0-100% ethyl acetate in DCM over 30 column volumes) provided (2-(benzyloxy)-6-methoxy-4-(5-methyloxazol-2-yl)phenyl)boronic acid (63 mg) as a white foam. MS=340.1 (M+1). $^1$H NMR (400 MHz, CHLOROFORM-d) δ ppm 7.28-7.46 (m, 5H), 7.25 (d, J=1.01 Hz, 1H), 7.08 (br. s, 1H), 6.85 (d, J=1.01 Hz, 1H), 5.17 (s, 2H), 3.95 (s, 3H), 2.38 (d, J=1.52 Hz, 3H).

Intermediate 3: Synthesis of tert-Butyl(3-methoxy-4-(4,4,5,5-tetramethyl-1,3,2-dioxaborolan-2-yl)phenoxy)dimethylsilane

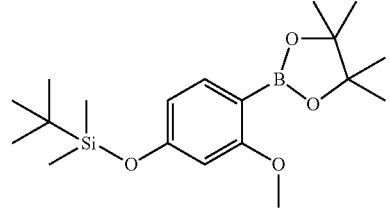 [SMILES: COc1cc(O[Si](C)(C)C(C)(C)C)ccc1B1OC(C)(C)C(C)(C)O1]

Step 1: (4-Bromo-3-methoxyphenoxy)(tert-butyl)dimethylsilane

4-Bromo-3-methoxyphenol (254 g, 1251 mmol) was dissolved in DCM (2500 mL) and treated with DIPEA (437 mL, 2502 mmol) under nitrogen atmosphere. tert-Butylchlorodimethylsilane (198 g, 1314 mmol) was added and the reaction mixture was stirred at room temperature overnight. The crude product was diluted with water and the organic layer was extracted then dried over sodium sulfate and concentrated.

Step 2: tert-Butyl(3-methoxy-4-(4,4,5,5-tetramethyl-1,3,2-dioxaborolan-2-yl)phenoxy)dimethylsilane Nitrogen was bubbled through a stirred mixture of potassium acetate (392 g, 3999 mmol), (4-bromo-3-methoxyphenoxy)(tert-butyl)dimethylsilane (472 g, 1250 mmol), 4,4,4',4',5,5,5',5'-octamethyl-2,2'-bi(1,3,2-dioxaborolane) (381 g, 1499 mmol), DPPF (55.4 g, 100 mmol), and PdCl$_2$(dppf)·CH$_2$Cl$_2$ adduct (82 g, 100 mmol) in dioxane (4500 mL). The reaction mixture was slowly heated to an internal temperature of 69° C., then left to stir at 69° C. for 16 hours before being slowly cooled over an hour to 20° C. The reaction mixture was filtered through celite, rinsed with EtOAc, and the solvent removed in vacuo to afford a black gel. The crude gel was dissolved in DCM, treated with DIPEA (90 mL) and tert-butylchlorodimethylsilane (70 g) and the resulting mixture left to stir at room temperature overnight. The mixture was diluted with water (1 L) and brine (1 L) and stirred for 30 mins. The organic phase was separated, dried over sodium sulfate, filtered, and concentrated in vacuo. The crude material was absorbed onto silica gel and purified by flash chromatography over silica using 20% EtOAc in heptanes (+1% TEA) as the eluent to afford the crude product as a black semi-solid. The crude material was again absorbed onto silica gel and purified by silica flash chromatography using 10% EtOAc in heptanes (+1% TEA) as the eluent to afford the title compound as an oil.

Intermediate 4: 5-Bromo-N-methyl-N-(2,2,6,6-tetramethylpiperidin-4-yl)-1,3,4-thiadiazol-2-amine To a stirred solution of 2,5-dibromo-1,3,4-thiadiazole (2.975 g, 12.2 mmol) and N,2,2,6,6-pentamethylpiperidin-4-amine (2.493 g, 14.64 mmol) in dioxane (40 mL) was added DIPEA (10.65 mL, 61 mmol) and the resulting mixture refluxed at 120° C. for 16 hours. The reaction mixture was cooled to room temperature then filtered under vacuum, rinsed with dioxane, and the filtrate concentrated in vacuo to afford the crude product as a pink/red oil. The crude material was purified by flash chromatography using 3% [7M NH$_3$ in MeOH]/DCM as the eluent to afford the title compound as a pink/red solid (2.924 g, 72% yield). LC-MS: Rt 0.70 min; MS m/z 335.2 [M+2H]$^+$ [Method A]. $^1$H NMR (400 MHz, DMSO-d$_6$) δ ppm 4.13-4.03 (m, 1H), 2.92 (s, 3H), 1.57 (dd, J=12.13, 3.54 Hz, 2H), 1.39 (t, J=12.13 Hz, 2H), 1.26 (br. s., 1H), 1.16 (s, 6H), 1.06 (s, 6H). LC-MS: Rt 1.12 min; MS m/z 335.2 [M+H]$^+$ [Method B].

By employing the method of Intermediate 4, using appropriate starting materials, the following intermediates were prepared:

| Intermediate | Compound | LCMS M + 1, Rt, Method | $^1$H NMR 400 MHz |
|---|---|---|---|
| 5 | (3aR,6aS)-tert-Butyl 5-(5-bromo-1,3,4-thiadiazol-2-yl)hexahydropyrrolo[3,4-c]pyrrole-2(1H)-carboxylate | 377.0 1.15 min D | $^1$H NMR (400 MHz, DMSO-d$_6$) δ ppm 3.70-3.58 (m, 2 H), 3.58-3.45 (m, 2 H), 3.30 (d, J = 12.13 Hz, 2 H), 3.18 (dd, J = 11.12, 3.54 Hz, 2 H), 3.02 (br. s., 2 H), 1.39 (s, 9 H) |
| 6 | 5-Bromo-N-(1,2,2,6,6-pentamethylpiperidin-4-yl)-1,3,4-thiadiazol-2-amine | 335.2, 0.72 min D | $^1$H NMR (400 MHz, DMSO-d$_6$) δ ppm 4.08 (tt, J = 12.32, 3.35 Hz, 1 H), 2.92 (s, 3 H), 1.57 (dd, J = 12.38, 3.28 Hz, 2 H), 1.39 (t, J = 12.13 Hz, 2 H), 1.26 (br. s., 1 H), 1.16 (s, 6 H), 1.06 (s, 6 H) |

SYNTHESIS OF EXAMPLES

Example 1

Synthesis of 5-(2-Methoxy-4-(1H-pyrazol-1-yl)phenyl)-N-methyl-N-(2,2,6,6-tetramethylpiperidin-4-yl)-1,3,4-thiadiazol-2-amine

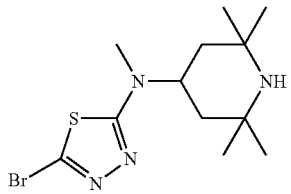 [SMILES: CN(c1nnc(Br)s1)C1CC(C)(C)NC(C)(C)C1]

To a stirred suspension of 1-(3-methoxy-4-(4,4,5,5-tetramethyl-1,3,2-dioxaborolan-2-yl)phenyl)-1H-pyrazole (Intermediate 1) (297 mg, 0.990 mmol) and 5-bromo-N-methyl-N-(2,2,6,6-tetramethylpiperidin-4-yl)-1,3,4-thiadiazol-2-amine (Intermediate 4) (300 mg, 0.900 mmol) in dioxane (4 mL) was added Pd(PPh$_3$)$_4$ (52 mg, 0.045 mmol) followed by a solution of Na$_2$CO$_3$ (191 mg, 1.800 mmol) in water (1 mL). The resulting mixture was purged with nitrogen, sealed, and heated at 120° C. for 30 minutes under microwave irradiation. The reaction mixture was diluted with EtOAc (100 mL) and washed with water (50 mL). The organic phase was separated, dried over MgSO$_4$, and filtered. The filtrate was concentrated in vacuo to afford the crude product as a yellow oil. The crude material was pre-absorbed onto silica gel and purified by flash chromatography over silica using 2.5% [7M NH$_3$ in MeOH]/DCM as the eluent to afford a pale brown glass-like solid which was re-dissolved in MeOH (10 mL) and SiliaMetS DMT (0.52 mmol/g, 433 mg) was added. The resulting suspension was placed in a shaker for 2.5 hours then the SiliaMetS DMT removed by filtration and the filtrate concentrated in vacuo to afford an orange/brown oil. The crude oil was re-dissolved in MeOH and loaded onto a 10 g SCX cartridge (pre-wet with MeOH). The cartridge was washed with MeOH (40 mL) then flushed with 7M NH$_3$ in MeOH (40 mL). The MeOH/NH$_3$ was removed in vacuo to afford a pale orange/brown glass-like solid. The crude glass-like solid was re-purified by mass directed preparative HPLC under basic conditions (5 mM NH$_4$OH) to afford the title compound as a pale pink glass-like solid (0.185 g, 48% yield). LC-MS: Rt 1.53 min; MS m/z 427.3 [M+H]$^+$ [Method B]. $^1$H NMR (400 MHz, DMSO-d$_6$) δ ppm 8.64 (d, J=2.53 Hz, 1H), 8.19 (d, J=8.59 Hz, 1H), 7.80 (d, J=1.52 Hz, 1H), 7.65 (d, J=2.02 Hz, 1H), 7.59 (dd, J=8.59, 2.02 Hz, 1H), 6.60 (dd, J=2.53, 1.52 Hz, 1H), 4.36 (tt, J=12.38, 3.28 Hz, 1H), 4.04 (s, 3H), 2.99 (s, 3H), 1.61 (dd, J=12.13, 3.03 Hz, 2H), 1.42 (t, J=12.38 Hz, 2H), 1.29 (br. s., 1H), 1.22 (s, 6H), 1.09 (s, 6H). HR-MS: Rt 1.54 mins; MS m/z 427.2260 [M+H]$^+$ [Method C].

By employing the method of Example 1, using appropriate starting materials, the following compounds were prepared:

| Example | Compound | LCMS M + 1, Rt, Method | $^1$H NMR 400 MHz |
|---|---|---|---|
| 2 | 6-(5-(Methyl(2,2,6,6-tetramethylpiperidin-4-yl)amino)-1,3,4-thiadiazol-2-yl)naphthalen-2-ol | 397.2, 0.52 min D | $^1$H NMR (400 MHz, DMSO-d$_6$) δ ppm 9.97 (br. s., 1 H), 8.14-8.11 (m, 1 H), 7.92-7.85 (m, 2 H), 7.76 (d, J = 8.59 Hz, 1 H), 7.18-7.11 (m, 2 H), 4.29-4.20 (m, 1 H), 3.01 (s, 3 H), 1.64 (dd, J = 12.13, 3.03 Hz, 2 H), 1.44 (t, J = 12.13 Hz, 2 H), 1.22 (s, 6 H), 1.09 (s, 6 H) |
| 3 | 5-(2-Methoxyquinolin-3-yl)-N-methyl-N-(2,2,6,6-tetramethylpiperidin-4-yl)-1,3,4-thiadiazol-2-amine | 412.3, 0.60 min D | $^1$H NMR (400 MHz, DMSO-d$_6$) δ ppm 8.97 (s, 1 H), 8.06 (d, J = 7.58 Hz, 1 H), 7.86-7.81 (m, 1 H), 7.73 (td, J = 7.71, 1.26 Hz, 1 H), 7.54-7.46 (m, 1 H), 4.40 (t, J = 12.38 Hz, 1 H), 4.14 (s, 3 H), 3.02 (s, 3 H), 1.65 (d, J = 9.60 Hz, 2 H), 1.48 (t, J = 11.87 Hz, 2 H), 1.25 (s, 6 H), 1.12 (s, 6 H) |

| Example | Compound | LCMS M + 1, Rt, Method | ¹H NMR 400 MHz |
|---|---|---|---|
| 4 | 5-(3-Methoxynaphthalen-2-yl)-N-methyl-N-(2,2,6,6-tetramethylpiperidin-4-yl)-1,3,4-thiadiazol-2-amine | 411.3, 0.59 min D | ¹H NMR (400 MHz, DMSO-d$_6$) δ ppm 8.64 (s, 1 H), 7.97 (d, J = 8.08 Hz, 1 H), 7.87 (d, J = 8.03 Hz, 1 H), 7.59-7.49 (m, 2 H), 7.41 (td, J = 7.45, 1.26 Hz, 1 H), 4.44 (br. s., 1 H), 4.05 (s, 3 H), 3.03 (s, 3 H), 1.80-1.02 (br. m., 16 H) |
| 5 | 5-(2-Methoxy-4-(1H-pyrazol-1-yl)phenyl)-N-(1,2,2,6,6-pentamethylpiperidin-4-yl)-1,3,4-thiadiazol-2-amine | 427.3, 0.55 min D | ¹H NMR (400 MHz, DMSO-d$_6$) δ ppm 8.64 (d, J = 2.53 Hz, 1 H), 8.19 (d, J = 8.59 Hz, 1 H), 7.80 (d, J = 1.52 Hz, 1 H), 7.65 (d, J = 2.02 Hz, 1 H), 7.59 (dd, J = 8.59, 2.02 Hz, 1 H), 6.63-6.59 (m, 1 H), 4.43-4.32 (m, 1 H), 4.04 (s, 3 H), 2.99 (s, 3 H), 1.63 (d, J = 11.12 Hz, 2 H), 1.43 (t, J = 10.11 Hz, 2 H), 1.23 (br. s., 6 H), 1.10 (br. s, 6 H) |

Example 6

Synthesis of 5-(2-Methoxy-4-(1-methyl-1H-pyrazol-4-yl)phenyl)-N-methyl-N-(2,2,6,6-tetramethylpiperidin-4-yl)-1,3,4-thiadiazol-2-amine

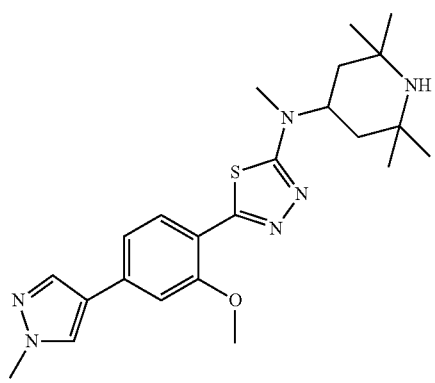

Step 1: 3-Methoxy-4-(5-(methyl(2,2,6,6-tetramethylpiperidin-4-yl)amino)-1,3,4-thiadiazol-2-yl)phenol To a stirred suspension of tert-butyl(3-methoxy-4-(4,4,5,5-tetramethyl-1,3,2-dioxaborolan-2-yl)phenoxy)dimethylsilane (Intermediate 3) (3.28 g, 9.00 mmol) and 5-bromo-N-methyl-N-(2,2,6,6-tetramethylpiperidin-4-yl)-1,3,4-thiadiazol-2-amine (Intermediate 4) (1 g, 6.00 mmol) in dioxane (48 mL) under nitrogen was added Pd(PPh$_3$)$_4$ (0.347 g, 0.30 mmol) followed by a solution of Na$_2$CO$_3$ (1.272 g, 12.00 mmol) in water (12 mL). The resulting mixture was refluxed at 120° C. for 18 hours. The reaction mixture was cooled to room temperature, then diluted with EtOAc (150 mL) and washed with water (100 mL). The organic phase was separated and the aqueous phase re-extracted with EtOAc (150 mL). The combined organics were dried over MgSO$_4$, filtered, and the filtrate concentrated in vacuo to afford an oily brown residue. The residue was suspended in EtOAc (10 mL) and sonicated, then the resulting suspension was filtered under vacuum to afford the crude product as an off-white solid. The crude mixture was purified by flash chromatography using 3% [7M NH$_3$ in MeOH]/DCM as the eluent to afford the title compound as a pale yellow glass-like solid (0.534 g, 23% yield). LC-MS: Rt 0.75 min; MS m/z 377.3 [M+H]+ [Method A]. $^1$H NMR (400 MHz, DMSO-d$_6$) δ ppm 9.99 (br. s., 1H), 7.88 (d, J=8.59 Hz, 1H), 6.54 (d, J=2.53 Hz, 1H), 6.50 (dd, J=8.34, 2.27 Hz, 1H), 4.34-4.25 (m, 1H), 3.86 (s, 3H), 2.94 (s, 3H), 1.59 (dd, J=11.62, 3.03 Hz, 2H), 1.40 (t, J=12.38 Hz, 2H), 1.26 (br. s., 1H), 1.20 (s, 6H), 1.08 (s, 6H).

Step 2: 3-Methoxy-4-(5-(methyl(2,2,6,6-tetramethylpiperidin-4-yl)amino)-1,3,4-thiadiazol-2-yl)phenyl trifluoromethanesulfonate A stirred suspension of 3-methoxy-4-(5-(methyl(2,2,6,6-tetramethylpiperidin-4-yl)amino)-1,3,4-thiadiazol-2-yl)phenol (533 mg, 1.416 mmol) and TEA (493 μL, 3.540 mmol) in DCM (15 mL) under nitrogen was cooled in an ice bath and 1,1,1-trifluoro-N-phenyl-N-((trifluoromethyl)sulfonyl)methanesulfonamide (531 mg, 1.486 mmol) was added. The resulting mixture was stirred at ice bath temperature for 10 minutes, then at room temperature for 18 hours. The reaction mixture was diluted with DCM (35 mL) and washed with saturated NaHCO$_{3(aq)}$ (20 mL). The organic phase was separated via a phase separator and concentrated in vacuo to afford the crude product as a white solid. The crude product was pre-absorbed onto silica gel and purified by flash chromatography using a gradient from 0-10% MeOH/DCM over 18 minutes to afford the title compound as a pale yellow solid (0.577 g, 77% yield). LC-MS: Rt 1.12 min; MS m/z 509.3 [M+H]+ [Method A]. $^1$H NMR (400 MHz, DMSO-d$_6$) δ ppm 8.24 (d, J=8.59 Hz, 1H), 7.42 (d, J=2.53 Hz, 1H), 7.21 (dd, J=8.84, 2.27 Hz, 1H), 4.44-4.33 (m, 1H), 4.00 (s, 3H), 2.99 (s, 3H), 1.62 (d, J=9.60 Hz, 2H), 1.43 (t, J=11.62 Hz, 2H), 1.28 (br. s., 1H), 1.22 (s, 6H), 1.09 (s, 6H).

Step 3: 5-(2-Methoxy-4-(1-methyl-1H-pyrazol-4-yl)phenyl)-N-methyl-N-(2,2,6,6-tetramethylpiperidin-4-yl)-1,3,4-thiadiazol-2-amine To a stirred solution of 1-methyl-4-(4,4,5,5-tetramethyl-1,3,2-dioxaborolan-2-yl)-1H-pyrazole (177 mg, 0.849 mmol) and 3-methoxy-4-(5-(methyl(2,2,6,6-tetramethylpiperidin-4-yl)amino)-1,3,4-thiadiazol-2-yl)phenyl trifluoromethanesulfonate (332 mg, 0.653 mmol) in dioxane (4 mL) was added Pd(PPh$_3$)$_4$ (38 mg, 0.033 mmol) followed by a solution of Na$_2$CO$_3$ (208 mg, 1.958 mmol) in water (1 mL). The resulting mixture was purged with nitrogen, sealed, and heated at 120° C. for 30 minutes under microwave irradiation. The reaction mixture was diluted with EtOAc (100 mL) and washed with water (50 mL). The organic phase was separated, dried over MgSO$_4$, and filtered. To the filtrate was added SiliaMetS DMT (541 mg, 0.61 mmol/g, 0.33 mmols) and the resulting suspension stirred at room temperature for 18 hours. The SiliaMetS DMT was removed by vacuum filtration, rinsed with EtOAc, and the filtrate concentrated in vacuo to afford the crude product as a pale yellow solid. The crude material was recrystallized from MeOH (3 mL) to afford the title compound as a white solid (0.166 g, 57% yield). LC-MS: Rt 0.86 min; MS m/z 441.4 [M+H]+ [Method A]. $^1$H NMR (400 MHz, DMSO-d$_6$) δ ppm 8.27 (s, 1H), 8.05 (d, J=8.08 Hz, 1H), 7.98 (s, 1H), 7.37 (d, J=1.52 Hz, 1H), 7.29 (dd, J=8.59, 1.52 Hz, 1H), 4.35 (tt, J=12.38, 3.28 Hz, 1H), 3.99 (s, 3H), 3.88 (s, 3H), 2.97 (s, 3H), 1.61 (dd, J=11.87, 3.28 Hz, 2H), 1.41 (t, J=12.13 Hz, 2H), 1.26 (s, 1H), 1.21 (s, 6H), 1.09 (s, 6H). LC-MS: Rt 1.60 min; MS m/z 440.4 [M+H]+ [Method B]. HR-MS: Rt 1.43 min; MS m/z 441.2419 [M+H]+ [Method C].

By employing the method of Example 6, using appropriate starting materials, the following compounds were prepared:

| Example | Compound | LCMS M + 1, Rt, Method | $^1$H NMR 400 MHz |
|---|---|---|---|
| 7 | 5-(2-Methoxy-4-(1H-pyrazol-4-yl)phenyl)-N-methyl-N-(2,2,6,6-tetramethylpiperidin-4-yl)-1,3,4-thiadiazol-2-amine | 427.3, 0.51 min D | $^1$H NMR (400 MHz, DMSO-d$_6$) δ ppm 13.03 (br. s., 1 H), 8.32 (br. s., 1 H), 8.05 (d, J = 8.08 Hz, 2 H), 7.41 (d, J = 1.52 Hz, 1 H), 7.34 (dd, J = 8.08, 1.52 Hz, 1 H), 4.35 (tt, J = 12.44, 2.97 Hz, 1 H), 4.00 (s, 3 H), 2.98 (s, 3 H), 1.61 (dd, J = 11.87, 3.28 Hz, 2 H), 1.47-1.36 (m, 2 H), 1.27 (br. s., 1 H), 1.21 (s, 6 H), 1.09 (s, 6 H) |

| Example | Compound | LCMS M + 1, Rt, Method | ¹H NMR 400 MHz |
|---|---|---|---|
| 8 | 4-(3-Methoxy-4-(5-(methyl(2,2,6,6-tetramethyl-piperidin-4-yl)amino)-1,3,4-thiadiazol-2-yl)phenyl)-1-methylpyridin-2(1H)-one | 468.4, 0.48 min D | ¹H NMR (400 MHz, DMSO-$d_6$) δ ppm 8.19 (d, J = 8.08 Hz, 1 H), 7.80 (d, J = 7.07 Hz, 1 H), 7.48 (d, J = 1.52 Hz, 1 H), 7.44 (dd, J = 8.08, 1.52 Hz, 1 H), 6.83 (d, J = 2.02 Hz, 1 H), 6.67 (dd, J = 7.07, 2.02 Hz, 1 H), 4.44-4.34 (m, 1 H), 4.05 (s, 3 H), 3.47 (s, 3 H), 2.99 (s, 3 H), 1.61 (dd, J = 12.13, 3.03 Hz, 2 H), 1.42 (t, J = 12.13 Hz, 2 H), 1.28 (br. s., 1 H), 1.22 (s, 6 H), 1.09 (s, 6 H) |
| 9 | 5-(3-Methoxy-4-(5-(methyl(2,2,6,6-tetramethyl-piperidin-4-yl)amino)-1,3,4-thiadiazol-2-yl)phenyl)pyridin-2-ol | 454.4, 0.46 min D | ¹H NMR (400 MHz, DMSO-$d_6$) δ ppm 11.93 (br, s, 1 H), 8.10 (d, J = 8.08 Hz, 1 H), 7.95 (dd, J = 9.60, 3.03 Hz, 1 H), 7.89 (d, J = 2.53 Hz, 1 H), 7.35 (d, J = 1.52 Hz, 1 H), 7.29 (dd, J = 8.34, 1.77 Hz, 1 H), 6.45 (d, J = 9.60 Hz, 1 H), 4.42-4.33 (m, 1 H), 4.02 (s, 3 H), 2.98 (s, 3 H), 1.63 (d, J = 9.09 Hz, 2 H), 1.44 (t, J = 11.12 Hz, 2 H), 1.23 (s, 6 H), 1.10 (s, 6 H) |
| 10 | 5-(3-Methoxy-4-(5-(methyl(2,2,6,6-tetramethyl-piperidin-4-yl)amino)-1,3,4-thiadiazol-2-yl)phenyl)-1-methylpyridin-2(1H)-one | 468.4, 0.48 min D | ¹H NMR (400 MHz, DMSO-$d_6$) δ ppm 8.29 (d, J = 2.53 Hz, 1 H), 8.12 (d, J = 8.08 Hz, 1 H), 7.95 (dd, J = 9.35, 2.78 Hz, 1 H), 7.37 (d, J = 1.52 Hz, 1 H), 7.31 (dd, J = 8.34, 1.77 Hz, 1 H), 6.51 (d, J = 9.60 Hz, 1 H), 4.41-4.32 (m, 1 H), 4.03 (s, 3 H), 3.53 (s, 3 H), 2.98 (s, 3 H), 1.61 (dd, J = 11.87, 3.28 Hz, 2 H), 1.42 (t, J = 12.13 Hz, 2 H), 1.27 (br. s., 1 H), 1.21 (s, 6 H), 1.09 (s, 6 H) |

| Example | Compound | LCMS M + 1, Rt, Method | ¹H NMR 400 MHz |
|---|---|---|---|
| 11 | N-Methyl-5-(2-methyl-4-(1-methyl-1H-pyrazol-4-yl)phenyl)-N-(2,2,6,6-tetramethylpiperidin-4-yl)-1,3,4-thiadiazol-2-amine | 425.4, 0.49 min D | ¹H NMR (400 MHz, DMSO-$d_6$) δ ppm 8.21 (s, 1 H), 7.92 (s, 1 H), 7.57 (s, 1 H), 7.54-7.46 (m, 2 H), 4.34-4.24 (m, 1 H), 3.87 (s, 3 H), 2.99 (s, 3 H), 2.53 (s, 3 H), 1.69-1.57 (m, 2 H), 1.44 (t, J = 11.87 Hz, 2 H), 1.21 (s, 6 H), 1.10 (s, 6 H) |
| 12 | 1-Methyl-4-(4-(5-(methyl(2,2,6,6-tetramethylpiperidin-4-yl)amino)-1,3,4-thiadiazol-2-yl)-3-(trifluoromethoxy)phenyl)pyridin-2(1H)-one | 522.3, 0.51 min D | ¹H NMR (400 MHz, DMSO-$d_6$) δ ppm 8.26 (d, J = 8.59 Hz, 1 H), 7.91 (dd, J = 8.34, 1.77 Hz, 1 H), 7.85-7.81 (m, 2 H), 6.81 (d, J = 2.02 Hz, 1 H), 6.65 (dd, J = 7.07, 2.02 Hz, 1 H), 4.36-4.27 (m, 1 H), 3.47 (s, 3 H), 3.04 (s, 3 H), 1.65 (d, J = 11.62 Hz, 2 H), 1.52-1.40 (m, 2 H), 1.21 (br. s., 6 H), 1.10 (br. s., 6 H) |

-continued

| Example | Compound | LCMS M + 1, Rt, Method | $^1$H NMR 400 MHz |
|---|---|---|---|
| 13 | 5-(4-(3,5-Dimethyl-1H-pyrazol-4-yl)-2-methoxy-phenyl)-N-methyl-N-(2,2,6,6-tetramethylpiperidin-4-yl)-1,3,4-thiadiazol-2-amine | 329.2, 0.47 min, D | $^1$H NMR (400 MHz, DMSO-$d_6$) δ ppm 12.37 (br. s., 1 H), 8.10 (d, J = 8.08 Hz, 1 H), 7.06 (s, 1 H), 7.04-7.00 (m, 1 H), 4.41-4.32 (m, 1 H), 3.96 (s, 3 H), 2.98 (s, 3 H), 2.29 (br. s., 3 H), 2.24 (br. s., 3 H), 1.62 (d, J = 10.61 Hz, 2 H), 1.42 (t, J = 11.62 Hz, 2 H), 1.27 (br. s., 1 H), 1.22 (s, 6 H), 1.09 (s, 6 H) |
| 14 | 5-(2-Methoxy-4-(1-methyl-1H-pyrazol-4-yl)phenyl)-N-methyl-N-(2,2,6,6-tetramethyl-piperidin-4-yl)-1,3,4-thiadiazol-2-amine | 479.4, 0.50 min, D | $^1$H NMR (400 MHz, DMSO-$d_6$) δ ppm 8.27 (s, 1 H), 8.05 (d, J = 8.08 Hz, 1 H), 7.98 (s, 1 H), 7.37 (d, J = 1.52 Hz, 1 H), 7.29 (dd, J = 8.59, 1.52 Hz, 1 H), 4.35 (tt, J = 12.38, 3.28 Hz, 1 H), 3.99 (s, 3 H), 3.88 (s, 3 H), 2.97 (s, 3H), 1.61 (dd, J = 11.87, 3.28 Hz, 2 H), 1.41 (t, J = 12.13 Hz, 2 H), 1.26 (s, 1 H), 1.21 (s, 6 H), 1.09 (s, 6 H) |

Example 15

Synthesis of 2-(5-(Methyl(2,2,6,6-tetramethylpiperidin-4-yl)amino)-1,3,4-thiadiazol-2-yl)-5-(1-methyl-1H-pyrazol-4-yl)phenol

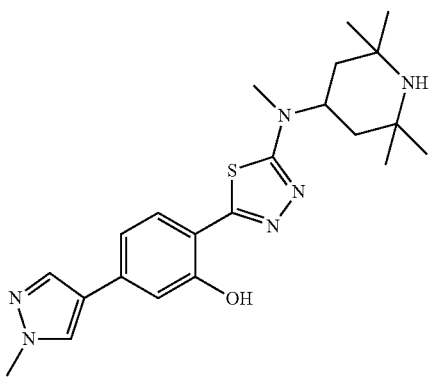

To a stirred solution of 5-(2-methoxy-4-(1-methyl-1H-pyrazol-4-yl)phenyl)-N-methyl-N-(2,2,6,6-tetramethylpiperidin-4-yl)-1,3,4-thiadiazol-2-amine (129 mg, 0.293 mmol) in NMP (3 mL) was added $Na_2CO_3$ (47 mg, 0.439 mmol) followed by PhSH (35 µL, 0.337 mmol). The resulting mixture was sealed, evacuated and back filled with nitrogen (×3), then heated at 190° C. for 20 minutes under microwave irradiation. The reaction mixture was diluted with MeOH (10 mL) and filtered through celite. The filtrate was acidified by addition of acetic acid (3 mL) and loaded onto a 2 g SCX cartridge (pre-wet with MeOH). The cartridge was washed with MeOH (15 mL) and flushed with 7M $NH_3$ in MeOH (15 mL). The MeOH/$NH_3$ was removed in vacuo to afford the crude product as a brown solid. The crude material was purified by UV-directed preparative HPLC under basic (5 mM $NH_4OH$) conditions, collecting at 352 nm, to afford the title compound as a pale brown glass-like solid (0.096 g, 77% yield). LC-MS: Rt 0.88 min; MS m/z 427.2 [M+H]$^+$ [Method A]. $^1$H NMR (400 MHz, DMSO-$d_6$) δ ppm 8.13 (s, 1H), 7.86-7.78 (m, 2H), 7.17-7.10 (m, 2H), 4.35-4.25 (m, 1H), 3.87 (s, 3H), 2.99 (s, 3H), 1.62 (dd, J=11.87, 3.28 Hz, 2H), 1.43 (t, J=12.13 Hz, 2H), 1.21 (s, 6H), 1.09 (s, 6H). LC-MS: Rt 1.69 min; MS m/z 427.4 [M+H]$^+$ [Method B]. HR-MS: Rt 1.49 mins; MS m/z 427.2660 [M+H]$^+$ [Method C].

By employing the methods of Example 6 and 15, using appropriate starting materials, the following compounds were prepared:

| Example | Compound | LCMS M + 1, Rt, Method | $^1$H NMR 400 MHz |
|---|---|---|---|
| 16 | 2-(5-(Methyl(2,2,6,6-tetramethylpiperidin-4-yl)amino)-1,3,4-thiadiazol-2-yl)-5-(1H-pyrazol-1-yl)phenol | 413.3, 0.55 min D | $^1$H NMR (400 MHz, DMSO-d$_6$) δ ppm 8.47 (d, J = 2.02 Hz, 1 H), 7.99 (d, J = 8.59 Hz, 1 H), 7.78-7.73 (m, 1 H), 7.47 (d, J = 1.52 Hz, 1 H), 7.36 (d, J = 8.59 Hz, 1 H), 6.58-6.53 (m, 1 H), 4.33 (t, J = 12.13 Hz, 1 H), 2.99 (s, 3 H), 1.69-1.58 (m, 2 H), 1.47 (t, J = 12.13 Hz, 2 H), 1.23 (s, 6 H), 1.12 (s, 6 H) |
| 17 | 5-(3-Hydroxy-4-(5-(methyl(2,2,6,6-tetramethyl-piperidin-4-yl)amino)-1,3,4-thiadiazol-2-yl)phenyl)-1-methylpyridin-2(1H)-one | 454.4, 0.47 min D | $^1$H NMR (400 MHz, DMSO-d$_6$) δ ppm 8.16 (d, J = 2.53 Hz, 1 H), 7.88 (d, J = 8.08 Hz, 1 H), 7.79 (dd, J = 9.35, 2.78 Hz, 1 H), 7.19-7.12 (m, 2 H), 6.49 (d, J = 9.09 Hz, 1 H), 4.37-4.28 (m, 1 H), 3.51 (s, 3 H), 3.00 (s, 3 H), 1.69-1.58 (m, 2 H), 1.54-1.37 (m, 2 H), 1.23 (s, 6 H), 1.11 (br. s., 6 H) |
| 18 | 4-(3-Hydroxy-4-(5-(methyl(2,2,6,6-tetramethyl-piperidin-4-yl)amino)-1,3,4-thiadiazol-2-yl)phenyl)-1-methylpyridin-2(1H)-one | 454.3, 0.48 min D | $^1$H NMR (400 MHz, DMSO-d$_6$) δ ppm 8.00 (d, J = 8.08 Hz, 1 H), 7.77 (d, J = 7.07 Hz, 1 H), 7.27-7.20 (m, 2 H), 6.61 (d, J = 2.02 Hz, 1 H), 6.51 (dd, J = 7.07, 2.02 Hz, 1 H), 4.40-4.29 (m, 1 H), 3.45 (s, 3 H), 3.00 (s, 3 H), 1.66-1.60 (m, 2 H), 1.45 (t, J = 11.87 Hz, 2 H), 1.22 (s, 6 H), 1.10 (s, 6 H) |

| Example | Compound | LCMS M + 1, Rt, Method | ¹H NMR 400 MHz |
|---|---|---|---|
| 19 | 5-(3-Hydroxy-4-(5-(methyl(2,2,6,6-tetramethyl-piperidin-4-yl)amino)-1,3,4-thiadiazol-2-yl)phenyl)pyridin-2-ol | 440.4, 0.45 min D | 1H NMR (400 MHz, DMSO-d₆) δ ppm 11.83 (br. s., 1 H), 7.88 (d, J = 8.59 Hz, 1 H), 7.80 (dd, J = 9.60, 2.53 Hz, 1 H), 7.71 (d, J = 2.02 Hz, 1 H), 7.16-7.09 (m, 2 H), 6.44 (d, J = 9.60 Hz, 1 H), 4.36-4.27 (m, 1 H), 2.99 (s, 3 H), 1.67-1.59 (m, 2 H), 1.50-1.37 (m, 2 H), 1.22 (s, 6 H), 1.10 (s, 6 H) |

Example 20

Synthesis of 3-(5-(Methyl(2,2,6,6-tetramethylpiperidin-4-yl)amino)-1,3,4-thiadiazol-2-yl)naphthalene-2,7-diol

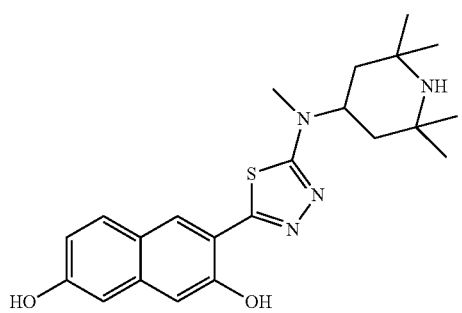 [SMILES: CN(c1nnc(-c2cc3ccc(O)cc3cc2O)s1)C1CC(C)(C)NC(C)(C)C1]

Step 1: 7-(Benzyloxy)-6-(5-(methyl(2,2,6,6-tetramethylpiperidin-4-yl)amino)-1,3,4-thiadiazol-2-yl)naphthalen-2-ol To a stirred solution of 7-(benzyloxy)-6-(4,4,5,5-tetramethyl-1,3,2-dioxaborolan-2-yl)naphthalen-2-ol (73 mg, 0.195 mmol) and 5-bromo-N-methyl-N-(2,2,6,6-tetramethylpiperidin-4-yl)-1,3,4-thiadiazol-2-amine (Intermediate 4) (84 mg, 0.150 mmol) in dioxane (2 mL) was added Pd(PPh₃)₄ (3.5 mg, 0.003 mmol) followed by a solution of Na₂CO₃ (63 mg, 0.599 mmol) in water (0.5 mL). The resulting mixture was purged with nitrogen, sealed, and heated at 120° C. for 1 hr under microwave irradiation. The reaction mixture was diluted with MeOH (20 mL), filtered via syringe filter, and the filtrate concentrated in vacuo to afford the crude product.

The crude mixture was pre-absorbed onto silica gel and purified over a 12 g silica cartridge using an ISCO Combi-Flash system running a gradient from 0-10% MeOH/DCM over 15 minutes. The relevant fractions were combined and concentrated in vacuo to afford the title compound as a yellow glass-like solid product (51 mg, 67.8% yield). LC-MS: Rt 1.04 min; MS m/z 503.4 [M+H]⁺ [Method B]. ¹H NMR (400 MHz, DMSO-d₆) δ ppm 9.92 (s, 1H) 8.53 (s, 1H) 7.81 (d, J=9.09 Hz, 1H) 7.56-7.63 (m, 2H) 7.32-7.48 (m, 4H) 7.08 (d, J=2.53 Hz, 1H) 6.97 (dd, J=8.84, 2.27 Hz, 1H) 5.33 (s, 2H) 3.92 (br. s., 1H) 2.94 (s, 3H) 1.69-0.97 (br. m., 16H).

Step 2: 3-(5-(Methyl(2,2,6,6-tetramethylpiperidin-4-yl)amino)-1,3,4-thiadiazol-2-yl)naphthalene-2,7-diol To a stirred, ice-bath cooled suspension of 7-(benzyloxy)-6-(5-(methyl(2,2,6,6-tetramethylpiperidin-4-yl)amino)-1,3,4-thiadiazol-2-yl)naphthalen-2-ol (49 mg, 0.112 mmol) in DCM (2 ml) under nitrogen was added BBr₃ (1M solution in DCM, 0.56 mL, 0.56 mmol). The reaction mixture was quenched by addition of MeOH (2 mL) and the resulting solution was warmed to room temperature, then loaded onto a 1 g SCX cartridge (pre-wet with MeOH). The cartridge was washed with MeOH (~15 mL) then flushed with 7M NH₃ in MeOH (~10 mL). The MeOH/NH₃ was removed in vacuo to afford the crude product. The crude product was taken up in 1:1 MeOH:DMSO (2 mL), filtered via syringe filter, and the filtrate purified by preparative HPLC, under neutral conditions, running a gradient from 10-90% MeCN/water over 15 minutes. The relevant fractions were combined and concentrated in vacuo to afford the title compound as a dark green/brown solid (20.6 mg, 49.2% yield). LC-MS: Rt 0.85 min; MS m/z 413.3 [M+H]⁺ [Method B]. ¹H NMR (400 MHz, DMSO-d₆) δ ppm 10.92 (br. s., 1H) 9.81 (br. s., 1H) 8.31 (s, 1H) 7.74 (d, J=9.09 Hz, 1H) 7.07 (s, 1H) 6.87-6.94 (m, 2H) 4.25-4.34 (m, 1H) 3.01 (s, 3H) 1.64 (dd, J=12.13, 3.03 Hz, 2H) 1.45 (t, J=12.13 Hz, 2H) 1.22 (s, 6H) 1.10 (s, 6H).

By employing the method of Example 20, using appropriate starting materials, the following compounds were prepared:

| Example | Compound | LCMS M + 1, Rt, Method | ¹H NMR 400 MHz |
|---|---|---|---|
| 21 | 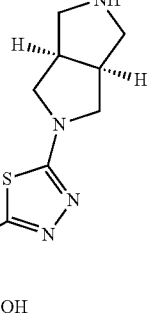<br>3-(5-((3aR,6aS)-Hexahydropyrrolo[3,4-c]pyrrol-2(1H)-yl)-1,3,4-thiadiazol-2-yl)naphthalene-2,7-diol | 355.1, 0.44 min D | ¹H NMR (400 MHz, DMSO-$d_6$) δ ppm 8.34 (s, 1 H), 7.75 (d, J = 9.09 Hz, 1 H), 7.07 (s, 1 H), 6.95-6.86 (m, 2 H), 3.70 (dd, J = 9.85, 6.82 Hz, 2 H), 3.33-3.26 (m, 2 H), 2.98-2.85 (m, 4 H), 2.70 (d, J = 8.08 Hz, 2 H) |
| 22 | 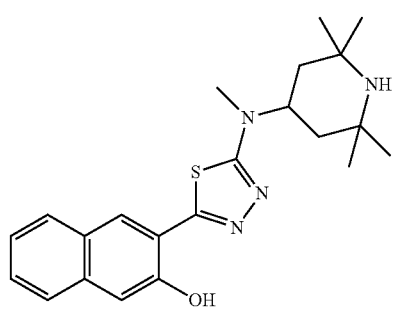 [SMILES: CN(c1nnc(-c2cc3ccccc3cc2O)s1)C1CC(C)(C)NC(C)(C)C1]<br>3-(5-(Methyl(2,2,6,6-tetramethylpiperidin-4-yl)amino)-1,3,4-thiadiazol-2-yl)naphthalen-2-ol.HBr | 397.3, 0.60 min D | ¹H NMR (400 MHz, DMSO-$d_6$) δ ppm 11.08 (br. s., 1 H), 8.76 (d, J = 12.13 Hz, 1 H), 8.55 (s, 1 H), 7.91 (d, J = 8.08 Hz, 1 H), 7.82-7.72 (m, 2 H), 7.48-7.43 (m, 1 H), 7.37-7.31 (m, 2 H), 4.63-4.53 (m, 1 H), 3.08 (s, 3 H), 2.03-1.90 (m, 4 H), 1.50 (s, 6 H), 1.45 (s, 6 H) |
| 23 | 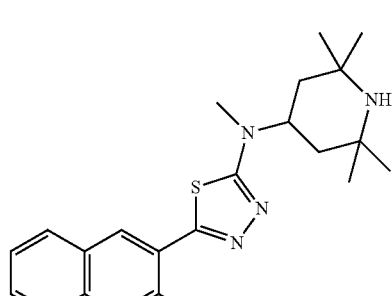<br>3-(5-(Methyl(2,2,6,6-tetramethylpiperidin-4-yl)amino)-1,3,4-thiadiazol-2-yl)quinolin-2-ol | 398.3, 0.52 min D | ¹H NMR (400 MHz, DMSO-$d_6$) δ ppm 12.38 (br. s., 1 H), 8.80 (s, 1 H), 7.89 (d, J = 7.07 Hz, 1 H), 7.62-7.56 (m, 1 H), 7.41 (d, J = 8.59 Hz, 1 H), 7.27 (t, J = 7.58 Hz, 1 H), 4.41-4.31 (m, 1 H), 3.00 (s, 3 H), 1.68-1.55 (m, 2 H), 1.44 (t, J = 11.62 Hz, 2 H), 1.23 (s, 6 H), 1.10 (s, 6 H) |

-continued

| Example | Compound | LCMS M + 1, Rt, Method | $^1$H NMR 400 MHz |
|---|---|---|---|
| 24 | 2-(5-(Methyl(2,2,6,6-tetramethylpiperidin-4-yl)amino)-1,3,4-thiadiazol-2-yl)-4-(1H-pyrazol-1-yl)phenol | 413.3, 0.55 min D | $^1$H NMR (400 MHz, DMSO-d$_6$) δ ppm 8.37 (d, J = 2.02 Hz, 1 H), 8.33 (d, J = 3.03 Hz, 1 H), 7.72-7.64 (m, 2 H), 7.04 (d, J = 8.59 Hz, 1 H), 6.50 (t, J = 2.02 Hz, 1 H), 4.38-4.29 (m, 1 H), 3.00 (s, 3 H), 1.64 (dd, J = 11.62, 3.03 Hz, 2 H), 1.45 (t, J = 12.13 Hz, 2 H), 1.22 (s, 6 H), 1.10 (s, 6 H) |

Example 25

Synthesis of 5-(2-Chloro-4-(1-methyl-1H-pyrazol-4-yl)phenyl)-N-methyl-N-(2,2,6,6-tetramethylpiperidin-4-yl)-1,3,4-thiadiazol-2-amine

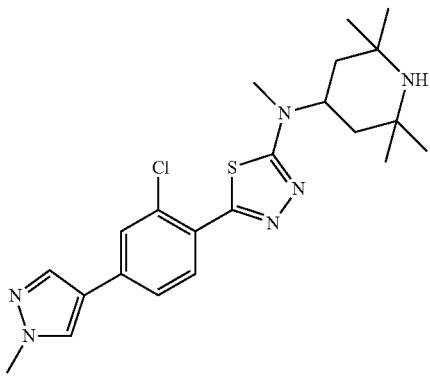

Step 1: 5-(4-Bromo-2-chlorophenyl)-1,3,4-thiadiazol-2-amine

A stirred mixture of 4-bromo-2-chlorobenzoic acid (2 g, 8.49 mmol) and hydrazinecarbothioamide (1.161 g, 12.74 mmol) was cooled under nitrogen in an ice-bath. POCl$_3$ (2.375 mL, 25.5 mmol) was then added dropwise. On completion of addition, the reaction mixture was warmed to 78° C. and left to stir for 3 hours. The reaction mixture was allowed to cool to room temperature then cooled further in an ice-bath. Quenching by addition of ice-water (50 mL) resulted in a solid/gum-like mass. This material was sonicated for 1.5 hours and the resulting suspension was diluted with a further 50 mL water and slurried for 16 hours. The suspension was filtered under vacuum and the solid rinsed with water, then re-suspended in saturated NaHCO$_{3(aq)}$ (100 mL). The suspension was slurried for 30 minutes then filtered under vacuum and rinsed with water to afford the crude product as an off-white solid. The crude product was pre-absorbed onto silica gel and purified by flash chromatography using a gradient from 0-10% MeOH/DCM over 30 minutes to afford the title compound as a pale yellow/off-white solid (1.087 g, 44% yield). LC-MS: Rt 1.09 min; MS m/z 292.0 [M+2H]$^+$ [Method A]. $^1$H NMR (400 MHz, DMSO-d$_6$) δ ppm 7.96 (d, J=8.59 Hz, 1H), 7.91 (d, J=2.02 Hz, 1H), 7.68 (dd, J=8.59, 2.02 Hz, 1H), 7.51 (s, 2H).

Step 2: 2-Bromo-5-(4-bromo-2-chlorophenyl)-1,3,4-thiadiazole 5-(4-Bromo-2-chlorophenyl)-1,3,4-thiadiazol-2-amine (1.087 g, 3.74 mmol) was added, portionwise over 5 minutes, to a stirred solution of CuBr$_2$ (1 g, 4.49 mmol) and t-BuNO$_2$ (0.661 mL, 5.61 mmol) in MeCN (11 mL) under nitrogen. On completion of addition, the reaction mixture was stirred at room temperature for 18 hours. The reaction mixture was quenched by addition of saturated NH$_4$Cl$_{(aq)}$ (40 mL) and extracted with EtOAc (100 mL). The organic phase was separated, dried over MgSO$_4$, and filtered. The filtrate was concentrated in vacuo to afford the title compound as a brown solid (1.193 g, 90% yield) with no further purification necessary. LC-MS: Rt 1.51 mins; MS m/z 354.8 M$^+$; [Method A]. $^1$H NMR (400 MHz, DMSO-d$_6$) δ ppm 8.12 (d, J=8.59 Hz, 1H), 8.07 (d, J=2.02 Hz, 1H), 7.80 (dd, J=8.59, 2.02 Hz, 1H).

Step 3: 5-(4-Bromo-2-chlorophenyl)-N-methyl-N-(2,2,6,6-tetramethylpiperidin-4-yl)-1,3,4-thiadiazol-2-amine A stirred solution of 2-bromo-5-(4-bromo-2-chlorophenyl)-1,3,4-thiadiazole (700 mg, 1.975 mmol) and 5-bromo- N-methyl-N-(2,2,6,6-tetramethylpiperidin-4-yl)-1,3,4-thiadiazol-2-amine (Intermediate 4) (1009 mg, 5.92 mmol) in NMP (4 mL) was heated to 120° C. for 3 hours. The reaction mixture was allowed to cool to room temperature then diluted with DCM (100 mL) and washed with saturated NaHCO$_{3(aq)}$ (100 mL). The organic phase was separated, dried over MgSO$_4$, and filtered. The filtrate was concentrated in vacuo to a brown liquid. The crude material was purified by silica flash chromatography, running a gradient from 0-10% [2M NH$_3$ in MeOH]/DCM over 30 minutes, collecting at 320 nm to afford the title compound as a light brown glass-like solid (750 mg, 86% yield). LC-MS: Rt 1.10 min; MS m/z 445.1 [M+2H]$^+$ [Method A]. $^1$H NMR (400 MHz, DMSO-d$_6$) δ ppm 7.96 (d, J=8.59 Hz, 1H), 7.93 (d, J=2.02 Hz, 1H), 7.70 (dd, J=8.59, 2.02 Hz, 1H), 4.36 (tt, J=12.38, 3.28 Hz, 1H) 3.01 (s, 3H), 1.62 (dd, J=12.13, 3.03 Hz, 2H), 1.43 (t, J=12.13 Hz, 2H), 1.28 (br. s., 1H), 1.20 (s, 6H), 1.09 (s, 6H).

Step 4: 5-(2-Chloro-4-(1-methyl-1H-pyrazol-4-yl) phenyl)-N-methyl-N-(2,2,6,6-tetramethylpiperidin-4-yl)-1,3,4-thiadiazol-2-amine To a stirred solution of 1-methyl-4-(4,4,5,5-tetramethyl-1,3,2-dioxaborolan-2-yl)-1H-pyrazole (129 mg, 0.620 mmol) and 5-(4-bromo-2-chlorophenyl)-N-methyl-N-(2,2,6,6-tetramethylpiperidin-4-yl)-1,3,4-thiadiazol-2-amine (250 mg, 0.563 mmol) in dioxane (4 mL) was added Pd(PPh$_3$)$_4$ (33 mg, 0.028 mmol), followed by a solution of Na$_2$CO$_3$ (179 mg, 1.69 mmol) in water (1 mL). The reaction mixture was purged with nitrogen, sealed, and heated at 80° C. for an hour under microwave irradiation. The reaction mixture was diluted with EtOAc (50 mL) and washed with saturated NaHCO$_{3(aq)}$ (25 mL). The organic phase was separated, dried over MgSO$_4$, and filtered. The filtrate was concentrated in vacuo to afford the crude product as a brown solid. The crude material was taken up in a 2:1 mixture of MeOH:DMSO (4.5 mL), passed through a syringe filter, and purified by UV-directed preparative HPLC under basic conditions (5 mM NH$_4$OH), collecting at 335 nm to afford the title compound as a white solid (138 mg, 55% yield). LC-MS: Rt 0.90 min; MS m/z 445.3 [M+H]$^+$ [Method A]. $^1$H NMR (400 MHz, DMSO-d$_6$) δ ppm 8.32 (s, 1H), 8.02 (s, 1H), 7.99 (d, J=8.08 Hz, 1H), 7.84 (d, J=1.52 Hz, 1H), 7.67 (dd, J=8.08, 1.52 Hz, 1H), 4.36 (tt, J=12.44, 3.47 Hz, 1H), 3.88 (s, 3H), 3.01 (s, 3H), 1.62 (dd, J=11.87, 3.28 Hz, 2H), 1.43 (t, J=12.13 Hz, 2H), 1.28 (br. s., 1H), 1.21 (s, 6H), 1.09 (s, 6H). LC-MS: Rt 1.84 mins; MS m/z 444.8 M$^+$ [Method B].

Example 26

Synthesis of 3-Chloro-2-(5-(methyl(2,2,6,6-tetramethylpiperidin-4-yl)amino)-1,3,4-thiadiazol-2-yl)-5-(1-methyl-1H-pyrazol-4-yl)phenol

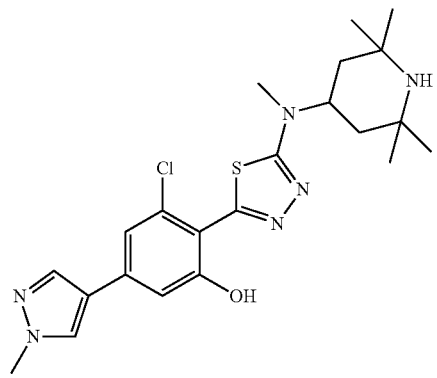

Step 1: 3-Chloro-2-(5-(methyl(2,2,6,6-tetramethylpiperidin-4-yl)amino)-1,3,4-thiadiazol-2-yl)-5-(1-methyl-1H-pyrazol-4-yl)phenol To a stirred solution of 5-(2-chloro-4-(1-methyl-1H-pyrazol-4-yl)phenyl)-N-methyl-N-(2,2,6,6-tetramethylpiperidin-4-yl)-1,3,4-thiadiazol-2-amine (Example 25) (125 mg, 0.281 mmol) in 1:1 AcOH:Ac$_2$O (2.8 mL) was added PhI(OAc)$_2$ (127 mg, 0.393 mmol) followed by Pd(OAc)$_2$ (6 mg, 0.028 mmol). The reaction mixture was warmed to 80° C. and stirred for 48 hours. The reaction mixture was cooled to room temperature, then diluted with MeOH (10 mL) and loaded onto a 2 g SCX cartridge (pre-wet with MeOH). The cartridge was washed with MeOH (10 mL) then flushed with 7M NH$_3$ in MeOH (10 mL). The MeOH/NH$_3$ was removed in vacuo to afford the crude product as a brown glass-like solid. The crude material was taken up in MeOH (3 mL), passed through a syringe filter, and purified by mass-directed preparative HPLC under basic conditions (5 mM NH$_4$OH) to give the crude product as a brown glass-like solid. The crude solid was re-dissolved in MeOH (3 mL) and re-purified by UV-directed preparative HPLC under acidic conditions (0.1% TFA), collecting at 348 nm. The combined fractions were loaded onto a 1 g SCX cartridge (pre-wet with MeOH) and the cartridge washed with MeOH (10 mL) then flushed with 7M NH$_3$ in MeOH (10 mL). The MeOH/NH$_3$ was removed in vacuo to afford the title compound as an off-white glass-like solid (6 mg, 5% yield). LC-MS: Rt 0.52 mins; MS m/z 461.3/463.2 [M+H]$^+$ [Method D]. $^1$H NMR (400 MHz, DMSO-d$_6$) δ ppm 8.26 (s, 1H), 7.95 (s, 1H), 7.32 (s, 1H), 7.15 (d, J=1.52 Hz, 1H), 4.35 (br. s., 1H), 3.87 (s, 3H), 3.01 (s, 3H), 1.65 (d, J=9.60 Hz, 2H), 1.48 (br. s., 2H), 1.22 (br. s., 6H), 1.11 (br. s., 6H).

By employing the method of Example 25, using appropriate starting materials, the following compounds were prepared:

| Example | Compound | LCMS M + 1, Rt, Method | $^1$H NMR 400 MHz |
|---|---|---|---|
| 27 LPE765 | 5-(2-chloro-4-(1-methyl-1H-pyrazol-4-yl)phenyl)-N-(2,2,6,6-tetramethylpiperidin-4-yl)-1,3,4-thiadiazol-2-amine | 431.1, 0.87 min D | $^1$H NMR (400 MHz, DMSO-d$_6$) δ ppm 13.12 (br. s., 1 H), 8.24 (br. s., 2 H), 7.99 (d, J = 8.08 Hz, 1 H), 7.90 (d, J = 1.52 Hz, 1 H), 7.76-7.67 (m, 1 H), 4.38 (t, J = 12.13 Hz, 1 H), 3.01 (s, 3 H), 1.73-1.58 (m, 2 H), 1.47 (t, J = 12.13 Hz, 2 H), 1.23 (s, 6 H), 1.11 (s, 6 H) |

Example 28

Synthesis of 3-Methoxy-2-(5-(methyl(2,2,6,6-tetramethylpiperidin-4-yl)amino)-1,3,4-thiadiazol-2-yl)-5-(5-methyloxazol-2-yl)phenol

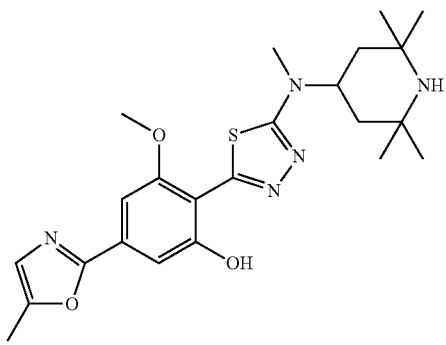

Step 1: 5-(2-(Benzyloxy)-6-methoxy-4-(5-methyloxazol-2-yl)phenyl)-N-methyl-N-(2,2,6,6-tetramethylpiperidin-4-yl)-1,3,4-thiadiazol-2-amine To a stirred solution of (2-(benzyloxy)-6-methoxy-4-(5-methyloxazol-2-yl)phenyl)boronic acid (Intermediate 2) (56 mg, 0.165 mmol) and 5-bromo-N-methyl-N-(2,2,6,6-tetramethylpiperidin-4-yl)-1,3,4-thiadiazol-2-amine (Intermediate 4) (50 mg, 0.150 mmol) in dioxane (1 mL) was added Pd(PPh$_3$)$_4$ (9 mg, 0.008 mmol), followed by a solution of Na$_2$CO$_3$ (32 mg, 0.300 mmol) in water (0.25 mL). The resulting mixture was purged with nitrogen, sealed, and heated at 120° C. for 30 minutes under microwave irradiation. The reaction mixture was diluted with MeOH (20 mL), filtered via syringe filter, and the filtrate concentrated in vacuo to afford the crude product as a pink/red oily residue. The crude material was purified by UV-directed preparative HPLC under acidic conditions (0.1% TFA), collecting at 311 nm to afford the TFA salt of the title compound as a yellow glass-like solid.

The TFA salt was re-dissolved in MeOH and loaded onto a 1 g SCX cartridge (pre-wet with MeOH). The cartridge was washed with MeOH (15 mL) then flushed with 7M NH$_3$ in MeOH (10 mL). The MeOH/NH$_3$ was removed in vacuo to afford the title compound as a clear glass-like solid (0.029 g, 35% yield). LC-MS: Rt 2.23 min; MS m/z 548.4 [M+H]$^+$ [Method B]. $^1$H NMR (400 MHz, DMSO-d$_6$) δ ppm 7.43-7.25 (m, 7H), 7.06 (s, 1H), 5.26 (s, 2H), 4.18-4.10 (m, 1H), 3.85 (s, 3H), 2.97 (s, 3H), 2.42 (s, 3H), 1.65-1.56 (m, 2H), 1.50-1.38 (m, 2H), 1.18 (s, 6H), 1.09 (s, 6H).

Step 2: 3-Methoxy-2-(5-(methyl(2,2,6,6-tetramethylpiperidin-4-yl)amino)-1,3,4-thiadiazol-2-yl)-5-(5-methyloxazol-2-yl)phenol A solution of 5-(2-(benzyloxy)-6-methoxy-4-(5-methyloxazol-2-yl)phenyl)-N-methyl-N-(2,2,6,6-tetramethylpiperidin-4-yl)-1,3,4-thiadiazol-2-amine (28.9 mg, 0.053 mmol) in 1:1 EtOAc:MeOH (5 mL) was added to a nitrogen flushed flask containing 10% Pd/C (2.9 mg, 10% by weight) and the resulting mixture placed under a hydrogen atmosphere and left to stir at room temperature for 72 hours. The reaction mixture was purged with nitrogen, diluted with EtOAc (10 mL), filtered through celite, then rinsed with EtOAc (50 mL). The filtrate was concentrated in vacuo to afford the crude product as a pale yellow solid. The crude material was purified by preparative HPLC under acidic conditions running a gradient from 20-95% MeCN/water (+0.1% TFA) over 15 minutes. The product containing fractions were loaded directly onto a 1 g SCX cartridge (pre-wet with MeOH) and the cartridge was washed with MeOH (10 mL) then flushed with 7M NH$_3$ in MeOH (10 mL). The MeOH/NH$_3$ was removed in vacuo to afford the title compound as an off-white/pale brown solid (9 mg, 39% yield). LC-MS: Rt 2.08 min; MS m/z 458.4 [M+H]$^+$ [Method B]. $^1$H NMR (400 MHz, DMSO-d$_6$) δ ppm 12.74 (br. s., 1H), 7.15 (s, 2H), 7.05 (d, J=1.01 Hz, 1H), 4.42-4.33 (m, 1H), 4.04 (s, 3H), 3.03 (s, 3H), 2.41 (d, J=1.01 Hz, 3H), 1.64 (dd, J=11.87, 3.28 Hz, 2H), 1.44 (t, J=12.13 Hz, 2H), 1.22 (s, 6H), 1.09 (s, 6H).

Example 29

Synthesis of 2-(2-Methoxy-4-(1H-pyrazol-1-yl)phenyl)-5-(1,2,3,6-tetrahydropyridin-4-yl)-1,3,4-thiadiazole

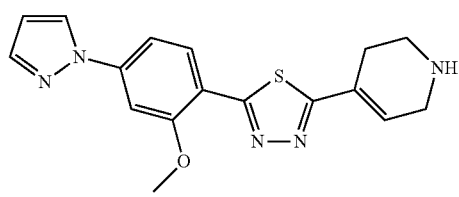 [SMILES: COc1cc(-n2cccn2)ccc1-c1nnc(C2=CCNCC2)s1]

Step 1: tert-Butyl 4-(5-bromo-1,3,4-thiadiazol-2-yl)-5,6-dihydropyridine-1(2H)-carboxylate To a 5 mL microwave vial was added tert-butyl 4-(4,4,5,5-tetramethyl-1,3,2-dioxaborolan-2-yl)-5,6-dihydropyridine-1(2H)-carboxylate (247 mg, 0.8 mmol), 2,5-dibromo-1,3,4-thiadiazole (98 mg, 0.4 mmol), $K_3PO_4$ (212 mg, 1.0 mmol), $Pd(PPh_3)_4$ (23 mg, 0.02 mmol), 1,4-dioxane (2 mL), and water (0.4 mL). The mixture was purged with $N_2$ for 10 min, then heated to 100° C. in the microwave for 1 hour. The mixture was diluted with EtOAc, washed with water and brine, dried over $Na_2SO_4$, and concentrated in vacuo. The residue was purified by column chromatography (EtOAc/Heptane) to afford 64 mg (46%) of tert-butyl 4-(5-bromo-1,3,4-thiadiazol-2-yl)-5,6-dihydropyridine-1(2H)-carboxylate: MS (M+2)=348.1; $^1$H NMR (400 MHz, CHLOROFORM-d) δ 6.46 (td, J=3.0, 1.9 Hz, 1H), 4.15 (d, J=3.0 Hz, 2H), 3.64 (t, J=5.6 Hz, 2H), 2.73 (m, 2H), 1.49 (s, 9H).

Step 2: tert-Butyl 4-(5-(2-methoxy-4-(1H-pyrazol-1-yl)phenyl)-1,3,4-thiadiazol-2-yl)-5,6-dihydropyridine-1(2H)-carboxylate To a 5 mL microwave vial was added tert-butyl 4-(5-bromo-1,3,4-thiadiazol-2-yl)-5,6-dihydropyridine-1(2H)-carboxylate (100 mg, 0.29 mmol), 1-(3-methoxy-4-(4,4,5,5-tetramethyl-1,3,2-dioxaborolan-2-yl)phenyl)-1H-pyrazole (173 mg, 0.58 mmol), $K_3PO_4$ (153 mg, 0.72 mmol), and $Pd(PPh_3)_4$ (17 mg, 0.015 mmol), 1,4-dioxane (2 mL), and water (0.4 mL). The mixture was purged with $N_2$ for 10 min and heated to 100° C. in the microwave for 1 hour. The mixture was diluted with EtOAc, washed with water and brine, dried over $Na_2SO_4$, and concentrated in vacuo. The residue was purified by column chromatography (EtOAc/Heptane) to give 87 mg (68.5%) of tert-butyl 4-(5-(2-methoxy-4-(1H-pyrazol-1-yl)phenyl)-1,3,4-thiadiazol-2-yl)-5,6-dihydropyridine-1(2H)-carboxylate: MS (M+1)=440.4; $^1$H NMR (400 MHz, CHLOROFORM-d) δ 8.57 (d, J=8.59 Hz, 1H), 8.03 (d, J=2.53 Hz, 1H), 7.78 (d, J=1.52 Hz, 1H), 7.62 (d, J=2.02 Hz, 1H), 7.32 (dd, J=2.02, 8.59 Hz, 1H), 6.59 (m, 1H), 6.51-6.55 (m, 1H), 4.15-4.22 (m, 2H), 4.11 (s, 3H), 3.69 (t, J=5.56 Hz, 2H), 2.78-2.90 (m, 2H), 1.51 (s, 9H).

Step 3: 2-(2-Methoxy-4-(1H-pyrazol-1-yl)phenyl)-5-(1,2,3,6-tetrahydropyridin-4-yl)-1,3,4-thiadiazole To a solution of tert-butyl 4-(5-(2-methoxy-4-(1H-pyrazol-1-yl)phenyl)-1,3,4-thiadiazol-2-yl)-5,6-dihydropyridine-1(2H)-carboxylate (80 mg, 0.18 mmol) in 1,4-dioxane (1 mL) was added 4 M HCl in 1,4-dioxane (0.9 mL). The mixture was stirred for 1 h. The mixture was then diluted with MeOH, loaded on the SCX, washed with MeOH, eluted with 2 N $NH_3$ in MeOH, and concentrated in vacuo. The residue was purified by column chromatography ($CH_2Cl_2$/MeOH) to give 32 mg of 2-(2-methoxy-4-(1H-pyrazol-1-yl)phenyl)-5-(1,2,3,6-tetrahydropyridin-4-yl)-1,3,4-thiadiazole: HRMS (M+1) calcd. for C17H17N5OS 340.1232, found 340.1228; $^1$H NMR (400 MHz, DMSO-$d_6$) δ 8.71 (d, J=2.53 Hz, 1H), 8.40 (d, J=8.59 Hz, 1H), 7.83 (d, J=1.52 Hz, 1H), 7.73 (d, J=2.02 Hz, 1H), 7.68 (dd, J=2.02, 8.59 Hz, 1H), 6.73 (m, 1H), 6.54-6.68 (m, 1H), 4.12 (s, 3H), 3.52 (m, 2H), 3.02 (t, J=5.81 Hz, 2H), 2.62 (m, 2H).

Example 30

Synthesis of 2-(5-(piperazin-1-yl)-1,3,4-thiadiazol-2-yl)-5-(1H-pyrazol-1-yl)phenol

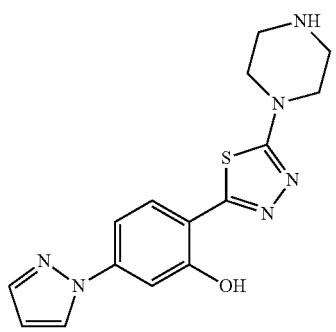 [SMILES: Oc1cc(-n2cccn2)ccc1-c1nnc(N2CCNCC2)s1]

Step 1: tert-Butyl 4-(5-bromo-1,3,4-thiadiazol-2-yl)piperazine-1-carboxylate DIPEA (430 μL, 2.460 mmol) was added to a stirred solution of 2,5-dibromo-1,3,4-thiadiazole (300 mg, 1.230 mmol) and tert-butyl piperazine-1-carboxylate (275 mg, 1.476 mmol) in dioxane (4 mL). The reaction mixture was heated at 120° C. for 2 hours. The reaction mixture was cooled to room temperature, filtered under vacuum, rinsed with dioxane, and the filtrate was concentrated in vacuo to afford the crude product as an orange oily residue. The crude material was purified by preparative HPLC under neutral conditions (ammonium formate modified) to afford the title compound as a yellow solid (331 mg, 77% yield). LC-MS: Rt 1.18 min; MS m/z 351.1 [M+2]$^+$ [Method A]. $^1$H NMR (400 MHz, DMSO-$d_6$) δ ppm 3.38-3.55 (m, 8H), 1.41 (s, 9H).

Step 2: tert-Butyl 4-(5-(2-methoxy-4-(1H-pyrazol-1-yl)phenyl)-1,3,4-thiadiazol-2-yl)piperazine-1-carboxylate To a stirred suspension of 1-(3-methoxy-4-(4,4,5,5-tetramethyl-1,3,2-dioxaborolan-2-yl)phenyl)-1H-pyrazole [Intermediate 1] (132 mg, 0.441 mmol) and tert-butyl 4-(5-bromo-1,3,4-thiadiazol-2-yl)piperazine-1-carboxylate (140 mg, 0.401 mmol) in dioxane (2 mL) was added $Pd(PPh_3)_4$ (23 mg, 20 μmol) followed by a solution of $Na_2CO_3$ (85 mg, 0.802 mmol) in water (0.5 mL). The reaction mixture was purged with nitrogen, sealed, and heated at 120° C. for 30 minutes under microwave irradiation. The reaction mixture was cooled to room temperature, diluted with DCM (20 mL), washed with water (10 mL), then the organic phase was separated and concentrated in vacuo to afford the crude product as a pale brown solid. The crude material was purified by flash chromatography using a 12 g silica cartridge running an EtOAc/heptane gradient to afford the title compound as a pale yellow/off-white solid (138 mg, 78% yield). LC-MS: Rt 1.34 min; MS m/z 443.3 [M+H]$^+$ [Method A]. $^1$H NMR (400 MHz, DMSO-d$_6$) δ ppm 8.65 (d, J=2.53 Hz, 1H), 8.21 (d, J=8.59 Hz, 1H), 7.80 (d, J=1.52 Hz, 1H), 7.66 (d, J=2.02 Hz, 1H), 7.60 (dd, J=8.59, 2.02 Hz, 1H), 6.59-6.62 (m, 1H), 4.05 (s, 3H), 3.51 (s, 8H), 1.43 (s, 9H).

Step 3: 2-(5-(piperazin-1-yl)-1,3,4-thiadiazol-2-yl)-5-(1H-pyrazol-1-yl)phenol

BBr$_3$ (1M solution in heptane, 1.56 mL, 1.56 mmol) was added to a stirred, nitrogen flushed solution of tert-butyl 4-(5-(2-methoxy-4-(1H-pyrazol-1-yl)phenyl)-1,3,4-thiadiazol-2-yl)piperazine-1-carboxylate (138 mg, 0.312 mmol) in DCM (6 mL) and the resulting bright yellow suspension was stirred at room temperature for 16 hours. The reaction mixture was quenched by addition of MeOH (10 mL) to give a suspension. The solid was collected by vacuum filtration, rinsed with MeOH, and re-dissolved in a mixture of DMSO and water. The solution was loaded onto a 5 g SCX cartridge (pre-wet with MeOH) and the cartridge was washed with DMSO/water (5 mL), MeOH (20 mL), then flushed with 7M NH$_3$ in MeOH (30 mL). The MeOH/NH$_3$ was removed in vacuo to afford the crude product as an off-white solid. The crude material was sonicated in MeOH (5 mL) and the resulting suspension filtered under vacuum to afford the title compound as an off-white solid (69 mg, 68% yield). LC-MS: Rt 0.76 min; MS m/z 329.2 [M+H]$^+$ [Method A]. $^1$H NMR (400 MHz, DMSO-d$_6$) δ ppm 8.50 (d, J=2.53 Hz, 1H), 8.03 (d, J=8.59 Hz, 1H), 7.77 (d, J=1.52 Hz, 1H), 7.52 (d, J=2.02 Hz, 1H), 7.42 (dd, J=8.59, 2.02 Hz, 1H), 6.55-6.61 (m, 1H), 3.42-3.48 (m, 4H), 2.80-2.91 (m, 4H).

Example 31

Synthesis of 5-(7-Methoxyquinolin-6-yl)-N-methyl-N-(2,2,6,6-tetramethylpiperidin-4-yl)-1,3,4-thiadiazol-2-amine

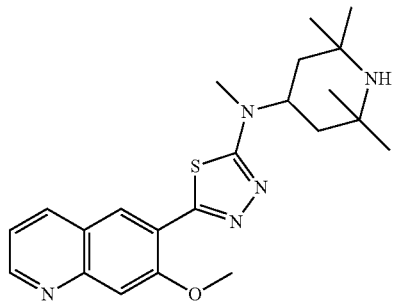

Step 1: 6-Bromo-7-methoxyquinoline

In a 100 mL round-bottom flask, a solution of concentrated sulfuric acid (2.1 mL, 39.6 mmol) in water (2.4 mL) was treated with 3-nitrobenzenesulfonic acid (2.06 g, 10.1 mmol) and glycerol (2.5 mL, 34.8 mmol) to give a thick grey suspension. The mixture was heated to 110° C. (oil bath) and 4-bromo-3-methoxyaniline (1.952 g, 9.66 mmol) was added portion-wise, resulting in an immobile slurry. Additional portions of water (3 mL), glycerol (3 mL), and concentrated sulfuric acid (3 mL) were added and the temperature increased to 140° C. After three hours the mixture had become a homogeneous dark brown solution, and LCMS analysis indicated reaction completion. The solution was cooled to RT, poured onto ice, and the pH was adjusted to 8 by addition of concentrated (30%) aqueous ammonium hydroxide. The mixture was partitioned between ethyl acetate and water, washed with water, brine, dried over magnesium sulfate and concentrated to a brown liquid. Purification by flash column chromatography (24 g silica gel, gradient of 0-20% ethyl acetate in dichloromethane over 25 column volumes) provided 6-bromo-7-methoxyquinoline (1.18 g, 46.2%) as a light brown fluffy solid. $^1$H NMR (400 MHz, CHLOROFORM-d) ppm 8.86 (dd, J=4.0, 1.5 Hz, 1H), 8.01-8.12 (m, 2H), 7.53 (s, 1H), 7.34 (dd, J=8.1, 4.5 Hz, 1H), 4.07 (s, 3H). NMR indicates the presence of about 10% 7-methyoxyquinoline. The mixture was taken on without further purification.

Step 2: (7-Methoxyquinolin-6-yl)boronic acid

To a solution of 6-bromo-7-methoxyquinoline (90% purity, 0.65 g, 2.73 mmol) cooled to −78° C. was added drop-wise nBuLi (1.6 M in heptanes, 1.877 mL, 3.00 mmol). The solution was stirred for 0.5 h after which time trimethyl borate (0.763 mL, 6.83 mmol) was added in a single portion. The solution was allowed to warm slowly to RT overnight. The crude reaction mixture was rotovapped to dryness, concentrated from heptane (2×), triturated with diethyl ether (3×) and concentrated to provide a crude mixture of (7-methoxyquinolin-6-yl)boronic acid as a tan colored solid (1.185 g, 214%). LCMS is clean, and based on the recovered mass the mixture was used without further purification assuming ~50% purity by weight. MS=204.1 (M+1). $^1$H NMR (400 MHz, METHANOL-d$_4$) ppm 8.48 (br s, 1H), 8.07 (d, J=8.1 Hz, 1H), 7.85 (s, 1H), 7.16 (dd, J=8.1, 4.5 Hz, 1H), 7.11 (s, 1H), 3.82 (s, 3H).

Step 3: 5-(7-Methoxyquinolin-6-yl)-N-methyl-N-(2,2,6,6-tetramethylpiperidin-4-yl)-1,3,4-thiadiazol-2-amine In a microwave tube, a mixture of 5-bromo-N-methyl-N-(2,2,6,6-tetramethylpiperidin-4-yl)-1,3,4-thiadiazol-2-amine (Intermediate 4) (100 mg, 0.300 mmol), (7-methoxyquinolin-6-yl)boronic acid (~50% by weight, 171 mg, 0.420 mmol) and sodium carbonate (95 mg, 0.90 mmol) in 3:1 dimethoxyethane/water (2.5 mL) was degassed with a dry stream of nitrogen for five minutes. Tetrakis(triphenylphosphine)palladium(0) (34.7 mg, 0.030 mmol) was added and the mixture heated in a microwave at 140° C. for 30 min. The mixture was diluted with water and extracted with DCM (6×). HCl in dioxane (1 M, 1.2 mL, 1.2 mmol) was added and the solution concentrated to dryness. SCX purification (2 g column, 7 M ammonia in MeOH elution) provided a brown residue which was further purified by flash column chromatography (12 g silica gel, 1-17% 1.4 N ammonia in MeOH gradient in DCM over 30 column volumes) to provide 5-(7-methoxyquinolin-6-yl)-N-methyl-N-(2,2,6,6-tetramethylpiperidin-4-yl)-1,3,4-thiadiazol-2-amine as a yellow solid (104 mg, 84%). MS=412.3 (M+1), Rt=0.45 min [Method D]. $^1$H NMR (400 MHz, METHANOL-d$_4$) ppm 8.83 (dd, J=4.3, 1.8 Hz, 1H), 8.71 (s, 1H), 8.42 (d, J=8.1 Hz, 1H), 7.57 (s, 1H), 7.48 (dd, J=8.3, 4.3 Hz, 1H), 4.43-4.57 (m, 1H), 4.16 (s, 3H), 3.11 (s, 3H), 1.81 (dd, J=12.6, 3.0 Hz, 2H), 1.58 (t, J=12.4 Hz, 2H), 1.37 (s, 6H), 1.25 (s, 6H).

Example 32

Synthesis of 6-(5-(Methyl(2,2,6,6-tetramethylpiperidin-4-yl)amino)-1,3,4-thiadiazol-2-yl)quinolin-7-ol

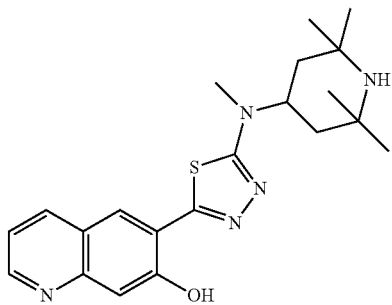

A mixture of 5-(7-methoxyquinolin-6-yl)-N-methyl-N-(2,2,6,6-tetramethylpiperidin-4-yl)-1,3,4-thiadiazol-2-amine (30 mg, 0.073 mmol) and pyridine hydrochloride (126 mg, 1.093 mmol) was heated in a microwave at 160° C. for 30 minutes. The resulting solid was dissolved into methanol and concentrated onto a mixture of silica gel (500 mg) and sodium bicarbonate (14.6 mmol, 122 mg) and subjected to flash column chromatography (4 g silica gel, 1-17% 1.4 N ammonia in MeOH gradient in DCM over 30 column volumes) to provide 6-(5-(methyl(2,2,6,6-tetramethylpiperidin-4-yl)amino)-1,3,4-thiadiazol-2-yl)quinolin-7-ol as a yellow solid (24 mg, 83%). MS=398.3 (M+1). $^1$H NMR (400 MHz, METHANOL-$d_4$) ppm 8.67 (d, J=3.0 Hz, 1H), 8.49 (s, 1H), 8.29 (d, J=7.6 Hz, 1H), 7.36 (s, 1H), 7.28 (dd, J=8.3, 4.3 Hz, 1H), 4.55 (t, J=12.1 Hz, 1H), 3.13 (s, 3H), 1.90 (dd, J=12.6, 3.0 Hz, 2H), 1.62-1.78 (m, 2H), 1.46 (s, 6H), 1.33 (s, 6H).

Synthesis of Intermediates

Intermediate 7: Synthesis of 2-bromo-5-((2,2,6,6-tetramethylpiperidin-4-yl)oxy)-1,3,4-thiadiazole

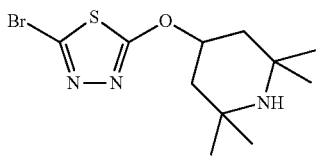 [SMILES: CC1(C)CC(Oc2nnc(Br)s2)CC(C)(C)N1]

LiHMDS (1M solution in TBME, 1.72 mL, 1.72 mmol) was added to a stirred, ice cooled suspension of 2,2,6,6-tetramethylpiperidin-4-ol (248 mg, 1.578 mmol) in DMF (5 mL) under nitrogen atmosphere. The resulting solution was stirred at 0° C. for 30 minutes then heated at 50° C. and for 3 hours. The reaction mixture was quenched by addition of MeOH (5 mL), acidified by addition of TFA, and loaded onto a 5 g SCX cartridge (pre-wet with MeOH). The cartridge was washed with MeOH (20 mL) then flushed with 7M $NH_3$ in MeOH (15 mL). The combined basic flushes were concentrated in vacuo to afford the crude product as a light brown solid. The crude material was pre-absorbed onto silica gel and purified by flash chromatography using a 12 g silica cartridge, running a MeOH/DCM gradient, to afford the title compound as a pale brown solid (227 mg, 49% yield). LC-MS Rt 0.72 min; MS m/z 322.1 [M+2]$^+$ [Method A]. $^1$H NMR (400 MHz, DMSO-$d_6$) δ ppm 5.26-5.38 (m, 1H), 2.01-2.17 (m, 2H), 1.42 (br. s., 1H) 1.23-1.32 (m, 2H), 1.17 (s, 6H), 1.10 (br. s., 6H).

Intermediate 8: Synthesis of 1-(3-methoxy-4-(4,4,5,5-tetramethyl-1,3,2-dioxaborolan-2-yl)phenyl)-N-methyl-1H-pyrazol-3-amine

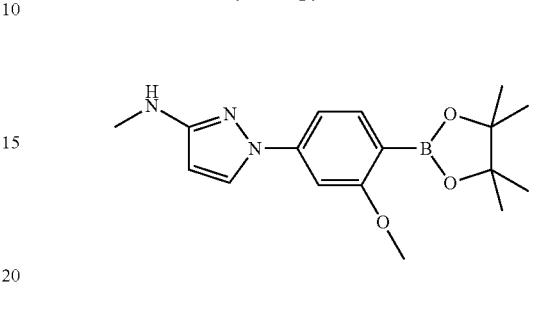

Step 1: 1-(4-Bromo-3-methoxyphenyl)-1H-pyrazol-3-amine

A mixture of 1-bromo-4-iodo-2-methoxybenzene (2.5 g, 7.99 mmol), 3-aminopyrazole (0.797 g, 9.59 mmol), salicylaldoxime (0.219 g, 1.598 mmol), $Cu_2O$ (91 mg, 0.479 mmol), and $Cs_2CO_3$ (3.9 g, 11.98 mmol) in DMF (8 mL) was degassed with $N_2$ and heated at 95° C. overnight. After cooling to RT, the mixture was filtered through celite and rinsed with EtOAc. The filtrate was washed with water and brine. The organic solution was dried over $Na_2SO_4$, filtered and concentrated in vacuo. The residue was purified by silica gel chromatography (10%-60% EtOAc in Heptane) to give 1-(4-bromo-3-methoxyphenyl)-1H-pyrazol-3-amine (800 mg, MS: 270.3 [M+H$^+$]).

Step 2: N-(1-(4-Bromo-3-methoxyphenyl)-1H-pyrazol-3-yl)-2,2,2-trifluoroacetamide To an ice cold solution of 1-(4-bromo-3-methoxyphenyl)-1H-pyrazol-3-amine (200 mg, 0.746 mmol) and pyridine (0.263 mL, 1.343 mmol) in DCM (5 mL) was added trifluoroacetic anhydride (0.124 mL, 0.895 mmol). The reaction mixture was stirred at room temperature for 3 h. The reaction mixture was diluted with DCM, washed with aqueous 1N HCl solution, aqueous saturated $NaHCO_3$, then dried over $Na_2SO_4$, filtered and concentrated under reduced pressure to give 320 mg of N-(1-(4-bromo-3-methoxyphenyl)-1H-pyrazol-3-yl)-2,2,2-trifluoroacetamide, which was used in the next step without further purification.

Step 3: N-(1-(4-Bromo-3-methoxyphenyl)-1H-pyrazol-3-yl)-2,2,2-trifluoro-N-methylacetamide To a mixture of N-(1-(4-bromo-3-methoxyphenyl)-1H-pyrazol-3-yl)-2,2,2-trifluoroacetamide (320 mg, 0.879 mmol) and $K_2CO_3$ (146 mg, 1.055 mmol) in DMF (2 mL) was added MeI (202 mg, 1.055 mmol). The reaction mixture was stirred at room temperature overnight. The reaction mixture was poured into water and extracted with $Et_2O$. The combined organic layers were washed with water, dried over $Na_2SO_4$, filtered and concentrated under reduced pressure to give N-(1-(4-bromo-3-methoxyphenyl)-1H-pyrazol-3-yl)-2,2,2-trifluoro-N-methylacetamide (300 mg, MS: 380.0 [M+H$^+$]).

Step 4: 1-(4-Bromo-3-methoxyphenyl)-N-methyl-1H-pyrazol-3-amine

To an ice cold solution of N-(1-(4-bromo-3-methoxyphenyl)-1H-pyrazol-3-yl)-2,2,2-trifluoro-N-methylacetamide (300 mg, 0.793 mmol) in EtOH (5 mL) was added a solution of 21% sodium ethoxide in EtOH (0.4 mL, 0.793 mmol). The mixture was stirred at room temperature overnight, then was poured into water. The mixture was extracted with EtOAc. The combined organic layers were washed with aqueous saturated NaHCO$_3$ solution, dried over Na$_2$SO$_4$, filtered and concentrated under reduced pressure to give 1-(4-bromo-3-methoxyphenyl)-N-methyl-1H-pyrazol-3-amine (200 mg, MS: 284.3 [M+H$^+$]).

Step 5: 1-(3-Methoxy-4-(4,4,5,5-tetramethyl-1,3,2-dioxaborolan-2-yl)phenyl)-N-methyl-1H-pyrazol-3-amine A degassed reaction mixture of 1-(4-bromo-3-methoxyphenyl)-N-methyl-1H-pyrazol-3-amine (200 mg, 0.709 mmol), bis(pinacolato)diboron (270 mg, 1.063 mmol), Pd(dppf)Cl$_2$ (51.9 mg, 0.071 mmol), dppf (39.3, 0.071 mmol) and potassium acetate (451 mg, 2.127 mmol) in 1,4-dioxane (5 mL) was heated at 90° C. overnight. After cooling to RT, the mixture was filtered through celite and washed with EtOAc. The filtrate was concentrated and the residue was purified by silica gel chromatography (10%-60% EtOAc in Heptane) to give 1-(3-methoxy-4-(4,4,5,5-tetramethyl-1,3,2-dioxaborolan-2-yl)phenyl)-N-methyl-1H-pyrazol-3-amine (160 mg, MS: 330.2 [M+H$^+$]).

Intermediate 9: Synthesis of 6-methoxy-5-(4,4,5,5-tetramethyl-1,3,2-dioxaborolan-2-yl)-2,3-dihydro-1H-inden-1-one

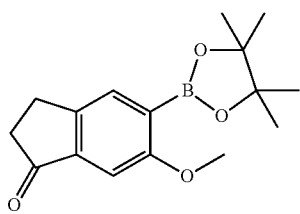 [SMILES: COc1cc2c(cc1B1OC(C)(C)C(C)(C)O1)CCC2=O]

To a 100 mL round bottom flask containing 1,4-dioxane (21 mL) was added 5-bromo-6-methoxy-2,3-dihydro-1H-inden-1-one (1.0 g, 4.15 mmol), bis(pinacolato)diboron (1.6 g, 6.22 mmol), and potassium acetate (1.3 g, 13.3 mmol). The suspension was degassed with nitrogen for 5 min, then 1,1'-bis(diphenylphosphino)ferrocene (0.23 g, 0.415 mmol) and PdCl$_2$(dppf) (0.30 g, 0.415 mmol) were added. The resulting suspension was heated at 80° C. for 18 h. The reaction was then cooled to room temperature, diluted with ethyl acetate, filtered through celite and concentrated in vacuo. The crude product was purified by silica gel chromatography to afford 6-methoxy-5-(4,4,5,5-tetramethyl-1,3,2-dioxaborolan-2-yl)-2,3-dihydro-1H-inden-1-one (1.1 g) MS [M+H$^+$]=289.4

Intermediate 10: Synthesis of 7-methoxy-6-(4,4,5,5-tetramethyl-1,3,2-dioxaborolan-2-yl)quinoline-2-carbonitrile

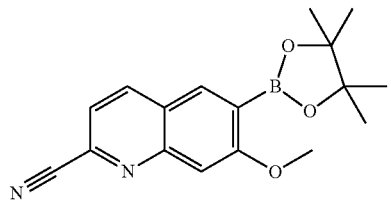 [SMILES: COc1cc2nc(C#N)ccc2cc1B1OC(C)(C)C(C)(C)O1]

Step 1: 6-Chloro-7-methoxyquinoline

A solution of sulfuric acid (35 mL) in water (35 mL) was treated with 3-nitrobenzenesulfonic acid (35.1 g, 159 mmol) and glycerol (80 ml, 1.1 mol) to give a thick grey suspension. The suspension was heated to 75° C. and 4-chloro-3-methoxyaniline (25.0 g, 159 mmol) was added. The mixture was stirred at 140° C. for 1 h. Additional quantities of water (35 mL), sulfuric acid (35 mL) and glycerol (40 mL) were added and the reaction was stirred an additional 2 h at 140° C. The solution was cooled to room temperature, poured onto ice, and the pH was adjusted to 13 by addition of concentrated ammonium hydroxide. The mixture was extracted with EtOAc (3×) and the extracts were washed with brine, dried over Na$_2$SO$_4$ and concentrated. Following the general procedure for quinoline purification described by Leir, C. M. *J. Org. Chem.*, 1977, 42, 911, the residue was dissolved into 2 M HCl (500 mL) and zinc chloride (43.2 g, 317 mmol) was added, resulting in immediate formation of a precipitate. The mixture was stirred for 30 min. The solids were isolated by filtration, washing with cold 2 M HCl, 2-propanol, then water. The solids were added to concentrated ammonium hydroxide (400 mL) and the mixture was stirred for 10 min. EtOAc was added and the mixture was stirred for 5 min. The mixture was extracted with EtOAc (3×) and the extracts were washed with brine, dried over Na$_2$SO$_4$ and concentrated to a dark brown residue consisting of a mixture of the two possible cyclization regioisomers. Silica gel chromatography (15-100% gradient of EtOAc in DCM) provided 6-chloro-7-methoxyquinoline (7.03 g) as a beige solid. MS (M+1)=194.1, $^1$H NMR (400 MHz, Methanol-d 4) δ 8.78 (dd, J=4.5, 1.6 Hz, 1H), 8.24 (dd, J=8.4, 1.4 Hz, 1H), 8.01 (s, 1H), 7.47 (s, 1H), 7.43 (dd, J=8.3, 4.5 Hz, 1H), 4.06 (s, 3H).

Step 2: 6-Chloro-7-methyoxyquinoline 1-oxide

In a 100 mL round bottom flask, 6-chloro-7-methoxyquinoline was dissolved in DCM (25.8 mL) and MTO (0.051 g, 0.207 mmol) was added. The reaction mixture was capped and vented with a needle, then placed in an ice bath to cool. Once cool, hydrogen peroxide (0.633 mL, 10.33 mmol) was added drop-wise. When the addition was complete, the reaction mixture was removed from cooling, warmed to room temperature and stirred overnight (18 h). MnO$_2$ (10 mg, 0.115 mmol) was added and the reaction mixture was stirred for an additional 2 h. The reaction mixture was filtered through celite, washing with DCM, then concentrated in vacuo to yield 6-chloro-7-methyoxyquinoline 1-oxide (1.036 g) MS [M+H$^+$]=210.3.

Step 3: 6-Chloro-7-methoxyquinoline-2-carbonitrile

A 50 mL flask containing acetonitrile (6.0 mL) was charged with 6-chloro-7-methoxyquinoline 1-oxide (0.25 g, 1.19 mmol), TEA (0.33 mL, 2.39 mmol), and trimethylsilyl cyanide (0.48 mL, 3.58 mmol). The reaction mixture was heated at 80° C. for 2 h, cooled to room temperature and concentrated in vacuo. The residue was basified using saturated $Na_2CO_3$ and the product was extracted with DCM. The organic layer was dried with $MgSO_4$, filtered and concentrated in vacuo to afford 6-chloro-7-methoxyquinoline-2-carbonitrile (0.20 g) MS [M+H$^+$]=219.4.

Step 4: 7-Methoxy-6-(4,4,5,5-tetramethyl-1,3,2-dioxaborolan-2-yl)quinoline-2-carbonitrile To a 5 mL microwave vial containing 1,4-dioxane (2.5 mL) was added 6-chloro-7-methoxyquinoline-2-carbonitrile (0.11 g, 0.503 mmol), bis(pinacolato)diboron (0.26 g, 1.01 mmol), and potassium acetate (0.30 g, 3.02 mmol). The suspension was degassed with nitrogen for 5 min. $PdCl_2$(dppf) dichloromethane adduct (0.04 g, 0.05 mmol) was added and the resulting suspension was heated at 100° C. for 2 h. The reaction was cooled to room temperature, diluted with ethyl acetate, filtered through celite and concentrated in vacuo to afford the crude product, 7-methoxy-6-(4,4,5,5-tetramethyl-1,3,2-dioxaborolan-2-yl)quinoline-2-carbonitrile MS [M+H$^+$]=311.2.

Synthesis of Examples

By employing similar methods as described for the preparation of Example 1, using appropriate starting materials, the following compounds were prepared:

| Example | Compound | LCMS M + 1, Rt, Method | $^1$H NMR 400 MHz |
|---|---|---|---|
| 33 | 3-methoxy-4-(5-(methyl(2,2,6,6-tetramethyl-piperidin-4-yl)amino)-1,3,4-thiadiazol-2-yl)benzonitrile | 386.2, 0.49 min, D | (DMSO-d$_6$) δ ppm 8.27 (d, J = 8.08 Hz, 1H), 7.73 (d, J = 1.52 Hz, 1H), 7.54 (dd, J = 8.34, 1.26 Hz, 1H), 4.35-4.45 (m, 1H), 4.01 (s, 3H), 3.00 (s, 3H), 1.61 (dd, J = 11.87, 3.28 Hz, 2H), 1.42 (t, J = 12.13 Hz, 2H), 1.28 (br. s., 1H), 1.21 (s, 6H), 1.08 (s, 6H) |
| 34 | 3-fluoro-4-(5-(methyl(2,2,6,6-tetramethylpiperidin-4-yl)amino)-1,3,4-thiadiazol-2-yl)benzonitrile | 374.2, 0.49 min, D | (DMSO-d$_6$) δ ppm 8.27 (t, J = 7.58 Hz, 1H), 8.08 (dd, J = 11.12, 1.01 Hz, 1H), 7.82 (dd, J = 8.34, 1.26 Hz, 1H), 4.41 (br. s., 1H), 3.04 (s, 3H), 1.59-1.70 (m, 2H), 1.50 (br. s., 2H), 1.24 (br. s., 6H), 1.12 (br. s., 6H) |

| Example | Compound | LCMS M + 1, Rt, Method | ¹H NMR 400 MHz |
|---|---|---|---|
| 35 | methyl 3-fluoro-4-(5-(methyl(2,2,6,6-tetramethyl-piperidin-4-yl)amino)-1,3,4-thiadiazol-2-yl) benzoate | 407.2, 0.53 min, D | (DMSO-d₆) δ ppm 8.26 (t, J = 7.83 Hz, 1H), 7.94-7.85 (m, 2H), 4.29-4.39 (m, 1H), 3.89 (s, 3H), 3.04 (s, 3H), 1.63 (dd, J = 11.87, 3.28 Hz, 2H), 1.44 (t, J = 12.13 Hz, 2H), 1.29 (s, 1H), 1.21 (s, 6H), 1.09 (s, 6H) |
| 36 | 5-(2-methoxy-4-(3-(methylamino)-1H-pyrazol-1-yl)phenyl)-N-methyl-N-(2,2,6,6-tetramethyl-piperidin-4-yl)-1,3,4-thiadiazol-2-amine | 456.3, 0.50 min, D | (DMSO-d₆) δ ppm 8.32 (d, J = 2.53 Hz, 1H), 8.08 (d, J = 8.59 Hz,1H), 7.39-7.46 (m, 2H), 5.86 (d, J = 2.53 Hz, 1H), 5.63-5.68 (m, 1H), 4.30-4.38 (m, 1H), 3.99 (s, 3H), 2.98 (s, 3H), 2.77 (d, J = 5.56 Hz, 3H), 1.62 (d, J = 10.61 Hz, 2H), 1.43 (t, J = 11.12 Hz, 2H), 1.22 (s, 6H), 1.10 (s, 6H) |
| 37 | 7-methoxy-6-(5-(methyl(2,2,6,6-tetramethyl-piperidin-4-yl)amino)-1,3,4-thiadiazol-2-yl) quinoline-2-carbonitrile | 437.2, 0.52 min, D | (Chloroform-d) δ 8.84 (s, 1H), 8.28 (d, J = 8.3 Hz, 1H), 7.48-7.65 (m, 2H), 4.47-4.65 (m, 1H), 4.13 (s, 3H), 3.09 (s, 3H), 1.82 (dd, J = 12.2, 3.4 Hz, 2H), 1.32-1.45 (m, 8H), 1.20 (s, 6H) |

By employing similar methods as described for the preparation of Example 6, using appropriate starting materials, the following compounds were prepared:

| Example | Compound | LCMS M + 1, Rt, Method | ¹H NMR 400 MHz |
|---------|----------|------------------------|----------------|
| 38 | 4-(3-methoxy-4-(5-((2,2,6,6-tetramethyl-piperidin-4-yl)oxy)-1,3,4-thiadiazol-2-yl)phenyl)-1-methylpyridin-2(1H)-one | 455.3, 0.48 min, D | (DMSO-$d_6$) δ ppm 8.24 (d, J = 8.59 Hz, 1H), 7.82 (d, J = 7.58 Hz, 1H), 7.47-7.54 (m, 2H), 6.85 (d, J = 2.02 Hz, 1H), 6.68 (dd, J = 7.07, 2.02 Hz, 1H), 5.37-5.45 (m, 1H), 4.08 (s, 3H), 3.47 (s, 3H), 2.15 (d, J = 10.11 Hz, 2H), 1.31 (br. s., 2H), 1.21 (br. s., 6H), 1.12 (br. s., 6H) |

By employing similar methods as described for the preparation of Example 25, using appropriate starting materials, the following compounds were prepared:

| Example | Compound | LCMS M + 1, Rt, Method | ¹H NMR 400 MHz |
|---------|----------|------------------------|----------------|
| 39 | 4-(3-chloro-4-(5-(methyl(2,2,6,6-tetramethyl-piperidin-4-yl)amino)-1,3,4-thiadiazol-2-yl)phenyl)-1-methylpyridin-2(1H)-one | 472.2 [M]⁺ 0.48 min, D | (DMSO-$d_6$) δ ppm 8.13 (d, J = 8.59 Hz, 1H), 7.98 (d, J = 2.02 Hz, 1H), 7.80-7.86 (m, 2H), 6.81 (d, J = 2.02 Hz, 1H), 6.66 (dd, J = 7.33, 2.27 Hz, 1H), 4.42 (br. s., 1H), 3.46 (s, 3H), 3.03 (s, 3H), 1.64 (br. s., 2H), 1.45 (br. s., 2H), 1.23 (br. s., 7H), 1.11 (br. s., 6H) |
| 40 | 5-(2-chloro-4-(1H-pyrazol-4-yl)phenyl)-N-methyl-N-(2,2,6,6-tetramethylpiperidin-4-yl)-1,3,4-thiadiazol-2-amine | 431.2, 0.49 min, D | (DMSO-$d_6$) δ ppm 8.23 (br. s., 2H), 7.99 (d, J = 8.08 Hz, 1H), 7.90 (d, J = 1.52 Hz, 1H), 7.67-7.78 (m, 1H), 4.29-4.44 (m, 1H), 3.01 (s, 3H), 1.62 (dd, J = 12.13, 3.03 Hz, 2H), 1.43 (t, J = 12.13 Hz, 2H), 1.21 (s, 6H), 1.09 (s, 6H) |

-continued

| Example | Compound | LCMS M + 1, Rt, Method | ¹H NMR 400 MHz |
|---|---|---|---|
| 41 | 5-(2-chloro-4-(4,5,6,7-tetrahydropyrazolo[1,5-a]pyridin-3-yl)phenyl)-N-methyl-N-(2,2,6,6-tetramethylpiperidin-4-yl)-1,3,4-thiadiazol-2-amine | 485.2 [M]⁺, 0.54 min, D | (DMSO-$d_6$) δ ppm 8.01 (d, J = 8.08 Hz, 1H), 7.89 (s, 1H), 7.66 (d, J = 1.52 Hz, 1H), 7.56 (dd, J = 8.34, 1.77 Hz, 1H), 4.31-4.44 (m, 1H), 4.11 (t, J = 6.06 Hz, 2H), 2.94-3.06 (m, 5H), 1.96-2.04 (m, 2H), 1.81-1.90 (m, 2H), 1.62 (dd, J = 11.87, 3.28 Hz, 2H), 1.43 (t, J = 12.38 Hz, 2H), 1.29 (br. s., 1H), 1.21 (s, 6H), 1.09 (s, 6H) |
| 42 | N-methyl-5-(5-(1-methyl-1H-pyrazol-4-yl)pyridin-2-yl)-N-(2,2,6,6-tetramethylpiperidin-4-yl)-1,3,4-thiadiazol-2-amine. Hydrochloride salt | 412.2, 0.46 min, D | (DMSO-$d_6$) δ ppm 9.03 (d, J = 11.12 Hz, 1H), 8.85 (d, J = 2.02 Hz, 1H), 8.33 (s, 1H), 8.07-8.13 (m, 1H), 7.93-8.07 (m, 3H), 4.44-4.55 (m, 1H), 3.90 (s, 3H), 3.07 (s, 3H), 1.87-2.02 (m, 4H), 1.50 (s, 6H), 1.45 (s, 6H) |
| 43 | 2-(2-chloro-4-(1-methyl-1H-pyrazol-4-yl)phenyl)-5-((2,2,6,6-tetramethylpiperidin-4-yl)oxy)-1,3,4-thiadiazole | 432.2, 0.54 min, A | (DMSO-$d_6$) δ ppm 8.35 (s, 1H), 8.02-8.07 (m, 2H), 7.90 (d, J = 2.02 Hz, 1H), 7.70-7.74 (m, 1H), 5.42 (tt, J = 11.31, 4.11 Hz, 1H), 3.88 (s, 3H), 2.16 (dd, J = 11.62, 4.04 Hz, 2H), 1.42 (br. s., 1H), 1.32 (t, J = 11.62 Hz, 2H), 1.20 (s, 6H), 1.11 (s, 6H) |

| Example | Compound | LCMS M + 1, Rt, Method | ¹H NMR 400 MHz |
|---|---|---|---|
| 44 | 5-(2-chloro-4-(6-methoxypyridin-3-yl)phenyl)-N-methyl-N-(2,2,6,6-tetramethylpiperidin-4-yl)-1,3,4-thiadiazol-2-amine | 472.2 [M]⁺, 0.58 min, D | (DMSO-d₆) δ ppm 8.62 (d, J = 2.02 Hz, 1H), 8.09-8.17 (m, 2H), 7.96 (d, J = 1.52 Hz, 1H), 7.80 (dd, J = 8.34, 1.77 Hz, 1H), 6.95 (d, J = 8.59 Hz, 1H), 4.35-4.44 (m, 1H), 3.92 (s, 3H), 3.02 (s, 3H), 1.63 (dd, J = 12.13, 3.03 Hz, 2H), 1.44 (t, J = 12.38 Hz, 2H), 1.29 (br. s., 1H), 1.21 (s, 6H), 1.09 (s, 6H) |
| 45 | 5-(4-(6-aminopyridin-3-yl)-2-fluorophenyl)-N-methyl-N-(2,2,6,6-tetramethylpiperidin-4-yl)-1,3,4-thiadiazol-2-amine | 441.3, 0.40 min, D | (DMSO-d₆) δ ppm 8.39 (d, J = 2.53 Hz, 1H), 8.07 (t, J = 8.34 Hz, 1H), 7.82 (dd, J = 8.59, 2.53 Hz, 1H), 7.57-7.69 (m, 2H), 6.53 (d, J = 9.09 Hz, 1H), 6.26 (s, 2H), 4.30-4.39 (m, 1H), 3.01 (s, 3H), 1.63 (d, J = 9.60 Hz, 2H), 1.44 (t, J = 11.62 Hz, 2H), 1.29 (br. s., 1H), 1.22 (s, 6H), 1.09 (s, 6H) |
| 46 | 5-(2-fluoro-4-(3-methyl-1H-pyrazol-5-yl)phenyl)-N-methyl-N-(2,2,6,6-tetramethylpiperidin-4-yl)-1,3,4-thiadiazol-2-amine | 429.3, 0.52 min, D | (DMSO-d₆) δ ppm 12.77 (br. s., 1H), 8.08 (t, J = 8.08 Hz, 1H), 7.69-7.78 (m, 2H), 6.58 (br. s., 1H), 4.29-4.39 (m, 1H), 3.02 (s, 3H), 2.28 (s, 3H), 1.63 (d, J = 12.13 Hz, 2H), 1.45 (t, J = 11.12 Hz, 2H), 1.29 (br. s., 1H), 1.22 (br. s., 6H), 1.10 (br. s., 6H) |

-continued

| Example | Compound | LCMS M + 1, Rt, Method | ¹H NMR 400 MHz |
|---------|----------|------------------------|----------------|
| 47 | 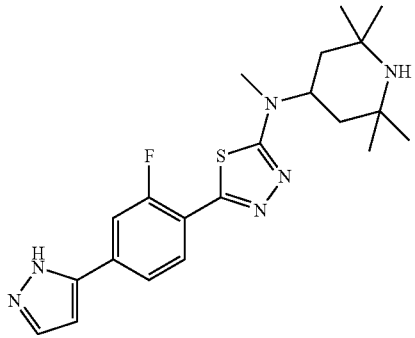 [SMILES: CN(c1nnc(-c2ccc(-c3ccn[nH]3)cc2F)s1)C1CC(C)(C)NC(C)(C)C1]<br>5-(2-fluoro-4-(1H-pyrazol-5-yl)phenyl)-N-methyl-N-(2,2,6,6-tetramethylpiperidin-4-yl)-1,3,4-thiadiazol-2-amine | 415.2, 0.49 min, D | (DMSO-$d_6$) δ ppm 13.10 (br. s., 1H), 8.11 (t, J = 8.08 Hz, 1H), 7.74-7.89 (m, 3H), 6.88 (s, 1H), 4.34 (t, J = 12.13 Hz, 1H), 3.02 (s, 3H), 1.63 (d, J = 9.09 Hz, 2H), 1.39-1.51 (m, 2H), 1.29 (br. s., 1H), 1.22 (s, 6H), 1.09 (s, 6H) |
| 48 | 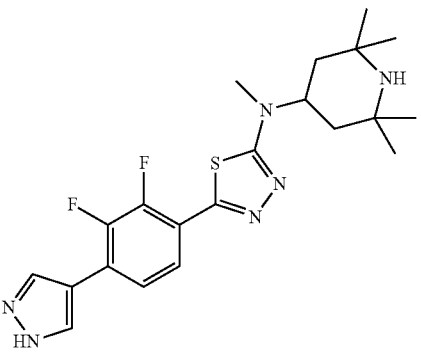 [SMILES: CN(c1nnc(-c2ccc(-c3cn[nH]c3)c(F)c2F)s1)C1CC(C)(C)NC(C)(C)C1]<br>5-(2,3-difluoro-4-(1H-pyrazol-4-yl)phenyl)-N-methyl-N-(2,2,6,6-tetramethylpiperidin-4-yl)-1,3,4-thiadiazol-2-amine | 433.3, 0.49 min, D | (DMSO-$d_6$) δ ppm 13.29 (br. s., 1H), 8.26 (br. s., 1H), 8.12 (br. s., 1H), 7.84 (td, J = 7.58, 1.52 Hz, 1H), 7.68-7.73 (m, 1H), 4.35 (tt, J = 12.57, 3.35 Hz, 1H), 3.02 (s, 3H), 1.63 (dd, J = 11.62, 3.03 Hz, 2H), 1.44 (t, J = 12.13 Hz, 2H), 1.29 (br. s., 1H), 1.21 (s, 6H), 1.09 (s, 6H) |
| 49 | 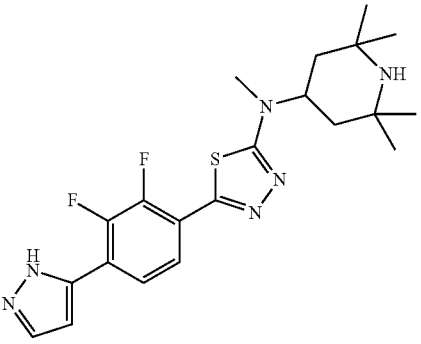 [SMILES: CN(c1nnc(-c2ccc(-c3ccn[nH]3)c(F)c2F)s1)C1CC(C)(C)NC(C)(C)C1]<br>5-(2,3-difluoro-4-(1H-pyrazol-5-yl)phenyl)-N-methyl-N-(2,2,6,6-tetramethylpiperidin-4-yl)-1,3,4-thiadiazol-2-amine | 433.2, 0.52 min, D | (DMSO-$d_6$) δ ppm 13.32 (br. s., 1H), 7.90 (d, J = 3.54 Hz, 3H), 6.75 (br. s., 1H), 4.30-4.39 (m, 1H), 3.03 (s, 3H), 1.63 (dd, J = 11.87, 3.28 Hz, 2H), 1.45 (t, J = 12.13 Hz, 2H), 1.29 (br. s., 1H), 1.21 (s, 6H), 1.09 (s, 6H) |

-continued

| Example | Compound | LCMS M + 1, Rt, Method | ¹H NMR 400 MHz |
|---|---|---|---|
| 50 | 5-(2,5-difluoro-4-(1H-pyrazol-4-yl)phenyl)-N-methyl-N-(2,2,6,6-tetramethylpiperidin-4-yl)-1,3,4-thiadiazol-2-amine | 433.3, 0.49 min, D | (DMSO-$d_6$) δ ppm 13.26 (br. s., 1H), 8.20 (br. s., 2H), 7.85-7.92 (m, 2H), 4.31-4.40 (m, 1H), 3.02 (s, 3H), 1.62 (dd, J = 12.13, 3.03 Hz, 2H), 1.44 (t, J = 12.13 Hz, 2H), 1.29 (br. s., 1H), 1.21 (s, 6H), 1.09 (s, 6H) |
| 51 | 5-(2,5-difluoro-4-(1H-pyrazol-5-yl)phenyl)-N-methyl-N-(2,2,6,6-tetramethylpiperidin-4-yl)-1,3,4-thiadiazol-2-amine | 433.2, 0.52 min, D | (DMSO-$d_6$) δ ppm 13.32 (br. s., 1H), 7.82-7.99 (m, 3H), 6.76 (br. s., 1H), 4.31-4.39 (m, 1H), 3.03 (s, 3H), 1.63 (dd, J = 11.62, 3.03 Hz, 2H), 1.40-1.49 (m, 2H), 1.29 (br. s., 1H), 1.21 (s, 6H), 1.09 (s, 6H) |
| 52 | 5-(2,6-difluoro-4-(1H-pyrazol-4-yl)phenyl)-N-methyl-N-(2,2,6,6-tetramethylpiperidin-4-yl)-1,3,4-thiadiazol-2-amine | 433.3, 0.47 min, D | (DMSO-$d_6$) δ ppm 13.16 (br. s., 1H), 8.29 (br. s., 2H), 7.58-7.67 (m, 2H), 4.29-4.38 (m, 1H), 3.01 (s, 3H), 1.63 (dd, J = 12.13, 3.03 Hz, 2H), 1.44 (t, J = 12.13 Hz, 2H), 1.29 (br. s., 1H), 1.20 (s, 6H), 1.09 (s, 6H) |

| Example | Compound | LCMS M + 1, Rt, Method | ¹H NMR 400 MHz |
|---|---|---|---|
| 53 | 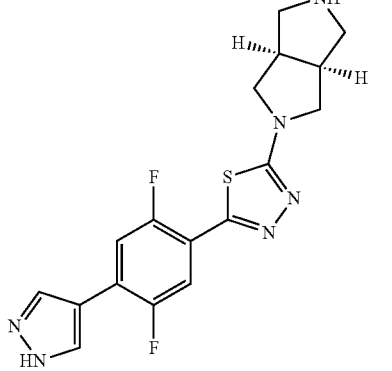<br>2-(2,5-difluoro-4-(1H-pyrazol-4-yl)phenyl)-5-((3aR,6aS)-hexahydropyrrolo[3,4-c]pyrrol-2(1H)-yl)-1,3,4-thiadiazole | 375.2, 0.43 min, D | (METHANOL-$d_4$) δ ppm 8.25 (s, 2H), 8.04 (dd, J = 11.62, 6.06 Hz, 1H), 7.80 (dd, J = 11.87, 6.32 Hz, 1H), 3.91 (dd, J = 10.36, 7.33 Hz, 2H), 3.60 (dd, J = 10.61, 3.03 Hz, 2H), 3.29-3.37 (m, 2H), 3.19-3.28 (m, 2H), 3.00 (dd, J = 11.37, 2.78 Hz, 2H) |
| 54 | 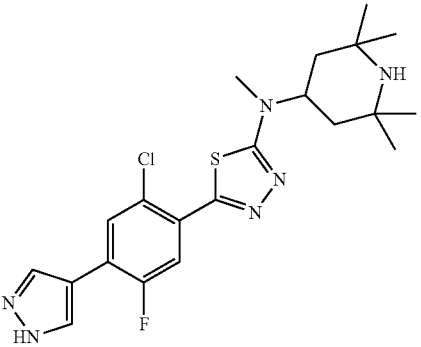 [SMILES: CN(c1nnc(-c2cc(F)c(-c3cn[nH]c3)cc2Cl)s1)C1CC(C)(C)NC(C)(C)C1]<br>5-(2-chloro-5-fluoro-4-(1H-pyrazol-4-yl)phenyl)-N-methyl-N-(2,2,6,6-tetramethylpiperidin-4-yl)-1,3,4-thiadiazol-2-amine | 449.1, 0.51 min, D | (DMSO-$d_6$) δ ppm 13.27 (br. s., 1H), 8.22 (br. s., 2H), 8.06 (d, J = 7.07 Hz, 1H), 7.91 (d, J = 11.62 Hz, 1H), 4.39 (t, J = 11.62 Hz, 1H), 3.02 (s, 3H), 1.64 (d, J = 10.11 Hz, 2H), 1.40-1.56 (m, 2H), 1.22 (s, 6H), 1.10 (s, 6H) |
| 55 | 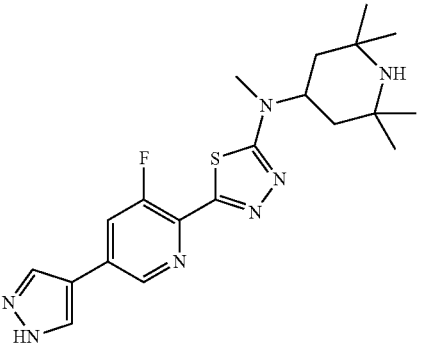 [SMILES: CN(c1nnc(-c2ncc(-c3cn[nH]c3)cc2F)s1)C1CC(C)(C)NC(C)(C)C1]<br>5-(3-fluoro-5-(1H-pyrazol-4-yl)pyridin-2-yl)-N-methyl-N-(2,2,6,6-tetramethylpiperidin-4-yl)-1,3,4-thiadiazol-2-amine | 416.2, 0.45 min, D | (DMSO-$d_6$) δ ppm 13.22 (br. s., 1H), 8.80 (t, J = 1.77 Hz, 1H), 8.32 (br. s., 2H), 8.16 (dd, J = 12.13, 1.52 Hz, 1H), 4.26-4.36 (m, 1H), 3.03 (s, 3H), 1.64 (dd, J = 12.13, 3.03 Hz, 2H), 1.45 (t, J = 12.13 Hz, 2H), 1.22 (s, 6H), 1.10 (s, 6H) |

| Example | Compound | LCMS M + 1, Rt, Method | ¹H NMR 400 MHz |
|---|---|---|---|
| 56 | 5-(4-(2-aminopyrimidin-4-yl)-2-chlorophenyl)-N-methyl-N-(2,2,6,6-tetramethylpiperidin-4-yl)-1,3,4-thiadiazol-2-amine | 458.2 [M]+, 0.51 min, D | (DMSO-$d_6$) δ ppm 8.37 (d, J = 5.05 Hz, 1H), 8.32 (d, J = 1.52 Hz, 1H), 8.13-8.20 (m, 2H), 7.25 (d, J = 5.56 Hz, 1H), 6.80 (s, 2H), 4.34-4.43 (m, 1H), 3.03 (s, 3H), 1.61-1.68 (m, 2H), 1.45 (t, J = 12.63 Hz, 2H), 1.22 (s, 6H), 1.10 (s, 6H) |
| 57 | 5-(5-(2-aminopyrimidin-4-yl)-2-chlorophenyl)-N-methyl-N-(2,2,6,6-tetramethylpiperidin-4-yl)-1,3,4-thiadiazol-2-amine | 458.2 [M]+, 0.47 min, D | (DMSO-$d_6$) δ ppm 8.43 (d, J = 1.52 Hz, 1H), 8.34-8.30 (m, 1H), 8.22 (d, J = 6.06 Hz, 1H), 8.15 (d, J = 8.08 Hz, 1H), 7.05 (br. s., 2H), 6.42 (d, J = 5.56 Hz, 1H), 4.30-4.42 (m, 1H), 3.03 (s, 3H), 1.64 (dd, J = 12.13, 3.03 Hz, 2H), 1.45 (t, J = 12.38 Hz, 2H), 1.22 (s, 6H), 1.10 (s, 6H) |

| Example | Compound | LCMS M + 1, Rt, Method | ¹H NMR 400 MHz |
|---|---|---|---|
| 58 | 5-(4-(2,4-dimethylthiazol-5-yl)-2,5-difluorophenyl)-N-methyl-N-(2,2,6,6-tetramethylpiperidin-4-yl)-1,3,4-thiadiazol-2-amine | 478.2, 0.57 min, D | (DMSO-$d_6$) δ ppm 7.98 (dd, J = 10.61, 6.06 Hz, 1H), 7.62 (dd, J = 11.12, 6.06 Hz, 1H), 4.33-4.45 (m, 1H), 3.03 (s, 3H), 2.66 (s, 3H), 2.33 (s, 3H), 1.63 (dd, J = 12.13, 3.03 Hz, 2H), 1.44 (t, J = 12.13 Hz, 2H), 1.30 (br. s, 1H), 1.21 (s, 6H), 1.09 (s, 6H) |
| 59 | 5-(4-(2,4-dimethylthiazol-5-yl)-2,3-difluorophenyl)-N-methyl-N-(2,2,6,6-tetramethylpiperidin-4-yl)-1,3,4-thiadiazol-2-amine | 478.2, 0.56 min, D | (METHANOL-$d_4$) δ ppm 7.88-8.06 (m, 1H), 7.27-7.45 (m, 1H), 4.47 (m, 1H), 3.11 (s, 3H), 2.72 (s, 3H), 2.32-2.42 (m, 3H), 1.79 (dd, J = 12.63, 3.03 Hz, 2H), 1.58 (t, J = 12.38 Hz, 2H), 1.35 (s, 6H), 1.24 (s, 6H) |

By employing similar methods as described for the preparation of Example 26, using appropriate starting materials, the following compounds were prepared:

| Example | Compound | LCMS M + 1, Rt, Method | ¹H NMR 400 MHz |
|---|---|---|---|
| 60 | 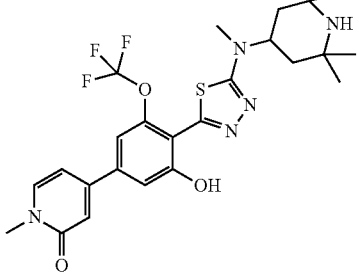<br>4-(3-hydroxy-4-(5-(methyl(2,2,6,6-tetra-methylpiperidin-4-yl)amino)-1,3,4-thiadiazol-2-yl)-5-(trifluoromethoxy)phenyl)-1-methylpyridin-2(1H)-one | 538.3, 0.53 min, D | (CHLOROFORM-d) δ ppm 12.77 (br. s., 1H), 7.30 (d, J = 7.07 Hz, 1H), 7.15 (d, J = 1.52 Hz, 1H), 6.98-7.02 (m, 1H), 6.74 (d, J = 1.52 Hz, 1H), 6.33 (dd, J = 7.07, 2.02 Hz, 1H), 4.31 (br. s., 1H), 3.52 (s, 3H), 3.05 (s, 3H), 1.76 (dd, J = 12.63, 3.03 Hz, 2H), 1.39 (br. s., 3H), 1.28 (s, 6H), 1.16 (br. s., 6H) |

Example 61

Synthesis of 5-(2-fluoro-6-methoxy-4-(1H-pyrazol-4-yl)phenyl)-N-methyl-N-(2,2,6,6-tetramethylpiperidin-4-yl)-1,3,4-thiadiazol-2-amine

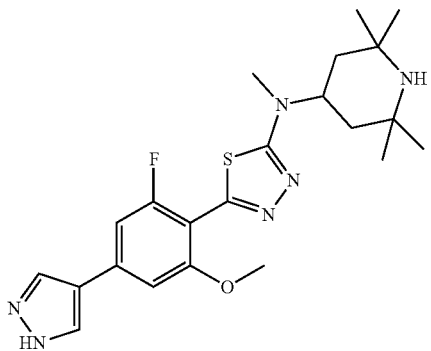 [SMILES: COc1cc(-c2cn[nH]c2)cc(F)c1-c1nnc(N(C)C2CC(C)(C)NC(C)(C)C2)s1]

Step 1: 5-(2-Fluoro-6-methoxyphenyl)-1,3,4-thiadiazol-2-amine

A stirred mixture of 2-fluoro-6-methoxybenzoic acid (2 g, 11.76 mmol) and hydrazinecarbothioamide (1.607 g, 17.63 mmol) was cooled under nitrogen atmosphere in an ice bath and POCl₃ (3.29 mL, 35.3 mmol) was added drop-wise. On completion of the addition, the reaction mixture was stirred at 78° C. for 3 hours. The reaction mixture was cooled in an ice bath and quenched by addition of ice water (~50 mL) to give a solid/gum-like mass. This solid was sonicated for 1.5 hours and the resulting suspension was diluted with a further 50 mL of water then slurried at room temperature for ~16 hours. The solid was collected by vacuum filtration, rinsed with water, re-suspended in saturated NaHCO$_{3(aq)}$ (~100 mL) and slurried for ~30 minutes. The resulting solid was collected by vacuum filtration, then rinsed with water to afford the crude product as an off-white solid. The crude material was pre-absorbed onto silica gel and purified by flash chromatography using a 120 g silica cartridge with a 0-10% MeOH/DCM gradient as the eluent to afford the title compound as a pale yellow solid (1.265 g, 45% yield). LC-MS: Rt 0.77 min; MS m/z 226.1 [M+H]⁺ [Method A]. ¹H NMR (400 MHz, DMSO-d₆) δ ppm 7.48 (td, J=8.34, 6.57 Hz, 1H), 7.29 (s, 2H), 7.02 (d, J=8.08 Hz, 1H), 6.91-6.99 (m, 1H), 3.85 (s, 3H).

Step 2: 2-Bromo-5-(2-fluoro-6-methoxyphenyl)-1,3,4-thiadiazole 5-(2-Fluoro-6-methoxyphenyl)-1,3,4-thiadiazol-2-amine (1.265 g, 5.62 mmol) was added, portion-wise, to a stirred solution of CuBr₂ (1.505 g, 6.74 mmol) and t-BuNO₂ (0.992 mL, 8.42 mmol) in MeCN (16 mL) under nitrogen and the reaction mixture was stirred at room temperature for ~18 hours. The reaction mixture was quenched by addition of saturated NH₄Cl$_{(aq)}$ (~40 mL) and extracted with EtOAc (100 mL). The organic phase was separated, dried over MgSO₄, and filtered. The filtrate was concentrated in vacuo to afford the title compound as a brown solid (1.401 g, 86% yield). LC-MS: Rt 1.15 min; MS m/z 289.0 [M]⁺; [Method A]. ¹H NMR (400 MHz, DMSO-d₆) δ ppm 7.63 (td, J=8.46, 6.32 Hz, 1H), 7.15 (d, J=8.59 Hz, 1H), 7.03-7.10 (m, 1H), 3.96 (s, 3H).

Step 3: 5-(2-Fluoro-6-methoxyphenyl)-N-methyl-N-(2,2,6,6-tetramethylpiperidin-4-yl)-1,3,4-thiadiazol-2-amine A stirred solution of 2-bromo-5-(2-fluoro-6-methoxyphenyl)-1,3,4-thiadiazole (335 mg, 1.159 mmol) and N,2,2,6,6-pentamethylpiperidin-4-amine (197 mg, 1.159 mmol) in NMP (2.5 mL) was heated at 120° C. for ~18 hours. The reaction mixture was diluted with saturated NaHCO$_{3(aq)}$ (30 mL), water (20 mL), and extracted with DCM (75 mL). The organic phase was separated, dried over MgSO₄ and filtered. The filtrate was concentrated in vacuo to afford the crude product as a brown oil/liquid. The crude material was purified by UV directed preparative HPLC under acidic conditions (0.1% TFA), collecting at 298 nm. The product containing fractions were combined and loaded onto a 5 g SCX cartridge (pre-wet with MeOH). The cartridge was washed with MeOH (30 mL) then flushed with 7M NH$_3$ in MeOH (20 mL). The MeOH/NH$_3$ was removed in vacuo to afford the title compound as an orange oil (121 mg, 28% yield). LC-MS: Rt 0.88 min; MS m/z 379.4 [M+H]$^+$; [Method A]. $^1$H NMR (400 MHz, DMSO-d$_6$) δ ppm 7.49 (td, J=8.34, 6.57 Hz, 1H), 7.03 (d, J=8.59 Hz, 1H), 6.97 (t, J=9.09 Hz, 1H), 4.26-4.36 (m, 1H), 3.86 (s, 3H), 2.98 (s, 3H), 1.62 (dd, J=11.62, 2.53 Hz, 2H), 1.42 (t, J=12.13 Hz, 2H), 1.27 (br. s., 1H), 1.20 (s, 6H), 1.09 (s, 6H).

Step 4: 5-(4-Bromo-2-fluoro-6-methoxyphenyl)-N-methyl-N-(2,2,6,6-tetramethylpiperidin-4-yl)-1,3,4-thiadiazol-2-amine Nitrogen was bubbled through a stirred solution of 5-(2-fluoro-6-methoxyphenyl)-N-methyl-N-(2,2,6,6-tetramethylpiperidin-4-yl)-1,3,4-thiadiazol-2-amine (121 mg, 0.32 mmol) and 4,4,4',4',5,5,5',5'-octamethyl-2,2'-bi(1,3,2-dioxaborolane) (122 mg, 0.48 mmol) in dioxane (2.5 mL) To this solution was added dtbpy (9 mg, 0.032 mmol) and [Ir(COD)(OMe)]$_2$ (11 mg, 0.016 mmol). The resulting solution was de-gassed by bubbling nitrogen through for a further 10 minutes, then heated at 90° C. for ~16 hours. The reaction mixture was concentrated in vacuo and the residue taken up in a 1:1 mixture of MeOH:water (4 mL). CuBr$_2$ (168 mg, 0.754 mmol) was added and the resulting suspension heated at 80° C. for ~18 hours. The reaction mixture was diluted with 28% NH$_4$OH$_{(aq)}$ (10 mL) and extracted with DCM (20 mL). The organic phase was separated and concentrated in vacuo to afford the crude product as a dark brown oil. The crude material was purified by UV directed preparative HPLC under acidic conditions (0.1% formic acid), collecting at 314 nm. The product containing fractions were combined and loaded onto a 2 g SCX cartridge (pre-wet with MeOH). The cartridge washed with MeOH (~15 mL) then flushed with 7M NH$_3$ in MeOH (10 mL). The MeOH/NH$_3$ was removed in vacuo to afford a light brown oil/glass-like solid as a crude mixture containing the title compound which was used without further purification. LC-MS: Rt 1.04 min; MS m/z 459.3 [M+2H]$^+$ [Method A].

Step 5: 5-(2-Fluoro-6-methoxy-4-(1H-pyrazol-4-yl)phenyl)-N-methyl-N-(2,2,6,6-tetramethylpiperidin-4-yl)-1,3,4-thiadiazol-2-amine Pd(Ph$_3$P)$_4$ (11 mg, 0.009 mmol) was added to a stirred suspension of 4-(4,4,5,5-tetramethyl-1,3,2-dioxaborolan-2-yl)-1H-pyrazole (55 mg, 0.282 mmol) and 5-(4-bromo-2-fluoro-6-methoxyphenyl)-N-methyl-N-(2,2,6,6-tetramethylpiperidin-4-yl)-1,3,4-thiadiazol-2-amine (86 mg, 0.188 mmol) in dioxane (1.5 mL), followed by a solution of NaHCO$_3$ (60 mg, 0.564 mmol) in water (0.375 mL). The reaction mixture was purged with nitrogen, sealed, and heated at 120° C. under microwave irradiation for 1 hour. The reaction mixture was diluted with DCM (20 mL) and washed with saturated NaHCO$_{3(aq)}$ (10 mL). The organic phase was separated and SiliaMetS-DMT (0.61 mmol/g, 145 mg, 0.09 mmol) was added. The resulting suspension was stirred at room temperature for ~2 hours then filtered. The filtrate was concentrated in vacuo to afford the crude product as a light brown oil. The crude material was purified by UV directed preparative HPLC under basic conditions (NH$_4$OH modified), collecting at 328 nm to afford the title compound as a white solid (26 mg, 32% yield). LC-MS: Rt 0.76 min; MS m/z 445.5 [M+H]$^+$ [Method A]. $^1$H NMR (400 MHz, DMSO-d$_6$) δ ppm 13.09 (br. s., 1H), 8.26 (br. s., 2H), 7.23-7.31 (m, 2H), 4.27-4.37 (m, 1H), 3.93 (s, 3H), 2.98 (s, 3H), 1.62 (dd, J=11.87, 3.28 Hz, 2H), 1.42 (t, J=12.13 Hz, 2H), 1.20 (s, 6H), 1.09 (s, 6H).

By employing similar methods as described for the preparation of Example 61, using appropriate starting materials, the following compounds were prepared:

| Example | Compound | LCMS M + 1, Rt, Method | $^1$H NMR 400 MHz |
|---|---|---|---|
| 62 | 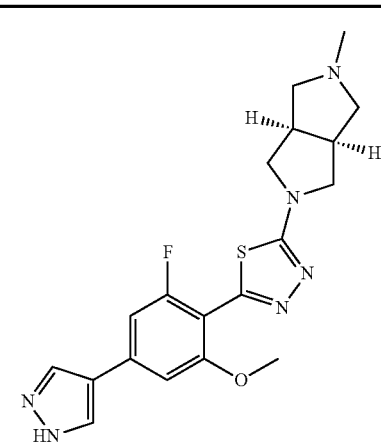<br>2-(2-fluoro-6-methoxy-4-(1H-pyrazol-4-yl)phenyl)-5-((3aR,6aS)-5-methylhexahydro-pyrrolo[3,4-c]pyrrol-2(1H)-yl)-1,3,4-thiadiazole | 401.1, 0.40 min, D | (CHLOROFORM-d) δ ppm 7.87 (s, 2H), 6.96 (d, J = 10.61 Hz, 1H), 6.85 (s, 1H), 3.94 (s, 3H), 3.77 (dd, J = 10.11, 7.58 Hz, 2H), 3.51 (dd, J = 10.61, 3.03 Hz, 2H), 3.08 (br. s., 2H), 2.67-2.78 (m, 2H), 2.63 (dd, J = 9.09, 2.53 Hz, 2H), 2.40 (s, 3H) |

| Example | Compound | LCMS M + 1, Rt, Method | ¹H NMR 400 MHz |
|---|---|---|---|
| 63 | 5-(2,3-difluoro-6-methoxy-4-(1H-pyrazol-4-yl)phenyl)-N-methyl-N-(2,2,6,6-tetramethyl-piperidin-4-yl)-1,3,4-thiadiazol-2-amine | 463.2, 0.50 min, D | (DMSO-d6) δ 13.30 (s, 1H), 8.24 (s, 2H), 7.29 (dd, J = 5.7, 2.0 Hz, 1H), 4.35 (tt, J = 12.5, 3.6 Hz, 1H), 3.95 (s, 3H), 3.00 (s, 3H), 1.63 (dd, J = 11.9, 3.5 Hz, 2H), 1.44 (t, J = 12.1 Hz, 2H), 1.21 (s, 6H), 1.09 (s, 6H) |

Example 64

Synthesis of 6-methoxy-2-(5-(methyl(2,2,6,6-tetramethylpiperidin-4-yl)amino)-1,3,4-thiadiazol-2-yl)-3,4-dihydroisoquinolin-1(2H)-one

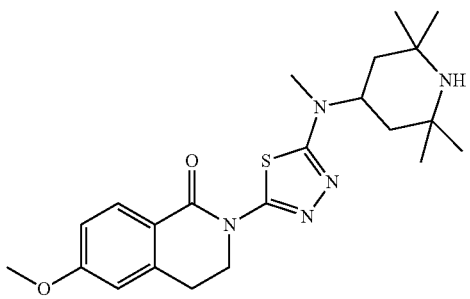

Step 1: 6-Methoxy-2-(5-(methyl(2,2,6,6-tetramethylpiperidin-4-yl)amino)-1,3,4-thiadiazol-2-yl)-3,4-dihydroisoquinolin-1(2H)-one To a stirred suspension of 6-methoxy-3,4-dihydroisoquinolin-1(2H)-one (50 mg, 0.282 mmol) and 5-bromo-N-methyl-N-(2,2,6,6-tetramethylpiperidin-4-yl)-1,3,4-thiadiazol-2-amine (Intermediate 4) (132 mg, 0.395 mmol) in DMF (0.7 mL) under nitrogen was added K₂CO₃ (78 mg, 0.564 mmol) followed by CuI (32 mg, 0.169 mmol). The reaction mixture was heated at 150° C. for ~18 hours. A further 1.4 eq of 5-bromo-N-methyl-N-(2,2,6,6-tetramethylpiperidin-4-yl)-1,3,4-thiadiazol-2-amine (132 mg, 0.395 mmol) and 0.6 eq of CuI (32 mg, 0.169 mmol) were added and stirring was continued at 150° C. for an additional 48 hours. The reaction mixture was diluted with EtOAc (10 mL) and filtered through celite. The filtrate was concentrated in vacuo to afford the crude product as a dark brown oil. The crude material was purified by UV directed preparative HPLC under acidic conditions (formic acid modified) collecting at 312 nm. The product containing fractions were combined and loaded onto a 2 g SCX cartridge (pre-wet with MeOH). The cartridge was washed with MeOH (~20 mL) then flushed with 10% DCM in [7M NH₃ in MeOH] (12 mL). The DCM/MeOH/NH₃ was removed in vacuo to afford the title compound as a pale yellow/brown glass-like solid (28 mg, 23% yield). LC-MS: Rt 0.91 min; MS m/z 430.5 [M+H]⁺ [Method A]. ¹H NMR (400 MHz, DMSO-d₆) δ ppm 7.88-7.97 (m, 1H), 6.96-7.03 (m, 2H), 4.35 (t, J=6.57 Hz, 2H), 4.16 (tt, J=12.19, 3.22 Hz, 1H), 3.85 (s, 3H), 3.14 (t, J=6.57 Hz, 2H), 2.91 (s, 3H), 1.58 (dd, J=12.13, 3.03 Hz, 2H), 1.42 (t, J=11.87 Hz, 2H), 1.20 (s, 6H), 1.09 (s, 6H).

Example 65

Synthesis of 5-(2-chloro-4-(1H-pyrazol-1-yl)phenyl)-N-methyl-N-(2,2,6,6-tetramethylpiperidin-4-yl)-1,3,4-thiadiazol-2-amine

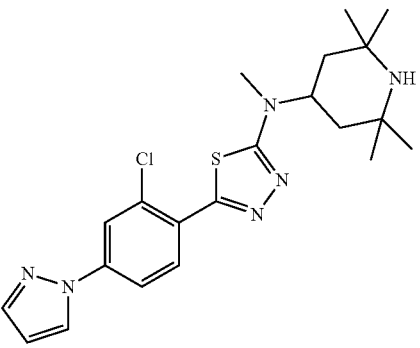 [SMILES: CN(c1nnc(-c2ccc(-n3cccn3)cc2Cl)s1)C1CC(C)(C)NC(C)(C)C1]

Step 1: 5-(2-Chloro-4-fluorophenyl)-N-methyl-N-(2,2,6,6-tetramethylpiperidin-4-yl)-1,3,4-thiadiazol-2-amine To a stirred suspension of (2-chloro-4-fluorophenyl)boronic acid (251 mg, 1.44 mmol) and 5-bromo-N-methyl-N-(2,2,6,6-tetramethylpiperidin-4-yl)-1,3,4-thiadiazol-2-amine (Intermediate 4) (400 mg, 1.2 mmol) in dioxane (10 mL) under nitrogen was added Pd(PPh₃)₄ (69 mg, 0.06 mmol)

followed by a solution of Na₂CO₃ (382 mg, 3.6 mmol) in water (2.5 mL). The reaction mixture was sealed and heated at 120° C. under microwave irradiation for 1 hour. The reaction mixture was diluted with DCM (100 mL) and washed with saturated NaHCO$_{3(aq)}$ (40 mL). The organic phase was separated, dried over MgSO₄, and filtered. The filtrate was diluted with MeOH (10 mL) and SiliaMetS-DMT (0.61 mmol/g, 0.984 mg, 0.6 mmol) was added. The resulting suspension was stirred at room temperature for ~18 hours then filtered. The filtrate was concentrated in vacuo to afford the crude product as a yellow/orange oil. The crude material was purified by flash chromatography using a 24 g silica cartridge running a gradient from 2-10% [2M NH₃ in MeOH]/DCM to afford the title compound as a pale yellow solid (312 mg, 68% yield). LC-MS: Rt 0.97 min; MS m/z 383.4 [M+H]⁺ [Method A]. ¹H NMR (400 MHz, DMSO-d₆) δ ppm 8.03 (dd, J=8.84, 6.32 Hz, 1H), 7.65 (dd, J=9.09, 2.53 Hz, 1H), 7.36-7.43 (m, 1H), 4.34 (tt, J=12.38, 3.28 Hz, 1H), 3.00 (s, 3H), 1.62 (dd, J=12.13, 3.03 Hz, 2H), 1.43 (t, J=12.38 Hz, 2H), 1.28 (br. s., 1H), 1.20 (s, 6H), 1.08 (s, 6H).

Step 2: 5-(2-Chloro-4-(1H-pyrazol-1-yl)phenyl)-N-methyl-N-(2,2,6,6-tetramethylpiperidin-4-yl)-1,3,4-thiadiazol-2-amine Cs₂CO₃ (128 mg, 0.392 mmol) was added to a stirred solution of 5-(2-chloro-4-fluorophenyl)-N-methyl-N-(2,2,6,6-tetramethylpiperidin-4-yl)-1,3,4-thiadiazol-2-amine (50 mg, 0.131 mmol) and 1H-pyrazole (13 mg, 0.196 mmol) in DMF (1.3 mL). The reaction mixture was stirred at room temperature for 4 days then warmed to 60° C. and stirred for an additional 18 hours. The reaction mixture was diluted with DCM (10 mL), filtered through celite, and the DCM was removed in vacuo to afford the crude product as a pale brown liquid. The crude material was purified by UV directed preparative HPLC under acidic conditions (formic acid modified), collecting at 324 nm. The product containing fractions were combined and loaded onto a 1 g SCX cartridge (pre-wet with MeOH). The cartridge was washed with MeOH (10 mL) then flushed with 10% DCM in [7M NH₃ in MeOH] (10 mL). The DCM/MeOH/NH₃ was removed in vacuo to afford the title compound as a clear glass-like solid (37 mg, 66% yield). LC-MS: Rt 0.97 min; MS m/z 431.5 [M+H]⁺ [Method A]. ¹H NMR (400 MHz, DMSO-d₆) δ ppm 8.67 (d, J=2.53 Hz, 1H), 8.14 (dd, J=5.56, 3.03 Hz, 2H), 7.97-8.02 (m, 1H), 7.83 (d, J=1.52 Hz, 1H), 6.64-6.60 (m, 1H), 4.37 (tt, J=12.25, 3.16 Hz, 1H), 3.02 (s, 3H), 1.63 (dd, J=12.13, 3.03 Hz, 2H), 1.45 (t, J=12.13 Hz, 2H), 1.21 (s, 6H), 1.09 (s, 6H).

By employing similar methods as described for the preparation of Example 65, using appropriate starting materials, the following compounds were prepared:

| Example | Compound | LCMS M + 1, Rt, Method | ¹H NMR 400 MHz |
|---|---|---|---|
| 66 | 5-(2-chloro-4-(1H-1,2,3-triazol-1-yl)phenyl)-N-methyl-N-(2,2,6,6-tetramethylpiperidin-4-yl)-1,3,4-thiadiazol-2-amine | 432.2, 0.50 min, D | (DMSO-d₆) δ ppm 8.99 (d, J = 1.52 Hz, 1H), 8.24-8.28 (m, 2H), 8.08-8.11 (m, 1H), 8.04 (d, J = 1.52 Hz, 1H), 4.38 (tt, J = 12.44, 2.97 Hz, 1H), 3.03 (s, 3H), 1.64 (dd, J = 11.87, 3.28 Hz, 2H), 1.45 (t, J = 12.38 Hz, 2H), 1.29 (br. s., 1H), 1.21 (s, 6H), 1.09 (s, 6H) |
| 67 | 5-(2-chloro-4-(2H-1,2,3-triazol-2-yl)phenyl)-N-methyl-N-(2,2,6,6-tetramethylpiperidin-4-yl)-1,3,4-thiadiazol-2-amine | 432.2, 0.58 min, D | (DMSO-d₆) δ ppm 8.22-8.27 (m, 3H), 8.20 (d, J = 2.53 Hz, 1H), 8.13 (dd, J = 8.59, 2.02 Hz, 1H), 4.37 (tt, J = 12.44, 2.97 Hz, 1H), 3.03 (s, 3H), 1.64 (dd, J = 12.13, 3.03 Hz, 2H), 1.44 (t, J = 12.13 Hz, 2H), 1.29 (br. s., 1H), 1.21 (s, 6H), 1.09 (s, 6H) |

-continued

| Example | Compound | LCMS M + 1, Rt, Method | ¹H NMR 400 MHz |
|---|---|---|---|
| 68 | 5-(2-chloro-4-(1H-1,2,4-triazol-1-yl)phenyl)-N-methyl-N-(2,2,6,6-tetramethylpiperidin-4-yl)-1,3,4-thiadiazol-2-amine | 432.2, 0.51 min, D | (DMSO-$d_6$) δ ppm 9.45 (s, 1H), 8.32 (s, 1H), 8.19-8.24 (m, 2H), 8.03-7.98 (m, 1H), 4.38 (tt, J = 12.25, 3.41 Hz, 1H), 3.02 (s, 3H), 1.63 (dd, J = 12.13, 3.54 Hz, 2H), 1.44 (t, J = 12.13 Hz, 2H), 1.30 (br. s., 1H), 1.21 (s, 6H), 1.09 (s, 6H) |
| 69 | 5-(4-(3-amino-1H-pyrazol-1-yl)-2-chlorophenyl)-N-methyl-N-(2,2,6,6-tetramethylpiperidin-4-yl)-1,3,4-thiadiazol-2-amine | 446.2 [M]⁺, 0.50 min, D | (DMSO-$d_6$) δ ppm 8.29 (d, J = 3.03 Hz, 1H), 8.01 (d, J = 8.59 Hz, 1H), 7.87 (d, J = 2.53 Hz, 1H), 7.71-7.77 (m, 1H), 5.83 (d, J = 2.53 Hz, 1H), 5.29 (s, 2H), 4.29-4.38 (m, 1H), 3.00 (s, 3H), 1.62 (dd, J = 11.87, 3.28 Hz, 2H), 1.43 (t, J = 12.38 Hz, 2H), 1.28 (s, 1H), 1.20 (s, 6H), 1.09 (s, 6H) |

Example 70

Synthesis of 2-(2-chloro-4-(1H-imidazol-1-yl)phenyl)-5-((3aR,6aS)-5-methylhexahydropyrrolo[3,4-c]pyrrol-2(1H)-yl)-1,3,4-thiadiazole

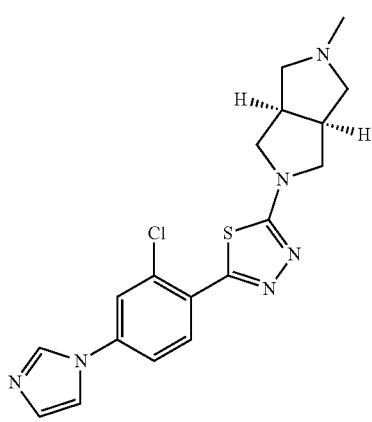 [SMILES: CN1C[C@@H]2CN(c3nnc(-c4ccc(-n5ccnc5)cc4Cl)s3)C[C@@H]2C1]

Step 1: 5-(2-Chloro-4-iodophenyl)-1,3,4-thiadiazol-2-amine

A stirred mixture of 2-chloro-4-iodobenzoic acid (2 g, 7.08 mmol) and hydrazinecarbothioamide (0.968 g, 10.62 mmol) was cooled under nitrogen in an ice bath. POCl₃ (1.98 mL, 21.24 mmol) was added drop-wise and the reaction mixture was heated at 78° C. for 3 hours. The reaction mixture was cooled in an ice bath before quenching by addition of ice water (50 mL). The resulting solid/cake was sonicated for 1 hour to give a free stirring suspension. This material was left to slurry at room temperature for ~18 hours then filtered under vacuum and rinsed with water to afford the crude product as a pale yellow/orange solid. The solid was re-suspended in saturated NaHCO₃(aq) (50 mL), slurried at room temperature for 2 hours, then collected by vacuum filtration to afford the title compound as a pale yellow solid (2.05 g, 86% yield). LC-MS: Rt 1.20 min; MS m/z 337.8 [M]⁺ [Method A]. ¹H NMR (400 MHz, DMSO-$d_6$) δ ppm 8.01 (d, J=1.52 Hz, 1H), 7.76-7.82 (m, 2H), 7.50 (s, 2H).

Step 2: 2-Bromo-5-(2-chloro-4-iodophenyl)-1,3,4-thiadiazole 5-(2-Chloro-4-iodophenyl)-1,3,4-thiadiazol-2-amine (2.05 g, 6.07 mmol) was added portion-wise to a stirred solution of CuBr$_2$ (1.628 g, 7.92 mmol) and t-BuNO$_2$ (1.07 mL, 9.11 mmol) in MeCN (15 mL) under nitrogen. The resulting mixture was stirred at room temperature for 18 hours. The reaction mixture was quenched by addition of saturated NH$_4$Cl$_{(aq)}$ (75 mL) and extracted with EtOAc (100 mL×2). The combined organic phases were concentrated in vacuo to afford the crude product as a pale brown solid. The crude material was pre-absorbed onto silica gel and purified by flash chromatography using a 120 g silica cartridge running a gradient from 0-20% EtOAc/heptane to afford the title compound as an off-white solid (1.795 g, 73% yield). MS m/z 402.6 [M+H]$^+$ $^1$H NMR (400 MHz, DMSO-d$_6$) δ ppm 8.15-8.19 (m, 1H), 7.91-7.97 (m, 2H).

Step 3: 2-(2-Chloro-4-iodophenyl)-5-((3aR,6aS)-5-methylhexahydropyrrolo[3,4-c]pyrrol-2(1H)-yl)-1,3,4-thiadiazole A stirred solution of 2-bromo-5-(2-chloro-4-iodophenyl)-1,3,4-thiadiazole (600 mg, 1.49 mmol) and (3aR,6aS)-2-methyloctahydropyrrolo[3,4-c]pyrrole (377 mg, 2.99 mmol) in NMP (4 mL) was heated at 120° C. for ~18 hours. The reaction mixture was cooled to room temperature then saturated NaHCO$_{3(aq)}$ (30 mL) was added. The resulting suspension was left to slurry for 1 hour before filtering under vacuum to afford the title compound as a pale brown solid which was used in the next step without further purification. LC-MS: Rt 1.06 min; MS m/z 446.8 [M]$^+$ $^1$H NMR (400 MHz, DMSO-d$_6$) δ ppm 8.03 (s, 1H), 7.77-7.86 (m, 2H), 3.71 (t, J=8.84 Hz, 2H), 3.36 (br. s., 2H), 2.97 (br. s., 2H), 2.40-2.54 (m, 4H), 2.22 (s, 3H).

Step 4: 2-(2-Chloro-4-(1H-imidazol-1-yl)phenyl)-5-((3aR,6aS)-5-methylhexahydropyrrolo[3,4-c]pyrrol-2(1H)-yl)-1,3,4-thiadiazole DMF (0.75 mL) was added to a nitrogen flushed flask containing copper(I) iodide (13 mg, 0.067 mmol), 2-(2-pyridyl)benzimidazole (13 mg, 0.067 mmol) and cesium carbonate (273 mg, 0.839 mmol). The resulting suspension was heated at 60° C. for 1 hour. 1H-Imidazole (23 mg, 0.336 mmol) and 2-(2-chloro-4-iodophenyl)-5-((3aR,6aS)-5-methylhexahydropyrrolo[3,4-c]pyrrol-2(1H)-yl)-1,3,4-thiadiazole (150 mg, 0.336 mmol) were added and the mixture was heated at 90° C. for ~18 hours. The reaction mixture was diluted with EtOAc (30 mL) and filtered through celite. The filtrate was concentrated in vacuo to afford a green oil. The crude material was taken up in MeOH (30 mL) and SiliaMetS-DMT (0.61 mmol/g, 1.098 g, 0.67 mmol) was added. The resulting suspension was stirred at room temperature for 72 hours then the SiliaMetS-DMT was removed by vacuum filtration and the filtrate was concentrated in vacuo to afford the crude product as a yellow oil. The crude material was purified by mass directed preparative HPLC under acidic conditions (TFA modified). The product containing fractions were combined, loaded onto a 1 g SCX cartridge (pre-wet with MeOH) and the cartridge washed with MeOH (10 mL) then flushed with 7M NH$_3$ in MeOH (10 mL). The MeOH/NH$_3$ was removed in vacuo to afford the title compound as a white solid (22 mg, 17% yield). LC-MS: Rt 0.52 min; MS m/z 387.0 [M+H]$^+$ [Method D]. $^1$H NMR (400 MHz, DMSO-d$_6$) δ ppm 8.44 (s, 1H), 8.15 (d, J=8.59 Hz, 1H), 8.06 (d, J=2.02 Hz, 1H), 7.91 (s, 1H), 7.83 (dd, J=8.59, 2.53 Hz, 1H), 7.15 (s, 1H), 3.72 (dd, J=10.36, 8.34 Hz, 2H), 3.37 (dd, J=10.36, 2.78 Hz, 2H), 3.00 (br. s., 2H), 2.56 (br. s., 4H), 2.26 (s, 3H).

By employing similar methods as described for the preparation of Example 70, using appropriate starting materials, the following compounds were prepared:

| Example | Compound | LCMS M + 1, Rt, Method | $^1$H NMR 400 MHz |
|---|---|---|---|
| 71 | 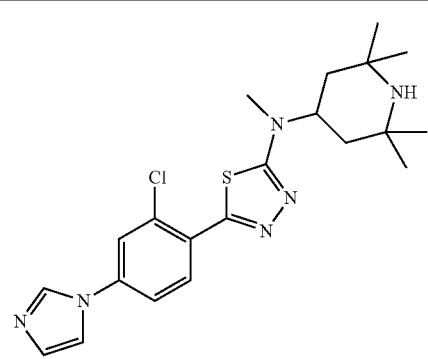  5-(2-chloro-4-(1H-imidazol-1-yl)phenyl)-N-methyl-N-(2,2,6,6-tetramethylpiperidin-4-yl)-1,3,4-thiadiazol-2-amine | 431.1, 0.41 min, D | (DMSO-d$_6$) δ ppm 8.44 (s, 1H), 8.13 (d, J = 8.59 Hz, 1H), 8.06 (d, J = 2.02 Hz, 1H), 7.92 (s, 1H), 7.83 (dd, J = 8.59, 2.02 Hz, 1H), 7.15 (s, 1H), 4.34-4.43 (m, 1H), 3.02 (s, 3H), 1.63 (dd, J = 12.13, 3.03 Hz, 2H), 1.44 (t, J = 12.13 Hz, 2H), 1.21 (s, 6H), 1.09 (s, 6H) |

| Example | Compound | LCMS M + 1, Rt, Method | 1H NMR 400 MHz |
|---|---|---|---|
| 72 | 5-(2-fluoro-4-(1H-imidazol-1-yl)phenyl)-N-methyl-N-(2,2,6,6-tetramethylpiperidin-4-yl)-1,3,4-thiadiazol-2-amine | 415.2, 0.40 min, D | (DMSO-$d_6$) δ ppm 8.44 (s, 1H), 8.18 (t, J = 8.59 Hz, 1H), 7.88-7.96 (m, 2H), 7.72 (dd, J = 8.59, 2.02 Hz, 1H), 7.15 (s, 1H), 4.32-4.41 (m, 1H), 3.02 (s, 3H), 1.63 (dd, J = 12.13, 3.03 Hz, 2H), 1.44 (t, J = 12.13 Hz, 2H), 1.21 (s, 6H), 1.09 (s, 6H) |

Example 73

Synthesis of 5-(2-methoxy-4-(1H-pyrazol-5-yl)phenyl)-N-methyl-N-(2,2,6,6-tetramethylpiperidin-4-yl)-1,3,4-thiadiazol-2-amine

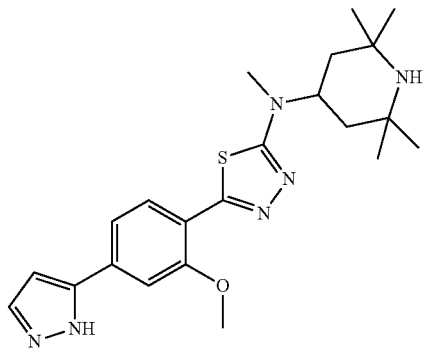 [SMILES: COc1cc(-c2ccn[nH]2)ccc1-c1nnc(N(C)C2CC(C)(C)NC(C)(C)C2)s1]

Step 1: 5-(4-Chloro-2-methoxyphenyl)-N-methyl-N-(2,2,6,6-tetramethylpiperidin-4-yl)-1,3,4-thiadiazol-2-amine Nitrogen was bubbled through a stirred solution of 5-bromo-N-methyl-N-(2,2,6,6-tetramethylpiperidin-4-yl)-1,3,4-thiadiazol-2-amine [Intermediate 4] (1 g, 3.00 mmol) and (4-chloro-2-methoxyphenyl)boronic acid (0.615 g, 3.30 mmol) in dioxane (20 mL). To this mixture was added Pd(PPh$_3$)$_4$ (0.173 g, 0.150 mmol) followed by a solution of Na$_2$CO$_3$ (0.954 g, 9.00 mmol) in water (5 mL). The reaction was heated at 80° C. for 18 hours. The reaction mixture was cooled to RT, diluted with EtOAc (150 mL) and washed with water (100 mL). The organic phase was separated, dried over MgSO$_4$, and filtered. The filtrate was concentrated in vacuo to afford the crude product as a dark red/brown oil which solidified on standing. The crude material was purified by flash chromatography using an 80 g silica cartridge running a gradient of [2M NH$_3$ in MeOH]/DCM to afford the title compound as an off-white solid (1.051 g, 89% yield). LC-MS: Rt 1.04 min; MS m/z 395.2 [M+H]$^+$ [Method A]. $^1$H NMR (400 MHz, DMSO-$d_6$) δ ppm 8.09 (d, J=8.59 Hz, 1H), 7.32 (d, J=2.02 Hz, 1H), 7.15 (dd, J=8.59, 2.02 Hz, 1H), 4.35 (tt, J=12.38, 3.54 Hz, 1H), 3.97 (s, 3H), 2.98 (s, 3H), 1.60 (dd, J=11.87, 3.28 Hz, 2H), 1.41 (t, J=12.13 Hz, 2H), 1.27 (s, 1H), 1.21 (s, 6H), 1.08 (s, 6H).

Step 2: 5-(2-Methoxy-4-(1H-pyrazol-5-yl)phenyl)-N-methyl-N-(2,2,6,6-tetramethylpiperidin-4-yl)-1,3,4-thiadiazol-2-amine To a stirred suspension of (1H-pyrazol-5-yl)boronic acid (14 mg, 0.139 mmol) and 5-(4-chloro-2-methoxyphenyl)-N-methyl-N-(2,2,6,6-tetramethylpiperidin-4-yl)-1,3,4-thiadiazol-2-amine (50 mg, 0.127 mmol) in dioxane (1 mL) was added Pd(PPh$_3$)$_4$ (7 mg, 0.006 mmol) followed by a solution of Na$_2$CO$_3$ (40 mg, 0.380 mmol) in water (0.25 mL). The reaction mixture was purged with nitrogen, sealed, and heated at 120° C. under microwave irradiation for 30 minutes, then again at 145° C. Additional catalyst and boronate were added and the mixture was heated for an additional 30 minutes under microwave irradiation at an increased temperature of 160° C. The reaction mixture was diluted with DCM (20 mL), washed with saturated NaHCO$_{3(aq)}$ (10 mL) and the organic phase was separated and concentrated in vacuo to afford the crude product as an oily residue. The crude material was purified by mass directed preparative HPLC under basic conditions (NH$_4$OH midified) to afford the title compound as a white solid (12.5 mg, 23% yield). LC-MS: Rt 0.81 min; MS m/z 427.3 [M+H]$^+$ [Method A]. $^1$H NMR (400 MHz, DMSO-$d_6$) δ ppm 12.99 (br. s., 1H), 8.12 (d, J=8.08 Hz, 1H), 7.82 (br. s., 1H), 7.60 (s, 1H), 7.54 (d, J=6.06 Hz, 1H), 6.84 (d, J=2.02 Hz, 1H), 4.31-4.41 (m, 1H), 4.01 (s, 3H), 2.99 (s, 3H), 1.61 (dd, J=12.13, 3.54 Hz, 2H), 1.42 (t, J=12.13 Hz, 2H), 1.27 (br. s., 1H), 1.22 (s, 6H), 1.09 (s, 6H).

By employing similar methods as described for the preparation of Example 73, using appropriate starting materials, the following compounds were prepared:

| Example | Compound | LCMS M + 1, Rt, Method | ¹H NMR 400 MHz |
|---|---|---|---|
| 74 | 5-(4-(2,4-dimethylthiazol-5-yl)-2-methoxyphenyl)-N-methyl-N-(2,2,6,6-tetramethylpiperidin-4-yl)-1,3,4-thiadiazol-2-amine | 472.3, 0.55 min, D | (DMSO-$d_6$) δ ppm 8.16 (d, J = 8.08 Hz, 1H), 7.20 (d, J = 2.02 Hz, 1 H), 7.16 (dd, J = 8.08, 1.52 Hz, 1 H), 4.33-4.42 (m, 1 H), 3.99 (s, 3 H), 2.99 (s, 3 H), 2.64 (s, 3 H), 2.45 (s, 3 H), 1.61 (dd, J = 11.87, 3.28 Hz, 2 H), 1.42 (t, J = 12.13 Hz, 2 H), 1.28 (br. s., 1 H), 1.22 (s, 6H), 1.09 (s, 6 H) |
| 75 | 5-(2-methoxy-4-(pyridin-3-yl)phenyl)-N-methyl-N-(2,2,6,6-tetramethylpiperidin-4-yl)-1,3,4-thiadiazol-2-amine | 438.3, 0.48 min, D | (DMSO-$d_6$) δ ppm 9.02 (d, J = 2.02 Hz, 1H), 8.61 (dd, J = 5.05, 1.52 Hz, 1H), 8.17-8.24 (m, 2H), 7.50-7.57 (m, 2H), 7.45-7.49 (m, 1H), 4.39 (tt, J = 12.51, 3.41 Hz, 1H), 4.06 (s, 3H), 3.00 (s, 3H), 1.62 (dd, J = 12.13, 3.03 Hz, 2H), 1.43 (t, J = 12.38 Hz, 2H), 1.28 (br. s., 1H), 1.22 (s, 6H), 1.09 (s, 6H) |
| 76 | 5-(2-fluoro-4-(1H-pyrazol-4-yl)phenyl)-N-methyl-N-(2,2,6,6-tetramethylpiperidin-4-yl)-1,3,4-thiadiazol-2-amine | 415.3, 0.48 min, D | (DMSO-$d_6$) δ ppm 13.09 (br. s., 1H), 8.34 (br. s., 1H), 8.11 (br. s., 1H), 8.04 (t, J = 8.08 Hz, 1H), 7.68 (dd, J = 12.88, 1.26 Hz, 1H), 7.61 (dd, J = 8.08, 1.52 Hz, 1H), 4.29-4.38 (m, 1H), 3.01 (s, 3H), 1.62 (dd, J = 12.13, 3.03 Hz, 2H), 1.43 (t, J = 12.13 Hz, 2H), 1.28 (br. s., 1H), 1.21 (s, 6H), 1.09 (s, 6H) |

| Example | Compound | LCMS M + 1, Rt, Method | ¹H NMR 400 MHz |
|---|---|---|---|
| 77 | 5-(2-methoxy-4-(2-methoxypyridin-4-yl)phenyl)-N-methyl-N-(2,2,6,6-tetramethyl-piperidin-4-yl)-1,3,4-thiadiazol-2-amine | 468.3, 0.56 min, D | (DMSO-$d_6$) δ ppm 8.26 (d, J = 5.05 Hz, 1H), 8.21 (d, J = 8.08 Hz, 1H), 7.55 (d, J = 1.52 Hz, 1H), 7.51 (dd, J = 8.08, 1.52 Hz, 1H), 7.42 (dd, J = 5.56, 1.52 Hz, 1H), 7.25-7.24 (m, 1H), 4.39 (tt, J = 12.51, 3.41 Hz, 1 H), 4.06 (s, 3 H), 3.91 (s, 3H), 3.00 (s, 3 H), 1.62 (dd, J = 12.13, 3.54 Hz, 2 H), 1.42 (t, J = 12.13 Hz, 2 H), 1.28 (br. s., 1 H), 1.22 (s, 6 H), 1.09 (s, 6 H) |
| 78 | 5-(2-methoxy-4-(6-methoxypyridin-3-yl)phenyl)-N-methyl-N-(2,2,6,6-tetramethyl-piperidin-4-yl)-1,3,4-thiadiazol-2-amine | 468.3, 0.56 min, D | (DMSO-$d_6$) δ ppm 8.62 (d, J = 2.02 Hz, 1H), 8.12-8.19 (m, 2H), 7.46 (d, J = 1.52 Hz, 1H), 7.40 (dd, J = 8.08, 1.52 Hz, 1H), 6.94 (d, J = 8.59 Hz, 1H), 4.39 (tt, J = 12.32, 3.09 Hz, 1H), 4.04 (s, 3H), 3.92 (s, 3H), 2.99 (s, 3H), 1.62 (dd, J = 11.87, 3.28 Hz, 2H), 1.42 (t, J = 12.13 Hz, 2H), 1.28 (br. s., 1H), 1.22 (s, 6H), 1.09 (s, 6H) |

Example 79

Synthesis of 2-(2-chloro-4-(1-methyl-1H-pyrazol-4-yl)phenyl)-5-((3aR,6aS)-5-methylhexahydropyrrolo[3,4-c]pyrrol-2(1H)-yl)-1,3,4-thiadiazole

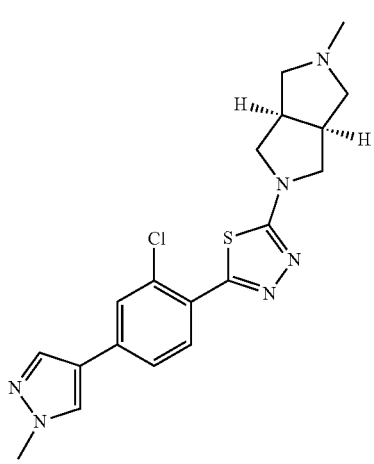 [SMILES: CN1C[C@@H]2CN(c3nnc(-c4ccc(-c5cnn(C)c5)cc4Cl)s3)C[C@@H]2C1]

Step 1: 5-(4-Bromo-2-chlorophenyl)-1,3,4-thiadiazol-2-amine

To an ice cooled mixture of 4-bromo-2-chlorobenzoic acid (2 g, 8.49 mmol) and hydrazinecarbothioamide (1.161 g, 12.74 mmol) was added phosphorous oxychloride (2.375 mL, 25.5 mmol) slowly, and the reaction was heated at 78° C. for 3 hours. After cooling to 0° C., ice water was added and the mixture was vigorously stirred for 1 hour. The resulting precipitate was filtered, washed with water then re-suspended in saturated NaHCO$_{3(aq)}$ and water (1:1) and stirred for 1 hour. The solid was filtered, washed with water, and dried in vacuo to afford the title compound which was used without further purification (2 g, 81% yield). MS m/z 291.9 [M+H]$^+$, ¹H NMR (400 MHz, DMSO-$d_6$) δ ppm 7.80-8.09 (m, 2H), 7.68 (dd, J=2.02, 8.59 Hz, 1H), 7.55 (br. s, 2H).

Step 2: 5-(2-Chloro-4-(1-methyl-1H-pyrazol-4-yl)phenyl)-1,3,4-thiadiazol-2-amine To a stirred solution of 1-methyl-4-(4,4,5,5-tetramethyl-1,3,2-dioxaborolan-2-yl)-1H-pyrazole (197 mg, 0.946 mmol) and 5-(4-bromo-2-chlorophenyl)-1,3,4-thiadiazol-2-amine (250 mg, 0.860 mmol) in dioxane (8 mL) was added Pd(PPh$_3$)$_4$ (50 mg, 0.043 mmol) followed by a solution of Na$_2$CO$_3$ (274 mg, 2.58 mmol) in water (2 mL). The reaction mixture was purged with nitrogen, sealed, and heated at 80° C. for 1 hour under microwave irradiation, then for an additional 2.5 hours at an increased temperature of 120° C. The reaction mixture was diluted with DCM (40 mL) and washed with saturated NaHCO$_{3(aq)}$ (40 mL). A few mLs of saturated NaCl$_{(aq)}$ were added to clear the resulting slight emulsion and the organic phase separated, dried over MgSO$_4$, and filtered. The filtrate was concentrated in vacuo to afford the crude product as a yellow solid. The crude material was pre-absorbed onto silica gel and purified by flash chromatography using a 24 g silica cartridge running a MeOH/DCM gradient to afford the title compound as a pale yellow solid (118 mg, 47% yield). LC-MS: Rt 0.83 min; MS m/z 292.0 [M+H]$^+$ [Method A]. $^1$H NMR (400 MHz, DMSO-d$_6$) δ ppm 8.31 (s, 1H), 7.97-8.03 (m, 2H), 7.83 (d, J=1.52 Hz, 1H), 7.65 (dd, J=8.34, 1.77 Hz, 1H), 7.41 (s, 2H), 3.87 (s, 3H).

Step 3: 2-Bromo-5-(2-chloro-4-(1-methyl-1H-pyrazol-4-yl)phenyl)-1,3,4-thiadiazole 5-(2-Chloro-4-(1-methyl-1H-pyrazol-4-yl)phenyl)-1,3,4-thiadiazol-2-amine (118 mg, 0.404 mmol) was added, portion-wise, to a stirred solution of CuBr$_2$ (108 mg, 0.485 mmol) and t-BuNO$_2$ (0.071 mL, 0.607 mmol) in MeCN (1 mL) under nitrogen atmosphere. On completion of the addition, the reaction was stirred at room temperature for 18 hours then quenched by addition of saturated NH$_4$Cl$_{(aq)}$ (20 mL), and EtOAc (10 mL) was added. The resulting bi-phasic suspension was filtered under vacuum, rinsed with water (10 mL), then EtOAc (10 mL). The filtrate was separated and the organic phase dried over MgSO$_4$, filtered, and re-combined with the solid from the first filtration. The solvent was removed in vacuo to afford the crude product as a light brown solid. The crude material was pre-absorbed onto silica gel and purified by flash chromatography using a 12 g silica cartridge running a EtOAc/heptane gradient to afford the title compound as a white solid 70.5 mg, 49% yield). MS m/z 356.8 [M+H]$^+$

Step 4: 2-(2-Chloro-4-(1-methyl-1H-pyrazol-4-yl)phenyl)-5-((3aR,6aS)-5-methylhexahydropyrrolo[3,4-c]pyrrol-2(1H)-yl)-1,3,4-thiadiazole A stirred suspension of 2-bromo-5-(2-chloro-4-(1-methyl-1H-pyrazol-4-yl)phenyl)-1,3,4-thiadiazole (70 mg, 0.197 mmol) and (3aR,6aS)-2-methyloctahydropyrrolo[3,4-c]pyrrole (75 mg, 0.590 mmol) in NMP (0.5 mL) was heated to 120° C. and the resulting solution was stirred for 16 hours. The reaction mixture was diluted with DCM (20 mL) and washed with saturated NaHCO$_{3(aq)}$ (20 mL). The organic phase was separated and the aqueous phase was re-extracted with DCM (20 mL). The combined organic phases were concentrated in vacuo to afford the crude product as a dark brown oily residue. The crude material was purified by mass directed preparative HPLC under acidic conditions (TFA modified) and the product containing fractions were loaded onto a 1 g SCX cartridge (pre-wet with MeOH). The cartridge was washed with MeOH (15 mL) then flushed with 7M NH$_3$ in MeOH (10 mL). The MeOH/NH$_3$ was removed in vacuo to afford the title compound as a light brown solid (10 mg, 13% yield). LC-MS: Rt 0.79 min; MS m/z 401.4 [M+H]$^+$ [Method D]. $^1$H NMR (400 MHz, DMSO-d$_6$) δ ppm 8.32 (s, 1H), 7.99-8.03 (m, 2H), 7.84 (d, J=2.02 Hz, 1H), 7.65-7.69 (m, 1H), 3.88 (s, 3H), 3.70 (dd, J=10.61, 8.08 Hz, 2H), 3.36 (dd, J=10.61, 3.03 Hz, 2H), 2.99 (br. s., 2H), 2.55 (br. s., 4H), 2.25 (s, 3H). $^1$H NMR (400 MHz, CHLOROFORM-d) δ ppm 8.21 (d, J=8.08 Hz, 1H), 7.81 (s, 1H), 7.69 (s, 1H), 7.57 (d, J=2.02 Hz, 1H), 7.46 (dd, J=8.34, 1.77 Hz, 1H), 3.99 (s, 3H), 3.79 (dd, J=9.85, 7.83 Hz, 2H), 3.53 (d, J=11.12 Hz, 2H), 3.12 (br. s., 2H), 2.76 (br. s., 2H), 2.58 (d, J=8.08 Hz, 2H), 2.41 (br. s., 3H).

By employing similar methods as described for the preparation of Example 79, using appropriate starting materials, the following compounds were prepared:

| Example | Compound | LCMS M + 1, Rt, Method | $^1$H NMR 400 MHz |
|---|---|---|---|
| 80 | 2-(2-chloro-4-(1H-pyrazol-4-yl)phenyl)-5-((3aR,6aS)-5-methylhexahydropyrrolo[3,4-c]pyrrol-2(1H)-yl)-1,3,4-thiadiazole | 387.2, 0.41 min, D | (METHANOL-d$_4$) δ ppm 7.99 (br. s., 2H), 7.92 (d, J = 8.59 Hz, 1H), 7.71 (s, 1H), 7.56 (d, J = 8.59 Hz, 1H), 3.60-3.70 (m, 2H), 3.32-3.43 (m, 2H), 3.03 (br. s., 2H), 2.62-2.73 (m, 2H), 2.47 (dd, J = 9.60, 3.03 Hz, 2H), 2.26 (s, 3H) |

-continued

| Example | Compound | LCMS M + 1, Rt, Method | ¹H NMR 400 MHz |
|---|---|---|---|
| 81 | 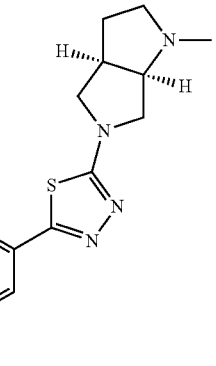<br>2-(2-chloro-4-(1H-pyrazol-4-yl)phenyl)-5-((3aR,6aR)-1-methylhexahydropyrrolo[3,4-b]pyrrol-5(1H)-yl)-1,3,4-thiadiazole | 387.1, 0.41 min, D | (METHANOL-$d_4$) δ ppm 8.00 (br. s., 2H), 7.93 (d, J = 8.08 Hz, 1H), 7.71 (d, J = 2.02 Hz, 1H), 7.57 (dd, J = 8.34, 1.77 Hz, 1H), 3.57-3.70 (m, 2H), 3.47-3.55 (m, 1H), 3.32-3.41 (m, 1H), 2.96-3.08 (m, 3H), 2.28-2.37 (m, 4H), 2.07-2.18 (m, 1H), 1.59-1.72 (m, 1H) |
| 82 | 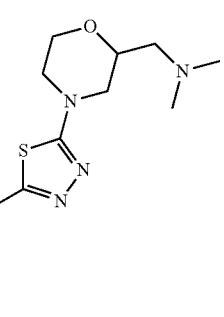<br>1-(4-(5-(2-chloro-4-(1H-pyrazol-4-yl)phenyl)-1,3,4-thiadiazol-2-yl)morpholin-2-yl)-N,N-dimethylmethanamine | 405.1, 0.44 min, D | (METHANOL-$d_4$) δ ppm 8.00 (br. s., 2H), 7.92 (d, J = 8.08 Hz, 1H), 7.71 (d, J = 1.52 Hz, 1H), 7.57 (dd, J = 8.08, 1.52 Hz, 1H), 3.93 (dd, J = 11.12, 3.03 Hz, 1H), 3.62-3.82 (m, 4H), 3.23-3.31 (m, 1H), 2.86-2.98 (m, 1H), 2.45 (dd, J = 13.14, 7.58 Hz, 1H), 2.34 (dd, J = 13.14, 3.54 Hz, 1H), 2.22 (s, 6H) |
| 83 | 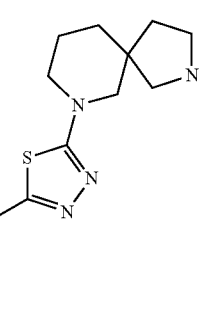<br>2-(2-chloro-4-(1H-pyrazol-4-yl)phenyl)-5-(2-methyl-2,7-diazaspiro[4.5]decan-7-yl)-1,3,4-thiadiazole | 415.1, 0.47 min, D | (METHANOL-$d_4$) δ ppm 7.95-8.07 (m, 2H) 7.87-7.94 (m, 1H) 7.70 (d, J = 1.52 Hz, 1H) 7.56 (dd, J = 8.34, 1.77 Hz, 1H) 3.43-3.57 (m, 2H) 3.30-3.42 (m, 2H) 2.62-2.73 (m, 1H) 2.45-2.58 (m, 2H) 2.28 (s, 3H) 1.53-1.75 (m, 6H) 1.18 (s, 1H) |

-continued

| Example | Compound | LCMS M + 1, Rt, Method | $^1$H NMR 400 MHz |
|---|---|---|---|
| 84 | 2-(2-fluoro-4-(1H-pyrazol-4-yl)phenyl)-5-((3aR,6aS)-5-methylhexahydropyrrolo[3,4-c]pyrrol-2(1H)-yl)-1,3,4-thiadiazole | 371.1, 0.40 min, D | (METHANOL-d$_4$) δ ppm 7.94-8.08 (m, 3H) 7.32-7.53 (m, 2H) 3.65 (dd, J = 10.36, 8.34 Hz, 2H) 3.39 (dd, J = 10.61, 3.03 Hz, 2H) 3.04 (br. s., 2H) 2.68 (dd, J = 9.60, 7.07 Hz, 2H) 2.47 (dd, J = 9.85, 3.28 Hz, 2H) 2.26 (s, 3H) |

Example 85

Synthesis of 2-(2-methoxy-4-(1-methyl-1H-pyrazol-4-yl)phenyl)-5-(2,6-diazaspiro[3.5]nonan-2-yl)-1,3,4-thiadiazole

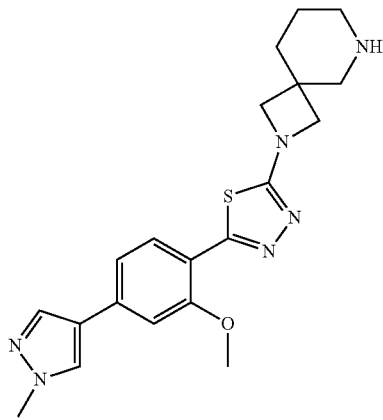 [SMILES: COc1cc(-c2cnn(C)c2)ccc1-c1nnc(N2CC3(CCCNC3)C2)s1]

Step 1: 5-(4-Iodo-2-methoxyphenyl)-1,3,4-thiadiazol-2-amine

To an ice cooled mixture of 4-iodo-2-methoxybenzoic acid (6.178 g, 22.22 mmol) and hydrazinecarbothioamide (2.43 g, 26.7 mmol) was added phosphorous oxychloride (6.21 mL, 66.7 mmol) slowly. The mixture was heated at 78° C. overnight. After cooling to 0° C., ice water was added and the mixture was vigorously stirred for 1 hour. The resulting precipitate was filtered, washed with water, and re-suspended in saturated NaHCO$_{3(aq)}$ and water (1:1) for 1 hour. The solid was filtered, washed with water, and dried in vacuo to afford the crude compound. The crude material was purified by flash chromatography (MeOH/CH$_2$Cl$_2$) to afford the title compound (1.2 g, 16% yield). MS m/z 334.0 [M+H]$^+$.

Step 2: 5-(2-Methoxy-4-(1-methyl-1H-pyrazol-4-yl)phenyl)-1,3,4-thiadiazol-2-amine To a stirred suspension of 1-methyl-4-(4,4,5,5-tetramethyl-1,3,2-dioxaborolan-2-yl)-1H-pyrazole (137 mg, 0.660 mmol) and 5-(4-iodo-2-methoxyphenyl)-1,3,4-thiadiazol-2-amine (200 mg, 0.6 mmol) in dioxane (4 mL) was added Pd(PPh$_3$)$_4$ (35 mg, 0.03 mmol) followed by a solution of Na$_2$CO$_3$ (191 mg, 1.801 mmol) in water (1 mL). The reaction was purged with nitrogen then heated at 80° C. for 18 hours. The reaction mixture was diluted with MeOH (20 mL), filtered through celite, and rinsed with DCM (20 mL). The filtrate was concentrated in vacuo to afford the crude product as an orange oily residue. The crude product was pre-absorbed onto silica gel and purified by flash chromatography using a 24 g silica cartridge, running a MeOH/DCM gradient to afford the title compound as a pale yellow solid (107 mg, 62% yield). LC-MS: Rt 0.81 min; MS m/z 288.1 [M+H]$^+$ [Method A]. $^1$H NMR (400 MHz, DMSO-d$_6$) δ ppm 8.27 (s, 1H), 8.05 (d, J=8.08 Hz, 1H), 7.98 (s, 1H), 7.36 (d, J=1.52 Hz, 1H), 7.28 (dd, J=8.08, 1.52 Hz, 1H), 7.13 (s, 2H), 3.99 (s, 3H), 3.88 (s, 3H).

Step 3: 2-Bromo-5-(2-methoxy-4-(1-methyl-1H-pyrazol-4-yl)phenyl)-1,3,4-thiadiazole 5-(2-Methoxy-4-(1-methyl-1H-pyrazol-4-yl)phenyl)-1,3,4-thiadiazol-2-amine (205 mg, 0.713 mmol) was added portion-wise to a stirred solution of CuBr$_2$ (191 mg, 0.865 mmol) and t-BuNO$_2$ (0.126 mL, 1.07 mmol) in MeCN (16 mL) under nitrogen atmosphere. On completion of the addition, the reaction mixture was stirred at room temperature for 18 hours then quenched by addition of saturated NH$_4$Cl$_{(aq)}$ (25 mL), diluted with water (25 mL), and extracted with EtOAc (100 mL×2) then DCM (100 mL). The combined organic phases were dried over MgSO$_4$, filtered, and the filtrate was concentrated in vacuo to afford the crude product as a light brown/orange solid. The crude material was pre-absorbed onto silica gel and purified by flash chromatography using a 12 g silica cartridge, running a MeOH/DCM to afford the title compound as a light yellow solid (80 mg, 32% yield). LC-MS: Rt 1.19 min; MS m/z 353.1 [M+2]$^+$ [Method A]. $^1$H NMR (400 MHz, DMSO-d₆) δ ppm 8.36 (s, 1H), 8.25 (d, J=8.59 Hz, 1H), 8.06 (s, 1H), 7.48 (d, J=1.52 Hz, 1H), 7.39 (dd, J=8.08, 1.52 Hz, 1H), 4.09 (s, 3H), 3.89 (s, 3H).

Step 4: 2-(2-Methoxy-4-(1-methyl-1H-pyrazol-4-yl) phenyl)-5-(2,6-diazaspiro[3.5]nonan-2-yl)-1,3,4-thiadiazole DIPEA (116 µL, 0.666 mmol) was added to a stirred suspension of 2-bromo-5-(2-methoxy-4-(1-methyl-1H-pyrazol-4-yl)phenyl)-1,3,4-thiadiazole (78 mg, 0.222 mmol) and tert-butyl 2,6-diazaspiro[3.5]nonane-6-carboxylate (acetic acid salt, 127 mg, 0.444 mmol) in NMP (444 µL) and the mixture was heated at 120° C. for 3 hours. The reaction mixture was diluted with DCM (10 mL), washed with saturated NaHCO₃(aq) (10 mL), and the organic phase was separated. TFA (342 µL, 4.44 mmol) was added and the resulting solution was stirred at room temperature for 18 hours. A further 1 mL TFA was added and the reaction mixture was warmed to 35° C. and stirred for 48 hours. The reaction mixture was loaded onto a 1 g SCX cartridge (pre-wet with MeOH) and the cartridge was washed with MeOH (10 mL) then flushed with 7M NH₃ in MeOH (10 mL). The MeOH/NH₃ was removed in vacuo to afford the crude product as a brown oil. The crude material was purified by UV directed preparative HPLC under acidic conditions (TFA modified) and the product containing fractions were loaded onto a 1 g SCX cartridge (pre-wet with MeOH). The cartridge was washed with MeOH (10 mL) and flushed with 7M NH₃ in MeOH (10 mL). The MeOH/NH₃ was removed in vacuo to afford the title compound a white foam-like solid (40.5 mg, 46% yield). LC-MS: Rt 0.83 min; MS m/z 397.1 [M+H]⁺ [Method D], ¹H NMR (400 MHz, DMSO-d₆) δ ppm 8.27 (s, 1H), 8.06 (d, J=8.08 Hz, 1H), 7.99 (s, 1H), 7.37 (d, J=1.52 Hz, 1H), 7.29 (dd, J=8.08, 1.52 Hz, 1H), 4.00 (s, 3H), 3.88 (s, 3H), 3.81 (d, J=7.58 Hz, 2H), 3.74 (d, J=7.58 Hz, 2H), 2.82 (s, 2H), 2.60 (t, J=5.05 Hz, 2H), 1.73 (t, J=5.56 Hz, 2H), 1.41 (quin, J=5.56 Hz, 2H).

By employing similar methods as described for the preparation of Example 85, using appropriate starting materials, the following compound was prepared:

Example 87

Synthesis of 2-(5-(methyl(2,2,6,6-tetramethylpiperidin-4-yl)amino)-1,3,4-thiadiazol-2-yl)-5-(1H-pyrazol-1-yl)phenol

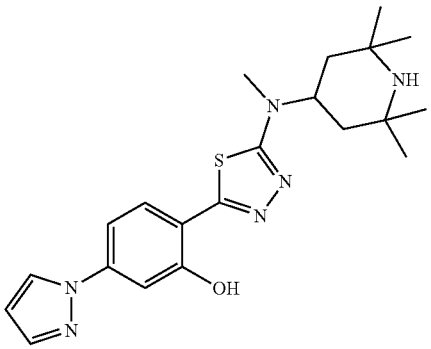 [SMILES: CN(c1nnc(-c2ccc(-n3cccn3)cc2O)s1)C1CC(C)(C)NC(C)(C)C1]

To a solution of 5-(2-methoxy-4-(1H-pyrazol-1-yl)phenyl)-N-methyl-N-(2,2,6,6-tetramethylpiperidin-4-yl)-1,3,4-thiadiazol-2-amine (Example 1) (30 mg, 0.070 mmol) in DCM (1.5 mL) was added BBr₃ (1M solution in heptane, 0.352 mL, 0.352 mmol). The resulting bright yellow suspension was stirred at room temperature for 2 h. The reaction mixture was quenched by addition of MeOH (5 mL) and the resulting solution was loaded onto a 1 g SCX cartridge (pre-wet with MeOH). The cartridge was washed with MeOH (10 mL) then flushed with 7M NH₃ in MeOH (15 mL). The solvent was evaporated in vacuo. The resulting crude material was sonicated in MeOH (2 mL) and the resulting suspension was filtered under vacuum to afford the title compound as a

| Example | Compound | LCMS M + 1, Rt, Method | ¹H NMR 400 MHz |
|---|---|---|---|
| 86 | 2-(2-methoxy-4-(1-methyl-1H-pyrazol-4-yl)phenyl)-5-(2,7-diazaspiro[3.5]nonan-2-yl)-1,3,4-thiadiazole | 397.2, 0.44 min, D | (DMSO-d₆) δ ppm 8.27 (s, 1H), 8.07 (d, J = 8.08 Hz, 1H), 7.99 (s, 1H), 7.37 (d, J = 1.52 Hz, 1H), 7.29 (dd, J = 8.08, 1.52 Hz, 1H), 4.00 (s, 3H), 3.88 (s, 3 H), 3.81 (s, 4H), 2.57-2.66 (m, 4H), 1.62-1.71 (m, 4H) | pale yellow solid (14.9 mg, 51.4% yield). LC-MS: Rt 0.55 min; MS m/z 413.3 [M+H]$^+$ [Method D]. $^1$H NMR (400 MHz, DMSO-d$_6$) δ ppm 8.47 (d, J=2.02 Hz, 1H), 7.99 (d, J=8.59 Hz, 1H), 7.73-7.78 (m, 1H), 7.47 (d, J=1.52 Hz, 1H), 7.36 (d, J=8.59 Hz, 1H), 6.53-6.58 (m, 1H), 4.33 (t, J=12.13 Hz, 1H), 2.99 (s, 3H), 1.58-1.69 (m, 2H), 1.47 (t, J=12.13 Hz, 2H), 1.23 (s, 6H), 1.12 (s, 6H).

By employing similar methods as described for the preparation of Example 87, using appropriate starting materials, the following compounds were prepared:

| Example | Compound | LCMS M + 1, Rt, Method | $^1$H NMR 400 MHz |
|---|---|---|---|
| 88 | 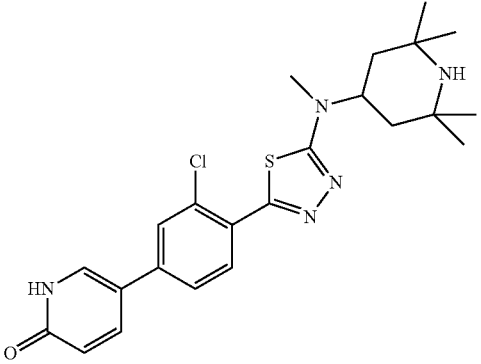<br>5-(3-chloro-4-(5-(methyl(2,2,6,6-tetramethylpiperidin-4-yl)amino)-1,3,4-thiadiazol-2-yl)phenyl)pyridin-2(1H)-one | 458.2 [M]$^+$, 0.48 min, D | (DMSO-d$_6$) δ ppm 8.03 (d, J = 8.59 Hz, 1H), 7.91-7.96 (m, 2H), 7.86 (d, J = 2.02 Hz, 1H), 7.70 (dd, J = 8.34, 1.77 Hz, 1H), 6.45 (d, J = 10.11 Hz, 1H), 4.34-4.42 (m, 1H), 3.01 (s, 3H), 1.61-1.67 (m, 2 H), 1.46 (t, J = 11.87 Hz, 2H), 1.22 (s, 6H), 1.10 (s, 6H) |
| 89 | 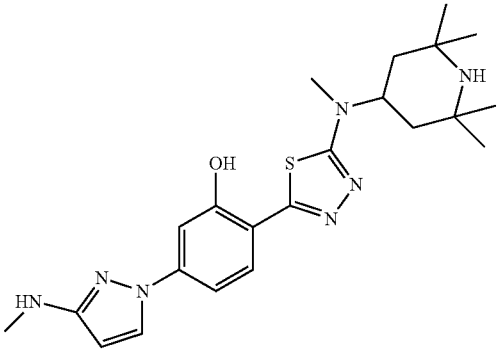<br>2-(5-(methyl(2,2,6,6-tetramethylpiperidin-4-yl)amino)-1,3,4-thiadiazol-2-yl)-5-(3-(methylamino)-1H-pyrazol-1-yl)phenol | 442.2, 0.49 min, D | (DMSO-d$_6$) δ ppm 8.16 (d, J = 2.53 Hz, 1H), 7.87 (d, J = 8.59 Hz, 1H), 7.33 (d, J = 2.02 Hz, 1H), 7.22 (dd, J = 8.84, 1.77 Hz, 1H), 5.81 (d, J = 2.53 Hz, 1H), 5.62 (q, J = 4.55 Hz, 1H), 4.24-4.36 (m, 1H), 2.98 (s, 3H), 2.75 (d, J = 5.05 Hz, 3H), 1.58-1.67 (m, 2H), 1.44 (t, J = 12.13 Hz, 2H), 1.22 (s, 6H), 1.10 (s, 6H) |

| Example | Compound | LCMS M + 1, Rt, Method | $^1$H NMR 400 MHz |
|---|---|---|---|
| 90 | 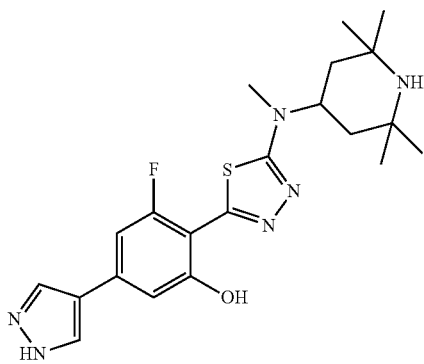<br>3-fluoro-2-(5-(methyl(2,2,6,6-tetramethylpiperidin-4-yl)amino)-1,3,4-thiadiazol-2-yl)-5-(1H-pyrazol-4-yl)phenol | 431.2, 0.50 min, D | (DMSO-d$_6$) δ ppm 13.08 (br. s., 1H), 8.19 (br. s., 2H), 7.12-7.26 (m, 2H), 4.29-4.41 (m, 1H), 3.02 (s, 3H), 1.64 (dd, J = 12.13, 3.03 Hz, 2H), 1.46 (t, J = 12.13 Hz, 2H), 1.22 (s, 6H), 1.10 (s, 6H) |
| 91 | 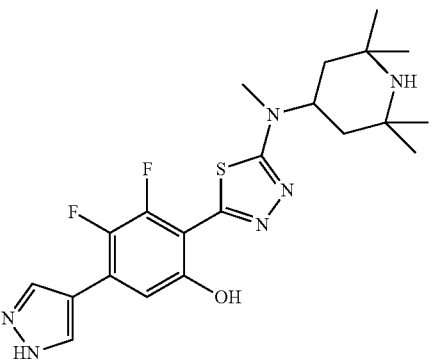<br>3,4-difluoro-2-(5-(methyl(2,2,6,6-tetramethylpiperidin-4-yl)amino)-1,3,4-thiadiazol-2-yl)-5-(1H-pyrazol-4-yl)phenol | 449.2, 0.52 min, D | (DMSO-d$_6$) δ 13.26 (s, 1H), 8.14 (s, 2H), 7.15 (d, J = 6.1 Hz, 1H), 4.45-4.28 (m, 1H), 3.03 (s, 3H), 1.65 (dd, J = 12.1, 3.5 Hz, 2H), 1.48 (t, J = 12.2 Hz, 2H), 1.23 (s, 6H), 1.11 (s, 6H) |

By employing similar methods as described for the preparation of Example 1 and Example 87, using appropriate starting materials, the following compound was prepared:

| Example | Compound | LCMS M + 1, Rt, Method | ¹H NMR 400 MHz |
|---|---|---|---|
| 92 | 6-hydroxy-5-(5-(methyl(2,2,6,6-tetramethylpiperidin-4-yl)amino)-1,3,4-thiadiazol-2-yl)-2,3-dihydro-1H-inden-1-one | 401.2, 0.48 min, D | ¹H NMR (400 MHz, DMSO-$d_6$) δ ppm 1.37-1.58 (m, 12H) 1.81-1.93 (m, 2H) 1.95-2.10 (m, 2H) 2.66 (dd, J = 6.53, 5.02 Hz, 2H) 2.97-3.12 (m, 5H) 4.35-4.70 (m, 1 H) 7.20 (s, 1H) 8.12 (d, J = 12.05 Hz, 1H) 8.20 (s, 1H) 9.17 (d, J = 11.80 Hz, 1H) 11.34 (br. s., 1H) |

By employing similar methods as described for the preparation of Example 25 and Example 87, using appropriate starting materials, the following compound was prepared:

| Example | Compound | LCMS M + 1, Rt, Method | ¹H NMR 400 MHz |
|---|---|---|---|
| 93 | 2-(5-(methyl(2,2,6,6-tetramethylpiperidin-4-yl)amino)-1,3,4-thiadiazol-2-yl)-5-(1H-pyrazol-4-yl)phenol | 413.2, 0.50 min, D | (DMSO-$d_6$) δ ppm 13.01 (br. s., 1H), 8.09 (br. s., 2H), 7.80 (d, J = 1.00 Hz, 1H), 7.04-7.33 (m, 2H), 4.12-4.45 (m, 1H), 2.99 (s, 3H), 1.62 (dd, J = 3.28, 11.87 Hz, 2H), 1.43 (t, J = 12.13 Hz, 2H), 1.19 (s, 6H), 1.09 (s, 6H) |

By employing similar methods as described for the preparation of Example 85 and Example 87, using appropriate starting materials, the following compounds were prepared:

| Example | Compound | LCMS M + 1, Rt, Method | $^1$H NMR 400 MHz |
|---|---|---|---|
| 94 | 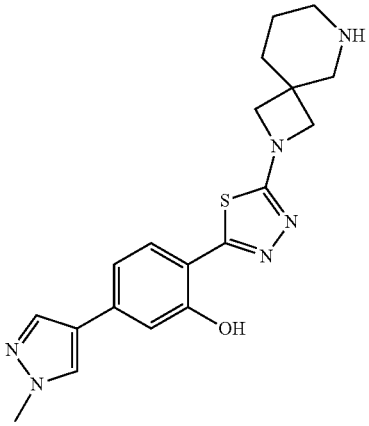<br>2-(5-(2,6-diazaspiro[3.5]nonan-2-yl)-1,3,4-thiadiazol-2-yl)-5-(1-methyl-1H-pyrazol-4-yl)phenol | 383.1, 0.45 min, D | (DMSO-d$_6$) δ ppm 10.90 (br. s., 1H), 8.06 (s, 1H), 7.72-7.80 (m, 2H), 7.03-7.10 (m, 2H), 3.78-3.87 (m, 7H), 2.94 (s, 1H), 2.56-2.72 (m, 2H), 2.29-2.45 (m, 2H), 1.67 (br. s., 2H), 1.51 (br. s., 2H) |
| 95 | 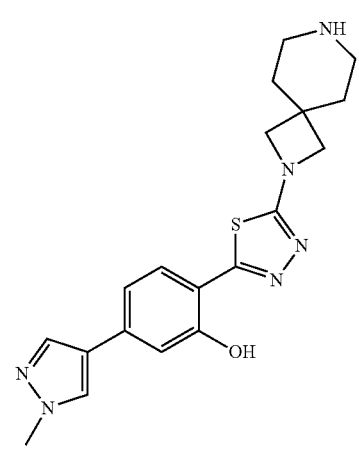<br>2-(5-(2,7-diazaspiro[3.5]nonan-2-yl)-1,3,4-thiadiazol-2-yl)-5-(1-methyl-1H-pyrazol-4-yl)phenol | 383.1, 0.44 min, D | (DMSO-d$_6$) δ ppm 8.12 (s, 1H), 7.86 (d, J = 8.08 Hz, 1H), 7.82 (s, 1H), 7.15-7.09 (m, 2H), 3.87 (s, 3H), 3.82 (s, 4H), 2.67 (t, J = 4.80 Hz, 4H), 1.65-1.75 (m, 4H) |

By employing similar methods as described for the preparation of Example 61 and Example 87, using appropriate starting materials, the following compounds were prepared:

| Example | Compound | LCMS M + 1, Rt, Method | ¹H NMR 400 MHz |
|---|---|---|---|
| 96 | 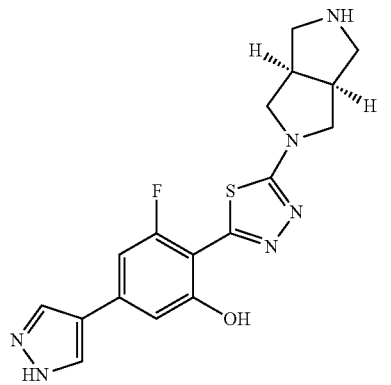<br>3-fluoro-2-(5-((3aR,6aS)-hexahydropyrrolo[3,4-c]pyrrol-2(1H)-yl)-1,3,4-thiadiazol-2-yl)-5-(1H-pyrazol-4-yl)phenol·Di-hydrochloride salt | 373.2, 0.43 min, D | (DMSO-$d_6$) δ ppm 9.26 (br. s., 2H), 8.20 (s, 2H), 7.23 (dd, J = 12.63, 1.52 Hz, 1H), 7.18 (s, 1 H), 3.78-3.70 (m, 2H), 3.57-3.59 (m, 4H), 3.43 (dd, J = 10.61, 6.06 Hz, 2H), 3.13-3.27 (m, H) |
| 97 | 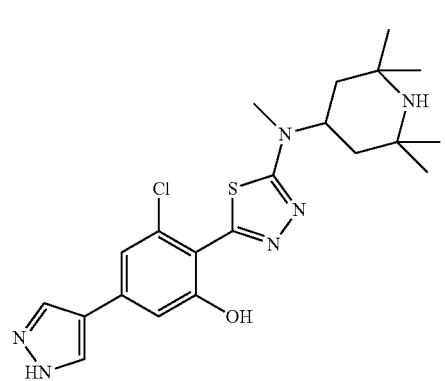<br>3-chloro-2-(5-(methyl(2,2,6,6-tetramethylpiperidin-4-yl)amino)-1,3,4-thiadiazol-2-yl)-5-(1H-pyrazol-4-yl)phenol | 477.2, 0.63 min, D | (DMSO-$d_6$) δ ppm 13.09 (br. s., 1H), 8.31 (br. s., 1H), 8.04 (br. s., 1H), 7.38 (d, J = 1.52 Hz, 1H), 7.21 (d, J = 2.02 Hz, 1H), 4.29-4.39 (m, 1H), 3.02 (s, 3H), 1.64 (dd, J = 11.87, 3.28 Hz, 2H), 1.46 (t, J = 12.38 Hz, 2H), 1.22 (s, 6H), 1.10 (s, 6H) |

Example 98

Synthesis of 2-(2-methoxy-4-(1H-pyrazol-1-yl)phenyl)-5-((2,2,6,6-tetramethylpiperidin-4-yl)methyl)-1,3,4-thiadiazole

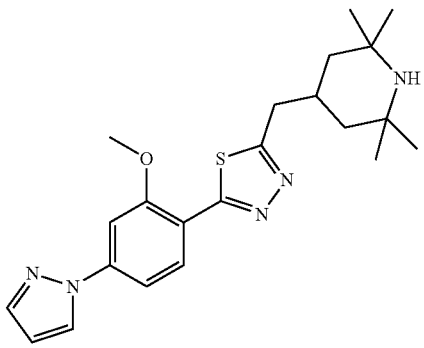 [SMILES: COc1cc(-n2cccn2)ccc1-c1nnc(CC2CC(C)(C)NC(C)(C)C2)s1]

Step 1: 5-((2,2,6,6-Tetramethylpiperidin-4-yl)methyl)-1,3,4-thiadiazol-2-amine A stirred mixture of 2-(2,2,6,6-tetramethylpiperidin-4-yl) acetic acid (410 mg, 2.057 mmol) and hydrazinecarbothioamide (281 mg, 3.09 mmol) was cooled under nitrogen in an ice bath. $POCl_3$ (0.575 mL, 6.17 mmol) was added drop-wise and the mixture was heated at 78° C. for 3 hours. The reaction mixture was cooled in an ice bath and quenched by addition of ice water (20 mL). The resulting mixture was sonicated for 20 minutes and the resulting suspension was stirred at room temperature for 72 hours. The resulting solution was basified by addition of NaOH (pellets added portion-wise over ~15 minutes). The resulting suspension was stirred at room temperature for 1 hour before filtering under vacuum and rinsing with water to afford the title compound as a pale brown solid (118 mg, 22% yield). LC-MS: Rt 0.44 min; MS m/z 255.3 [M+H]$^+$ [Method A]. $^1$H NMR (400 MHz, DMSO-$d_6$) δ ppm 6.98 (s, 2H), 2.66 (d, J=7.07 Hz, 2H), 2.03 (br. s., 1H), 1.49 (d, J=10.61 Hz, 2H), 1.08 (s, 6H), 0.99 (br. s., 6H), 0.78 (t, J=12.13 Hz, 2H).

Step 2: 2-Bromo-5-((2,2,6,6-tetramethylpiperidin-4-yl)methyl)-1,3,4-thiadiazole 5-((2,2,6,6-tetramethylpiperidin-4-yl)methyl)-1,3,4-thiadiazol-2-amine (117 mg, 0.46 mmol) was added portionwise to a stirred solution of $CuBr_2$ (123 mg, 0.552 mmol) and t-BuNO$_2$ (0.081 mL, 0.69 mmol) in MeCN (1 mL) under nitrogen atmosphere. On completion of the addition, the reaction mixture was stirred at room temperature for 18 hours then a further 1.5 eq of t-BuNO$_2$ (0.081 mL, 0.69 mmol) was added. The reaction mixture was stirred at room temperature for 10 minutes, and a further 1.2 eq of $CuBr_2$ (123 mg, 0.552 mmol) was added. The reaction mixture was stirred at room temperature for a further 18 hours, then quenched by addition of saturated NH$_4$Cl$_{(aq)}$ (10 mL) and extracted with DCM (20 mL). The organic phase was separated and concentrated in vacuo to afford the crude product as a brown oil. The crude material was purified by UV directed preparative HPLC under acidic conditions (formic acid modified) and the product containing fractions were loaded onto a 1 g SCX cartridge (pre-wet with MeOH). The cartridge was washed with MeOH (10 mL) then flushed with 7M NH$_3$ in MeOH (10 mL). The MeOH/NH$_3$ was removed in vacuo to afford the title compound as a brown oil (35 mg, 23% yield). LC-MS: Rt 0.66 min; MS m/z 320.2 [M+2]$^+$ [Method A]. $^1$H NMR (400 MHz, DMSO-$d_6$) δ ppm 2.99 (d, J=7.07 Hz, 2H), 2.11-2.22 (m, 1H), 1.44-1.52 (m, 2H), 1.07 (s, 6H), 0.98 (s, 6H), 0.82 (t, J=12.38 Hz, 2H).

Step 3: 2-(2-Methoxy-4-(1H-pyrazol-1-yl)phenyl)-5-((2,2,6,6-tetramethylpiperidin-4-yl)methyl)-1,3,4-thiadiazole To a stirred suspension of 1-(3-methoxy-4-(4,4,5,5-tetramethyl-1,3,2-dioxaborolan-2-yl)phenyl)-1H-pyrazole [Intermediate 4] [39 mg, 0.128 mmol) and 2-bromo-5-((2,2,6,6-tetramethylpiperidin-4-yl)methyl)-1,3,4-thiadiazole (34 mg, 0.107 mmol) in dioxane (1 mL) was added Pd(PPh$_3$)$_4$ (6 mg, 0.005 mmol), followed by a solution of Na$_2$CO$_3$ (34 mg, 0.32 mmol) in water (0.25 mL). The reaction mixture was purged with nitrogen, sealed, and heated at 120° C. for 1 hour under microwave irradiation. The reaction mixture was diluted with DCM (20 mL) and washed with saturated NaHCO$_{3(aq)}$ (10 mL). The organic phase was separated and concentrated in vacuo to afford the crude product as a brown oily residue. The crude material was purified by UV directed preparative HPLC under acidic conditions (formic acid modified) and the product containing fractions were loaded onto a 1 g SCX cartridge (pre-wet with MeOH). The cartridge was washed with MeOH (10 mL) then flushed with 7M NH$_3$ in MeOH (10 mL). The MeOH/NH$_3$ was removed in vacuo to afford the title compound as a slightly off-white solid 28.6 mg, 65% yield). LC-MS: Rt 0.88 min; MS m/z 412.5 [M+H]$^+$ [Method A]. $^1$H NMR (400 MHz, DMSO-$d_6$) δ ppm 8.70 (d, J=2.53 Hz, 1H), 8.39 (d, J=8.59 Hz, 1H), 7.83 (d, J=1.01 Hz, 1H), 7.73 (d, J=1.52 Hz, 1H), 7.67 (dd, J=8.59, 2.02 Hz, 1H), 6.64-6.61 (m, 1H), 4.11 (s, 3H), 3.01 (d, J=6.57 Hz, 2H), 2.17-2.28 (m, 1H), 1.53 (dd, J=12.63, 2.53 Hz, 2H), 1.09 (s, 6H), 1.00 (s, 6H), 0.86 (t, J=12.38 Hz, 2H).

Example 99

Synthesis of 2-(2,3-difluoro-4-(1H-pyrazol-4-yl)phenyl)-5-(2,7-diazaspiro[3.5]nonan-2-yl)-1,3,4-thiadiazole

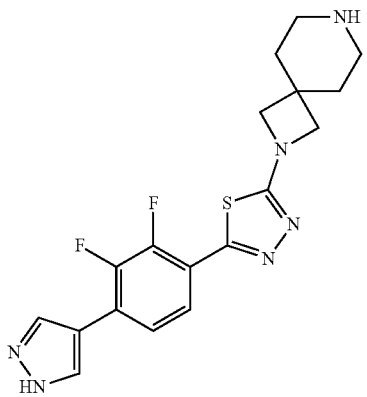 [SMILES: Fc1c(-c2cn[nH]c2)ccc(-c2nnc(N3CC4(CCNCC4)C3)s2)c1F]

Step 1: tert-Butyl 2-(5-bromo-1,3,4-thiadiazol-2-yl)-2,7-diazaspiro[3.5]nonane-7-carboxylate A stirred suspension of 2,5-dibromo-1,3,4-thiadiazole (245 mg, 1.004 mmol), tert-butyl 2,7-diazaspiro[3.5]nonane- 7-carboxylate (290 mg, 1.105 mmol) and DIPEA (702 μL, 1.02 mmol) in dioxane (2.5 mL) was heated at 120° C. for 1 hour. The reaction mixture was diluted with water (10 mL), extracted with DCM (20 mL), and the organic phase was concentrated onto silica gel. The crude material was purified by flash chromatography using a 24 g silica cartridge running an EtOAc/heptane gradient to afford the title compound as a yellow oil (343 mg, 88% yield). LC-MS: Rt 1.25 min; MS m/z 391.2 [M+2]$^+$ [Method A]. $^1$H NMR (400 MHz, Chloroform-d) δ 3.87 (s, 4H), 3.34-3.43 (m, 4H), 1.73-1.85 (m, 4H), 1.46 (s, 9H).

Step 2: tert-Butyl 2-(5-(4-(benzyloxy)-2,3-difluorophenyl)-1,3,4-thiadiazol-2-yl)-2,7-diazaspiro[3.5]nonane-7-carboxylate Nitrogen was bubbled through a stirred solution of (4-(benzyloxy)-2,3-difluorophenyl)boronic acid (356 mg, 1.349 mmol) and tert-butyl 2-(5-bromo-1,3,4-thiadiazol-2-yl)-2,7-diazaspiro[3.5]nonane-7-carboxylate (343 mg, 0.881 mmol) in dioxane (8 mL). To this solution was added Pd(PPh$_3$)$_4$ (52 mg, 0.045 mmol) followed by a solution of Na$_2$CO$_3$ (286 mg, 2.7 mmol) in water (2 mL). The reaction mixture was sealed and heated at 100° C. for 1 hour under microwave irradiation. The reaction mixture was diluted with EtOAc (150 mL) and washed with water (75 mL). The organic phase was separated, dried over MgSO$_4$, and filtered. The filtrate was concentrated in vacuo to afford the crude product as a light orange/brown solid. The crude material was pre-absorbed onto silica gel and purified by flash chromatography using a 40 g silica cartridge running an EtOAc/heptane gradient to afford the title compound as a white solid (169 mg, 35% yield). LC-MS: Rt 1.62 min; MS m/z 529.4 [M+H]$^+$ [Method A]. $^1$H NMR (400 MHz, DMSO-d$_6$) δ 7.75-7.82 (m, 1H), 7.46-7.51 (m, 2H), 7.36-7.45 (m, 3H), 7.24-7.32 (m, 1H), 5.30 (s, 2H), 3.89 (s, 4H), 3.24-3.31 (m, 4H), 1.66-1.78 (m, 4H), 1.40 (s, 9H).

Step 3: tert-Butyl 2-(5-(2,3-difluoro-4-hydroxyphenyl)-1,3,4-thiadiazol-2-yl)-2,7-diazaspiro[3.5]nonane-7-carboxylate A suspension of tert-butyl 2-(5-(4-(benzyloxy)-2,3-difluorophenyl)-1,3,4-thiadiazol-2-yl)-2,7-diazaspiro[3.5]nonane-7-carboxylate (169 mg, 0.32 mmol) in a 1:3 mixture of MeOH:EtOAc (12 mL) was added to a nitrogen flushed flask containing 10% Pd/C (17 mg). The reaction mixture was placed under hydrogen atmosphere (50 psi) on a Parr shaker for 18 hours. Additional 10% Pd/C (169 mg) was added and the reaction was re-subjected to hydrogenation at 50 psi using a Parr shaker for a further 5 days. The reaction mixture was placed under an inert atmosphere (nitrogen), diluted with 10% MeOH/DCM (50 mL), filtered through celite, and rinsed with DCM. The filtrate was concentrated in vacuo to afford a pale brown solid which was re-dissolved in a 1:1 mixture MeOH:DCM (8 mL) and re-subjected to hydrogenation for 4 days at 50 psi using a Parr shaker and 10% Pd/C (169 mg) as the catalyst. The reaction mixture was diluted with 10% MeOH/DCM (50 mL), filtered through celite, and rinsed with DCM. The filtrate was concentrated in vacuo to afford the crude product as a slightly off-white solid. The crude material was purified by flash chromatography using a 12 g silica cartridge running a MeOH/DCM gradient to afford the title compound as an off-white solid (47 mg, 34% yield). LC-MS: Rt 1.27 min; MS m/z 439.3 [M+H]$^+$ [Method A]. $^1$H NMR (400 MHz, DMSO-d$_6$) δ 11.00 (s, 1H), 7.65 (td, J=8.5, 2.2 Hz, 1H), 6.92 (td, J=8.5, 1.9 Hz, 1H), 3.87 (s, 4H), 3.20-3.31 (m, 4H), 1.67-1.78 (m, 4H), 1.40 (s, 9H).

Step 4: tert-Butyl 2-(5-(2,3-difluoro-4-(((trifluoromethyl)sulfonyl)oxy)phenyl)-1,3,4-thiadiazol-2-yl)-2,7-diazaspiro[3.5]nonane-7-carboxylate A stirred solution of tert-butyl 2-(5-(2,3-difluoro-4-hydroxyphenyl)-1,3,4-thiadiazol-2-yl)-2,7-diazaspiro[3.5]nonane-7-carboxylate (59 mg, 1.35 mmol) and TEA (47 μl, 0.366 mmol) in DCM (1.3 mL) under nitrogen was cooled in an ice bath. To this solution was added 1,1,1-trifluoro-N-phenyl-N-((trifluoromethyl)sulfonyl)methanesulfonamide (51 mg, 0.141 mmol). The reaction mixture was stirred at ice bath temperature for 10 minutes then warmed to room temperature for 18 hours. A further 0.5 eq of 1,1,1-trifluoro-N-phenyl-N-((trifluoromethyl)sulfonyl)methanesulfonamide (24 mg, 0.067 mmol) was added and the reaction mixture was stirred for an additional 3 hours. The reaction mixture was diluted with DCM (20 mL) and washed with saturated NaHCO$_{3(aq)}$ (10 mL). The organic phase was separated and concentrated in vacuo to afford the crude product as a slightly off-white solid. The crude material was purified by flash chromatography using a 12 g silica cartridge running an EtOAc/heptane gradient to afford the title compound as a white solid (68 mg, 89% yield). LC-MS: Rt 1.63 min; MS m/z 571.3 [M+H]$^+$ [Method A]. $^1$H NMR (400 MHz, Chloroform-d) δ 8.12 (ddd, J=9.4, 7.1, 2.5 Hz, 1H), 7.25-7.21 (m, 1H), 3.97 (s, 4H), 3.36-3.47 (m, 4H), 1.77-1.89 (m, 4H), 1.47 (s, 9H).

Step 5: tert-Butyl 2-(5-(2,3-difluoro-4-(1H-pyrazol-4-yl)phenyl)-1,3,4-thiadiazol-2-yl)-2,7-diazaspiro[3.5]nonane-7-carboxylate A mixture of tert-butyl 2-(5-(2,3-difluoro-4-(((trifluoromethyl)sulfonyl)oxy)phenyl)-1,3,4-thiadiazol-2-yl)-2,7-diazaspiro[3.5]nonane-7-carboxylate (68 mg, 0.119 mmol) and 4-(4,4,5,5-tetramethyl-1,3,2-dioxaborolan-2-yl)-1H-pyrazole (35 mg, 0.179 mmol) in dioxane (1 mL) was stirred under nitrogen atmosphere. To this suspension was added Pd(PPh$_3$)$_4$ (7 mg, 0.006 mmol) followed by a solution of Na$_2$CO$_3$ (38 mg, 0.358 mmol) in water (0.25 mL). The reaction mixture was sealed and heated at 120° C. for 1 hour under microwave irradiation. The reaction mixture was diluted with water (10 mL) and extracted with DCM (20 mL). The organic phase was separated and concentrated in vacuo to afford the crude product as an off-white solid. The crude material was purified by UV directed preparative HPLC under basic conditions (NH$_4$OH modified) to afford he title compound as a white solid (11 mg, 19% yield). MS m/z 489.1 [M+H]$^+$, $^1$H NMR (400 MHz, DMSO-d$_6$) δ 13.30 (s, 1H), 8.18 (s, 2H), 7.85 (ddd, J=8.6, 6.7, 1.8 Hz, 1H), 7.70 (ddd, J=8.7, 7.0, 1.8 Hz, 1H), 3.91 (s, 4H), 3.28-3.31 (m, 4H), 1.74 (t, J=5.6 Hz, 4H), 1.40 (s, 9H).

Step 6: 2-(2,3-Difluoro-4-(1H-pyrazol-4-yl)phenyl)-5-(2,7-diazaspiro[3.5]nonan-2-yl)-1,3,4-thiadiazole Hydrochloride Salt HCl (4M solution in dioxane, 113 μL, 0.45 mmol) was added to a stirred suspension of tert-butyl 2-(5-(2,3-difluoro-4-(1H-pyrazol-4-yl)phenyl)-1,3,4-thiadiazol-2-yl)-2,7-diazaspiro[3.5]nonane-7-carboxylate (11 mg, 0.023 mmol) in dioxane (1 mL). The reaction mixture was stirred at room temperature for 18 hours then diluted with a roughly 1:1 mixture of MeOH:DCM (10 mL) and a drop of water was added. The resulting suspension was solubilized by addition of DMSO (5 mL) and the solution was loaded onto a 0.5 g SCX cartridge (pre-wet with MeOH). The cartridge was washed with MeOH (10 mL) then flushed with 10% DCM in [7M NH₃ in MeOH] (10 mL). The DCM/MeOH/NH₃ was removed in vacuo to afford the title compound as an off-white solid (7.4 mg, 85% yield). LC-MS: Rt 0.66 min; MS m/z 389.2 [M+H]⁺ [Method A]. ¹H NMR (400 MHz, DMSO-d₆) δ 13.30 (s, 1H), 8.18 (s, 2H), 7.84 (ddd, J=8.6, 6.8, 1.7 Hz, 1H), 7.70 (ddd, J=8.6, 7.1, 1.7 Hz, 1H), 3.87 (s, 4H), 2.65 (t, J=5.0 Hz, 4H), 1.70 (t, J=5.4 Hz, 4H).

Example 100

Synthesis of 2-(5-(2,7-diazaspiro[3.5]nonan-2-yl)-1,3,4-thiadiazol-2-yl)-3-fluoro-5-(1H-pyrazol-4-yl)phenol

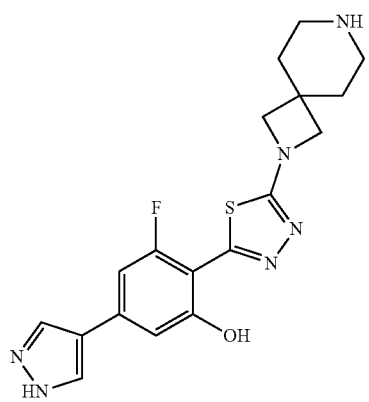 [SMILES: Oc1cc(-c2cn[nH]c2)cc(F)c1-c1nnc(N2CC3(CCNCC3)C2)s1]

Step 1: 5-(4-Bromo-2,6-difluorophenyl)-1,3,4-thiadiazol-2-amine

A stirred mixture of 4-bromo-2,6-difluorobenzoic acid (5 g, 21.1 mmol) and hydrazinecarbothioamide (2.88 g, 31.6 mmol) was cooled under nitrogen in an ice bath. POCl₃ (5.9 mL, 63.3 mmol) was added drop-wise and the reaction was stirred at ice bath temperature for 15 minutes then heated at 78° C. for 3 hours. The reaction mixture was cooled in an ice bath then quenched by addition of ice water (150 mL). The resulting solid was sonicated for 30 minutes to give a free stirring suspension which was left to slurry at room temperature for 72 hours. The solid was collected by vacuum filtration, rinsed with water, and re-suspended in saturated NaHCO₃₍aq₎ (150 mL). This suspension was stirred at room temperature for 18 hours then the solid was collected by vacuum filtration, rinsed with water, and dried in a vacuum oven for 24 hours to give the title compound (5.174 g, 84% yield) which was used in the next step without further purification. LC-MS: Rt 0.99 min; MS m/z 294.2 [M+2]⁺ [Method A]. ¹H NMR (400 MHz, DMSO-d₆) δ ppm 7.68 (d, J=8.08 Hz, 2H), 7.57 (s, 2H).

Step 2: 5-(2-(Benzyloxy)-4-bromo-6-fluorophenyl)-1,3,4-thiadiazol-2-amine

A stirred suspension of NaH (60% dispersion in mineral oil, 151 mg, 3.77 mmol) in THF (10 mL) was cooled under nitrogen in an ice bath. To this suspension was added a solution of benzyl alcohol (0.372 mL, 3.59 mmol) in THF (5 mL) drop-wise. On completion of addition, the resulting suspension was stirred at ice bath temperature for 5 minutes, then room temperature for 10 minutes, before being slowly added to a stirred, ice-bath cooled suspension of 5-(4-bromo-2,6-difluorophenyl)-1,3,4-thiadiazol-2-amine (1 g, 3.42 mmol) in THF (20 mL). The resulting yellow/brown suspension was stirred at ice bath temperature for 15 minutes, room temperature for 1 hour then heated at 50° C. for 18 hours. The reaction was quenched by addition of saturated NH₄Cl₍aq₎ (30 mL), diluted with water (30 mL), and extracted with EtOAc (100 mL). The organic phase was separated, dried over MgSO₄, and filtered. The filtrate was concentrated onto silica gel and the crude material was purified by flash chromatography using an 80 g silica cartridge running an EtOAc/heptane gradient to afford the title compound as a pale yellow solid (488 mg, 37% yield). LC-MS: Rt 1.19 min; MS m/z 282.0 M⁺ [Method A]. ¹H NMR (400 MHz, DMSO-d₆) δ 7.27-7.47 (m, 9H), 5.28 (s, 2H).

Step 3: 2-(2-(Benzyloxy)-4-bromo-6-fluorophenyl)-5-bromo-1,3,4-thiadiazole 5-(2-(Benzyloxy)-4-bromo-6-fluorophenyl)-1,3,4-thiadiazol-2-amine (487 mg, 1.281 mmol) was added portionwise to a stirred solution of CuBr₂ (343 mg, 1.537 mmol) and t-BuNO₂ (226 μL, 1.921 mmol) in MeCN (4.2 mL) under nitrogen. The reaction mixture was stirred at room temperature for 18 hours. The reaction was quenched by addition of water (40 mL), then 28% NH₄OH₍aq₎ (5 mL) was added, and the resulting suspension was extracted with DCM (50 mL). The organic phase was separated and concentrated onto silica gel. The crude material was purified by flash chromatography using a 40 g silica cartridge running an EtOAc/heptane gradient to afford the title compound as a white solid (253 mg, 44% yield). LC-MS: Rt 1.53 min; MS m/z 445.0 [M+H]⁺ [Method A]. ¹H NMR (400 MHz, DMSO-d₆) δ 7.31-7.56 (m, 7H), 5.38 (s, 2H).

Step 4: tert-Butyl 2-(5-(2-(benzyloxy)-4-bromo-6-fluorophenyl)-1,3,4-thiadiazol-2-yl)-2,7-diazaspiro[3.5]nonane-7-carboxylate To a stirred suspension of 2-(2-(benzyloxy)-4-bromo-6-fluorophenyl)-5-bromo-1,3,4-thiadiazole (252 mg, 0.567 mmol) and tert-butyl 2,7-diazaspiro[3.5]nonane-7-carboxylate hydrochloride (179 mg, 0.681 mmol) in dioxane (2.8 mL) was added TEA (237 μL, 1.702 mmol) and the mixture was heated at 120° C. for 3 hours. The reaction mixture was cooled to RT, diluted with water (20 mL), extracted with DCM (20 mL). The organic phase was concentrated in vacuo to afford the crude product as a yellow oily residue. The crude material was purified by flash chromatography using a 40 g silica cartridge running an EtOAc/heptane gradient to afford the title compound as a white solid (150 mg, 45% yield). LC-MS: Rt 1.62 min; MS m/z 591.3 [M+H]⁺ [Method A]. ¹H NMR (400 MHz, DMSO-d₆) δ 7.29-7.47 (m, 7H), 5.31 (s, 2H), 3.83 (s, 4H), 3.17-3.30 (m, 4H), 1.65-1.77 (m, 4H), 1.40 (s, 9H).

Step 5: tert-Butyl 2-(5-(2-(benzyloxy)-6-fluoro-4-(1H-pyrazol-4-yl)phenyl)-1,3,4-thiadiazol-2-yl)-2,7-diazaspiro[3.5]nonane-7-carboxylate A mixture of tert-butyl 2-(5-(2-(benzyloxy)-4-bromo-6-fluorophenyl)-1,3,4-thiadiazol-2-yl)-2,7-diazaspiro[3.5]nonane-7-carboxylate (150 mg, 0.254 mmol) and 4-(4,4,5,5-tetramethyl-1,3,2-dioxaborolan-2-yl)-1H-pyrazole (74 mg, 0.382 mmol) in dioxane (2 mL) was stirred under nitrogen atmosphere. To this suspension was added Pd(PPh₃)₄ (15 mg, 0.013 mmol) followed by a solution of Na₂CO₃ (81 mg, 0.763 mmol) in water (0.5 mL). The reaction mixture was sealed and heated at 120° C. for 1 hour under microwave irradiation. A further 1.5 eq of 4-(4,4,5,5-tetramethyl-1,3,2-dioxaborolan-2-yl)-1H-pyrazole (74 mg, 0.382 mmol) was added and the reaction was heated for an additional hour at 120° C. under microwave irradiation. A further 1.5 eq of 4-(4,4,5,5-tetramethyl-1,3,2-dioxaborolan-2-yl)-1H-pyrazole (74 mg, 0.382 mmol) was added, followed by an additional 0.05 eq of Pd(PPh$_3$)$_4$ (15 mg, 0.013 mmol) and the reaction mixture was heated for 1 hour at 120° C. under microwave irradiation. The reaction mixture was diluted with water (15 mL) and extracted with DCM (20 mL). The organic phase was concentrated in vacuo to afford the crude product as a pale brown oil. The crude material was purified by flash chromatography using a 24 g silica cartridge running a MeOH/DCM gradient to afford a pale brown oil. The oil was purified using a 24 g silica running an EtOAc/heptane gradient to afford the title compound as a clear glass-like solid (86 mg, 58% yield). MS m/z 577.2 [M+H]$^+$, $^1$H NMR (400 MHz, DMSO-d$_6$) δ 13.10 (s, 1H), 8.39 (d, J=1.8 Hz, 1H), 8.09 (d, J=2.0 Hz, 1H), 7.47-7.57 (m, 2H), 7.33-7.44 (m, 4H), 7.28 (dd, J=11.6, 1.5 Hz, 1H), 5.35 (s, 2H), 3.82 (s, 4H), 3.18-3.32 (m, 4H), 1.63-1.77 (m, 4H), 1.40 (s, 9H).

Step 6: tert-Butyl 2-(5-(2-fluoro-6-hydroxy-4-(1H-pyrazol-4-yl)phenyl)-1,3,4-thiadiazol-2-yl)-2,7-diazaspiro[3.5]nonane-7-carboxylate A solution of tert-butyl 2-(5-(2-(benzyloxy)-6-fluoro-4-(1H-pyrazol-4-yl)phenyl)-1,3,4-thiadiazol-2-yl)-2,7-diazaspiro[3.5]nonane-7-carboxylate (86 mg, 0.149 mmol) in a 1:1: mixture MeOH:DCM (3 mL) was added to a nitrogen flushed flask containing 10% Pd/C (8.6 mg). The reaction mixture was placed under a hydrogen atmosphere (balloon) and stirred at room temperature for 18 hours. The reaction mixture was flushed with nitrogen and an additional 8.6 mg of 10% Pd/C was added. The reaction was diluted with 1:1 MeOH:DCM (3 mL), and again placed under a hydrogen atmosphere (balloon) and stirred at room temperature for an additional 5 days. The reaction mixture was flushed with nitrogen, diluted with 10% MeOH in DCM (50 mL) and filtered through celite. The filtrate was concentrated in vacuo to afford a pale brown/off-white solid. The solid was re-dissolved in 25% MeOH in DCM (10 mL) and added to a nitrogen flushed flash containing 10% Pd/C (8.6 mg). The reaction mixture was placed under a hydrogen atmosphere (balloon) and left to stir at room temperature for 18 hours. The reaction mixture was diluted with 10% MeOH in DCM (50 mL) and filtered through celite. The filtrate was concentrated in vacuo to afford the crude product as a brown solid. The crude material was purified by flash chromatography using a 10 g silica cartridge running a MeOH/DCM gradient and collecting by mass to afford an the title compound as a pale brown solid (54 mg, 74% yield). LC-MS: Rt 1.33 min; MS m/z 487.3 [M+H]$^+$ [Method A]. $^1$H NMR (400 MHz, DMSO-d$_6$) δ 13.09 (s, 1H), 11.92 (s, 1H), 8.36 (d, J=1.7 Hz, 1H), 8.04 (d, J=1.9 Hz, 1H), 7.22 (dd, J=12.6, 1.6 Hz, 1H), 7.14-7.19 (m, 1H), 3.92 (s, 4H), 3.28-3.31 (m, 4H), 1.69-1.79 (m, 4H), 1.40 (s, 9H).

Step 7: 2-(5-(2,7-Diazaspiro[3.5]nonan-2-yl)-1,3,4-thiadiazol-2-yl)-3-fluoro-5-(1H-pyrazol-4-yl)phenol HCl (4M solution in dioxane, 545 μL, 2.179 mmol) was added to a stirred suspension of tert-butyl 2-(5-(2,3-difluoro-4-(1H-pyrazol-4-yl)phenyl)-1,3,4-thiadiazol-2-yl)-2,7-diazaspiro[3.5]nonane-7-carboxylate (53 mg, 0.109 mmol) in dioxane (4 mL). The reaction mixture was stirred at room temperature for 2 hours then diluted with dioxane (2 mL), MeOH (5 mL), DMSO (5 mL) and a small amount of water, then loaded onto a 2 g SCX cartridge (pre-wet with MeOH). The cartridge was washed with MeOH (15 mL) then flushed with 10% DCM in [7M NH$_3$ in MeOH] (20 mL). The DCM/MeOH/NH$_3$ was removed in vacuo to afford the crude product as a brown solid. The crude material was heated in MeOH (5 mL) and the resulting suspension was cooled to room temperature then filtered under vacuum and rinsed with MeOH to afford the title compound as a pale brown solid (23 mg, 55% yield). LC-MS: Rt 0.68 min; MS m/z 387.2 [M+H]$^+$ [Method A]. $^1$H NMR (400 MHz, DMSO-d$_6$) δ 13.07 (s, 1H), 8.17 (s, 2H), 7.15-7.05 (m, 2H), 3.87 (s, 4H), 2.70 (t, J=5.1 Hz, 4H), 1.73 (t, J=5.3 Hz, 4H).

Example 101

Synthesis of 4-methoxy-1-methyl-3-(5-(methyl(2,2,6,6-tetramethylpiperidin-4-yl)amino)-1,3,4-thiadiazol-2-yl)quinolin-2(1H)-one

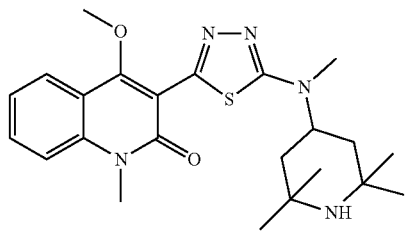

Step 1:
3-Bromo-4-methoxy-1-methylquinolin-2(1H)-one

To a solution of 4-methoxy-1-methylquinolin-2(1H)-one (2 g, 10.57 mmol) in THF (5 mL) at 0° C. under N$_2$ atmosphere was added N-bromosuccinimide (2.26 g, 12.68 mmol) in portions over a period of 1 hour. The suspension was stirred at 0° C. for 1 hour then at room temperature for 2 hours. The solvent was removed in vacuo and CH$_2$Cl$_2$ was added to re-dissolve the residue. The solution was washed twice with a cold saturated NaHCO$_3$ solution and with cold H$_2$O then dried over anhydrous MgSO$_4$. The solvent was removed in vacuo and the resulting solid residue was triturated several times with Et$_2$O. The resulting solid was dried in vacuo to afford 3-bromo-4-methoxy-1-methylquinolin-2(1H)-one (2.7 g, MS: 269.9 [M+H$^+$])

Step 2: (4-Methoxy-1-methyl-2-oxo-1,2-dihydroquinolin-3-yl)boronic acid

To a solution of 3-bromo-4-methoxy-1-methylquinolin-2(1H)-one (2.7 g, 10.07 mmol) in THF (5 mL) was added n-butyllithium (2.5 M in Hexane, 4.03 mL) under nitrogen atmosphere at −78° C. and the reaction mixture was maintained at this temperature for 1 h. A cooled solution of trimethyl borate (1.35 mL, 12.08 mmol) was added at −78° C., and the reaction mixture was maintained at this temperature for 2 h. The reaction mixture was warmed to room temperature and stirred overnight. The reaction mixture was diluted with 1M HCl and a white solid precipitated from the solution. The precipitate was filtered, washed with water and EtOAc, then dried under high vacuum to provide (4-methoxy-1-methyl-2-oxo-1,2-dihydroquinolin-3-yl)boronic acid (1.5 g, MS: 234.1 [M+H$^+$].)

Step 3: 4-Methoxy-1-methyl-3-(5-(methyl(2,2,6,6-tetramethylpiperidin-4-yl)amino)-1,3,4-thiadiazol-2-yl)quinolin-2(1H)-one A degassed reaction mixture of (4-methoxy-1-methyl-2-oxo-1,2-dihydroquinolin-3-yl)boronic acid (500 mg, 2.15 mmol), 5-bromo-N-methyl-N-(2,2,6,6-tetramethylpiperidin-4-yl)-1,3,4-thiadiazol-2-amine (858 mg, 2.57 mmol), tetrakis (triphenylphosphine)palladium(0) (248 mg, 0.215 mmol) and Na$_2$CO$_3$ (682 mg, 6.44 mmol) in 1,4-dioxane (5 mL) and water (1 mL) was heated via microwave irradiation at 100° C. for 1 h. After cooling to room temperature, the mixture was filtered through celite, washed with MeOH then the filtrate was concentrated. The residue was purified by silica gel chromatography (2%~10% 2M NH$_3$ in MeOH/DCM) to give 4-methoxy-1-methyl-3-(5-(methyl(2,2,6,6-tetramethylpiperidin-4-yl)amino)-1,3,4-thiadiazol-2-yl)quinolin-2(1H)-one (240 mg, MS: 442.1 [M+H$^+$].) (4 mg, MS: 442.0 [M+H$^+$], LCMS Rt=1.25 min (LCMS method D); $^1$H NMR (400 MHz, METHANOL-d$_4$) δ ppm 8.55 (s, 1H), 8.14 (dd, J=8.08, 1.52 Hz, 1H), 7.72-7.81 (m, 1H), 7.61-7.69 (m, 1H), 7.33-7.45 (m, 1H), 4.61 (br. s., 1H), 3.94 (s, 3H), 3.78 (s, 3H), 3.11 (s, 3H), 1.95 (d, J=12.13 Hz, 2H), 1.79 (br. s., 2H), 1.50 (s, 6H), 1.39 (br. s., 6H).

Example 102

Synthesis of 4-hydroxy-1-methyl-3-(5-(methyl(2,2,6,6-tetramethylpiperidin-4-yl)amino)-1,3,4-thiadiazol-2-yl)quinolin-2(1H)-one

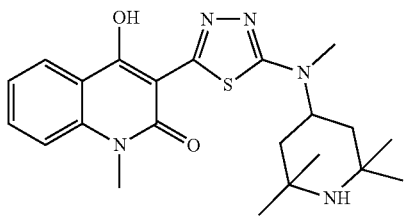

By employing the methods of Example 15, Example 101 was reacted with PhSH to provide 5-(1H-imidazole-1-yl)-2-(6-(methyl(2,2,6,6-tetramethyl-piperidin-4-yl)amino-)pyridazin-3-yl)phenol as a pale yellow powder (2 mg, MS: 428.2 [M+H$^+$], LCMS Rt=0.57 min (LCMS method D); $^1$H NMR (400 MHz, METHANOL-d$_4$) δ ppm 8.22 (d, J=8.08 Hz, 1H), 7.68 (t, J=8.08 Hz, 1H), 7.53 (d, J=8.59 Hz, 1H), 7.31 (t, J=7.33 Hz, 1H), 4.38 (br. s., 1H), 3.72 (s, 3H), 3.07 (s, 3H), 1.80 (dd, J=12.63, 3.03 Hz, 2H), 1.52-1.65 (m, 2H) 1.37 (s, 6H) 1.23-1.29 (m, 6H).

Example 103

Synthesis of 3-(5-(methyl(2,2,6,6-tetramethylpiperidin-4-yl)amino)-1,3,4-thiadiazol-2-yl)quinolin-2(1H)-one

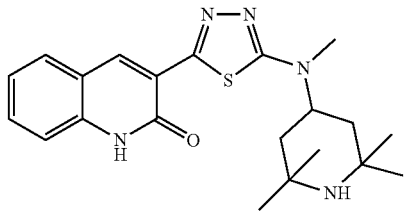

Step 1: (2-Oxo-1,2-dihydroquinolin-3-yl)boronic acid

To a microwave vial was added 3-bromo-2-hydroxyquinoline (50 mg, 0.223 mmol), bis(pinacolato)diboron (113 mg, 0.446 mmol), potassium acetate (66 mg, 0.669 mmol), PdCl$_2$ (dppf).CH$_2$Cl$_2$ (18.22 mg, 0.022 mmol), and dppf (12.37 mg, 0.022 mmol), followed by addition of 1,4-dioxane (6 mL). The reaction mixture was purged with N$_2$ and stirred under N$_2$ atmosphere at 90° C. overnight. The reaction mixture was filtered through a disposable filter funnel, concentrated in vacuo, and purified by silica gel chromotography (10% to 60% EtOAc in heptane) to afford (2-oxo-1,2-dihydroquinolin-3-yl)boronic acid (30 mg, MS: 190.1 [M+H+].)

Step 2: 3-(5-(Methyl(2,2,6,6-tetramethylpiperidin-4-yl)amino)-1,3,4-thiadiazol-2-yl)quinolin-2(1H)-one Following a similar procedure as described for Step 3 in Example 101, (2-oxo-1,2-dihydroquinolin-3-yl)boronic acid and 5-bromo-N-methyl-N-(2,2,6,6-tetramethylpiperidin-4-yl)-1,3,4-thiadiazol-2-amine (858 mg, 2.57 mmol) were reacted to provide the crude product, which was purified by preparative HPLC under basic condition to give 3-(5-(methyl (2,2,6,6-tetramethylpiperidin-4-yl)amino)-1,3,4-thiadiazol-2-yl)quinolin-2(1H)-one (14 mg, MS: 398.2 [M+H$^+$], LCMS Rt=0.51 min (LCMS method D); $^1$H NMR (400 MHz, METHANOL-d$_4$) δ ppm 8.74 (s, 1H), 7.67-7.80 (m, 1H), 7.47-7.57 (m, 1H), 7.31 (d, J=8.08 Hz, 1H), 7.19-7.27 (m, 1H), 4.34 (br. s., 1H), 2.99 (s, 3H), 1.71 (dd, J=12.63, 3.03 Hz, 2H), 1.50 (t, J=12.38 Hz, 2H), 1.28 (s, 6H), 1.10-1.23 (m, 6H).

Example 104

Synthesis of 1-methyl-3-(5-(methyl(2,2,6,6-tetramethylpiperidin-4-yl)amino)-1,3,4-thiadiazol-2-yl)quinolin-2(1H)-one

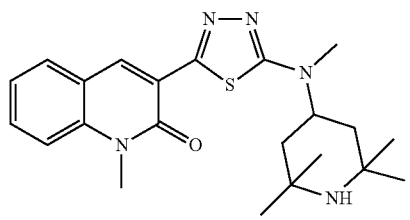

Step 1: 3-Bromo-1-methylquinolin-2(1H)-one

To a solution of 3-bromo-2-hydroxyquinoline (50 mg, 0.223 mmol) in DMF (1 mL) was added methyl iodide (0.017 mL, 0.268 mmol) and potassium carbonate (46.3 mg, 0.335 mmol.) at room temperature. The reaction mixture was stirred for 16 hours at room temperature. Water was added and the solution was extracted with ethyl acetate. The organic layer was washed with water then aqueous saturated sodium chloride solution. The organic layer was dried over sodium sulfate, filtered, and concentrated in vacuo. The resulting residue was purified by silica gel column chromatography (developing solvent: hexane/ethyl acetate=/1) to give 3-bromo-1-methylquinolin-2(1H)-one (52 mg, MS: 238.1 [M+H$^+$].)

Step 2: 1-Methyl-3-(5-(methyl(2,2,6,6-tetramethylpiperidin-4-yl)amino)-1,3,4-thiadiazol-2-yl)quinolin-2(1H)-one By employing the methods of Example 103, 1-methyl-3-(5-(methyl(2,2,6,6-tetramethylpiperidin-4-yl)amino)-1,3,4-thiadiazol-2-yl)quinolin-2(1H)-one was obtained as a pale yellow powder (28 mg, MS: 412.2 [M+H$^+$], LCMS Rt=0.62 min (LCMS method D); $^1$H NMR (400 MHz, METHANOL-d$_4$) δ ppm 8.85 (s, 1H), 7.90 (d, J=7.58 Hz, 1H), 7.73-7.81 (m, 1H), 7.66-7.72 (m, 1H), 7.42 (t, J=7.58 Hz, 1H), 4.73-4.84 (m, 1H), 3.88 (s, 3H), 3.10-3.19 (m, 3H), 2.07 (dd, J=13.64, 3.54 Hz, 2H), 1.96 (t, J=12.88 Hz, 2H), 1.61-1.69 (m, 6H), 1.46-1.57 (m, 6H).

Example 105

Synthesis of 2-(2-chloro-4-(1H-pyrazol-4-yl)phenyl)-5-((3aR,6aS)-hexahydropyrrolo[3,4-c]pyrrol-2(1H)-yl)-1,3,4-thiadiazole Hydrochloride Salt

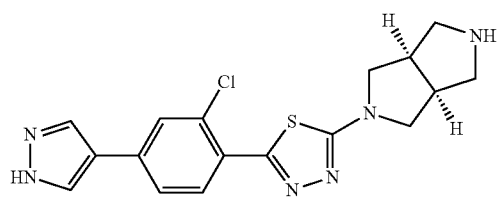 [SMILES: Clc1cc(-c2cn[nH]c2)ccc1-c1nnc(N2C[C@H]3CNC[C@H]3C2)s1]

Step 1: 5-(4-Bromo-2-chlorophenyl)-1,3,4-thiadiazol-2-amine

To an ice-cooled mixture of 4-bromo-2-chlorobenzoic acid (3 g, 12.74 mmol) and hydrazinecarbothioamide (2.17 g, 23.81 mmol) was added phosphorous oxychloride (3.56 mL, 38.2 mmol) slowly. The mixture was heated at 78° C. overnight. After cooling to 0° C., ice water was added. The mixture was vigorously stirred for 1 h. The resulting precipitate was filtered and washed with water then re-suspended in a saturated NaHCO$_3$ solution and water (1:1) for 1 h. The solid was filtered, washed with water, and concentrated in vacuo to give 5-(4-bromo-2-chlorophenyl)-1,3,4-thiadiazol-2-amine (2.4 g, MS: 291.8 [M+H$^+$].)

Step 2: 5-(2-Chloro-4-(1H-pyrazol-4-yl)phenyl)-1,3,4-thiadiazol-2-amine

To a microwave vial was added 5-(4-bromo-2-chlorophenyl)-1,3,4-thiadiazol-2-amine (500 mg, 1.721 mmol), 4-pyrazole boronic acid pinacle ester (668 mg, 3.44 mmol), cesium carbonate (1.68 g, 5.16 mmol), Pd$_2$(dba)$_3$.CH$_2$Cl$_2$ (178 mg, 0.172 mmol), and Xphos (82 mg, 0.172 mmol), followed by addition of 1,4-dioxane (2 mL)/H$_2$O (0.5 mL). The vial was purged with N$_2$ 3 times and the reaction mixture was heated via microwave irradiation at 100° C. for 1 h. The reaction mixture was filtered through a disposable filter funnel, washed with EtOAc, concentrated in vacuo, and purified by silica gel chromotography (2% to 15% MeOH/DCM) to afford 5-(2-chloro-4-(1H-pyrazol-4-yl)phenyl)-1,3,4-thiadiazol-2-amine (250 mg, MS: 278.0 [M+H+].)

Step 3: (3aR,6aS)-tert-Butyl 5-(5-(2-chloro-4-(1H-pyrazol-4-yl)phenyl)-1,3,4-thiadiazol-2-yl)hexahydropyrrolo[3,4-c]pyrrole-2(1H)-carboxylate 5-(2-Chloro-4-(1H-pyrazol-4-yl)phenyl)-1,3,4-thiadiazol-2-amine (250 mg, 0.9 mmol) was added, portion-wise over about 5 minutes, to a stirred solution of CuBr$_2$ (241 mg, 1.08 mmol) and tert-butyl nitrite (139 mg, 1.35 mmol) in MeCN (5 mL) under nitrogen atmosphere. On completion of the addition, the reaction mixture was left to stir at room temperature for 18 hours. The reaction mixture was quenched by addition of saturated NH$_4$Cl$_{(aq)}$ and extracted with EtOAc. The organic phase was separated and concentrated in vacuo to afford 2-bromo-5-(2-chloro-4-(1H-pyrazol-4-yl)phenyl)-1,3,4-thiadiazole a brown solid, which was used without further purification. A degassed reaction mixture of 2-bromo-5-(2-chloro-4-(1H-pyrazol-4-yl)phenyl)-1,3,4-thiadiazole (40 mg, 0.117 mmol), cis-2-boc-hexahydropyrollo[3,4-c]pyrrole (24.86 mg, 0.117 mmol), potassium fluoride (7.48 mg, 0.129 mmol), 18-crown-6 (30.9 mg, 0.117 mmol) and DIEA (0.041 ml, 0.234 mmol) in NMP (1 mL) was heated under microwave irradiation at 190° C. for 1 h. After cooling to RT, the mixture was filtered through celite, washed with MeOH, and the filtrate was concentrated. The residue was dissolved in DMSO and purified by preparative HPLC under basic conditions to give (3aR,6aS)-tert-butyl 5-(5-(2-chloro-4-(1H-pyrazol-4-yl)phenyl)-1,3,4-thiadiazol-2-yl)hexahydropyrrolo[3,4-c]pyrrole-2(1H)-carboxylate (10 mg, MS: 473.0 [M+H+].)

Step 4: 2-(2-Chloro-4-(1H-pyrazol-4-yl)phenyl)-5-((3aR,6aS)-hexahydropyrrolo[3,4-c]pyrrol-2(1H)-yl)-1,3,4-thiadiazole Hydrochloride Salt A solution of (3aR,6aS)-tert-butyl 5-(5-(2-chloro-4-(1H-pyrazol-4-yl)phenyl)-1,3,4-thiadiazol-2-yl)hexahydropyrrolo[3,4-c]pyrrole-2(1H)-carboxylate (10 mg, 0.021 mmol) in 1,4-dioxane (2 mL) was treated with 4M HCl in dioxane (1 mL) and stirred at room temperature for 3 h. The reaction mixture was concentrated in vacuo to give the title compound (2 mg, MS: 373.1 [M+H⁺], LCMS Rt=0.44 min (LCMS method D); ¹H NMR (400 MHz, METHANOL-d₄) δ ppm 7.99 (br. s., 2H), 7.92 (d, J=8.59 Hz, 1H), 7.71 (d, J=2.02 Hz, 1H), 7.53-7.60 (m, 1H), 3.68 (dd, J=10.86, 7.83 Hz, 2H), 3.36 (dd, J=10.86, 3.28 Hz, 2H), 3.03-3.11 (m, 2H), 2.97-3.03 (m, 2H), 2.75 (dd, J=11.12, 3.03 Hz, 2H).

By employing similar methods as described for the preparation of Example 105, using appropriate starting materials, the following compounds were prepared:

| Example | Compound | LCMS M + 1, Rt, Method | ¹H NMR 400 MHz |
|---|---|---|---|
| 106 | 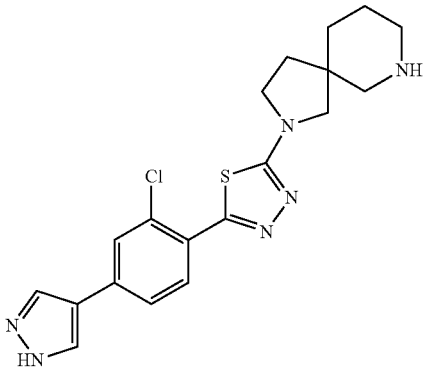<br>2-(2-chloro-4-(1H-pyrazol-4-yl)phenyl)-5-(2,7-diazaspiro[4.5]decan-2-yl)-1,3,4-thiadiazole•Hydrochloride Salt | 401.1, 0.47 min, D | METHANOL-d₄ δ ppm 7.99 (br. s., 2H) 7.92 (d, J = 8.08 Hz, 1H) 7.70 (d, J = 1.52 Hz, 1H) 7.56 (dd, J = 8.08, 1.52 Hz, 1H) 3.49-3.58 (m, 2H) 3.45 (d, J = 10.11 Hz, 1H) 3.28 (d, J = 10.61 Hz, 1H) 2.60-2.75 (m ,4H) 1.98 (dt, J = 13.01, 6.38 Hz, 1H) 1.86 (dt, J = 12.76, 7.77 Hz, 1H) 1.48-1.66 (m, 4H) |
| 107 | 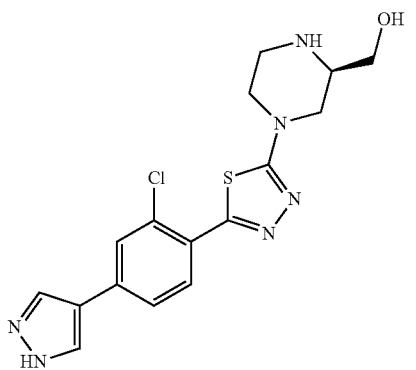<br>(R)-(4-(5-(2-chloro-4-(1H-pyrazol-4-yl)phenyl)-1,3,4-thiadiazol-2-yl)piperazin-2-yl)methanol•Hydrochloride Salt | 377.1, 0.41 min, D | METHANOL-d₄ δ ppm 8.00 (br. s., 2H) 7.91 (d, J = 8.08 Hz, 1H) 7.72 (d, J = 2.02 Hz, 1H) 7.57 (dd, J = 8.34, 1.77 Hz, 1H) 3.74-3.90 (m, 2H) 3.52 (d, J = 5.56 Hz, 1H) 3.47-3.51 (m, 2H) 2.99-3.06 (m, 1 H) 2.91-2.99 (m, 1H) 2.84-2.90 (m, 2H) |

Example 108

Synthesis of 2-(5-(methyl(2,2,6,6-tetramethylpiperidin-4-yl)amino)-1,3,4-thiadiazol-2-yl)benzo[b]thiophene-5-carbonitrile

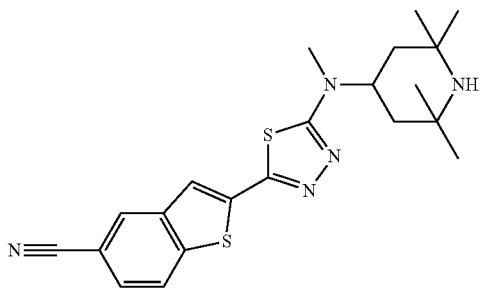

In a microwave vial, a mixture of 5-bromo-N-methyl-N-(2,2,6,6-tetramethylpiperidin-4-yl)-1,3,4-thiadiazol-2-amine (Intermediate 4, 150 mg, 0.450 mmol), (5-cyanobenzo[b]thiophen-2-yl)boronic acid (128 mg, 0.630 mmol) and sodium carbonate (119 mg, 1.125 mmol) in 4:1 dimethoxyethane/water (3.7 mL) was degassed for 5 minutes. Tetrakis(triphenylphosphine)palladium(0) (52.0 mg, 0.045 mmol) was added and the mixture was heated under microwave irradiation at 140° C. for 0.5 h. The mixture was partitioned between DCM and water then extracted with DCM (4×). The DCM extracts were acidified by addition of HCl in dioxane (4.0 M solution, 113 μl, 0.450 mmol) and concentrated to dryness. SCX purification (1 g column, 7 M ammonia in MeOH elution), followed by flash column chromatography (4 g silica gel, 1-20% 7 N ammonia in MeOH gradient, in DCM) provided 2-(5-(methyl(2,2,6,6-tetramethylpiperidin-4-yl)amino)-1,3,4-thiadiazol-2-yl)benzo[b]thiophene-5-carbonitrile (49 mg) as a light yellow solid. LC/MS Rt=0.52 min. MS=412.1 (M+1) [Method D]. $^1$H NMR (400 MHz, METHANOL-$d_4$) δ ppm 8.27 (d, J=1.0 Hz, 1H), 8.11 (d, J=8.6 Hz, 1H), 7.82 (s, 1H), 7.68 (dd, J=8.6, 1.5 Hz, 1H), 4.43 (t, J=12.4 Hz, 1H), 3.12 (s, 3H), 1.82 (dd, J=12.6, 3.0 Hz, 2H), 1.60 (t, J=12.1 Hz, 2H), 1.37 (s, 6H), 1.25 (s, 6H).

Example 109

Synthesis of 5-(3-chlorobenzo[b]thiophen-2-yl)-N-methyl-N-(2,2,6,6-tetramethylpiperidin-4-yl)-1,3,4-thiadiazol-2-amine

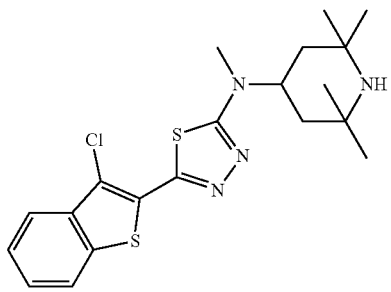

Step 1: 5-(Benzo[b]thiophen-2-yl)-N-methyl-N-(2,2,6,6-tetramethylpiperidin-4-yl)-1,3,4-thiadiazol-2-amine 5-Bromo-N-methyl-N-(2,2,6,6-tetramethylpiperidin-4-yl)-1,3,4-thiadiazol-2-amine (Intermediate 4, 150 mg, 0.450 mmol) was coupled with benzo[b]thiophen-2-ylboronic acid (112 mg, 0.630 mmol) using the method of Example 108 for Suzuki coupling. SCX purification (2 g column, 7 M ammonia in MeOH elution) followed by flash column chromatography (12 g silica gel, 1-20% gradient of 3.5 M ammonia in methanol, in DCM) provided 5-(benzo[b]thiophen-2-yl)-N-methyl-N-(2,2,6,6-tetramethylpiperidin-4-yl)-1,3,4-thiadiazol-2-amine as a light yellow solid (48 mg). MS=387.0 (M+1). $^1$H NMR (400 MHz, METHANOL-$d_4$) δ ppm 7.82-7.95 (m, 2H), 7.72 (s, 1H), 7.37-7.46 (m, 2H), 4.40 (t, J=12.4 Hz, 1H), 3.11 (s, 3H), 1.82 (dd, J=12.6, 3.5 Hz, 2H), 1.59 (t, J=12.4 Hz, 2H), 1.37 (s, 6H), 1.25 (s, 6H).

Step 2: 5-(3-Chlorobenzo[b]thiophen-2-yl)-N-methyl-N-(2,2,6,6-tetramethylpiperidin-4-yl)-1,3,4-thiadiazol-2-amine A mixture of 5-(benzo[b]thiophen-2-yl)-N-methyl-N-(2,2,6,6-tetramethylpiperidin-4-yl)-1,3,4-thiadiazol-2-amine (37 mg, 0.096 mmol) and N-chlorosuccinimide (15.34 mg, 0.115 mmol) in DCE:AcOH (1:1) (1 mL) was heated at 90° C. for six hours. The reaction was cooled to RT, diluted with saturated sodium bicarbonate, extracted with ethyl acetate (3×), and DCM (2×). The combined organic extracts were washed with brine, dried over magnesium sulfate and concentrated to a crystalline yellow solid. Purification by flash column chromatography (4 g silica gel, 1-17% 3.5 N ammonia in MeOH gradient in DCM over 30 column volumes) provided 5-(3-chlorobenzo[b]thiophen-2-yl)-N-methyl-N-(2,2,6,6-tetramethylpiperidin-4-yl)-1,3,4-thiadiazol-2-amine as a yellow solid (18 mg). LC/MS Rt=0.58 min. MS=420.9 (M−1). $^1$H NMR (400 MHz, METHANOL-$d_4$) δ ppm 7.84-7.99 (m, 2H), 7.47-7.60 (m, 2H), 4.53 (m, 1H), 3.14 (s, 3H), 1.83 (d, J=9.6 Hz, 2H), 1.55-1.68 (m, 2H), 1.38 (s, 6H), 1.26 (s, 6H).

LCMS Conditions:
Method A:
Waters Acquity UPLC system
Waters Acquity UPLC BEH 1.7 μm 2.1×50 mm (Part#: 186002350)
Flow rate: 1 mL/min
Temperature: 50° C. (column temp)
Mobile Phase Compositions:
A: Water+0.05% formic acid+3.75 mM ammonium acetate.
B: Acetonitrile+0.04% formic acid.
Gradient: (from 2 to 98% B in 1.7 min)
Method B:
Waters Acquity UPLC system
Waters Acquity BEH 1.7 μm 2.1×50 mm (Part#: 186002350)
Flow rate: 1 mL/min
Temperature: 50° C. (column temp)
Mobile Phase Compositions:
A: Water+3.75 mM ammonium acetate+2% ACN.
B: Acetonitrile.

Gradient: (from 2 to 98% B in 4.4 min)
Method C:
Waters Acquity G2 Xevo QTof-Rs(FWHM)>20000
Waters Acquity CSH 1.7 μm 2.1×50 mm (Part#: 186005296)
Flow rate: 1 mL/min
Temperature: 50° C. (column temp)
Mobile Phase Compositions:
A: Water+3.75 mM ammonium acetate+0.001% formic acid.
B: Acetonitrile.
Gradient: (from 2 to 98% B in 4.4 min)
Method D:
Waters Acquity UPLC system
Waters Acquity UPLC BEH C18 1.7 um, 2.1×30 mm (Part#: 186002349)
Flow rate: 1 mL/min
Temperature: 55° C. (column temp)
Mobile Phase Compositions:
A: 0.05% formic acid in water.
B: 0.04% formic acid in methanol.
Gradient:

| Time (min) | Flow (mL/min) | % A | % B |
|---|---|---|---|
| 0 | 1.000 | 95.0 | 5.0 |
| 0.10 | 1.000 | 95.0 | 5.0 |
| 0.50 | 1.000 | 20.0 | 80.0 |
| 0.60 | 1.000 | 5.0 | 95.0 |
| 0.80 | 1.000 | 5.0 | 95.0 |
| 0.90 | 1.000 | 95.0 | 5.0 |
| 1.15 | 1.000 | 95.0 | 5.0 |

Abbreviations

| | |
|---|---|
| ~ | about or to |
| 1H NMR | proton nuclear magnetic resonance |
| Chloroform-d | deuterated chloroform; CDCl3 |
| d | doublet |
| DCM | dichloromethane |
| DIPEA, DIEA | diisopropylethylamine |
| DMF | dimethylformamide |
| DMSO-d6 | deuterated dimethylsulfoxide |
| DPPF | 1,1'-bis(diphenylphosphino)ferrocene |
| dtbpy | 4,4'-di-tert-butyl-2,2'-dipyridyl |
| Eq, eq | equivalents |
| Et | ethyl |
| Ether, Et2O | diethyl ether |
| EtOAc | ethylacetate |
| EtOH | ethanol |
| EtONa | sodium ethoxide |
| g | gram |
| h, hr | hour |
| HPLC | high performance liquid chromatography |
| HR-MS | high resolution mass spectrometry |
| [Ir(COD)(OMe)]2 | (1,5-Cyclooctadiene)(methoxy)iridium(I) dimer |
| L | liter |
| LC-MS | liquid chromatography mass spectrometry |
| LiHMDS | lithium hexamethyldisilazide |
| m | multiplet |
| Me | methyl |
| MeCN | acetonitrile |
| MeI | methyl iodide |
| MeOD, Methanol-d4 | deuterated methanol |
| MeOH | methanol |
| MHz | megahertz |
| mL | milliliter |
| mol | mole |
| mmol | millimole |
| mol | micromole |
| MTO | Methyltrioxorhenium(VII) |
| nBuLi | n-butyl lithium |
| nm | nanometers |
| NMP | N-methylpiperidone |
| Pd(PPh3)4 | tetrakis(triphenylphosphine)palladium(0) |
| Pd/C | palladium on carbon |
| PdCl2(dppf)•CH2Cl2 adduct | [1,1'-Bis(diphenylphosphino)ferrocene]dichloropalladium(II), complex with dichloromethane |
| Pd2(dba)3•CH2Cl2 | Tris(dibenzylideneacetone)dipalladium(0)-chloroform adduct |
| PhSH | thiophenol |
| ppm | parts per million |
| psi | pounds per square inch |
| RT | room temperature |
| s | singlet |
| SCX | strong cation exchange |
| SiliaMetS DMT | silica bound 2,4,6-trimercaptotriazine |
| TBAF | tetrabutylammonium fluoride |
| TBME | tert-butyl methyl ether |
| t-BuNO2 | tert-butyl nitrite |
| TEA | triethylamine |
| TFA | trifluoroacetic acid |
| THF | tetrahydrofuran |
| UV | ultraviolet light |
| uW | microwave |
| XPhos | 2-Dicyclohexylphosphino-2',4',6'-triisopropylbiphenyl |

Biological Example 1

A cellular SMN ELISA was used to measure the effects of low molecular weight compounds on SMN protein elevation. Cells from a myoblast cell line derived from the SMNdelta7 mouse model (kind gift from Steve Burden, NYU) were seeded into a 384-well plate at a density of 3000 cells/well and treated with compounds for 24 hours. ELISA capture plates were prepared by coating 384-well plates (Immulon 4HBX) with 0.5 ug/mL of anti-SMN mAb (BD Science, Catalog number 610647) at 4° C. overnight. The plates were washed 5 times with 110 uL of PBS-Tween (0.05% Tween-20, PBST), blocked with 100 uL of 1% BSA in PBST for 2 hours and washed (5 times) with 100 uL of PBST. After 24 hours of compound treatment cells were lysed in a modified RIPA-buffer, on ice for 1 hour. 20 uL of lysate and 20 uL of 1% BSA were then added to the ELISA capture plates and incubated at 4° C. overnight. Plates were washed (5 times) with PBST and then incubated with 1:100 dilution of primary rabbit anti-SMN polyclonal antibody (Santa cruz, Catalog number SC-15320) at room temperature for 1 hour and subsequently washed (5 times) with 110 uL of PBST. This was followed by addition of 1:100 Goat anti-Rabbit IgG-HRP linked (Cell Signaling, Catalog number 7074) secondary antibody for 1 hour. Plates were then washed with PBST and incubated with 40 uL TMB substrate (Cell Signaling, Catalog number 7004L) at room temperature for 1-10 minutes with shaking. The reaction was stopped by addition of 40 uL of stop solution (Cell signaling, Catalog number 7002L) and absorption was measured at 450 nm. Data was reported as fold activation over DMSO control and $EC_{50}$. ELISA assay condition: compound concentration range 100 pM-10 uM.

Activity Table: ELISA data generated using Biological Example

| Example # | Structure | Chemical Name | SMN Activity Fold, EC$_{50}$ |
|---|---|---|---|
| 1 | 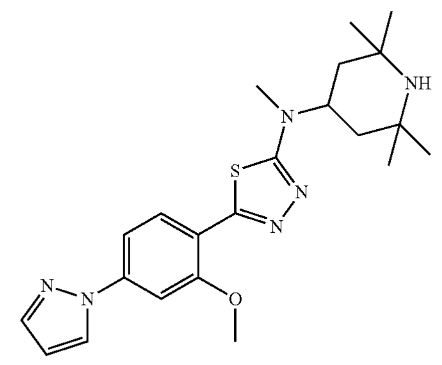 [SMILES: COc1cc(-n2cccn2)ccc1-c1nnc(N(C)C2CC(C)(C)NC(C)(C)C2)s1] | 5-(2-Methoxy-4-(1H-pyrazol-1-yl)phenyl)-N-methyl-N-(2,2,6,6-tetramethylpiperidin-4-yl)-1,3,4-thiadiazol-2-amine | 2.45, 63 nM |
| 2 | 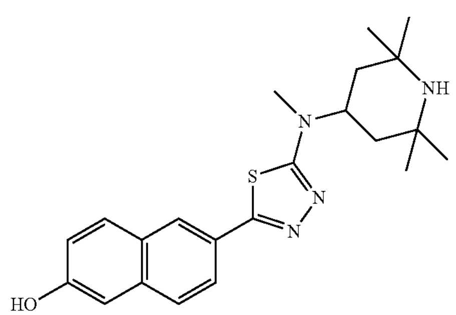 [SMILES: CN(c1nnc(-c2ccc3cc(O)ccc3c2)s1)C1CC(C)(C)NC(C)(C)C1] | 6-(5-(Methyl(2,2,6,6-tetramethylpiperidin-4-yl)amino)-1,3,4-thiadiazol-2-yl)naphthalen-2-ol | 2.66, 436 nM |
| 3 | 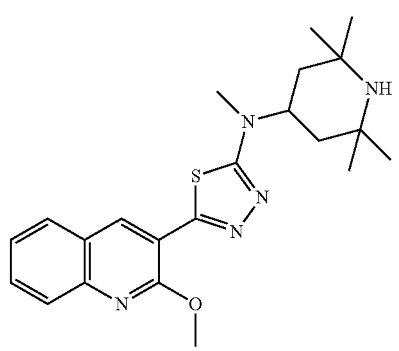 [SMILES: COc1nc2ccccc2cc1-c1nnc(N(C)C2CC(C)(C)NC(C)(C)C2)s1] | 5-(2-Methoxyquinolin-3-yl)-N-methyl-N-(2,2,6,6-tetramethylpiperidin-4-yl)-1,3,4-thiadiazol-2-amine | 2.67, 337 nM |
| 4 | 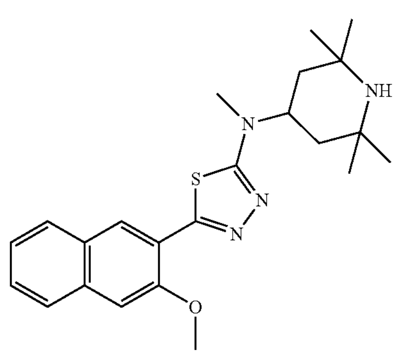 [SMILES: COc1cc2ccccc2cc1-c1nnc(N(C)C2CC(C)(C)NC(C)(C)C2)s1] | 5-(3-Methoxynaphthalen-2-yl)-N-methyl-N-(2,2,6,6-tetramethylpiperidin-4-yl)-1,3,4-thiadiazol-2-amine | 2.48, 887 nM |

Activity Table: ELISA data generated using Biological Example

| Example # | Structure | Chemical Name | SMN Activity Fold, EC$_{50}$ |
|---|---|---|---|
| 5 | 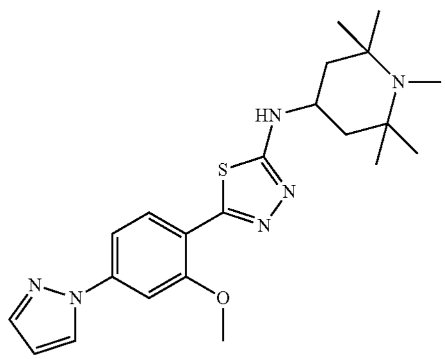 [SMILES: COc1cc(-n2cccn2)ccc1-c1nnc(NC2CC(C)(C)N(C)C(C)(C)C2)s1] | 5-(2-Methoxy-4-(1H-pyrazol-1-yl)phenyl)-N-(1,2,2,6,6-pentamethylpiperidin-4-yl)-1,3,4-thiadiazol-2-amine | 2.88, 87 nM |
| 6 | 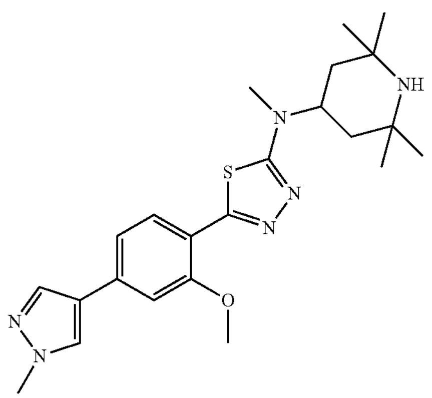 [SMILES: COc1cc(-c2cnn(C)c2)ccc1-c1nnc(N(C)C2CC(C)(C)NC(C)(C)C2)s1] | 5-(2-Methoxy-4-(1-methyl-1H-pyrazol-4-yl)phenyl)-N-methyl-N-(2,2,6,6-tetramethylpiperidin-4-yl)-1,3,4-thiadiazol-2-amine: | 2.49, 44 nM |
| 7 | 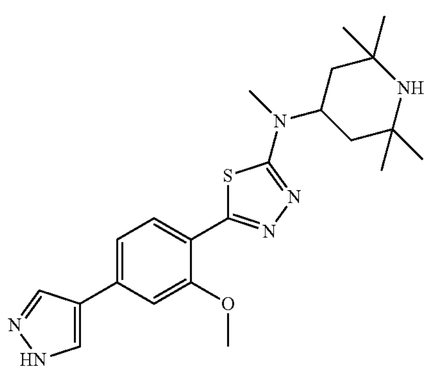 [SMILES: COc1cc(-c2cn[nH]c2)ccc1-c1nnc(N(C)C2CC(C)(C)NC(C)(C)C2)s1] | 5-(2-Methoxy-4-(1H-pyrazol-4-yl)phenyl)-N-methyl-N-(2,2,6,6-tetramethylpiperidin-4-yl)-1,3,4-thiadiazol-2-amine | 2.86, 38 nM |
| 8 | 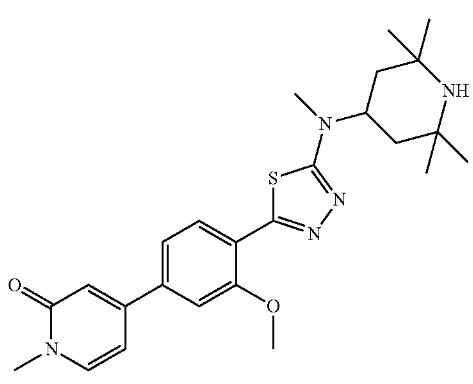 [SMILES: COc1cc(-c2ccn(C)c(=O)c2)ccc1-c1nnc(N(C)C2CC(C)(C)NC(C)(C)C2)s1] | 4-(3-Methoxy-4-(5-(methyl(2,2,6,6-tetramethylpiperidin-4-yl)amino)-1,3,4-thiadiazol-2-yl)phenyl)-1-methylpyridin-2(1H)-one | 3.20, 134 nM |

| Example # | Structure | Chemical Name | SMN Activity Fold, $EC_{50}$ |
|---|---|---|---|
| 9 | 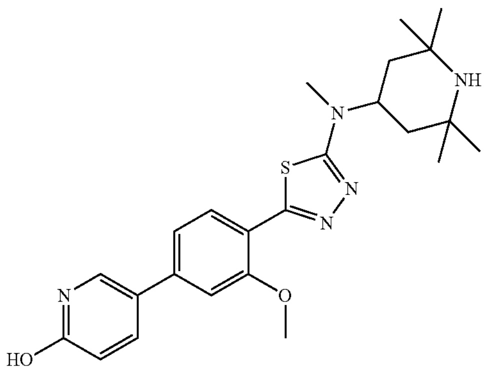 [SMILES: COc1cc(-c2ccc(O)nc2)ccc1-c1nnc(N(C)C2CC(C)(C)NC(C)(C)C2)s1] | 5-(3-Methoxy-4-(5-(methyl(2,2,6,6-tetramethylpiperidin-4-yl)amino)-1,3,4-thiadiazol-2-yl)phenyl)pyridin-2-ol | 2.46, 784 nM |
| 10 | 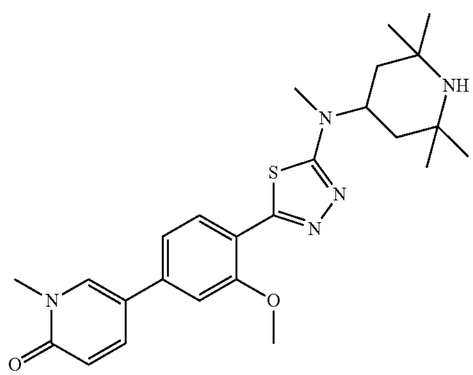 [SMILES: COc1cc(-c2ccc(=O)n(C)c2)ccc1-c1nnc(N(C)C2CC(C)(C)NC(C)(C)C2)s1] | 5-(3-Methoxy-4-(5-(methyl(2,2,6,6-tetramethylpiperidin-4-yl)amino)-1,3,4-thiadiazol-2-yl)phenyl)-1-methylpyridin-2(1H)-one | 2.65, 79 nM |
| 11 | 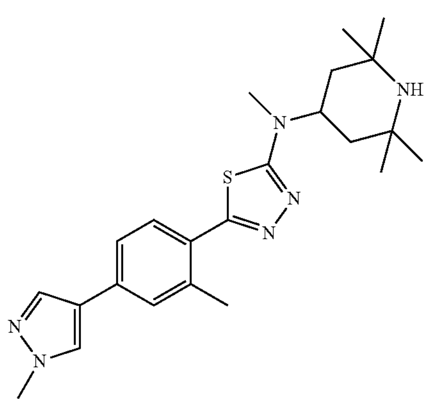 [SMILES: Cc1cc(-c2cnn(C)c2)ccc1-c1nnc(N(C)C2CC(C)(C)NC(C)(C)C2)s1] | N-Methyl-5-(2-methyl-4-(1-methyl-1H-pyrazol-4-yl)phenyl)-N-(2,2,6,6-tetramethylpiperidin-4-yl)-1,3,4-thiadiazol-2-amine | 2.84, 684 nM |

Activity Table: ELISA data generated using Biological Example

| Example # | Structure | Chemical Name | SMN Activity Fold, $EC_{50}$ |
|---|---|---|---|
| 12 | 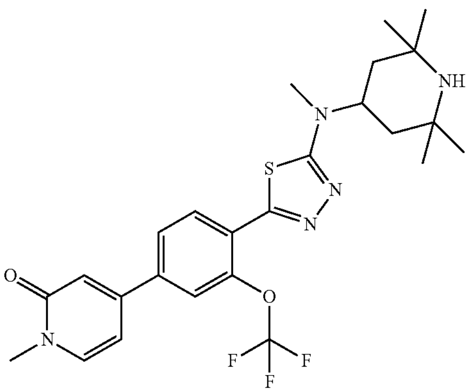 | 1-Methyl-4-(4-(5-(methyl(2,2,6,6-tetramethylpiperidin-4-yl)amino)-1,3,4-thiadiazol-2-yl)-3-(trifluoromethoxy)phenyl)pyridin-2(1H)-one | 2.20, 895 nM |
| 13 | 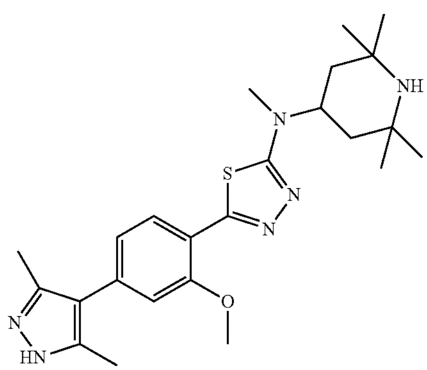 [SMILES: COc1cc(-c2c(C)n[nH]c2C)ccc1-c1nnc(N(C)C2CC(C)(C)NC(C)(C)C2)s1] | 5-(4-(3,5-Dimethyl-1H-pyrazol-4-yl)-2-methoxyphenyl)-N-methyl-N-(2,2,6,6-tetramethylpiperidin-4-yl)-1,3,4-thiadiazol-2-amine | inactive |
| 14 | 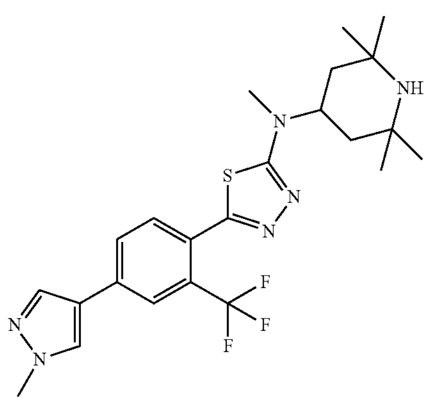 [SMILES: CN(c1nnc(-c2ccc(-c3cnn(C)c3)cc2C(F)(F)F)s1)C1CC(C)(C)NC(C)(C)C1] | 5-(2-Methoxy-4-(1-methyl-1H-pyrazol-4-yl)phenyl)-N-methyl-N-(2,2,6,6-tetramethylpiperidin-4-yl)-1,3,4-thiadiazol-2-amine | inactive |

Activity Table: ELISA data generated using Biological Example

Activity Table: ELISA data generated using Biological Example

| Example # | Structure | Chemical Name | SMN Activity Fold, EC$_{50}$ |
|---|---|---|---|
| 15 | 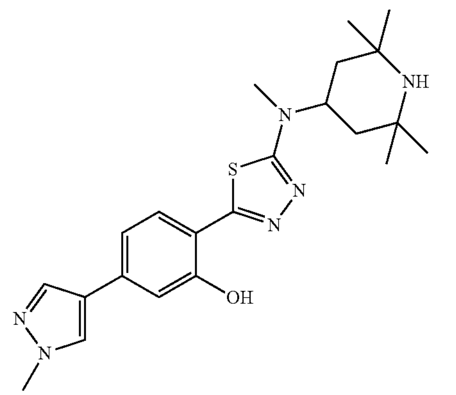 [SMILES: CN(c1nnc(-c2ccc(-c3cnn(C)c3)cc2O)s1)C1CC(C)(C)NC(C)(C)C1] | 2-(5-(Methyl(2,2,6,6-tetramethylpiperidin-4-yl)amino)-1,3,4-thiadiazol-2-yl)-5-(1-methyl-1H-pyrazol-4-yl)phenol | 3.14, 32 nM |
| 16 | 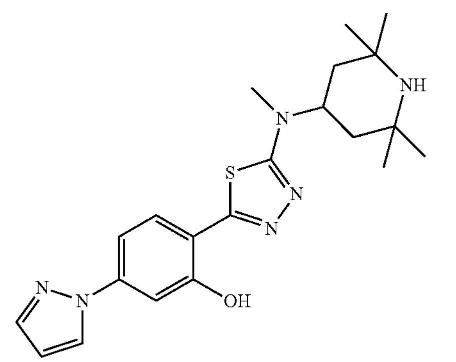 [SMILES: CN(c1nnc(-c2ccc(-n3cccn3)cc2O)s1)C1CC(C)(C)NC(C)(C)C1] | 2-(5-(Methyl(2,2,6,6-tetramethylpiperidin-4-yl)amino)-1,3,4-thiadiazol-2-yl)-5-(1H-pyrazol-1-yl)phenol | 2.76, 171 nM |
| 17 | 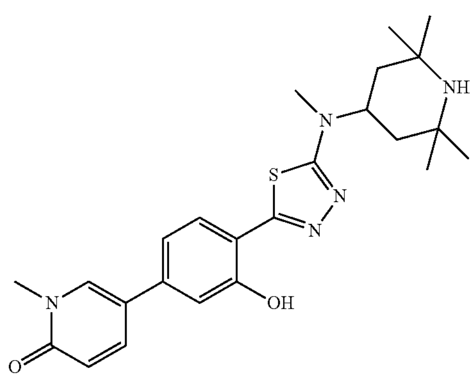 | 5-(3-Hydroxy-4-(5-(methyl(2,2,6,6-tetramethylpiperidin-4-yl)amino)-1,3,4-thiadiazol-2-yl)phenyl)-1-methylpyridin-2(1H)-one | 2.74, 36 nM |
| 18 | 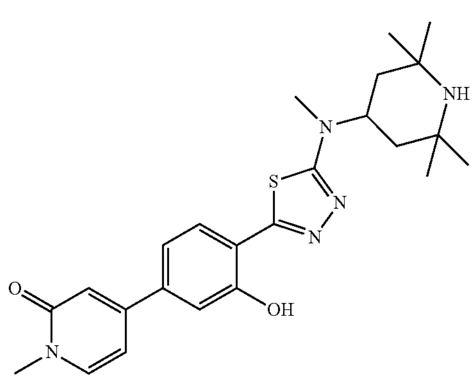 [SMILES: CN(c1nnc(-c2ccc(-c3ccn(C)c(=O)c3)cc2O)s1)C1CC(C)(C)NC(C)(C)C1] | 4-(3-Hydroxy-4-(5-(methyl(2,2,6,6-tetramethylpiperidin-4-yl)amino)-1,3,4-thiadiazol-2-yl)phenyl)-1-methylpyridin-2(1H)-one | 3.36, 61 nM |

Activity Table: ELISA data generated using Biological Example

| Example # | Structure | Chemical Name | SMN Activity Fold, $EC_{50}$ |
|---|---|---|---|
| 19 | 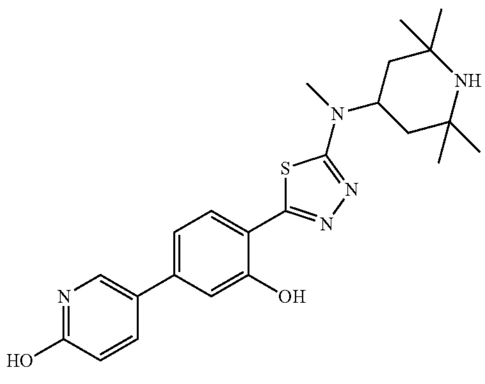 [SMILES: CN(c1nnc(-c2ccc(-c3ccc(O)nc3)cc2O)s1)C1CC(C)(C)NC(C)(C)C1] | 5-(3-Hydroxy-4-(5-(methyl(2,2,6,6,-tetramethylpiperidin-4-yl)amino)-1,3,4-thiadiazol-2-yl)phenyl)pyridin-2-ol | 2.85, 51 nM |
| 20 | 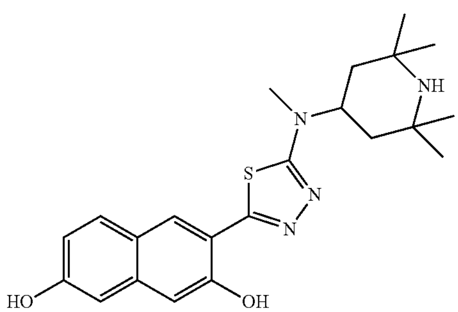 [SMILES: CN(c1nnc(-c2cc3ccc(O)cc3cc2O)s1)C1CC(C)(C)NC(C)(C)C1] | 3-(5-(Methyl(2,2,6,6-tetramethylpiperidin-4-yl)amino)-1,3,4-thiadiazol-2-yl)naphthalene-2,7-diol | 2.63, 48 nM |
| 21 | 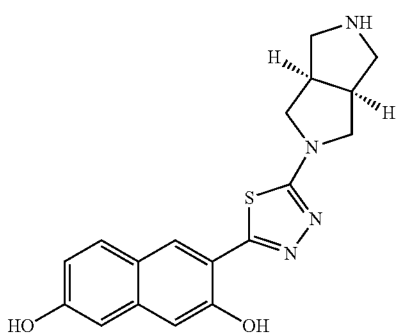 [SMILES: Oc1ccc2cc(-c3nnc(N4C[C@H]5CNC[C@H]5C4)s3)c(O)cc2c1] | 3-(5-((3aR,6aS)-Hexahydropyrrolo[3,4-c]pyrrol-2(1H)-yl)-1,3,4-thiadiazol-2-yl)naphthalene-2,7-diol | 2.66, 323 nM |
| 22 | 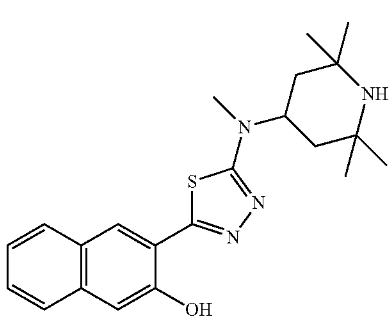 [SMILES: CN(c1nnc(-c2cc3ccccc3cc2O)s1)C1CC(C)(C)NC(C)(C)C1] | 3-(5-(Methyl(2,2,6,6-tetramethylpiperidin-4-yl)amino)-1,3,4-thiadiazol-2-yl)naphthalen-2-ol•hydrobromide salt | 2.70, 253 nM |

-continued

Activity Table: ELISA data generated using Biological Example

| Example # | Structure | Chemical Name | SMN Activity Fold, EC$_{50}$ |
|---|---|---|---|
| 23 | 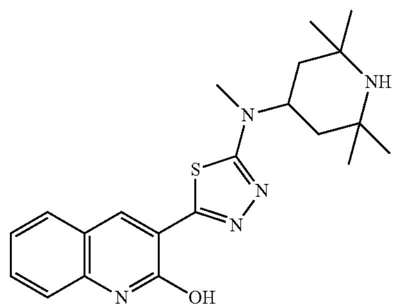 [SMILES: CN(c1nnc(-c2cc3ccccc3nc2O)s1)C1CC(C)(C)NC(C)(C)C1] | 3-(5-(Methyl(2,2,6,6-tetramethylpiperidin-4-yl)amino)-1,3,4-thiadiazol-2-yl)quinolin-2-ol | 2.66, 231 nM |
| 24 | 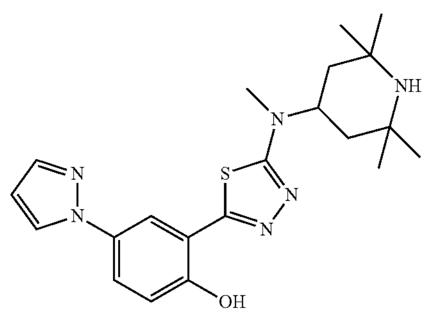 [SMILES: CN(c1nnc(-c2cc(-n3cccn3)ccc2O)s1)C1CC(C)(C)NC(C)(C)C1] | 2-(5-(Methyl(2,2,6,6-tetramethylpiperidin-4-yl)amino)-1,3,4-thiadiazol-2-yl)-4-(1H-pyrazol-1-yl)phenol | 2.28, 987 nM |
| 25 | 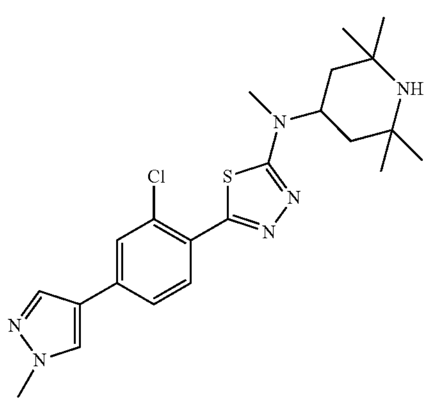 [SMILES: CN(c1nnc(-c2ccc(-c3cnn(C)c3)cc2Cl)s1)C1CC(C)(C)NC(C)(C)C1] | 5-(2-Chloro-4-(1-methyl-1H-pyrazol-4-yl)phenyl)-N-methyl-N-(2,2,6,6-tetramethylpiperidin-4-yl)-1,3,4-thiadiazol-2-amine | 2.49, 132 nM |
| 26 | 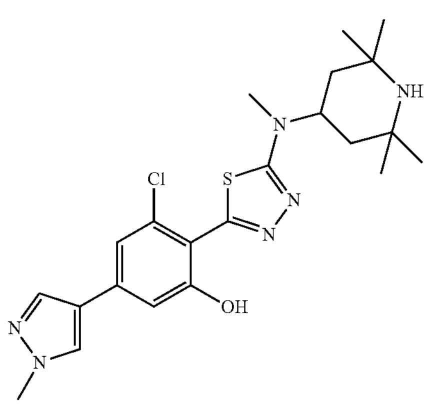 [SMILES: CN(c1nnc(-c2c(O)cc(-c3cnn(C)c3)cc2Cl)s1)C1CC(C)(C)NC(C)(C)C1] | 3-Chloro-2-(5-(methyl(2,2,6,6-tetramethylpiperidin-4-yl)amino)-1,3,4-thiadiazol-2-yl)-5-(1-methyl-1H-pyrazol-4-yl)phenol | 2.26, 3 nM |

Activity Table: ELISA data generated using Biological Example

| Example # | Structure | Chemical Name | SMN Activity Fold, $EC_{50}$ |
|---|---|---|---|
| 27 | 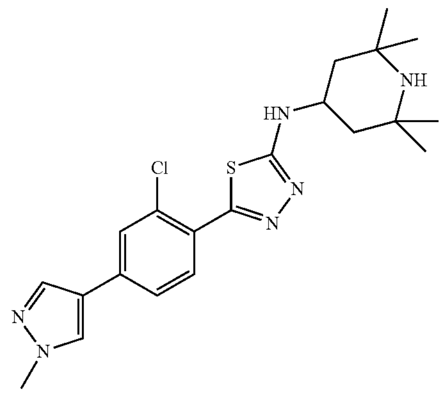 [SMILES: Cn1cc(-c2ccc(-c3nnc(NC4CC(C)(C)NC(C)(C)C4)s3)c(Cl)c2)cn1] | 5-(2-chloro-4-(1-methyl-1H-pyrazol-4-yl)phenyl)-N-(2,2,6,6-tetramethylpiperidin-4-yl)-1,3,4-thiadiazol-2-amine | 2.48, 193 nM |
| 28 | 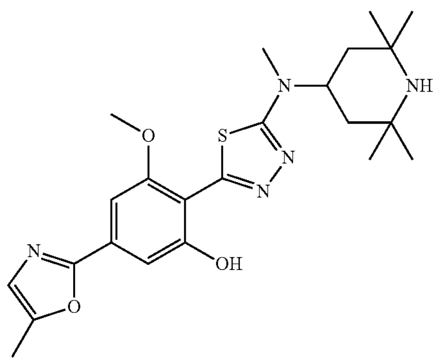 [SMILES: COc1cc(-c2ncc(C)o2)cc(O)c1-c1nnc(N(C)C2CC(C)(C)NC(C)(C)C2)s1] | 3-Methoxy-2-(5-(methyl(2,2,6,6-tetramethylpiperidin-4-yl)amino)-1,3,4-thiadiazol-2-yl)-5-(5-methyloxazol-2-yl)phenol | 2.70, 20 nM |
| 29 | 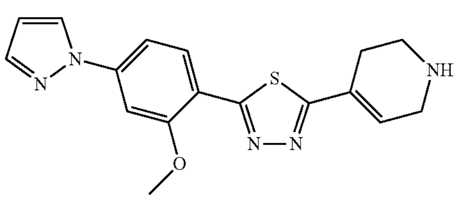 [SMILES: COc1cc(-n2cccn2)ccc1-c1nnc(C2=CCNCC2)s1] | 2-(2-Methoxy-4-(1H-pyrazol-1-yl)phenyl)-5-(1,2,3,6-tetrahydropyridin-4-yl)-1,3,4-thiadiazole | 2.46, 879 nM |
| 30 | 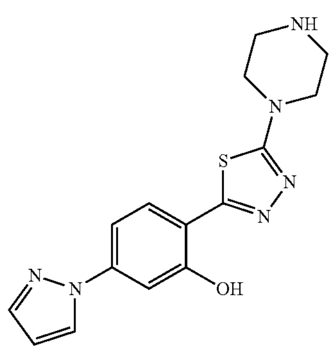 [SMILES: Oc1cc(-n2cccn2)ccc1-c1nnc(N2CCNCC2)s1] | 2-(5-(piperazin-1-yl)-1,3,4-thiadiazol-2-yl)-5-(1H-pyrazol-1-yl)phenol | 1.98, 6560 nM |

| Example # | Structure | Chemical Name | SMN Activity Fold, $EC_{50}$ |
|---|---|---|---|
| 31 | 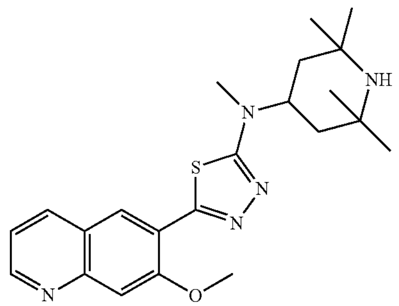 | 5-(7-Methoxyquinolin-6-yl)-N-methyl-N-(2,2,6,6-tetramethylpiperidin-4-yl)-1,3,4-thiadiazol-2-amine | 2.43, 113 nM |
| 32 | 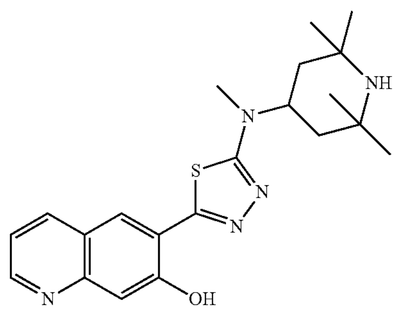 | 6-(5-(Methyl(2,2,6,6-tetramethylpiperidin-4-yl)amino)-1,3,4-thiadiazol-2-yl)quinolin-7-ol | 2.48, 256 nM |
| 33 | 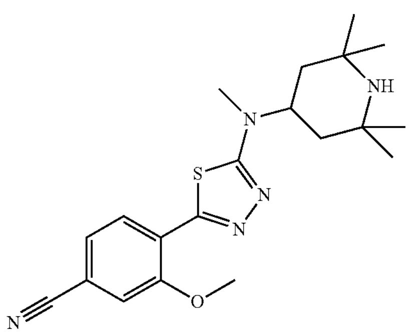 [SMILES: COc1cc(C#N)ccc1-c1nnc(N(C)C2CC(C)(C)NC(C)(C)C2)s1] | 3-methoxy-4-(5-(methyl(2,2,6,6-tetramethylpiperidin-4-yl)amino)-1,3,4-thiadiazol-2-yl)benzonitrile | 2.16, 1040 nM |
| 34 | 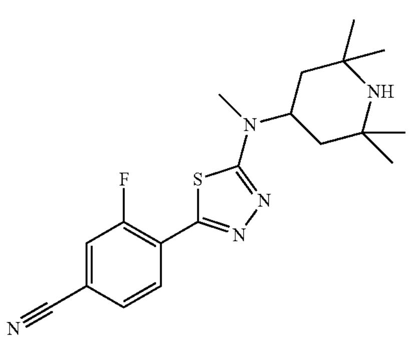 [SMILES: CN(c1nnc(-c2ccc(C#N)cc2F)s1)C1CC(C)(C)NC(C)(C)C1] | 3-fluoro-4-(5-(methyl(2,2,6,6-tetramethylpiperidin-4-yl)amino)-1,3,4-thiadiazol-2-yl)benzonitrile | 2.32, >10000 nM |

| Activity Table: ELISA data generated using Biological Example | | | |
|---|---|---|---|
| Example # | Structure | Chemical Name | SMN Activity Fold, $EC_{50}$ |
| 35 | | methyl 3-fluoro-4-(5-(methyl(2,2,6,6-tetramethylpiperidin-4-yl)amino)-1,3,4-thiadiazol-2-yl)benzoate | 2.81, 864 nM |
| 36 | | 5-(2-methoxy-4-(3-(methylamino)-1H-pyrazol-1-yl)phenyl)-N-methyl-N-(2,2,6,6-tetramethylpiperidin-4-yl)-1,3,4-thiadiazol-2-amine | 2.15, 163 nM |
| 37 | | 7-methoxy-6-(5-(methyl(2,2,6,6-tetramethylpiperidin-4-yl)amino)-1,3,4-thiadiazol-2-yl)quinoline-2-carbonitrile | 2.19, 78 nM |
| 38 | | 4-(3-methoxy-4-(5-((2,2,6,6-tetramethylpiperidin-4-yl)oxy)-1,3,4-thiadiazol-2-yl)phenyl)-1-methylpyridin-2(1H)-one | 2.12, 1523 nM |

Activity Table: ELISA data generated using Biological Example

| Example # | Structure | Chemical Name | SMN Activity Fold, $EC_{50}$ |
|---|---|---|---|
| 39 | 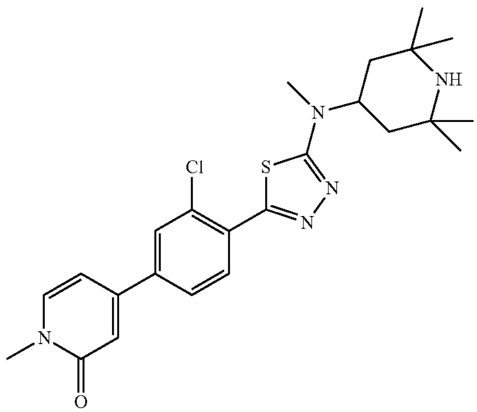 | 4-(3-chloro-4-(5-(methyl(2,2,6,6-tetramethylpiperidin-4-yl)amino)-1,3,4-thiadiazol-2-yl)phenyl)-1-methylpyridin-2(1H)-one | 2.31, 50 nM |
| 40 | 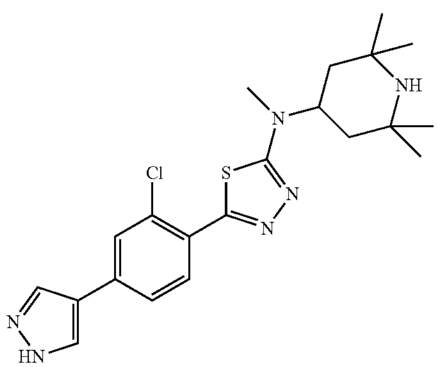 [SMILES: CN(c1nnc(-c2ccc(-c3cn[nH]c3)cc2Cl)s1)C1CC(C)(C)NC(C)(C)C1] | 5-(2-chloro-4-(1H-pyrazol-4-yl)phenyl)-N-methyl-N-(2,2,6,6-tetramethylpiperidin-4-yl)-1,3,4-thiadiazol-2-amine | 2.55, 34 nM |
| 41 | 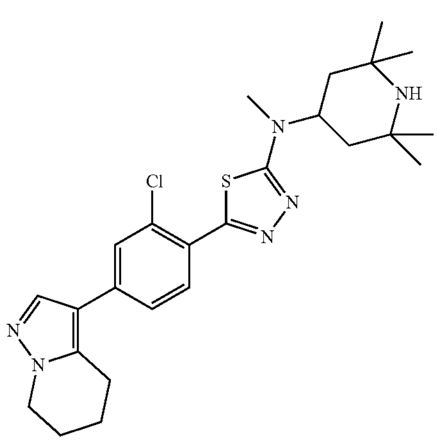 [SMILES: CN(c1nnc(-c2ccc(-c3cnn4c3CCCC4)cc2Cl)s1)C1CC(C)(C)NC(C)(C)C1] | 5-(2-chloro-4-(4,5,6,7-tetrahydropyrazolo[1,5-a]pyridin-3-yl)phenyl)-N-methyl-N-(2,2,6,6-tetramethylpiperidin-4-yl)-1,3,4-thiadiazol-2-amine | 2.44, 507 nM |

-continued

Activity Table: ELISA data generated using Biological Example

| Example # | Structure | Chemical Name | SMN Activity Fold, $EC_{50}$ |
|---|---|---|---|
| 42 | 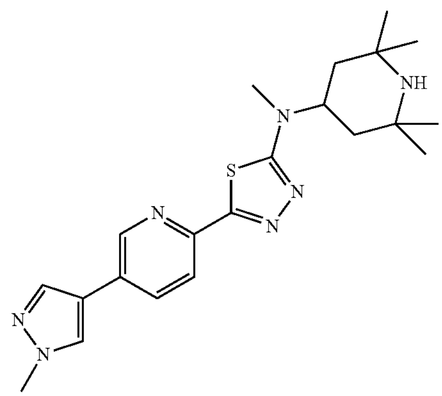 [SMILES: CN(c1nnc(-c2ccc(-c3cnn(C)c3)cn2)s1)C1CC(C)(C)NC(C)(C)C1] | N-methyl-5-(5-(1-methyl-1H-pyrazol-4-yl)pyridin-2-yl)-N-(2,2,6,6-tetramethylpiperidin-4-yl)-1,3,4-thiadiazol-2-amine•Hydrochloride salt | 2.32, 675 nM |
| 43 | 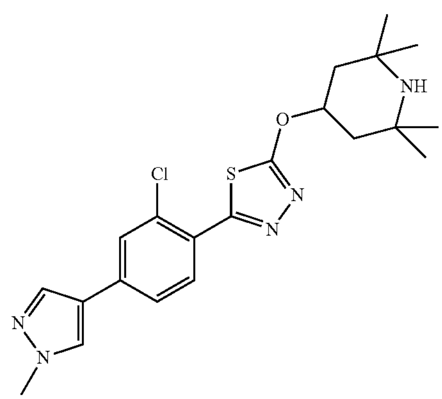 [SMILES: Cn1cc(-c2ccc(-c3nnc(OC4CC(C)(C)NC(C)(C)C4)s3)c(Cl)c2)cn1] | 2-(2-chloro-4-(1-methyl-1H-pyrazol-4-yl)phenyl)-5-((2,2,6,6-tetramethylpiperidin-4-yl)oxy)-1,3,4-thiadiazole | 2.28, 446 nM |
| 44 | 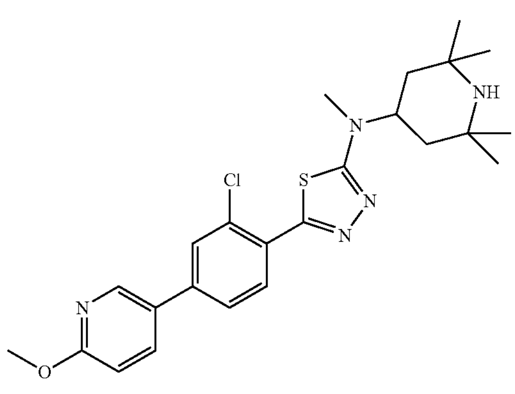 | 5-(2-chloro-4-(6-methoxypyridin-3-yl)phenyl)-N-methyl-N-(2,2,6,6-tetramethylpiperidin-4-yl)-1,3,4-thiadiazol-2-amine | 2.26, 4917 nM |

-continued

Activity Table: ELISA data generated using Biological Example

| Example # | Structure | Chemical Name | SMN Activity Fold, $EC_{50}$ |
|---|---|---|---|
| 45 | 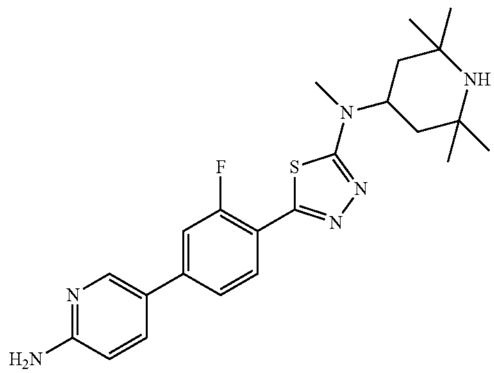 [SMILES: CN(c1nnc(-c2ccc(-c3ccc(N)nc3)cc2F)s1)C1CC(C)(C)NC(C)(C)C1] | 5-(4-(6-aminopyridin-3-yl)-2-fluorophenyl)-N-methyl-N-(2,2,6,6-tetramethylpiperidin-4-yl)-1,3,4-thiadiazol-2-amine | 2.26, 163 nM |
| 46 | 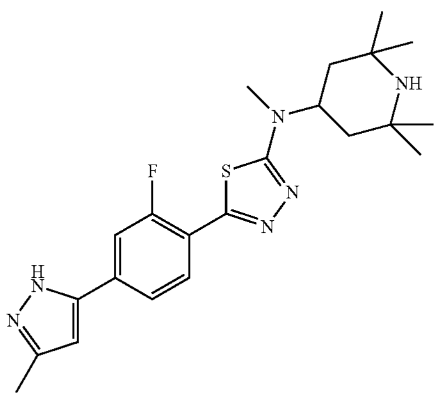 [SMILES: Cc1cc(-c2ccc(-c3nnc(N(C)C4CC(C)(C)NC(C)(C)C4)s3)c(F)c2)[nH]n1] | 5-(2-fluoro-4-(3-methyl-1H-pyrazol-5-yl)phenyl)-N-methyl-N-(2,2,6,6-tetramethylpiperidin-4-yl)-1,3,4-thiadiazol-2-amine | 2.32, 122 nM |
| 47 | 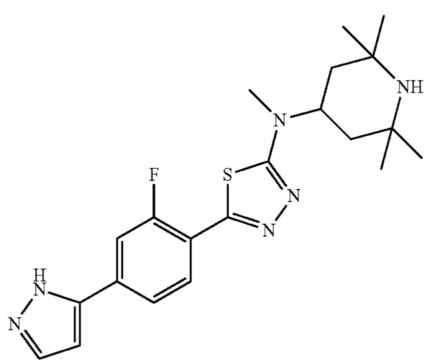 [SMILES: CN(c1nnc(-c2ccc(-c3ccn[nH]3)cc2F)s1)C1CC(C)(C)NC(C)(C)C1] | 5-(2-fluoro-4-(1H-pyrazol-5-yl)phenyl)-N-methyl-N-(2,2,6,6-tetramethylpiperidin-4-yl)-1,3,4-thiadiazol-2-amine | 2.29, 152 nM |
| 48 | 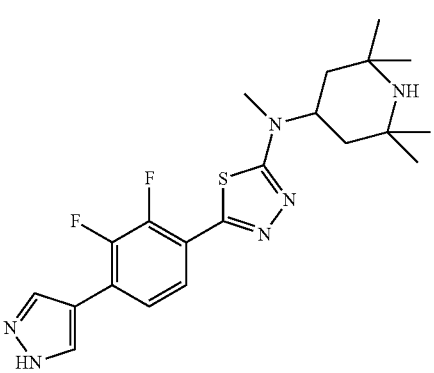 [SMILES: CN(c1nnc(-c2ccc(-c3cn[nH]c3)c(F)c2F)s1)C1CC(C)(C)NC(C)(C)C1] | 5-(2,3-difluoro-4-(1H-pyrazol-4-yl)phenyl)-N-methyl-N-(2,2,6,6-tetramethylpiperidin-4-yl)-1,3,4-thiadiazol-2-amine | 3.04, 33 nM |

Activity Table: ELISA data generated using Biological Example

| Example # | Structure | Chemical Name | SMN Activity Fold, EC$_{50}$ |
|---|---|---|---|
| 49 | 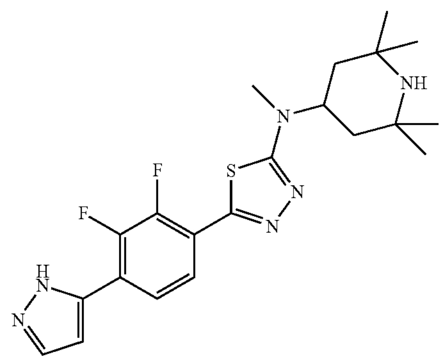 [SMILES: CN(c1nnc(-c2ccc(-c3ccn[nH]3)c(F)c2F)s1)C1CC(C)(C)NC(C)(C)C1] | 5-(2,3-difluoro-4-(1H-pyrazol-5-yl)phenyl)-N-methyl-N-(2,2,6,6-tetramethylpiperidin-4-yl)-1,3,4-thiadiazol-2-amine | 2.42, 81 nM |
| 50 | 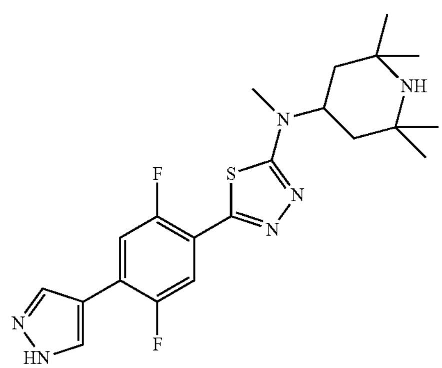 [SMILES: CN(c1nnc(-c2cc(F)c(-c3cn[nH]c3)cc2F)s1)C1CC(C)(C)NC(C)(C)C1] | 5-(2,5-difluoro-4-(1H-pyrazol-4-yl)phenyl)-N-methyl-N-(2,2,6,6-tetramethylpiperidin-4-yl)-1,3,4-thiadiazol-2-amine | 3.07, 20 nM |
| 51 | 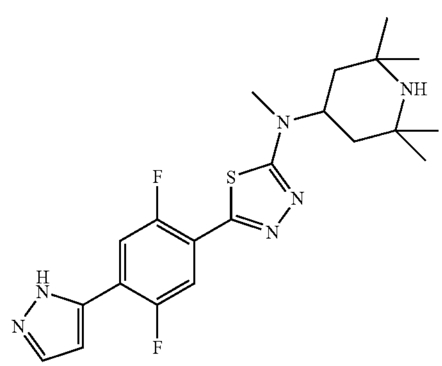 [SMILES: CN(c1nnc(-c2cc(F)c(-c3ccn[nH]3)cc2F)s1)C1CC(C)(C)NC(C)(C)C1] | 5-(2,5-difluoro-4-(1H-pyrazol-5-yl)phenyl)-N-methyl-N-(2,2,6,6-tetramethylpiperidin-4-yl)-1,3,4-thiadiazol-2-amine | 2.86, 85 nM |
| 52 | 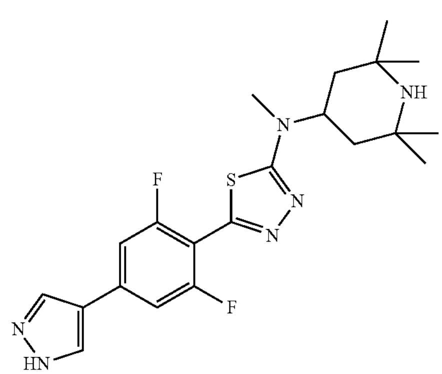 [SMILES: CN(c1nnc(-c2c(F)cc(-c3cn[nH]c3)cc2F)s1)C1CC(C)(C)NC(C)(C)C1] | 5-(2,6-difluoro-4-(1H-pyrazol-4-yl)phenyl)-N-methyl-N-(2,2,6,6-tetramethylpiperidin-4-yl)-1,3,4-thiadiazol-2-amine | 3.30, 61 nM |

Activity Table: ELISA data generated using Biological Example

| Example # | Structure | Chemical Name | SMN Activity Fold, EC$_{50}$ |
|---|---|---|---|
| 53 | 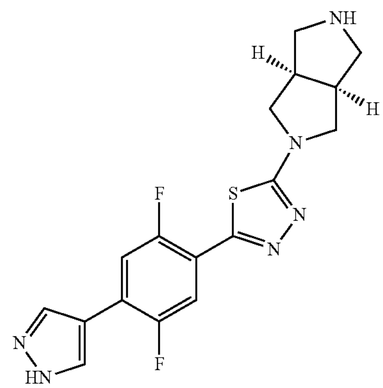 [SMILES: Fc1cc(-c2nnc(N3C[C@H]4CNC[C@H]4C3)s2)c(F)cc1-c1cn[nH]c1] | 2-(2,5-difluoro-4-(1H-pyrazol-4-yl)phenyl)-5-((3aR,6aS)-hexahydropyrrolo[3,4-c]pyrrol-2(1H)-yl)-1,3,4-thiadiazole | 2.56, 70 nM |
| 54 | 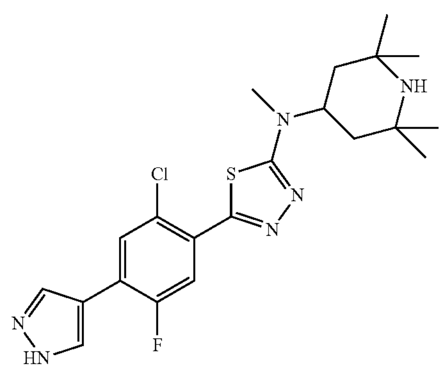 [SMILES: CN(c1nnc(-c2cc(F)c(-c3cn[nH]c3)cc2Cl)s1)C1CC(C)(C)NC(C)(C)C1] | 5-(2-chloro-5-fluoro-4-(1H-pyrazol-4-yl)phenyl)-N-methyl-N-(2,2,6,6-tetramethylpiperidin-4-yl)-1,3,4-thiadiazol-2-amine | 3.16, 47 nM |
| 55 | 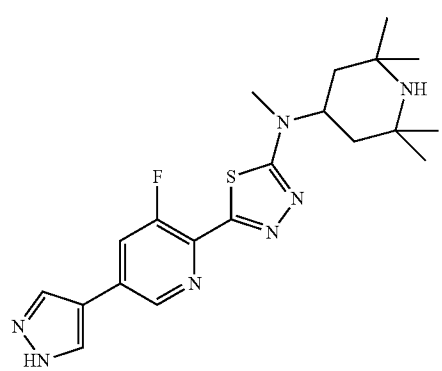 [SMILES: CN(c1nnc(-c2ncc(-c3cn[nH]c3)cc2F)s1)C1CC(C)(C)NC(C)(C)C1] | 5-(3-fluoro-5-(1H-pyrazol-4-yl)pyridin-2-yl)-N-methyl-N-(2,2,6,6-tetramethylpiperidin-4-yl)-1,3,4-thiadiazol-2-amine | 2.75, 1011 nM |
| 56 | 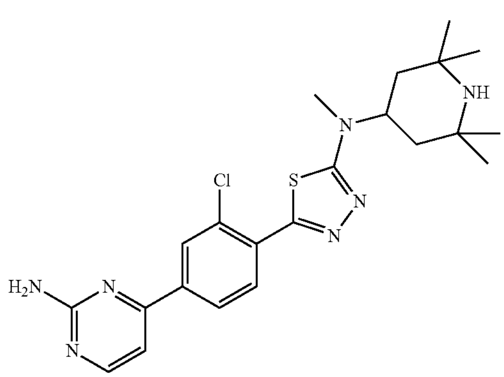 [SMILES: CN(c1nnc(-c2ccc(-c3ccnc(N)n3)cc2Cl)s1)C1CC(C)(C)NC(C)(C)C1] | 5-(4-(2-aminopyrimidin-4-yl)-2-chlorophenyl)-N-methyl-N-(2,2,6,6-tetramethylpiperidin-4-yl)-1,3,4-thiadiazol-2-amine | 2.47, 41 nM |

| Example # | Structure | Chemical Name | SMN Activity Fold, $EC_{50}$ |
|---|---|---|---|
| 57 | 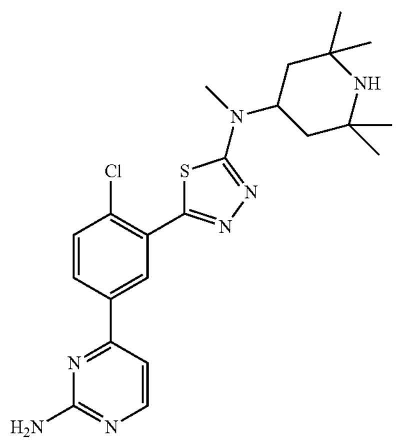 [SMILES: CN(c1nnc(-c2cc(-c3ccnc(N)n3)ccc2Cl)s1)C1CC(C)(C)NC(C)(C)C1] | 5-(5-(2-aminopyrimidin-4-yl)-2-chlorophenyl)-N-methyl-N-(2,2,6,6-tetramethylpiperidin-4-yl)-1,3,4-thiadiazol-2-amine | 2.55, 94 nM |
| 58 | 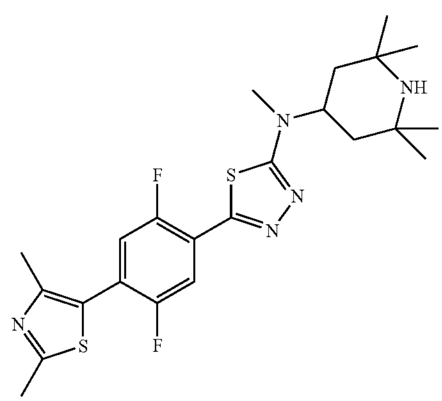 [SMILES: Cc1nc(C)c(-c2cc(F)c(-c3nnc(N(C)C4CC(C)(C)NC(C)(C)C4)s3)cc2F)s1] | 5-(4-(2,4-dimethylthiazol-5-yl)-2,5-difluorophenyl)-N-methyl-N-(2,2,6,6-tetramethylpiperidin-4-yl)-1,3,4-thiadiazol-2-amine | 2.41, 386 nM |
| 59 | 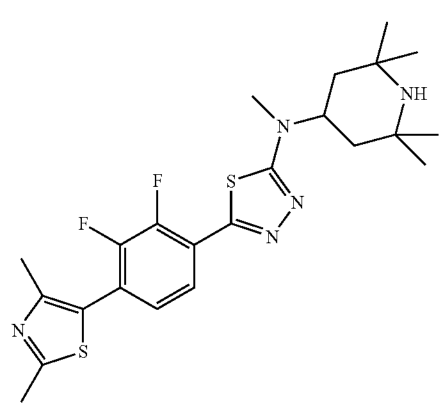 [SMILES: Cc1nc(C)c(-c2ccc(-c3nnc(N(C)C4CC(C)(C)NC(C)(C)C4)s3)c(F)c2F)s1] | 5-(4-(2,4-dimethylthiazol-5-yl)-2,3-difluorophenyl)-N-methyl-N-(2,2,6,6-tetramethylpiperidin-4-yl)-1,3,4-thiadiazol-2-amine | 2.69, 1501 nM |

Activity Table: ELISA data generated using Biological Example

Activity Table: ELISA data generated using Biological Example

| Example # | Structure | Chemical Name | SMN Activity Fold, $EC_{50}$ |
|---|---|---|---|
| 60 | 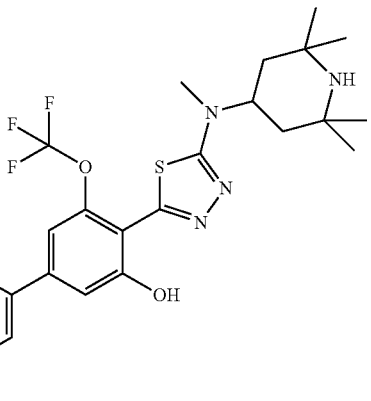 | 4-(3-hydroxy-4-(5-(methyl(2,2,6,6-tetramethylpiperidin-4-yl)amino)-1,3,4-thiadiazol-2-yl)-5-(trifluoromethoxy)phenyl)-1-methylpyridin-2(1H)-one | 2.69, 53 nM |
| 61 | 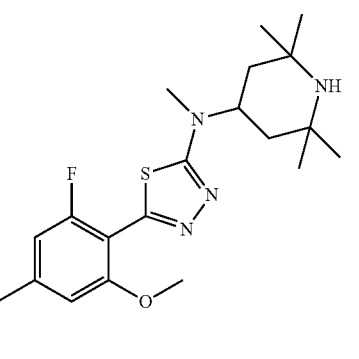 | 5-(2-fluoro-6-methoxy-4-(1H-pyrazol-4-yl)phenyl)-N-methyl-N-(2,2,6,6-tetramethylpiperidin-4-yl)-1,3,4-thiadiazol-2-amine | 2.36, 95 nM |
| 62 | 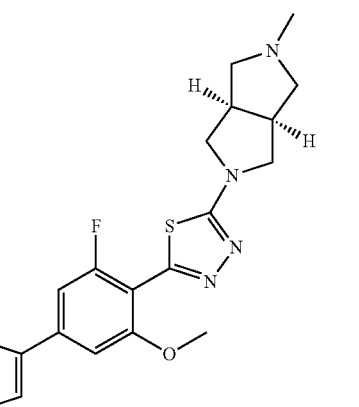 | 2-(2-fluoro-6-methoxy-4-(1H-pyrazol-4-yl)phenyl)-5-((3aR,6aS)-5-methylhexahydropyrrolo[3,4-c]pyrrol-2(1H)-yl)-1,3,4-thiadiazole | 2.01, 3642 nM |

Activity Table: ELISA data generated using Biological Example

| Example # | Structure | Chemical Name | SMN Activity Fold, EC$_{50}$ |
|---|---|---|---|
| 63 | 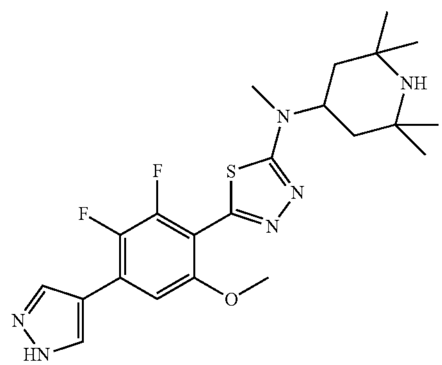 [SMILES: COc1cc(-c2cn[nH]c2)c(F)c(F)c1-c1nnc(N(C)C2CC(C)(C)NC(C)(C)C2)s1] | 5-(2,3-difluoro-6-methoxy-4-(1H-pyrazol-4-yl)phenyl)-N-methyl-N-(2,2,6,6-tetramethylpiperidin-4-yl)-1,3,4-thiadiazol-2-amine | 3.13, 47 nM |
| 64 | 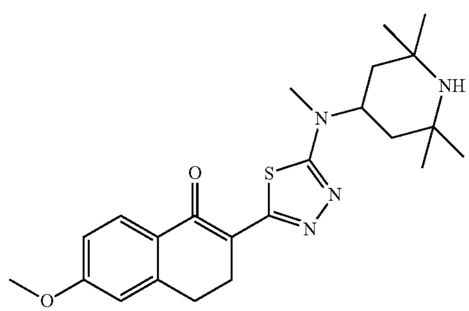 | 6-methoxy-2-(5-(methyl(2,2,6,6-tetramethylpiperidin-4-yl)amino)-1,3,4-thiadiazol-2-yl)-3,4-dihydroisoquinolin-1(2H)-one | 2.51, 1620 nM |
| 65 | 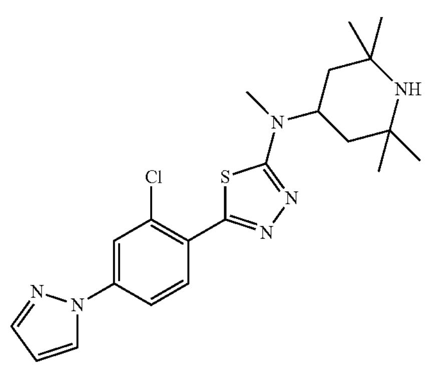 [SMILES: CN(c1nnc(-c2ccc(-n3cccn3)cc2Cl)s1)C1CC(C)(C)NC(C)(C)C1] | 5-(2-chloro-4-(1H-pyrazol-1-yl)phenyl)-N-methyl-N-(2,2,6,6-tetramethylpiperidin-4-yl)-1,3,4-thiadiazol-2-amine | 2.37, 273 nM |
| 66 | 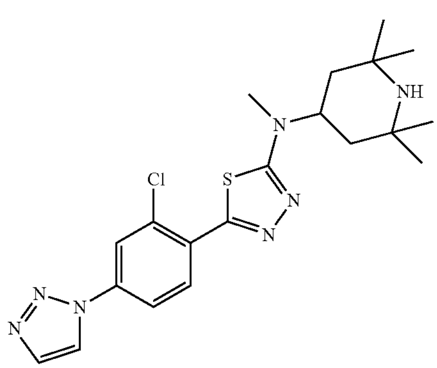 [SMILES: CN(c1nnc(-c2ccc(-n3ccnn3)cc2Cl)s1)C1CC(C)(C)NC(C)(C)C1] | 5-(2-chloro-4-(1H-1,2,3-triazol-1-yl)phenyl)-N-methyl-N-(2,2,6,6-tetramethylpiperidin-4-yl)-1,3,4-thiadiazol-2-amine | 2.32, 130 nM |

| Example # | Structure | Chemical Name | SMN Activity Fold, EC$_{50}$ |
|---|---|---|---|
| 67 | 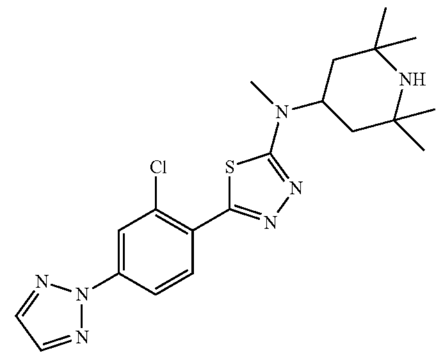 [SMILES: CN(c1nnc(-c2ccc(-n3nccn3)cc2Cl)s1)C1CC(C)(C)NC(C)(C)C1] | 5-(2-chloro-4-(2H-1,2,3-triazol-2-yl)phenyl)-N-methyl-N-(2,2,6,6-tetramethylpiperidin-4-yl)-1,3,4-thiadiazol-2-amine | 2.45, 159 nM |
| 68 | 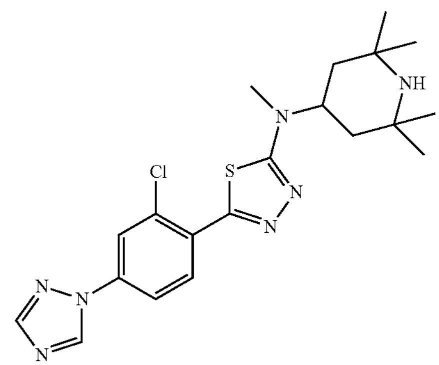 [SMILES: CN(c1nnc(-c2ccc(-n3cncn3)cc2Cl)s1)C1CC(C)(C)NC(C)(C)C1] | 5-(2-chloro-4-(1H-1,2,4-triazol-1-yl)phenyl)-N-methyl-N-(2,2,6,6-tetramethylpiperidin-4-yl)-1,3,4-thiadiazol-2-amine | 2.64, 79 nM |
| 69 | 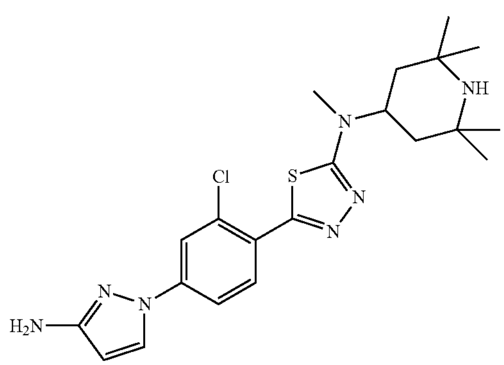 [SMILES: CN(c1nnc(-c2ccc(-n3ccc(N)n3)cc2Cl)s1)C1CC(C)(C)NC(C)(C)C1] | 5-(4-(3-amino-1H-pyrazol-1-yl)-2-chlorophenyl)-N-methyl-N-(2,2,6,6-tetramethylpiperidin-4-yl)-1,3,4-thiadiazol-2-amine | 2.44, 171 nM |
| 70 | 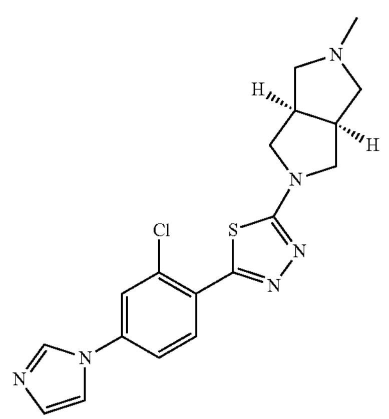 [SMILES: CN1C[C@@H]2CN(c3nnc(-c4ccc(-n5ccnc5)cc4Cl)s3)C[C@@H]2C1] | 2-(2-chloro-4-(1H-imidazol-1-yl)phenyl)-5-((3aR,6aS)-5-methylhexahydropyrrolo[3,4-c]pyrrol-2(1H)-yl)-1,3,4-thiadiazole | 2.17, 2571 nM |

Activity Table: ELISA data generated using Biological Example

-continued

Activity Table: ELISA data generated using Biological Example

| Example # | Structure | Chemical Name | SMN Activity Fold, $EC_{50}$ |
|---|---|---|---|
| 71 | 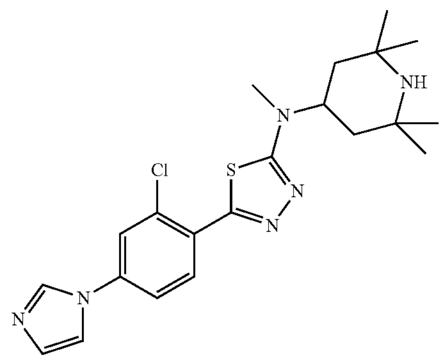 [SMILES: CN(c1nnc(-c2ccc(-n3ccnc3)cc2Cl)s1)C1CC(C)(C)NC(C)(C)C1] | 5-(2-chloro-4-(1H-imidazol-1-yl)phenyl)-N-methyl-N-(2,2,6,6-tetramethylpiperidin-4-yl)-1,3,4-thiadiazol-2-amine | 2.40, 32 nM |
| 72 | 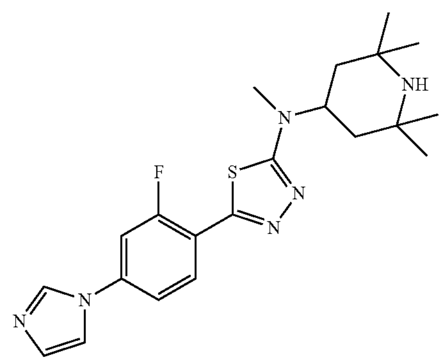 [SMILES: CN(c1nnc(-c2ccc(-n3ccnc3)cc2F)s1)C1CC(C)(C)NC(C)(C)C1] | 5-(2-fluoro-4-(1H-imidazol-1-yl)phenyl)-N-methyl-N-(2,2,6,6-tetramethylpiperidin-4-yl)-1,3,4-thiadiazol-2-amine | 2.50, 91 nM |
| 73 | 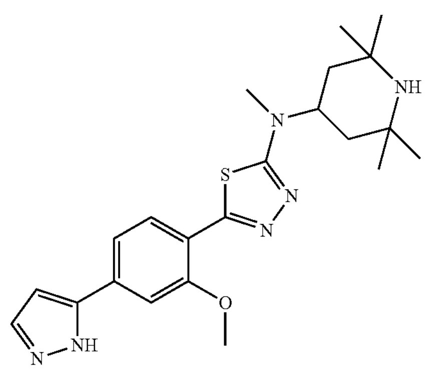 [SMILES: COc1cc(-c2ccn[nH]2)ccc1-c1nnc(N(C)C2CC(C)(C)NC(C)(C)C2)s1] | 5-(2-methoxy-4-(1H-pyrazol-5-yl)phenyl)-N-methyl-N-(2,2,6,6-tetramethylpiperidin-4-yl)-1,3,4-thiadiazol-2-amine | 2.73, 110 nM |
| 74 | 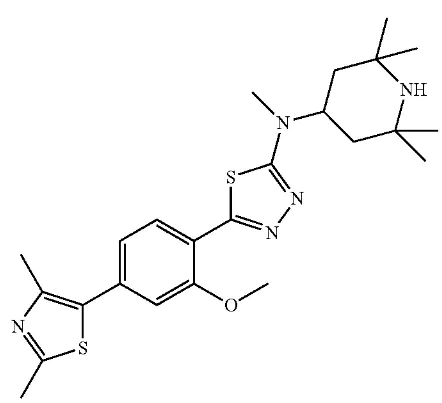 [SMILES: COc1cc(-c2sc(C)nc2C)ccc1-c1nnc(N(C)C2CC(C)(C)NC(C)(C)C2)s1] | 5-(4-(2,4-dimethylthiazol-5-yl)-2-methoxyphenyl)-N-methyl-N-(2,2,6,6-tetramethylpiperidin-4-yl)-1,3,4-thiadiazol-2-amine | 2.64, 85 nM |

Activity Table: ELISA data generated using Biological Example

| Example # | Structure | Chemical Name | SMN Activity Fold, EC$_{50}$ |
|---|---|---|---|
| 75 | 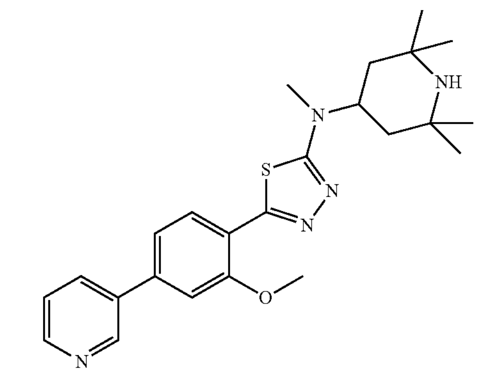 [SMILES: COc1cc(-c2cccnc2)ccc1-c1nnc(N(C)C2CC(C)(C)NC(C)(C)C2)s1] | 5-(2-methoxy-4-(pyridin-3-yl)phenyl)-N-methyl-N-(2,2,6,6-tetramethylpiperidin-4-yl)-1,3,4-thiadiazol-2-amine | 2.44, 235 nM |
| 76 | 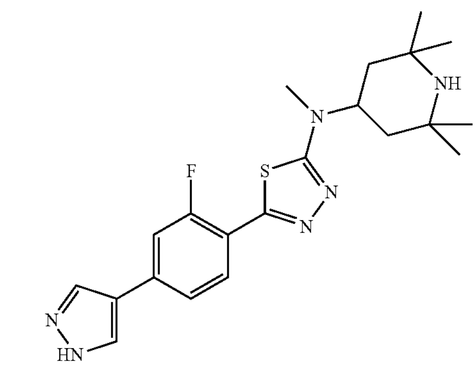 [SMILES: CN(c1nnc(-c2ccc(-c3cn[nH]c3)cc2F)s1)C1CC(C)(C)NC(C)(C)C1] | 5-(2-fluoro-4-(1H-pyrazol-4-yl)phenyl)-N-methyl-N-(2,2,6,6-tetramethylpiperidin-4-yl)-1,3,4-thiadiazol-2-amine | 3.06, 43 nM |
| 77 | 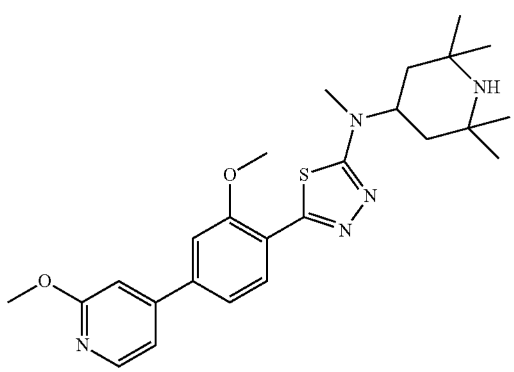 | 5-(2-methoxy-4-(2-methoxypyridin-4-yl)phenyl)-N-methyl-N-(2,2,6,6-tetramethylpiperidin-4-yl)-1,3,4-thiadiazol-2-amine | 3.33, 52 nM |
| 78 | 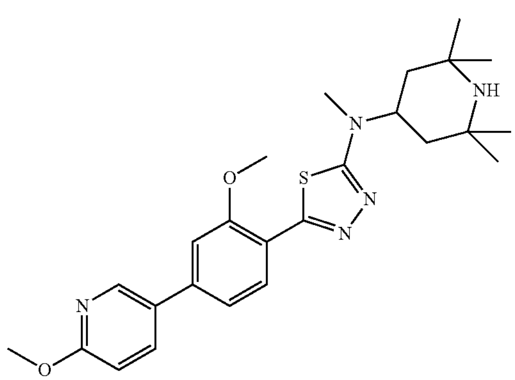 | 5-(2-methoxy-4-(6-methoxypyridin-3-yl)phenyl)-N-methyl-N-(2,2,6,6-tetramethylpiperidin-4-yl)-1,3,4-thiadiazol-2-amine | 2.52, 165 nM |

| Example # | Structure | Chemical Name | SMN Activity Fold, $EC_{50}$ |
|---|---|---|---|
| 79 | 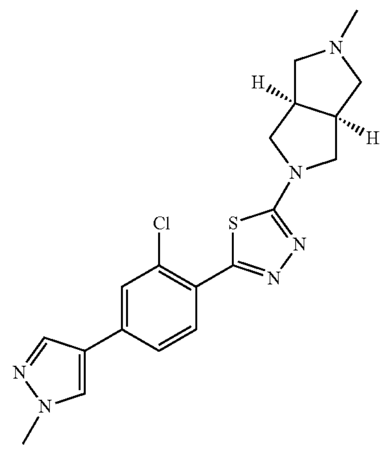 [SMILES: CN1C[C@@H]2CN(c3nnc(-c4ccc(-c5cnn(C)c5)cc4Cl)s3)C[C@@H]2C1] | 2-(2-chloro-4-(1-methyl-1H-pyrazol-4-yl)phenyl)-5-((3aR,6aS)-5-methylhexahydropyrrolo[3,4-c]pyrrol-2(1H)-yl)-1,3,4-thiadiazole | 2.76, 150 nM |
| 80 | 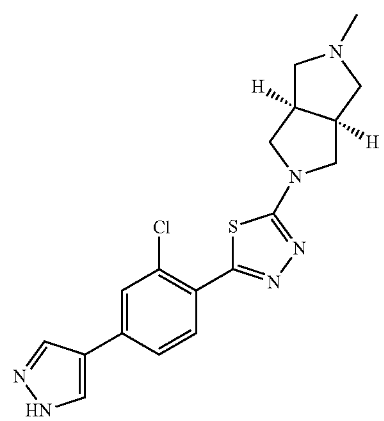 [SMILES: CN1C[C@@H]2CN(c3nnc(-c4ccc(-c5cn[nH]c5)cc4Cl)s3)C[C@@H]2C1] | 2-(2-chloro-4-(1H-pyrazol-4-yl)phenyl)-5-((3aR,6aS)-5-methylhexahydropyrrolo[3,4-c]pyrrol-2(1H)-yl)-1,3,4-thiadiazole | 2.70, 149 nM |
| 81 | 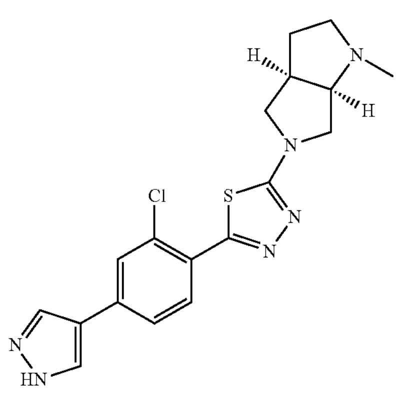 [SMILES: CN1CC[C@@H]2CN(c3nnc(-c4ccc(-c5cn[nH]c5)cc4Cl)s3)C[C@@H]21] | 2-(2-chloro-4-(1H-pyrazol-4-yl)phenyl)-5-((3aR,6aR)-1-methylhexahydropyrrolo[3,4-b]pyrrol-5(1H)-yl)-1,3,4-thiadiazole | 2.38, 1538 nM |

Activity Table: ELISA data generated using Biological Example
| Example # | Structure | Chemical Name | SMN Activity Fold, $EC_{50}$ |
|---|---|---|---|
| 82 | 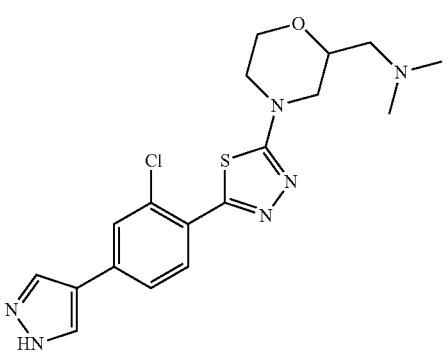 [SMILES: CN(C)CC1CN(c2nnc(-c3ccc(-c4cn[nH]c4)cc3Cl)s2)CCO1] | 1-(4-(5-(2-chloro-4-(1H-pyrazol-4-yl)phenyl)-1,3,4-thiadiazol-2-yl)morpholin-2-yl)-N,N-dimethylmethanamine | 2.50, 994 nM |
| 83 | 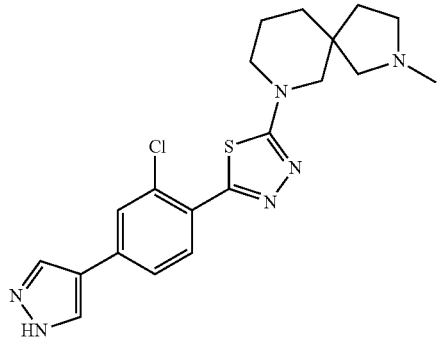 [SMILES: CN1CCC2(CCCN(c3nnc(-c4ccc(-c5cn[nH]c5)cc4Cl)s3)C2)C1] | 2-(2-chloro-4-(1H-pyrazol-4-yl)phenyl)-5-(2-methyl-2,7-diazaspiro[4.5]decan-7-yl)-1,3,4-thiadiazole | 2.59, 3280 nM |
| 84 | 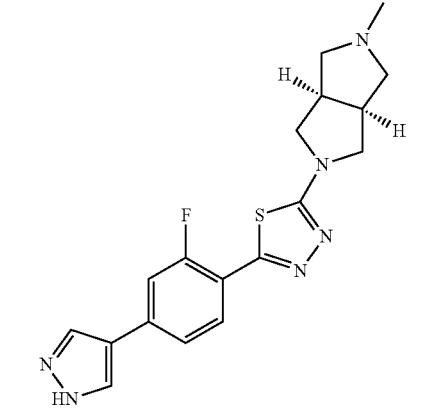 [SMILES: CN1C[C@@H]2CN(c3nnc(-c4ccc(-c5cn[nH]c5)cc4F)s3)C[C@@H]2C1] | 2-(2-fluoro-4-(1H-pyrazol-4-yl)phenyl)-5-((3aR,6aS)-5-methylhexahydropyrrolo[3,4-c]pyrrol-2(1H)-yl)-1,3,4-thiadiazole | 2.11, 193 nM |

-continued

Activity Table: ELISA data generated using Biological Example

| Example # | Structure | Chemical Name | SMN Activity Fold, $EC_{50}$ |
|---|---|---|---|
| 85 | 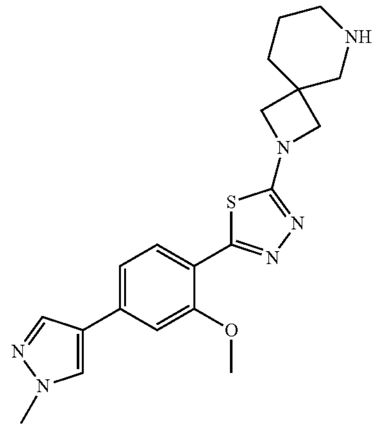 [SMILES: COc1cc(-c2cnn(C)c2)ccc1-c1nnc(N2CC3(CCCNC3)C2)s1] | 2-(2-methoxy-4-(1-methyl-1H-pyrazol-4-yl)phenyl)-5-(2,6-diazaspiro[3.5]nonan-2-yl)-1,3,4-thiadiazole | 2.22, 282 nM |
| 86 | 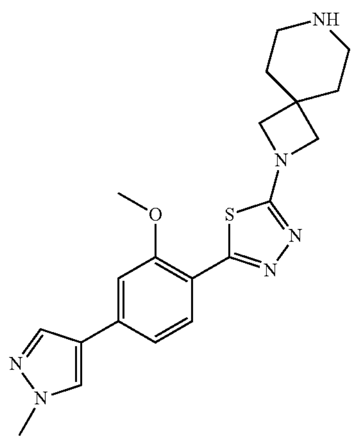 [SMILES: COc1cc(-c2cnn(C)c2)ccc1-c1nnc(N2CC3(CCNCC3)C2)s1] | 2-(2-methoxy-4-(1-methyl-1H-pyrazol-4-yl)phenyl)-5-(2,7-diazaspiro[3.5]nonan-2-yl)-1,3,4-thiadiazole | 2.33, 152 nM |
| 87 | 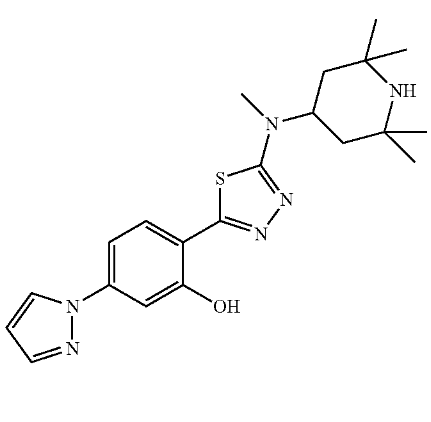 [SMILES: CN(c1nnc(-c2ccc(-n3cccn3)cc2O)s1)C1CC(C)(C)NC(C)(C)C1] | 2-(5-(Methyl(2,2,6,6-tetramethylpiperidin-4-yl)amino)-1,3,4-thiadiazol-2-yl)-5-(1H-pyrazol-1-yl)phenol | 2.76, 171 nM |

| Example # | Structure | Chemical Name | SMN Activity Fold, $EC_{50}$ |
|---|---|---|---|
| 88 | 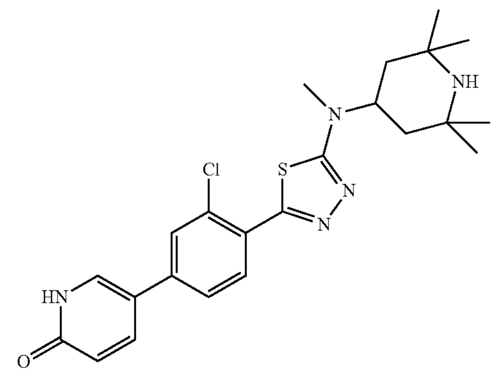 [SMILES: CN(c1nnc(-c2ccc(-c3ccc(=O)[nH]c3)cc2Cl)s1)C1CC(C)(C)NC(C)(C)C1] | 5-(3-chloro-4-(5-(methyl(2,2,6,6-tetramethylpiperidin-4-yl)amino)-1,3,4-thiadiazol-2-yl)phenyl)pyridin-2(1H)-one | 2.22, 160 nM |
| 89 | 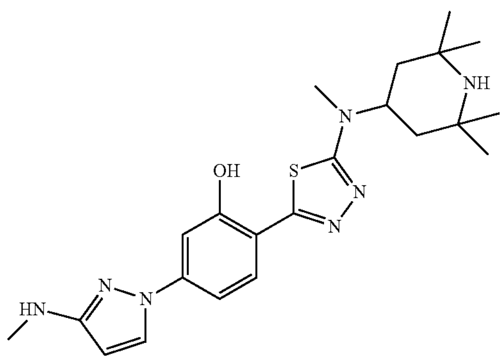 | 2-(5-(methyl(2,2,6,6-tetramethylpiperidin-4-yl)amino)-1,3,4-thiadiazol-2-yl)-5-(3-(methylamino)-1H-pyrazol-1-yl)phenol | 2.85, 106 nM |
| 90 | 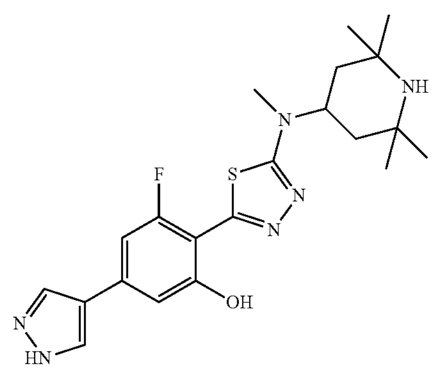 [SMILES: CN(c1nnc(-c2c(O)cc(-c3cn[nH]c3)cc2F)s1)C1CC(C)(C)NC(C)(C)C1] | 3-fluoro-2-(5-(methyl(2,2,6,6-tetramethylpiperidin-4-yl)amino)-1,3,4-thiadiazol-2-yl)-5-(1H-pyrazol-4-yl)phenol | 2.57, 6 nM |
| 91 | 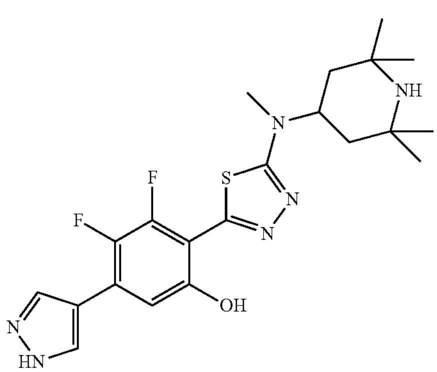 [SMILES: CN(c1nnc(-c2c(O)cc(-c3cn[nH]c3)c(F)c2F)s1)C1CC(C)(C)NC(C)(C)C1] | 3,4-difluoro-2-(5-(methyl(2,2,6,6-tetramethylpiperidin-4-yl)amino)-1,3,4-thiadiazol-2-yl)-5-(1H-pyrazol-4-yl)phenol | 2.67, 3 nM |

Activity Table: ELISA data generated using Biological Example

Activity Table: ELISA data generated using Biological Example

| Example # | Structure | Chemical Name | SMN Activity Fold, EC$_{50}$ |
|---|---|---|---|
| 92 | 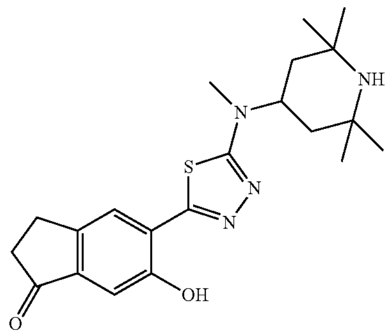 [SMILES: CN(c1nnc(-c2cc3c(cc2O)C(=O)CC3)s1)C1CC(C)(C)NC(C)(C)C1] | 6-hydroxy-5-(5-(methyl(2,2,6,6-tetramethylpiperidin-4-yl)amino)-1,3,4-thiadiazol-2-yl)-2,3-dihydro-1H-inden-1-one | 2.50, 91 nM |
| 93 | 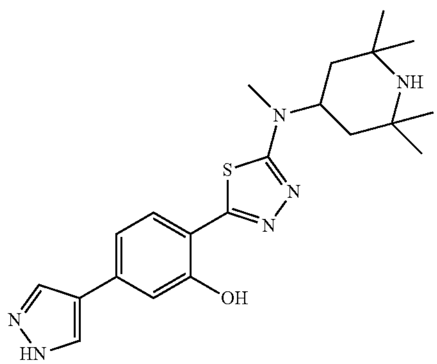 [SMILES: CN(c1nnc(-c2ccc(-c3cn[nH]c3)cc2O)s1)C1CC(C)(C)NC(C)(C)C1] | 2-(5-(methyl(2,2,6,6-tetramethylpiperidin-4-yl)amino)-1,3,4-thiadiazol-2-yl)-5-(1H-pyrazol-4-yl)phenol | 2.47, 404 nM |
| 94 | 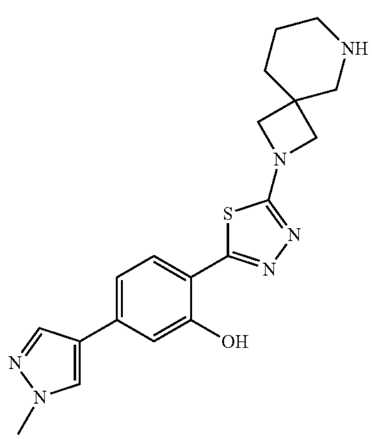 [SMILES: Cn1cc(-c2ccc(-c3nnc(N4CC5(CCCNC5)C4)s3)c(O)c2)cn1] | 2-(5-(2,6-diazaspiro[3.5]nonan-2-yl)-1,3,4-thiadiazol-2-yl)-5-(1-methyl-1H-pyrazol-4-yl)phenol | 2.59, 155 nM |

| Example # | Structure | Chemical Name | SMN Activity Fold, EC$_{50}$ |
|---|---|---|---|
| 95 | 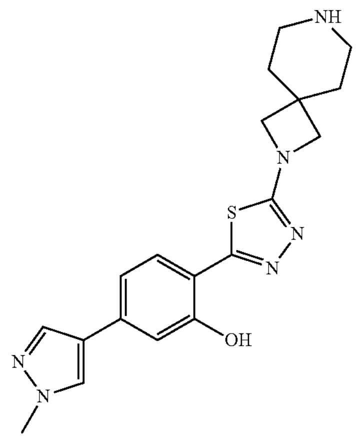 [SMILES: Cn1cc(-c2ccc(-c3nnc(N4CC5(CCNCC5)C4)s3)c(O)c2)cn1] | 2-(5-(2,7-diazaspiro[3.5]nonan-2-yl)-1,3,4-thiadiazol-2-yl)-5-(1-methyl-1H-pyrazol-4-yl)phenol | 2.44, 53 nM |
| 96 | 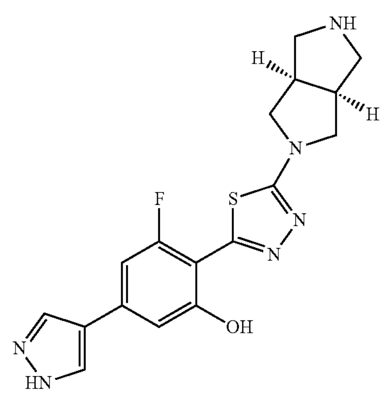 [SMILES: Oc1cc(-c2cn[nH]c2)cc(F)c1-c1nnc(N2C[C@H]3CNC[C@H]3C2)s1] | 3-fluoro-2-(5-((3aR,6aS)-hexahydropyrrolo[3,4-c]pyrrol-2(1H)-yl)-1,3,4-thiadiazol-2-yl)-5-(1H-pyrazol-4-yl)phenol•Di-hydrochloride salt | 2.85, 9 nM |
| 97 | 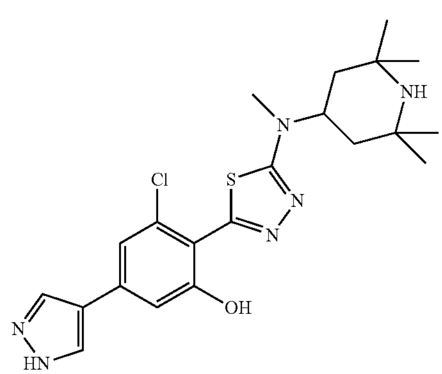 [SMILES: CN(c1nnc(-c2c(O)cc(-c3cn[nH]c3)cc2Cl)s1)C1CC(C)(C)NC(C)(C)C1] | 3-chloro-2-(5-(methyl(2,2,6,6-tetramethylpiperidin-4-yl)amino)-1,3,4-thiadiazol-2-yl)-5-(1H-pyrazol-4-yl)phenol | 2.45, 3 nM |

-continued

Activity Table: ELISA data generated using Biological Example

| Example # | Structure | Chemical Name | SMN Activity Fold, EC$_{50}$ |
|---|---|---|---|
| 98 | 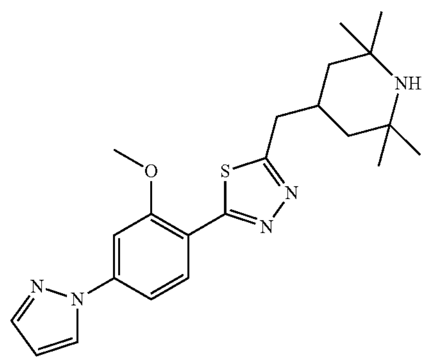 [SMILES: COc1cc(-n2cccn2)ccc1-c1nnc(CC2CC(C)(C)NC(C)(C)C2)s1] | 2-(2-methoxy-4-(1H-pyrazol-1-yl)phenyl)-5-((2,2,6,6-tetramethylpiperidin-4-yl)methyl)-1,3,4-thiadiazole | 2.19, 818 nM |
| 99 | 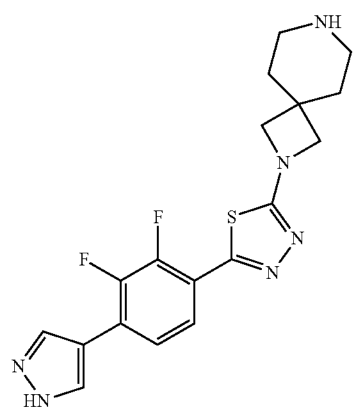 [SMILES: Fc1c(-c2cn[nH]c2)ccc(-c2nnc(N3CC4(CCNCC4)C3)s2)c1F] | 2-(2,3-difluoro-4-(1H-pyrazol-4-yl)phenyl)-5-(2,7-diazaspiro[3.5]nonan-2-yl)-1,3,4-thiadiazole | |
| 100 | 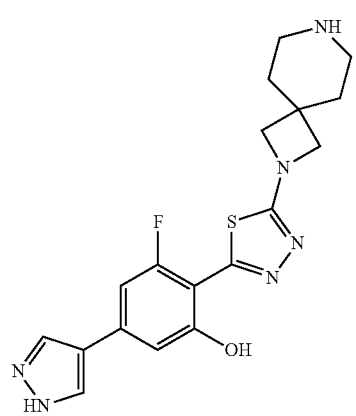 [SMILES: Oc1cc(-c2cn[nH]c2)cc(F)c1-c1nnc(N2CC3(CCNCC3)C2)s1] | 2-(5-(2,7-diazaspiro[3.5]nonan-2-yl)-1,3,4-thiadiazol-2-yl)-3-fluoro-5-(1H-pyrazol-4-yl)phenol | |
| 101 | 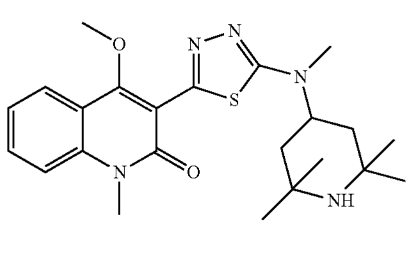 | 4-methoxy-1-methyl-3-(5-(methyl(2,2,6,6-tetramethylpiperidin-4-yl)amino)-1,3,4-thiadiazol-2-yl)quinolin-2(1H)-one | 2.51, 742 nM |

-continued

Activity Table: ELISA data generated using Biological Example

| Example # | Structure | Chemical Name | SMN Activity Fold, $EC_{50}$ |
|---|---|---|---|
| 102 | 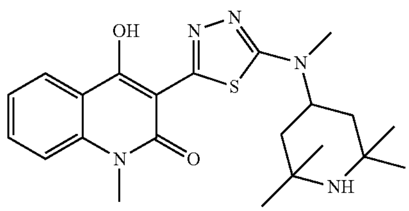 | 4-hydroxy-1-methyl-3-(5-(methyl(2,2,6,6-tetramethylpiperidin-4-yl)amino)-1,3,4-thiadiazol-2-yl)quinolin-2(1H)-one | 2.71, 24 nM |
| 103 | 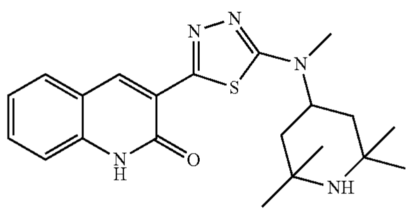 | 3-(5-(methyl(2,2,6,6-tetramethylpiperidin-4-yl)amino)-1,3,4-thiadiazol-2-yl)quinolin-2(1H)-one | 2.47, 161 nM |
| 104 | 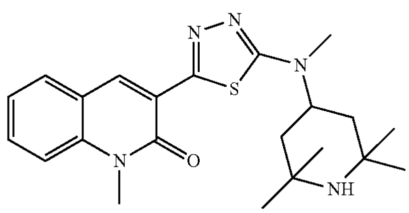 | 1-methyl-3-(5-(methyl(2,2,6,6-tetramethylpiperidin-4-yl)amino)-1,3,4-thiadiazol-2-yl)quinolin-2(1H)-one | 2.76, 100 nM |
| 105 | 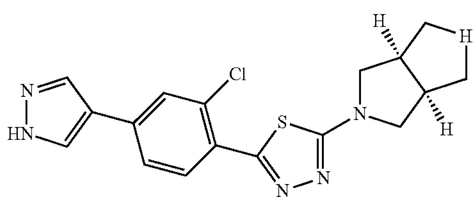 | 2-(2-chloro-4-(1H-pyrazol-4-yl)phenyl)-5-((3aR,6aS)-hexahydropyrrolo[3,4-c]pyrrol-2(1H)-yl)-1,3,4-thiadiazole•Hydrochloride Salt | 2.21, 181 nM |
| 106 | 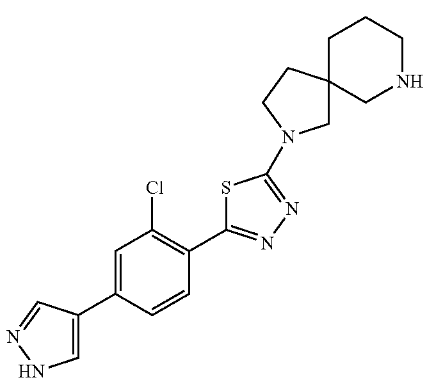 [SMILES: Clc1cc(-c2cn[nH]c2)ccc1-c1nnc(N2CCC3(CCCNC3)C2)s1] | 2-(2-chloro-4-(1H-pyrazol-4-yl)phenyl)-5-(2,7-diazaspiro[4.5]decan-2-yl)-1,3,4-thiadiazole•Hydrochloride Salt | 2.50, 1656 nM |

Activity Table: ELISA data generated using Biological Example

| Example # | Structure | Chemical Name | SMN Activity Fold, EC$_{50}$ |
|---|---|---|---|
| 107 | 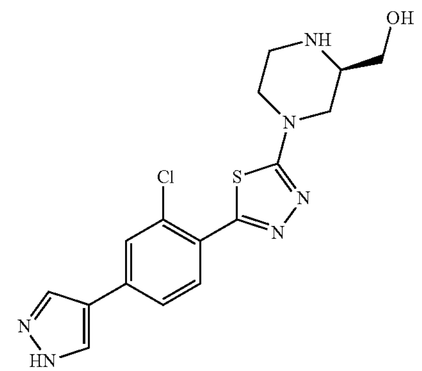 [SMILES: OC[C@H]1CN(c2nnc(-c3ccc(-c4cn[nH]c4)cc3Cl)s2)CCN1] | (R)-(4-(5-(2-chloro-4-(1H-pyrazol-4-yl)phenyl)-1,3,4-thiadiazol-2-yl)piperazin-2-yl)methanol•Hydrochloride Salt | 2.06, 4535 nM |
| 108 | 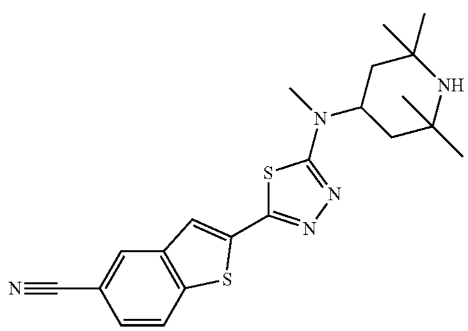 | 2-(5-(methyl(2,2,6,6-tetramethylpiperidin-4-yl)amino)-1,3,4-thiadiazol-2-yl)benzo[b]thiophene-5-carbonitrile | 2.72, 539 nM |
| 109 | 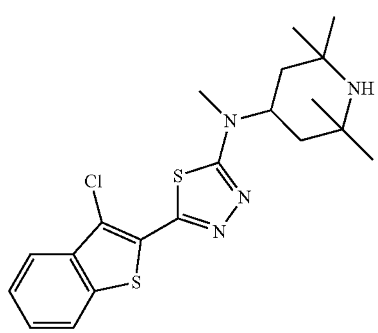 | 5-(3-chlorobenzo[b]thiophen-2-yl)-N-methyl-N-(2,2,6,6-tetramethylpiperidin-4-yl)-1,3,4-thiadiazol-2-amine | 2.75, 534 nM |

What is claimed is:

1. A compound, or salt thereof, which compound is represented by Formula (X)

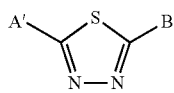

(X)

wherein

A' is phenyl which is substituted with 0, 1, 2, or 3 substituents independently selected from $C_1$-$C_4$alkyl, wherein 2 $C_1$-$C_4$alkyl groups can combine with the atoms to which they are bound to form a 5-6 membered ring and is substituted with 0 or 1 substituent selected from oxo, oxime and hydroxy, halo$C_1$-$C_4$alkyl, dihalo$C_1$-$C_4$alkyl, trihalo$C_1$-$C_4$alkyl, $C_1$-$C_4$alkoxy, $C_1$-$C_4$alkoxy-$C_3$-$C_7$cycloalkyl, halo$C_1$-$C_4$alkoxy, dihalo$C_1$-$C_4$alkoxy, trihalo$C_1$-$C_4$alkoxy, hydroxy, cyano, halogen, amino, mono-$C_1$-$C_4$alkylamino, di-$C_1$-$C_4$alkylamino, heteroaryl, $C_1$-$C_4$alkyl substituted with hydroxy, $C_1$-$C_4$alkoxy substituted with aryl, —C(O)NHC$_1$-$C_4$alkyl-heteroaryl, —NHC(O)—$C_1$-$C_4$alkyl-heteroaryl, $C_1$-$C_4$alkylC(O)NH-heteroaryl, $C_1$-$C_4$alkylNHC(O)-heteroaryl, 3-7 membered cycloalkyl, 5-7 membered cycloalkenyl and 5, 6 or 9 membered heterocycle containing 1 or 2 heteroatoms, independently, selected from S, O and N, wherein heteroaryl has 5, 6 or 9 ring atoms, 1, 2 or 3 ring heteroatoms selected from N, O and S, and substituted with 0, 1, or 2 substituents independently selected from oxo, hydroxy, nitro, halogen, $C_1$-$C_4$alkyl, $C_1$-$C_4$alkenyl, $C_1$-$C_4$alkoxy, $C_3$-$C_7$cycloalkyl, $C_1$-$C_4$alkyl-OH, triha-lo$C_1$-$C_4$alkyl, mono-$C_1$-$C_4$alkylamino, di-$C_1$-$C_4$alkylamino, —C(O)NH$_2$, —NH$_2$, —NO$_2$, hydroxyC1-C$_4$alkylamino, hydroxyC$_1$-C$_4$alkyl, 4-7 member heterocycleC$_1$-C$_4$alkyl, aminoC$_1$-C$_4$alkyl, mono-C$_1$-C$_4$alkyl and di-C$_1$-C$_4$alkylaminoC$_1$-C$_4$alkyl; or A' is 6 member heteroaryl having 1-3 ring nitrogen atoms, which 6 member heteroaryl is substituted by phenyl or a heteroaryl having 5 or 6 ring atoms, 1 or 2 ring heteroatoms independently selected from N, O and S, and substituted with 0, 1, or 2 substituents independently selected from C$_1$-C$_4$alkyl, mono-C$_1$-C$_4$alkylamino, di-C$_1$-C$_4$alkylamino, hydroxyC$_1$-C$_4$alkylamino, hydroxyC$_1$-C$_4$alkyl, aminoC$_1$-C$_4$alkyl, mono-C$_1$-C$_4$alkylaminoC$_1$-C$_4$alkyl and di-C$_1$-C$_4$alkylaminoC$_1$-C$_4$alkyl; or A' is bicyclic heteroaryl having 9 to 10 ring atoms and 1, 2, or 3 ring heteroatoms independently selected from N, O or S, which bicyclic heteroaryl is substituted with 0, 1, or 2 substituents independently selected from oxo, cyano, halogen, hydroxy, C$_1$-C$_4$alkyl, C$_2$-C$_4$alkenyl, C$_2$-C$_4$alkynyl, C$_1$-C$_4$alkoxy, C$_1$-C$_4$alkoxy substituted with hydroxy, C$_1$-C$_4$alkoxy, amino, mono-C$_1$-C$_4$alkylamino and di-C$_1$-C$_4$alkylamino;

B is

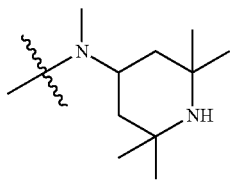

2. A compound, or salt thereof, which compound is represented by Formula (I)

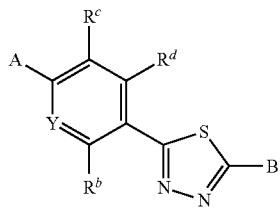

wherein

Y is N or C—R$^a$;

R$^a$ is hydrogen or C$_1$-C$_4$alkyl;

R$^b$ is hydrogen, C$_1$-C$_4$alkyl, C$_1$-C$_4$alkoxy, hydroxy, cyano, halogen, trihalo C$_1$-C$_4$alkyl or trihalo C$_1$-C$_4$alkoxy;

R$^c$ and R$^d$ are each, independently, hydrogen, C$_1$-C$_4$alkyl, C$_1$-C$_4$alkoxy, hydroxy, trihalo C$_1$-C$_4$alkyl, trihalo C$_1$-C$_4$alkoxy or heteroaryl;

A is 5 member heteroaryl having 1-3 ring heteroatoms independently selected from N, O and S, and substituted with 0, 1, or 2 substituents independently selected from C$_1$-C$_4$alkyl, hydroxyl, mono-C$_1$-C$_4$alkylamino, di-C$_1$-C$_4$alkylamino, hydroxyC$_1$-C$_4$alkylamino, hydroxyC$_1$-C$_4$alkyl, aminoC$_1$-C$_4$alkyl, mono-C$_1$-C$_4$alkylaminoC$_1$-C$_4$alkyl and di-C$_1$-C$_4$alkylaminoC$_1$-C$_4$alkyl;

B is a group of the formula:

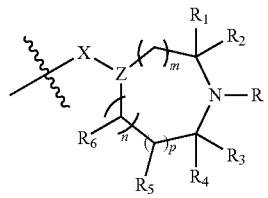

wherein m, n and p are independently selected from 0 or 1;

R, R$_1$, R$_2$, R$_3$, and R$_4$ are independently selected from the group consisting of hydrogen, C$_1$-C$_4$alkyl, which alkyl is optionally substituted with hydroxy, amino, mono-C$_1$-C$_4$akylamino and di-C$_1$-C$_4$akylamino;

R$_5$ and R$_6$ are independently selected from hydrogen and fluorine; or

R and R$_3$, taken in combination form a fused 5 or 6 member heterocyclic ring having 0 or 1 additional ring heteroatoms selected from N, O or S;

R$_1$ and R$_3$, taken in combination form a C$_1$-C$_3$alkylene group;

R$_1$ and R$_5$, taken in combination form a C$_1$-C$_3$alkylene group;

R$_3$ and R$_4$, taken in combination with the carbon atom to which they attach, form a spirocyclicC$_3$-C$_6$cycloalkyl;

X is CR$_{A'}$R$_{B'}$, NR$_7$ or a bond;

R$_7$ is hydrogen, or C$_1$-C$_4$alkyl;

R$_{A'}$ and R$_{B'}$ are independently selected from hydrogen and C$_1$-C$_4$alkyl, or R$_{A'}$ and R$_{B'}$, taken in combination, form a divalent C$_2$-C$_5$alkylene group;

Z is CR$_8$ or N; when Z is N, X is a bond;

R$_8$ is hydrogen or taken in combination with R$_6$ form a double bond; or

B is a group of the formula:

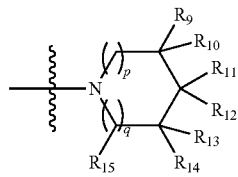

wherein p is selected from the group consisting of 0, 1 and 2;

q is 0;

R$_9$ and R$_{13}$ are independently selected from hydrogen and C$_1$-C$_4$alkyl;

R$_{10}$ and R$_{14}$ are independently selected from hydrogen, amino, mono-C$_1$-C$_4$akylamino, di-C$_1$-C$_4$akylamino and C$_1$-C$_4$alkyl, which alkyl is optionally substituted with hydroxy, amino, mono-C$_1$-C$_4$akylamino or di-C$_1$-C$_4$akylamino;

R$_{11}$ is hydrogen, C$_1$-C$_4$alkyl, amino, mono-C$_1$-C$_4$akylamino or di-C$_1$-C$_4$akylamino;

R$_{12}$ is hydrogen or C$_1$-C$_4$alkyl; or

R$_9$ and R$_{11}$, taken in combination form a saturated azacycle having 4 to 7 ring atoms which is optionally substituted with 1-3 C$_1$-C$_4$alkyl groups; or R$_{11}$ and R$_{12}$, taken in combination form a saturated azacycle having 4 to 7 ring atoms which is optionally substituted with 1-3 C$_1$-C$_4$alkyl groups.

3. A compound, or a salt thereof, according to claim 2, wherein A is selected from:

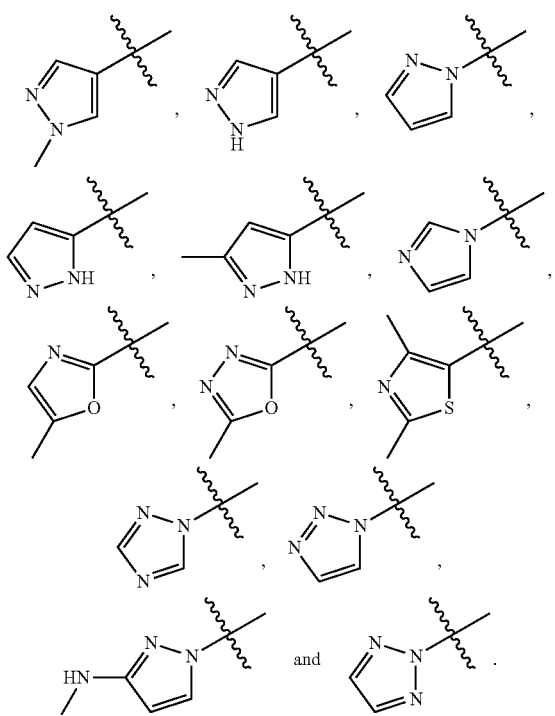

4. A compound or salt thereof selected from the group consisting of:
   5-(2-Methoxy-4-(1H-pyrazol-1-yl)phenyl)-N-methyl-N-(2,2,6,6-tetramethylpiperidin-4-yl)-1,3,4-thiadiazol-2-amine;
   6-(5-(Methyl(2,2,6,6-tetramethylpiperidin-4-yl)amino)-1,3,4-thiadiazol-2-yl)naphthalen-2-ol;
   5-(2-Methoxyquinolin-3-yl)-N-methyl-N-(2,2,6,6-tetramethylpiperidin-4-yl)-1,3,4-thiadiazol-2-amine;
   5-(3-Methoxynaphthalen-2-yl)-N-methyl-N-(2,2,6,6-tetramethylpiperidin-4-yl)-1,3,4-thiadiazol-2-amine;
   5-(2-Methoxy-4-(1H-pyrazol-1-yl)phenyl)-N-(1,2,2,6,6-pentamethylpiperidin-4-yl)-1,3,4-thiadiazol-2-amine;
   5-(2-Methoxy-4-(1-methyl-1H-pyrazol-4-yl)phenyl)-N-methyl-N-(2,2,6,6-tetramethylpiperidin-4-yl)-1,3,4-thiadiazol-2-amine;
   5-(2-Methoxy-4-(1H-pyrazol-4-yl)phenyl)-N-methyl-N-(2,2,6,6-tetramethylpiperidin-4-yl)-1,3,4-thiadiazol-2-amine;
   4-(3-Methoxy-4-(5-(methyl(2,2,6,6-tetramethylpiperidin-4-yl)amino)-1,3,4-thiadiazol-2-yl)phenyl)-1-methylpyridin-2(1H)-one;
   5-(3-Methoxy-4-(5-(methyl(2,2,6,6-tetramethylpiperidin-4-yl)amino)-1,3,4-thiadiazol-2-yl)phenyl)pyridin-2-ol;
   5-(3-Methoxy-4-(5-(methyl(2,2,6,6-tetramethylpiperidin-4-yl)amino)-1,3,4-thiadiazol-2-yl)phenyl)-1-methylpyridin-2(1H)-one;
   N-Methyl-5-(2-methyl-4-(1-methyl-1H-pyrazol-4-yl)phenyl)-N-(2,2,6,6-tetramethylpiperidin-4-yl)-1,3,4-thiadiazol-2-amine;
   1-Methyl-4-(4-(5-(methyl(2,2,6,6-tetramethylpiperidin-4-yl)amino)-1,3,4-thiadiazol-2-yl)-3-(trifluoromethoxy)phenyl)pyridin-2(1H)-one;
   5-(4-(3,5-Dimethyl-1H-pyrazol-4-yl)-2-methoxyphenyl)-N-methyl-N-(2,2,6,6-tetramethylpiperidin-4-yl)-1,3,4-thiadiazol-2-amine;
   5-(2-Methoxy-4-(1-methyl-1H-pyrazol-4-yl)phenyl)-N-methyl-N-(2,2,6,6-tetramethylpiperidin-4-yl)-1,3,4-thiadiazol-2-amine;
   2-(5-(Methyl(2,2,6,6-tetramethylpiperidin-4-yl)amino)-1,3,4-thiadiazol-2-yl)-5-(1-methyl-1H-pyrazol-4-yl)phenol;
   2-(5-(Methyl(2,2,6,6-tetramethylpiperidin-4-yl)amino)-1,3,4-thiadiazol-2-yl)-5-(1H-pyrazol-1-yl)phenol;
   5-(3-Hydroxy-4-(5-(methyl(2,2,6,6-tetramethylpiperidin-4-yl)amino)-1,3,4-thiadiazol-2-yl)phenyl)-1-methylpyridin-2(1H)-one;
   4-(3-Hydroxy-4-(5-(methyl(2,2,6,6-tetramethylpiperidin-4-yl)amino)-1,3,4-thiadiazol-2-yl)phenyl)-1-methylpyridin-2(1H)-one;
   5-(3-Hydroxy-4-(5-(methyl(2,2,6,6-tetramethylpiperidin-4-yl)amino)-1,3,4-thiadiazol-2-yl)phenyl)pyridin-2-ol;
   3-(5-(Methyl(2,2,6,6-tetramethylpiperidin-4-yl)amino)-1,3,4-thiadiazol-2-yl)naphthalene-2,7-diol;
   3-(5-((3aR,6aS)-Hexahydropyrrolo[3,4-c]pyrrol-2(1H)-yl)-1,3,4-thiadiazol-2-yl)naphthalene-2,7-diol;
   3-(5-(Methyl(2,2,6,6-tetramethylpiperidin-4-yl)amino)-1,3,4-thiadiazol-2-yl)naphthalen-2-ol.hydrobromide salt;
   3-(5-(Methyl(2,2,6,6-tetramethylpiperidin-4-yl)amino)-1,3,4-thiadiazol-2-yl)quinolin-2-ol;
   2-(5-(Methyl(2,2,6,6-tetramethylpiperidin-4-yl)amino)-1,3,4-thiadiazol-2-yl)-4-(1H-pyrazol-1-yl)phenol;
   5-(2-Chloro-4-(1-methyl-1H-pyrazol-4-yl)phenyl)-N-methyl-N-(2,2,6,6-tetramethylpiperidin-4-yl)-1,3,4-thiadiazol-2-amine;
   3-Chloro-2-(5-(methyl(2,2,6,6-tetramethylpiperidin-4-yl)amino)-1,3,4-thiadiazol-2-yl)-5-(1-methyl-1H-pyrazol-4-yl)phenol;
   5-(2-chloro-4-(1-methyl-1H-pyrazol-4-yl)phenyl)-N-(2,2,6,6-tetramethylpiperidin-4-yl)-1,3,4-thiadiazol-2-amine;
   3-Methoxy-2-(5-(methyl(2,2,6,6-tetramethylpiperidin-4-yl)amino)-1,3,4-thiadiazol-2-yl)-5-(5-methyloxazol-2-yl)phenol;
   2-(2-Methoxy-4-(1H-pyrazol-1-yl)phenyl)-5-(1,2,3,6-tetrahydropyridin-4-yl)-1,3,4-thiadiazole
   2-(5-(piperazin-1-yl)-1,3,4-thiadiazol-2-yl)-5-(1H-pyrazol-1-yl)phenol;
   5-(7-Methoxyquinolin-6-yl)-N-methyl-N-(2,2,6,6-tetramethylpiperidin-4-yl)-1,3,4-thiadiazol-2-amine;
   6-(5-(Methyl(2,2,6,6-tetramethylpiperidin-4-yl)amino)-1,3,4-thiadiazol-2-yl)quinolin-7-ol;
   3-methoxy-4-(5-(methyl(2,2,6,6-tetramethylpiperidin-4-yl)amino)-1,3,4-thiadiazol-2-yl)benzonitrile;
   3-fluoro-4-(5-(methyl(2,2,6,6-tetramethylpiperidin-4-yl)amino)-1,3,4-thiadiazol-2-yl)benzonitrile;
   methyl 3-fluoro-4-(5-(methyl(2,2,6,6-tetramethylpiperidin-4-yl)amino)-1,3,4-thiadiazol-2-yl)benzoate;
   5-(2-methoxy-4-(3-(methylamino)-1H-pyrazol-1-yl)phenyl)-N-methyl-N-(2,2,6,6-tetramethylpiperidin-4-yl)-1,3,4-thiadiazol-2-amine;
   7-methoxy-6-(5-(methyl(2,2,6,6-tetramethylpiperidin-4-yl)amino)-1,3,4-thiadiazol-2-yl)quinoline-2-carbonitrile;
   4-(3-methoxy-4-(5-((2,2,6,6-tetramethylpiperidin-4-yl)oxy)-1,3,4-thiadiazol-2-yl)phenyl)-1-methylpyridin-2(1H)-one;
   4-(3-chloro-4-(5-(methyl(2,2,6,6-tetramethylpiperidin-4-yl)amino)-1,3,4-thiadiazol-2-yl)phenyl)-1-methylpyridin-2(1H)-one;
   5-(2-chloro-4-(1H-pyrazol-4-yl)phenyl)-N-methyl-N-(2,2,6,6-tetramethylpiperidin-4-yl)-1,3,4-thiadiazol-2-amine;

5-(2-chloro-4-(4,5,6,7-tetrahydropyrazolo[1,5-a]pyridin-3-yl)phenyl)-N-methyl-N-(2,2,6,6-tetramethylpiperidin-4-yl)-1,3,4-thiadiazol-2-amine;
N-methyl-5-(5-(1-methyl-1H-pyrazol-4-yl)pyridin-2-yl)-N-(2,2,6,6-tetramethylpiperidin-4-yl)-1,3,4-thiadiazol-2-amine Hydrochloride salt;
2-(2-chloro-4-(1-methyl-1H-pyrazol-4-yl)phenyl)-5-((2,2,6,6-tetramethylpiperidin-4-yl)oxy)-1,3,4-thiadiazole;
5-(2-chloro-4-(6-methoxypyridin-3-yl)phenyl)-N-methyl-N-(2,2,6,6-tetramethylpiperidin-4-yl)-1,3,4-thiadiazol-2-amine;
5-(4-(6-aminopyridin-3-yl)-2-fluorophenyl)-N-methyl-N-(2,2,6,6-tetramethylpiperidin-4-yl)-1,3,4-thiadiazol-2-amine;
5-(2-fluoro-4-(3-methyl-1H-pyrazol-5-yl)phenyl)-N-methyl-N-(2,2,6,6-tetramethylpiperidin-4-yl)-1,3,4-thiadiazol-2-amine;
5-(2-fluoro-4-(1H-pyrazol-5-yl)phenyl)-N-methyl-N-(2,2,6,6-tetramethylpiperidin-4-yl)-1,3,4-thiadiazol-2-amine;
5-(2,3-difluoro-4-(1H-pyrazol-4-yl)phenyl)-N-methyl-N-(2,2,6,6-tetramethylpiperidin-4-yl)-1,3,4-thiadiazol-2-amine;
5-(2,3-difluoro-4-(1H-pyrazol-5-yl)phenyl)-N-methyl-N-(2,2,6,6-tetramethylpiperidin-4-yl)-1,3,4-thiadiazol-2-amine;
5-(2,5-difluoro-4-(1H-pyrazol-4-yl)phenyl)-N-methyl-N-(2,2,6,6-tetramethylpiperidin-4-yl)-1,3,4-thiadiazol-2-amine;
5-(2,5-difluoro-4-(1H-pyrazol-5-yl)phenyl)-N-methyl-N-(2,2,6,6-tetramethylpiperidin-4-yl)-1,3,4-thiadiazol-2-amine;
5-(2,6-difluoro-4-(1H-pyrazol-4-yl)phenyl)-N-methyl-N-(2,2,6,6-tetramethylpiperidin-4-yl)-1,3,4-thiadiazol-2-amine;
2-(2,5-difluoro-4-(1H-pyrazol-4-yl)phenyl)-5-((3aR,6aS)-hexahydropyrrolo[3,4-c]pyrrol-2(1H)-yl)-1,3,4-thiadiazole;
5-(2-chloro-5-fluoro-4-(1H-pyrazol-4-yl)phenyl)-N-methyl-N-(2,2,6,6-tetramethylpiperidin-4-yl)-1,3,4-thiadiazol-2-amine;
5-(3-fluoro-5-(1H-pyrazol-4-yl)pyridin-2-yl)-N-methyl-N-(2,2,6,6-tetramethylpiperidin-4-yl)-1,3,4-thiadiazol-2-amine;
5-(4-(2-aminopyrimidin-4-yl)-2-chlorophenyl)-N-methyl-N-(2,2,6,6-tetramethylpiperidin-4-yl)-1,3,4-thiadiazol-2-amine;
5-(5-(2-aminopyrimidin-4-yl)-2-chlorophenyl)-N-methyl-N-(2,2,6,6-tetramethylpiperidin-4-yl)-1,3,4-thiadiazol-2-amine;
5-(4-(2,4-dimethylthiazol-5-yl)-2,5-difluorophenyl)-N-methyl-N-(2,2,6,6-tetramethylpiperidin-4-yl)-1,3,4-thiadiazol-2-amine;
5-(4-(2,4-dimethylthiazol-5-yl)-2,3-difluorophenyl)-N-methyl-N-(2,2,6,6-tetramethylpiperidin-4-yl)-1,3,4-thiadiazol-2-amine;
4-(3-hydroxy-4-(5-(methyl(2,2,6,6-tetramethylpiperidin-4-yl)amino)-1,3,4-thiadiazol-2-yl)-5-(trifluoromethoxy)phenyl)-1-methylpyridin-2(1H)-one;
5-(2-fluoro-6-methoxy-4-(1H-pyrazol-4-yl)phenyl)-N-methyl-N-(2,2,6,6-tetramethylpiperidin-4-yl)-1,3,4-thiadiazol-2-amine;
2-(2-fluoro-6-methoxy-4-(1H-pyrazol-4-yl)phenyl)-5-((3aR,6aS)-5-methylhexahydropyrrolo[3,4-c]pyrrol-2(1H)-yl)-1,3,4-thiadiazole;
5-(2,3-difluoro-6-methoxy-4-(1H-pyrazol-4-yl)phenyl)-N-methyl-N-(2,2,6,6-tetramethylpiperidin-4-yl)-1,3,4-thiadiazol-2-amine;
6-methoxy-2-(5-(methyl(2,2,6,6-tetramethylpiperidin-4-yl)amino)-1,3,4-thiadiazol-2-yl)-3,4-dihydroisoquinolin-1(2H)-one;
5-(2-chloro-4-(1H-pyrazol-1-yl)phenyl)-N-methyl-N-(2,2,6,6-tetramethylpiperidin-4-yl)-1,3,4-thiadiazol-2-amine;
5-(2-chloro-4-(1H-1,2,3-triazol-1-yl)phenyl)-N-methyl-N-(2,2,6,6-tetramethylpiperidin-4-yl)-1,3,4-thiadiazol-2-amine;
5-(2-chloro-4-(2H-1,2,3-triazol-2-yl)phenyl)-N-methyl-N-(2,2,6,6-tetramethylpiperidin-4-yl)-1,3,4-thiadiazol-2-amine;
5-(2-chloro-4-(1H-1,2,4-triazol-1-yl)phenyl)-N-methyl-N-(2,2,6,6-tetramethylpiperidin-4-yl)-1,3,4-thiadiazol-2-amine;
5-(4-(3-amino-1H-pyrazol-1-yl)-2-chlorophenyl)-N-methyl-N-(2,2,6,6-tetramethylpiperidin-4-yl)-1,3,4-thiadiazol-2-amine;
2-(2-chloro-4-(1H-imidazol-1-yl)phenyl)-5-((3aR,6aS)-5-methylhexahydropyrrolo[3,4-c]pyrrol-2(1H)-yl)-1,3,4-thiadiazole;
5-(2-chloro-4-(1H-imidazol-1-yl)phenyl)-N-methyl-N-(2,2,6,6-tetramethylpiperidin-4-yl)-1,3,4-thiadiazol-2-amine;
5-(2-fluoro-4-(1H-imidazol-1-yl)phenyl)-N-methyl-N-(2,2,6,6-tetramethylpiperidin-4-yl)-1,3,4-thiadiazol-2-amine;
5-(2-methoxy-4-(1H-pyrazol-5-yl)phenyl)-N-methyl-N-(2,2,6,6-tetramethylpiperidin-4-yl)-1,3,4-thiadiazol-2-amine;
5-(4-(2,4-dimethylthiazol-5-yl)-2-methoxyphenyl)-N-methyl-N-(2,2,6,6-tetramethylpiperidin-4-yl)-1,3,4-thiadiazol-2-amine;
5-(2-methoxy-4-(pyridin-3-yl)phenyl)-N-methyl-N-(2,2,6,6-tetramethylpiperidin-4-yl)-1,3,4-thiadiazol-2-amine;
5-(2-fluoro-4-(1H-pyrazol-4-yl)phenyl)-N-methyl-N-(2,2,6,6-tetramethylpiperidin-4-yl)-1,3,4-thiadiazol-2-amine;
5-(2-methoxy-4-(2-methoxypyridin-4-yl)phenyl)-N-methyl-N-(2,2,6,6-tetramethylpiperidin-4-yl)-1,3,4-thiadiazol-2-amine;
5-(2-methoxy-4-(6-methoxypyridin-3-yl)phenyl)-N-methyl-N-(2,2,6,6-tetramethylpiperidin-4-yl)-1,3,4-thiadiazol-2-amine;
2-(2-chloro-4-(1-methyl-1H-pyrazol-4-yl)phenyl)-5-((3aR,6aS)-5-methylhexahydropyrrolo[3,4-c]pyrrol-2(1H)-yl)-1,3,4-thiadiazole;
2-(2-chloro-4-(1H-pyrazol-4-yl)phenyl)-5-((3aR,6aS)-5-methylhexahydropyrrolo[3,4-c]pyrrol-2(1H)-yl)-1,3,4-thiadiazole;
2-(2-chloro-4-(1H-pyrazol-4-yl)phenyl)-5-((3aR,6aR)-1-methylhexahydropyrrolo[3,4-b]pyrrol-5(1H)-yl)-1,3,4-thiadiazole;
1-(4-(5-(2-chloro-4-(1H-pyrazol-4-yl)phenyl)-1,3,4-thiadiazol-2-yl)morpholin-2-yl)-N,N-dimethylmethanamine;
2-(2-chloro-4-(1H-pyrazol-4-yl)phenyl)-5-(2-methyl-2,7-diazaspiro[4.5]decan-7-yl)-1,3,4-thiadiazole;
2-(2-fluoro-4-(1H-pyrazol-4-yl)phenyl)-5-((3aR,6aS)-5-methylhexahydropyrrolo[3,4-c]pyrrol-2(1H)-yl)-1,3,4-thiadiazole;
2-(2-methoxy-4-(1-methyl-1H-pyrazol-4-yl)phenyl)-5-(2,6-diazaspiro[3.5]nonan-2-yl)-1,3,4-thiadiazole;

2-(2-methoxy-4-(1-methyl-1H-pyrazol-4-yl)phenyl)-5-(2,7-diazaspiro[3.5]nonan-2-yl)-1,3,4-thiadiazole;
2-(5-(Methyl(2,2,6,6-tetramethylpiperidin-4-yl)amino)-1,3,4-thiadiazol-2-yl)-5-(1H-pyrazol-1-yl)phenol;
5-(3-chloro-4-(5-(methyl(2,2,6,6-tetramethylpiperidin-4-yl)amino)-1,3,4-thiadiazol-2-yl)phenyl)pyridin-2(1H)-one;
2-(5-(methyl(2,2,6,6-tetramethylpiperidin-4-yl)amino)-1,3,4-thiadiazol-2-yl)-5-(3-(methylamino)-1H-pyrazol-1-yl)phenol;
3-fluoro-2-(5-(methyl(2,2,6,6-tetramethylpiperidin-4-yl)amino)-1,3,4-thiadiazol-2-yl)-5-(1H-pyrazol-4-yl)phenol;
3,4-difluoro-2-(5-(methyl(2,2,6,6-tetramethylpiperidin-4-yl)amino)-1,3,4-thiadiazol-2-yl)-5-(1H-pyrazol-4-yl)phenol;
6-hydroxy-5-(5-(methyl(2,2,6,6-tetramethylpiperidin-4-yl)amino)-1,3,4-thiadiazol-2-yl)-2,3-dihydro-1H-inden-1-one;
2-(5-(methyl(2,2,6,6-tetramethylpiperidin-4-yl)amino)-1,3,4-thiadiazol-2-yl)-5-(1H-pyrazol-4-yl)phenol;
2-(5-(2,6-diazaspiro[3.5]nonan-2-yl)-1,3,4-thiadiazol-2-yl)-5-(1-methyl-1H-pyrazol-4-yl)phenol;
2-(5-(2,7-diazaspiro[3.5]nonan-2-yl)-1,3,4-thiadiazol-2-yl)-5-(1-methyl-1H-pyrazol-4-yl)phenol;
3-fluoro-2-(5-((3aR,6aS)-hexahydropyrrolo[3,4-c]pyrrol-2(1H)-yl)-1,3,4-thiadiazol-2-yl)-5-(1H-pyrazol-4-yl) phenol Di-hydrochloride salt;
3-chloro-2-(5-(methyl(2,2,6,6-tetramethylpiperidin-4-yl)amino)-1,3,4-thiadiazol-2-yl)-5-(1H-pyrazol-4-yl)phenol;
2-(2-methoxy-4-(1H-pyrazol-1-yl)phenyl)-5-((2,2,6,6-tetramethylpiperidin-4-yl)methyl)-1,3,4-thiadiazole;
2-(2,3-difluoro-4-(1H-pyrazol-4-yl)phenyl)-5-(2,7-diazaspiro[3.5]nonan-2-yl)-1,3,4-thiadiazole;
2-(5-(2,7-diazaspiro[3.5]nonan-2-yl)-1,3,4-thiadiazol-2-yl)-3-fluoro-5-(1H-pyrazol-4-yl)phenol;
4-methoxy-1-methyl-3-(5-(methyl(2,2,6,6-tetramethylpiperidin-4-yl)amino)-1,3,4-thiadiazol-2-yl)quinolin-2(1H)-one;
4-hydroxy-1-methyl-3-(5-(methyl(2,2,6,6-tetramethylpiperidin-4-yl)amino)-1,3,4-thiadiazol-2-yl)quinolin-2(1H)-one;
3-(5-(methyl(2,2,6,6-tetramethylpiperidin-4-yl)amino)-1,3,4-thiadiazol-2-yl)quinolin-2(1H)-one;
1-methyl-3-(5-(methyl(2,2,6,6-tetramethylpiperidin-4-yl)amino)-1,3,4-thiadiazol-2-yl)quinolin-2(1H)-one;
2-(2-chloro-4-(1H-pyrazol-4-yl)phenyl)-5-((3aR,6aS)-hexahydropyrrolo[3,4-c]pyrrol-2(1H)-yl)-1,3,4-thiadiazole Hydrochloride Salt;
2-(2-chloro-4-(1H-pyrazol-4-yl)phenyl)-5-(2,7-diazaspiro[4.5]decan-2-yl)-1,3,4-thiadiazole Hydrochloride Salt;
(R)-(4-(5-(2-chloro-4-(1H-pyrazol-4-yl)phenyl)-1,3,4-thiadiazol-2-yl)piperazin-2-yl)methanol Hydrochloride Salt;
2-(5-(methyl(2,2,6,6-tetramethylpiperidin-4-yl)amino)-1,3,4-thiadiazol-2-yl)benzo[b]thiophene-5-carbonitrile; and
5-(3-chlorobenzo[b]thiophen-2-yl)-N-methyl-N-(2,2,6,6-tetramethylpiperidin-4-yl)-1,3,4-thiadiazol-2-amine.

5. A pharmaceutical composition comprising a therapeutically effective amount of a compound according to claim 1, or a pharmaceutically acceptable salt thereof and one or more pharmaceutically acceptable carriers.

6. A combination comprising a therapeutically effective amount of a compound according to claim 1, or a pharmaceutically acceptable salt thereof and one or more therapeutically active co-agents.

7. A method to treat or ameliorate an SMN-deficiency-related condition, comprising administering to a subject in need thereof an effective amount of a compound or salt thereof of claim 1.

8. The method of claim 7, wherein said SMN-deficiency-related condition is Spinal Muscular Atrophy.

9. A pharmaceutical composition comprising a therapeutically effective amount of a compound according to claim 2, or a pharmaceutically acceptable salt thereof and one or more pharmaceutically acceptable carriers.

10. A pharmaceutical composition comprising a therapeutically effective amount of a compound according to claim 4, or a pharmaceutically acceptable salt thereof and one or more pharmaceutically acceptable carriers.

11. A combination comprising a therapeutically effective amount of a compound according to claim 2 or a pharmaceutically acceptable salt thereof and one or more therapeutically active co-agents.

12. A combination comprising a therapeutically effective amount of a compound according to claim 4 or a pharmaceutically acceptable salt thereof and one or more therapeutically active co-agents.

13. A method to treat or ameliorate an SMN-deficiency-related condition, comprising administering to a subject in need thereof an effective amount of a compound or salt thereof of claim 2.

14. The method of claim 13, wherein said SMN-deficiency-related condition is Spinal Muscular Atrophy.

15. A method to treat or ameliorate an SMN-deficiency-related condition, comprising administering to a subject in need thereof an effective amount of a compound or salt thereof of claim 4.

16. The method of claim 15, wherein said SMN-deficiency-related condition is Spinal Muscular Atrophy.

* * * * *